(12) United States Patent
Klein et al.

(10) Patent No.: US 11,098,099 B2
(45) Date of Patent: Aug. 24, 2021

(54) INTERLEUKIN-2 FUSION PROTEINS AND USES THEREOF

(71) Applicant: Hoffmann-La Roche Inc., Nutley, NJ (US)

(72) Inventors: Christian Klein, Bonstetten (CH); Pablo Umana, Wollerau (CH); Ekkehard Moessner, Kreuzlingen (CH); Ralf Hosse, Cham (CH); Laurence Bernard Peterson, Cambridge (GB); Linda Wicker, Cambridge (GB)

(73) Assignee: HOFFMANN-LA ROCHE INC., Little Falls, NJ (US)

( * ) Notice: Subject to any disclaimer, the term of this patent is extended or adjusted under 35 U.S.C. 154(b) by 282 days.

(21) Appl. No.: 14/613,831

(22) Filed: Feb. 4, 2015

(65) Prior Publication Data

US 2015/0218260 A1    Aug. 6, 2015

Related U.S. Application Data

(60) Provisional application No. 61/936,564, filed on Feb. 6, 2014.

(51) Int. Cl.
*C07K 14/55* (2006.01)

(52) U.S. Cl.
CPC .......... *C07K 14/55* (2013.01); *C07K 2317/52* (2013.01); *C07K 2319/00* (2013.01); *C07K 2319/30* (2013.01)

(58) Field of Classification Search
CPC ................ A61K 38/2013; C07K 14/55; C07K 2319/30; C07K 2319/00
See application file for complete search history.

(56) References Cited

U.S. PATENT DOCUMENTS

| | | | |
|---|---|---|---|
| 5,650,150 A | 7/1997 | Gillies | |
| 6,955,807 B1* | 10/2005 | Shanafelt | C07K 14/55 424/85.2 |
| 8,969,526 B2 | 3/2015 | Baehner et al. | |
| 9,266,938 B2 | 2/2016 | Ast et al. | |
| 9,447,159 B2 | 9/2016 | Ast et al. | |
| 10,184,009 B2 | 1/2019 | Ast et al. | |
| 10,202,464 B2 | 2/2019 | Ast et al. | |
| 2004/0175357 A1 | 9/2004 | Shanafelt et al. | |
| 2004/0229338 A1 | 11/2004 | King et al. | |
| 2010/0021477 A1 | 1/2010 | Tsui et al. | |
| 2010/0260765 A1 | 10/2010 | Barry et al. | |
| 2011/0274650 A1* | 11/2011 | Gavin | C07K 14/55 424/85.2 |
| 2012/0251531 A1* | 10/2012 | Baehner | C07K 16/2896 424/133.1 |
| 2013/0195795 A1 | 1/2013 | Gavin et al. | |
| 2015/0218260 A1 | 8/2015 | Klein et al. | |
| 2015/0239981 A1 | 8/2015 | Baehner et al. | |
| 2016/0090407 A1 | 3/2016 | Hosse et al. | |
| 2016/0208017 A1 | 7/2016 | Ast et al. | |
| 2016/0263240 A1 | 9/2016 | Ast et al. | |
| 2017/0137530 A1 | 5/2017 | Baehner et al. | |
| 2018/0009868 A1 | 1/2018 | Hosse et al. | |

FOREIGN PATENT DOCUMENTS

| | | | |
|---|---|---|---|
| WO | 85/00817 | 2/1985 | |
| WO | 99/43713 | 9/1999 | |
| WO | 999/60128 A1 | 11/1999 | |
| WO | 2003/048334 A2 | 6/2003 | |
| WO | 2005/007121 A2 | 1/2005 | |
| WO | 2005/086798 | 9/2005 | |
| WO | WO 2005086798 A2 * | 9/2005 | ............. C07K 14/55 |
| WO | 2006/058077 | 6/2006 | |
| WO | 2008/003473 | 1/2008 | |
| WO | 2009/061853 A2 | 5/2009 | |
| WO | 2009/135615 A2 | 11/2009 | |
| WO | 2009/135615 A3 | 11/2009 | |
| WO | 2009/135615 A8 | 11/2009 | |
| WO | 2010/085495 A1 | 7/2010 | |
| WO | 2012/062228 A2 | 5/2012 | |
| WO | 2012/107417 | 8/2012 | |
| WO | WO-2012107417 A1 * | 8/2012 | ............. C07K 14/55 |
| WO | 2012/123381 A1 | 9/2012 | |

(Continued)

OTHER PUBLICATIONS

Bowie et al. Deciphering the Message in Protein Sequences: Tolerance to Amino Acid Substitutions. Science, 1990, 247:1306-1310.*
Burgess et al. Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue. J. Cell Biol. 111:2129-2138, 1990.*
Bork. Powers and pitfalls in sequence analysis: the 70% hurdle. Genome Research, 2000; 10:398-400.*
Strohl. Optimization of Fc-mediated effector functions of monoclonal antibodies. Current Opinion in Biotechnology. 20:685-691, Nov. 2009.*
Presta. Molecular engineering and design of therapeutic antibodies. Current Opinion in Immunology. 20(4):460-470. Aug. 2008.*
Strohl. Current Opinion in Biotechnology. 20:685-691, Nov. 2009 (Year: 2009).*

(Continued)

*Primary Examiner* — Vanessa L. Ford
*Assistant Examiner* — Sandra E Dillahunt
(74) *Attorney, Agent, or Firm* — Jonathan P. Aumais

(57) ABSTRACT

The present invention generally relates to fusion proteins of immunoglobulins and interleukin-2 (IL-2). More particularly, the invention concerns fusion proteins of immunoglobulins and mutant IL-2 that exhibit improved properties for use as therapeutic agents, e.g. in the treatment of autoimmune diseases and immune-mediated inflammatory diseases. In addition, the present invention relates to polynucleotides encoding such fusion proteins, and vectors and host cells comprising such polynucleotides. The invention further relates to methods for producing the fusion proteins of the invention, and to methods of using them in the treatment of disease.

28 Claims, 54 Drawing Sheets

Specification includes a Sequence Listing.

(56) References Cited

FOREIGN PATENT DOCUMENTS

| WO | 2012/130831 | A1 | | 10/2012 | | |
| WO | 2012/146628 | A1 | | 11/2012 | | |
| WO | WO-2012146628 | A1 | * | 11/2012 | ......... | C07K 16/2866 |
| WO | 2012/178137 | A1 | | 12/2012 | | |
| WO | WO-2012178137 | A1 | * | 12/2012 | ............. | C07K 14/55 |
| WO | WO 2012178137 | A1 | * | 12/2012 | ....... | A61K 47/48569 |
| WO | 2014/023752 | A1 | | 2/2014 | | |
| WO | 2014/153063 | A1 | | 9/2014 | | |
| WO | 2014/153111 | A2 | | 9/2014 | | |
| WO | 2016/022671 | A1 | | 2/2016 | | |

OTHER PUBLICATIONS

Presta. Current Opinion in Immunology. 20(4):460-470. Aug. 2008 (Year: 2008).*
Bowie et al. Science, 1990, 247:1306-1310 (Year: 1990).*
Burgess et al. J. Cell Biol. 111:2129-2138, 1990 (Year: 1990).*
Lazar et al. Mol. Cell. Biol., 8:1247-1252, 1988 (Year: 1988).*
Bork. Genome Research, 2000; 10:398-400 (Year: 2000).*
International Search Report and Written Opinion on patentability for International Patent Application No. PCT/EP2015/052312.
Bork et al., "Powers and Pitfalls in Sequence Analysis: the 70% Hurdle" Genorme Res. 10:398-400 ( 2000).
Bowie et al., "Deciphering the message in protein sequences: tolerance to amino acid substitutions" Science 247(4948):1306-10 ( 1990).
Burgess et al., "Possible dissociation of the heparin-binding and mitogenic activities of heparin-binding (Acidic Fibroblast) gtowth factor-1 from its receptor-binding activities by site-directed mutagenesis of a single lysine residue" Journal of Cell Biology 111:2129-2138 ( 1990).
Presta et al., "Molecular engineering and design of therapeutic antibodies" Current Opinion in Immunology 20:460-470 ( 2008).
Strohl, R., "Optimization of Fc-mediated effector functions of monoclonal antibodies" Current Opinion in Biotechnology 20(6):685-691 (2009).
(Extended European Search Report for European Patent Application No. 18201416.7 dated May 15, 2019).

Armour et al., "Recombinant human IgG molecules lacking Fcÿ receptor I binding and monocyte triggering activities," Eur. J. Immunol. 1999. 29: 2613-2624.
Brandenburg et al., "IL-2 induces in vivo suppression by CD4\\\superscript:+\\\CD25\\\superscript:+\\\Foxp3\\\superscript:+\\\regulatory T cells" Eur. J. Immunol. 38:1643-1653 (2008).
De La Rosa et al., "Interleukin-2 is essential for CD4\\\superscript:+\\\CD25\\\superscript:+\\\regulatory T cell function" Eur. J. Immunol. 34:2480-2488 ( 2004).
Gillies et al., "Improving the Efficacy of Antibody-Interleukin 2 Fusion Proteins by Reducing Their Interaction with Fc Receptors," Cancer Research, vol. 59(9), pp. 2159-2166 (1999).
Harvill et al, "An IgG3-IL2 fusion protein activates complement, binds FcTRI, generates LAK activity and shows enhanced binding to the high affinity IL-2R," Immunotechnology, vol. 1(2), pp. 95-105 (1995).
Helguera et al., "Vaccination with novel combinations of anti-HER2/neu cytokines fusion proteins and soluble protein antigen elicits a protective immune response against HER2/neu expressing tumors," Vaccine 24 (2006) 304-316.
Kim et al., "Immunoglobulin-Cytokine Fusion Molecules: The New Generation of Immunomodulating Agents," Transplantation Proceedings, 30, 4031-4036 (1998).
Kunzendorf et al., "Suppression of Cell-mediated and Humoral Immune Responses by an Interleukin-2-Immunoglobulin Fusion Protein in Mice" J. Clin. Invest. 97(5):1204-1210 (Mar. 1996).
Shields et al., "High Resolution Mapping of the Binding Site on Human IgG1 for FcyRI, FcyRII, FcyRIII, and FcRn and design of IgG1 variants with improved binding to the RcyR" J Biol Chem 276(9):6591-6604 (Mar 2, 2001).
The International Search Report and Written Opinion, dated Nov. 4, 2013, in the corresponding PCT Patent Application No. PCT/EP2013/066516.
Wang et al., "Structure of the quaternary complex of interleukin-2 with its α, beta, and γc receptors" Science 310(5751):1159-1163 ( 2005).
Peterson et al., "A long-lived IL-2 mutein that selectively activates and expands regulatory T cells as a therapy for autoimmune disease" Journal of Autoimmunity 95:1-14 2018.

* cited by examiner

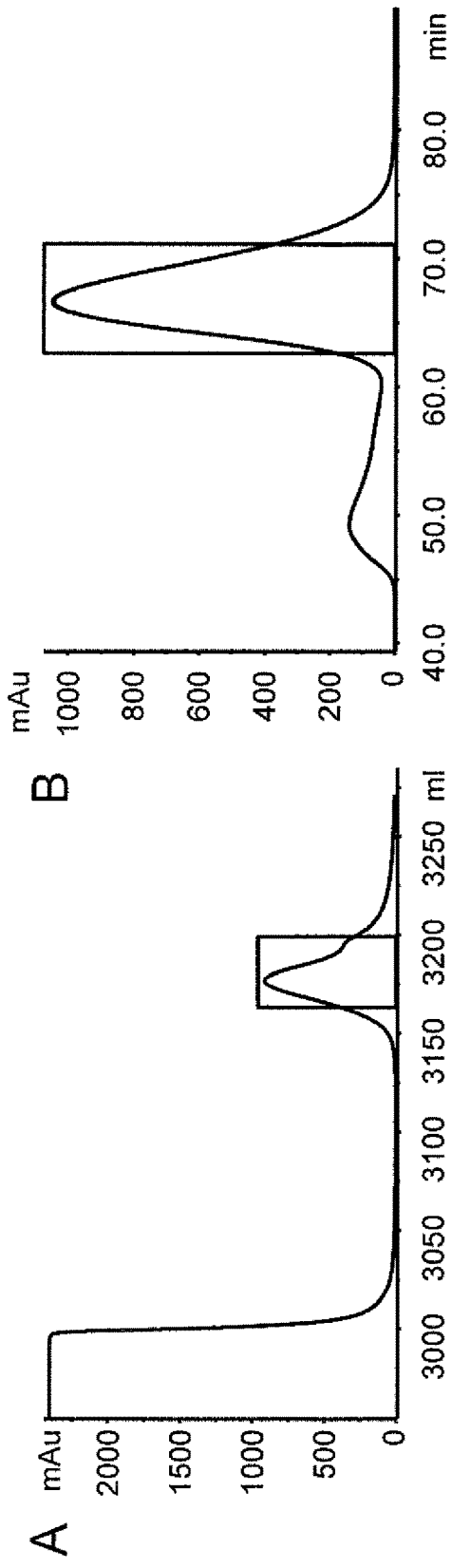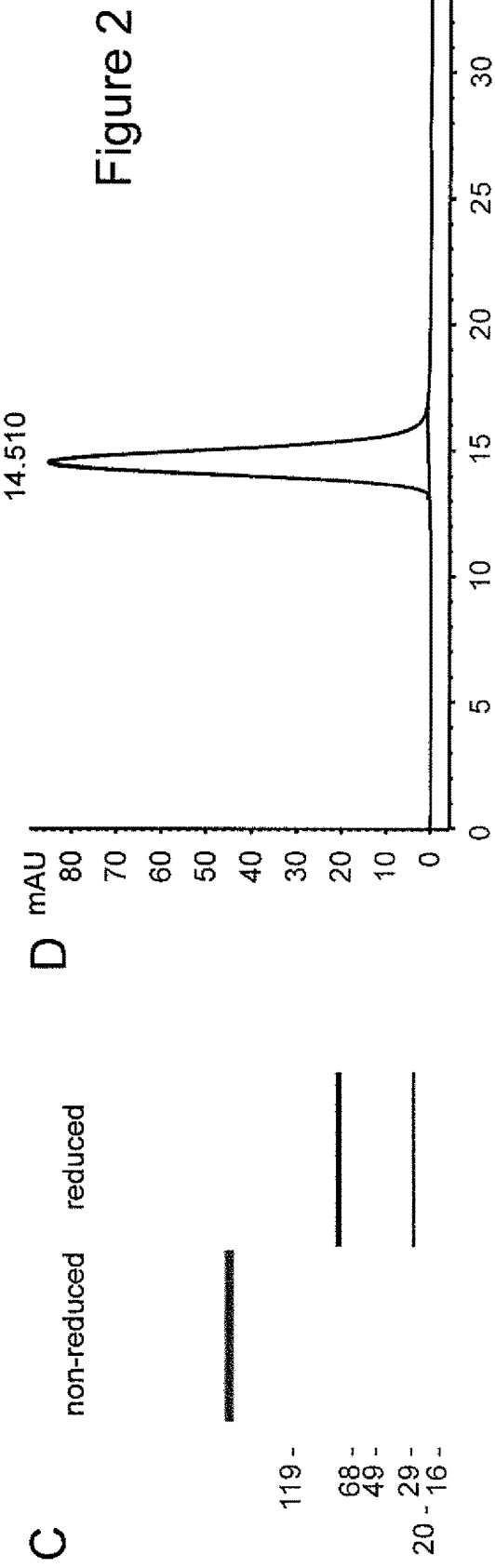
Figure 2

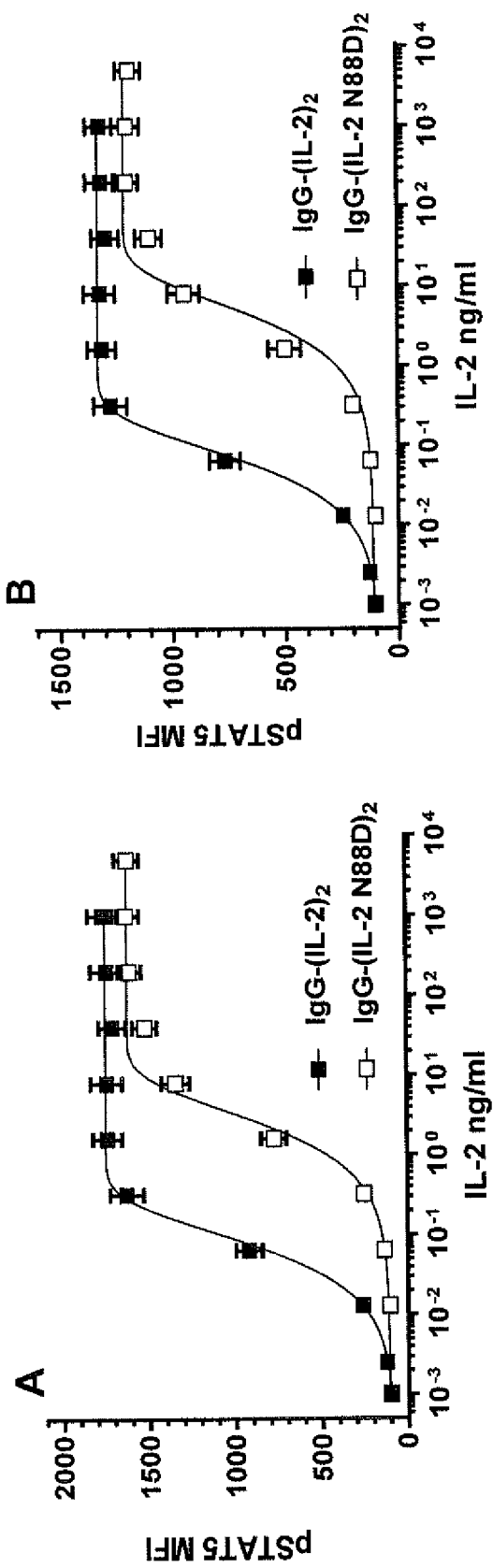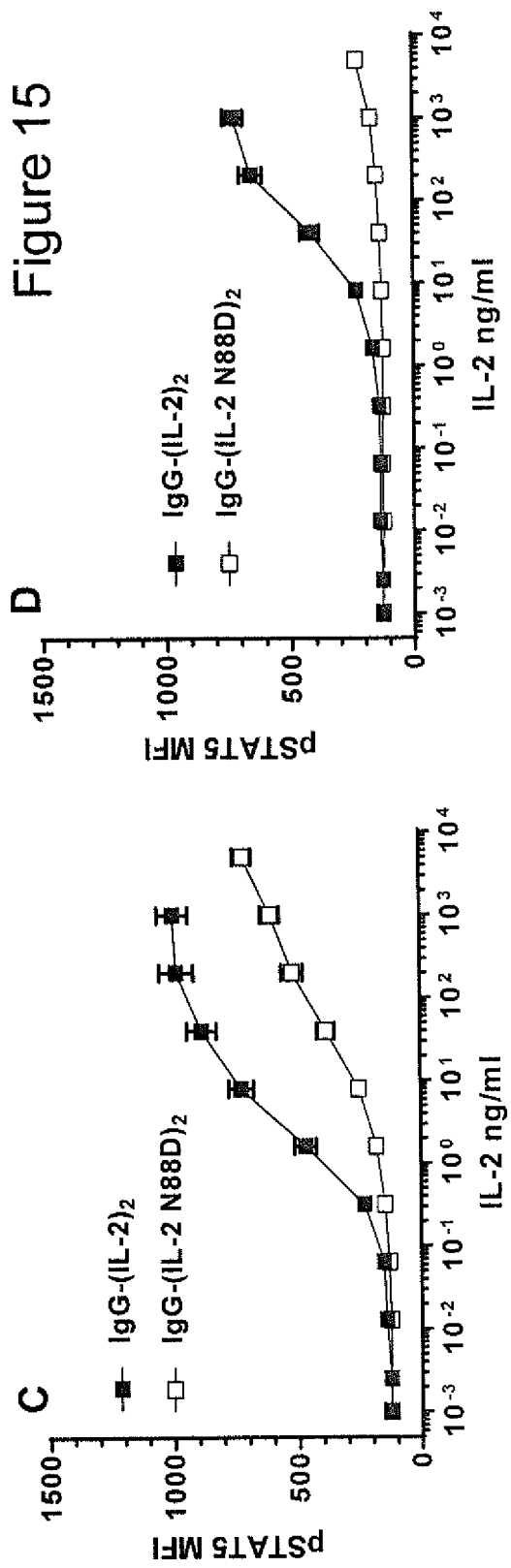
Figure 15

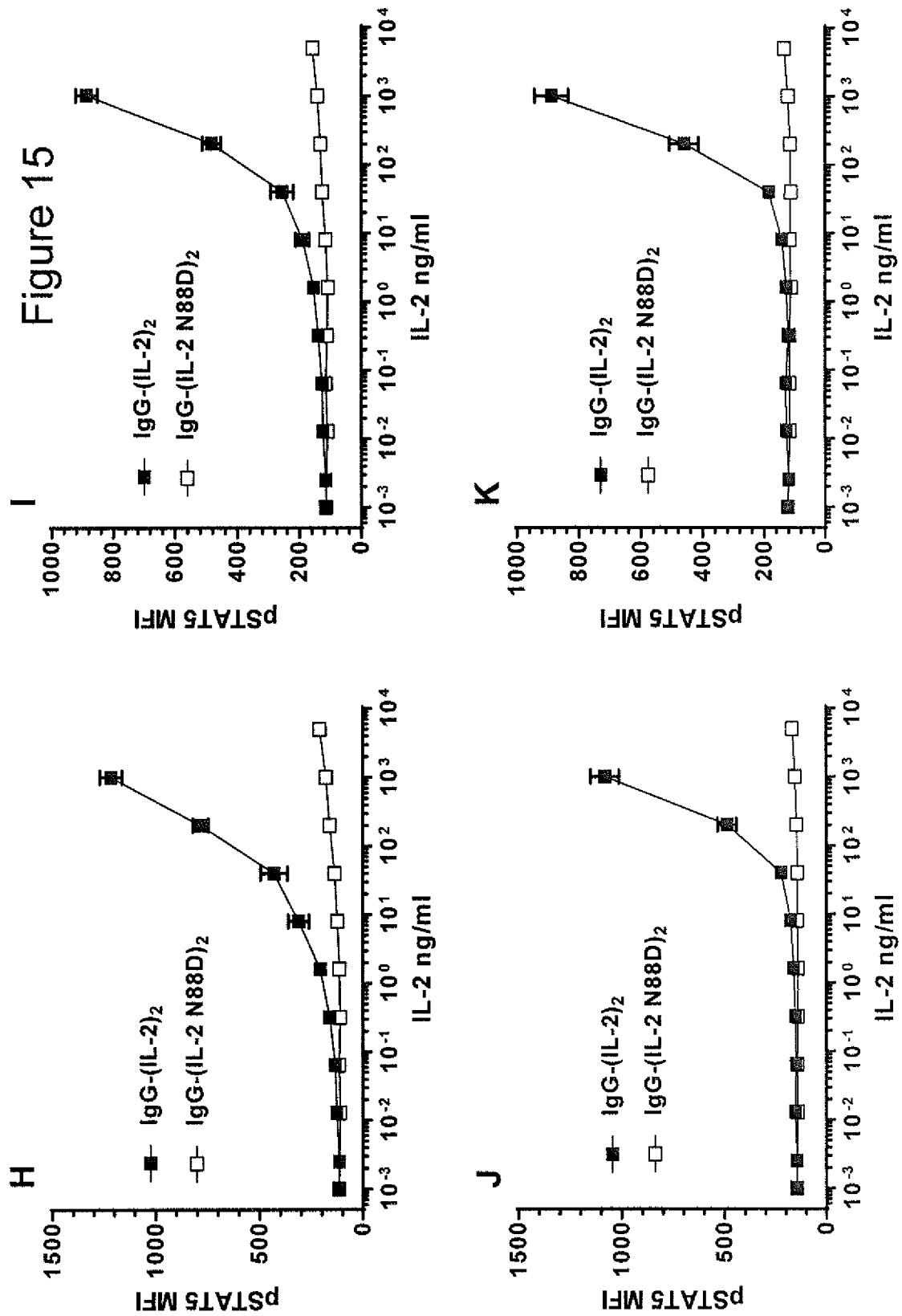

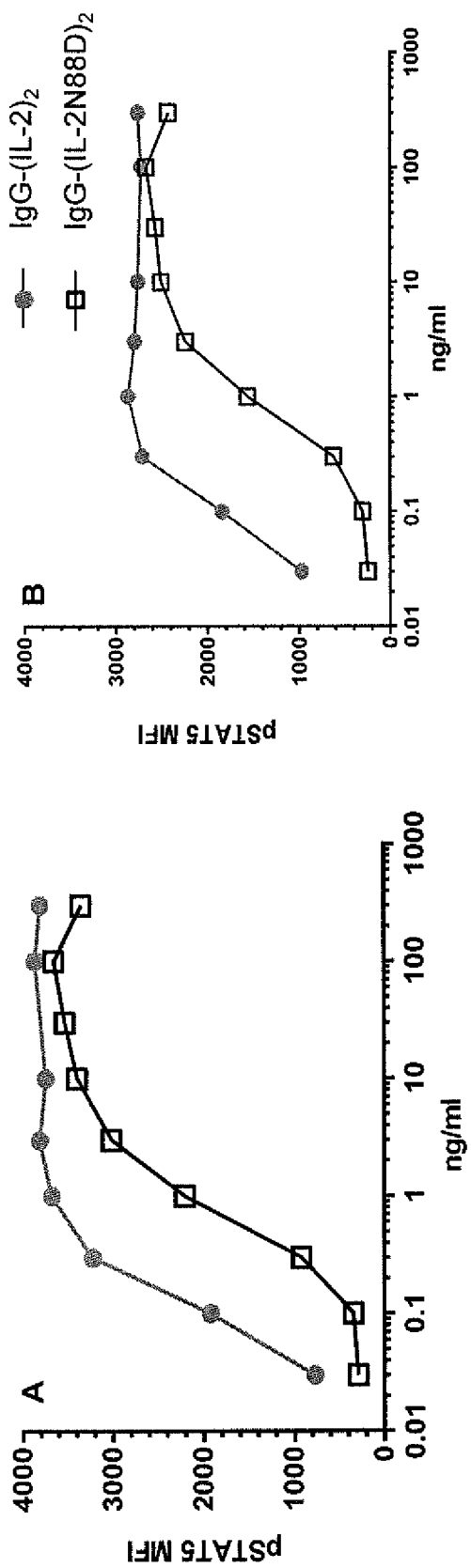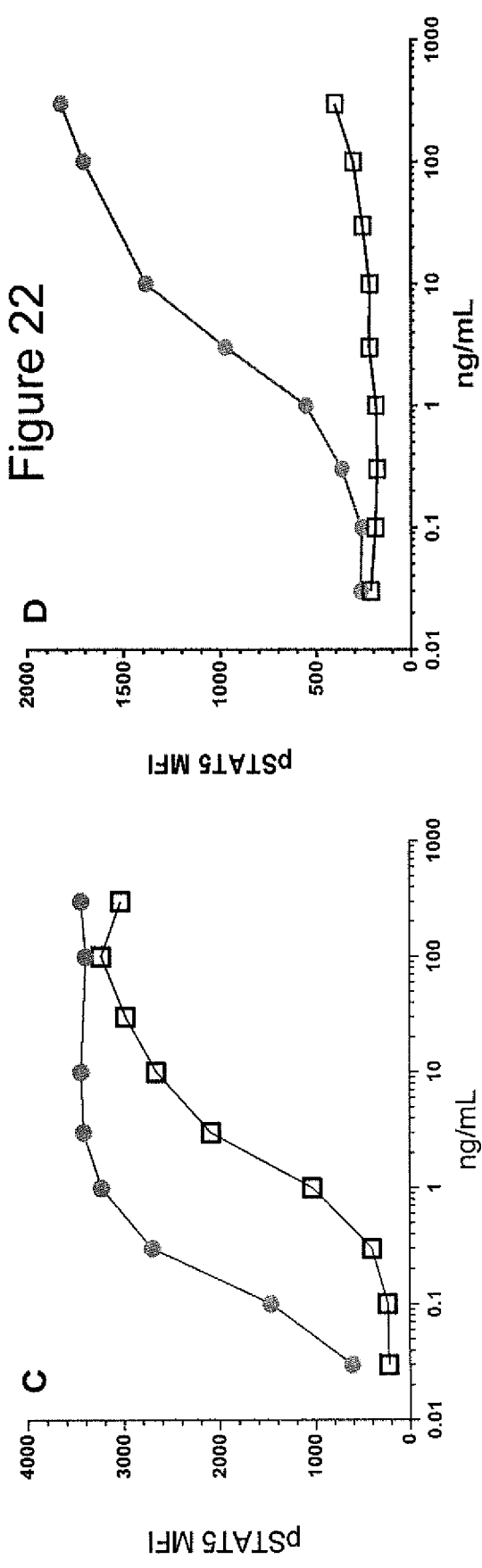
Figure 22

Figure 38
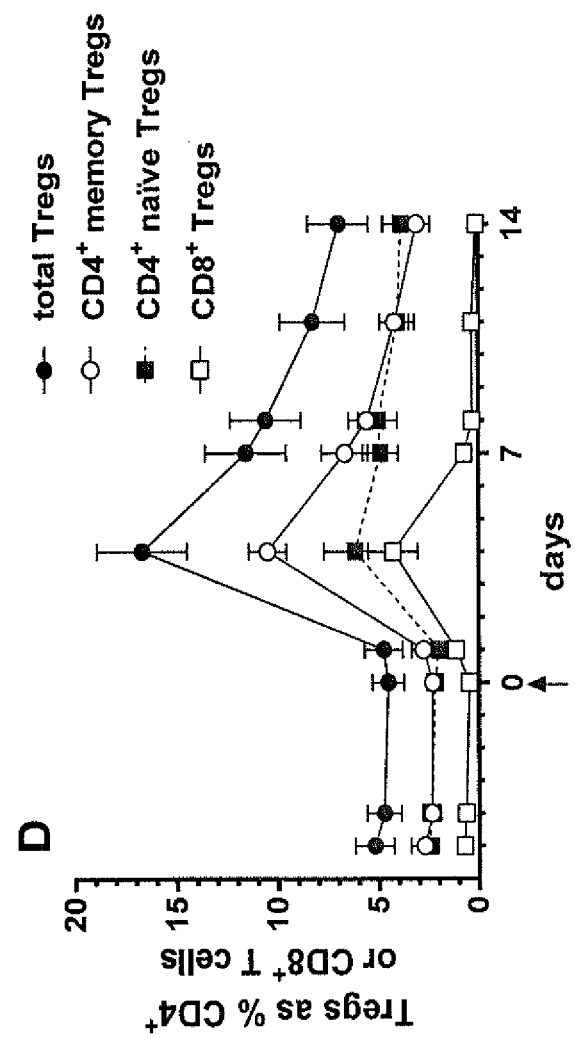
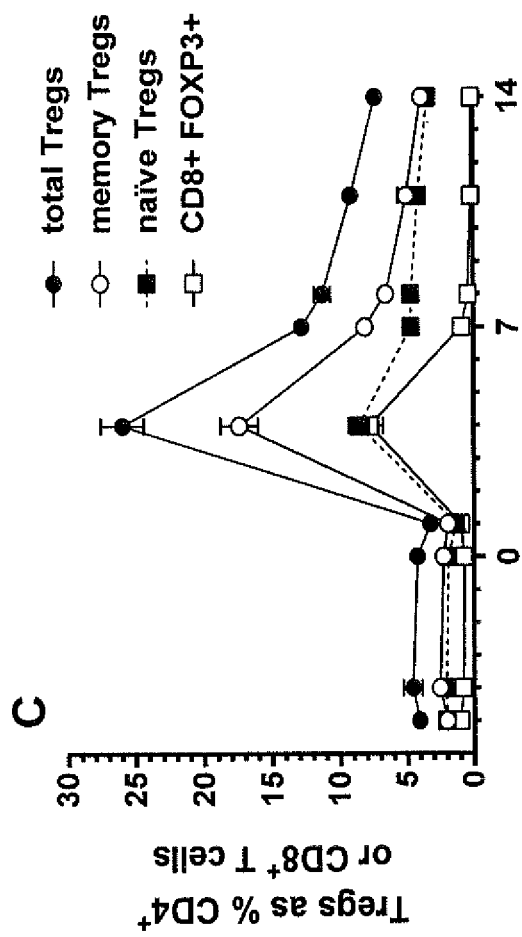

INTERLEUKIN-2 FUSION PROTEINS AND USES THEREOF

CROSS REFERENCE

This U.S. utility application claims priority under 35 USC § 119(e) to U.S. Provisional Application Ser. No. 61/936,564, filed on Feb. 6, 2014.

FIELD OF THE INVENTION

The present invention generally relates to fusion proteins of immunoglobulins and interleukin-2 (IL-2). More particularly, the invention concerns fusion proteins of immunoglobulins and mutant IL-2 that exhibit improved properties for use as therapeutic agents, e.g. in the treatment of autoimmune diseases and immune-mediated inflammatory diseases. In addition, the present invention relates to polynucleotides encoding such fusion proteins, and vectors and host cells comprising such polynucleotides. The invention further relates to methods for producing the fusion proteins of the invention, and to methods of using them in the treatment of disease.

BACKGROUND

Regulatory T cells (Tregs) represent specific subsets of T lymphocytes that are crucial for the maintenance of self-tolerance. These $CD4^+CD25^{hi}$ cells with suppressor function can be distinguished from effector T cells by the intracellular expression of the transcription factor FOXP3, as well as other cell markers such as $CD127^{low}$, $CTLA-4^+$, LAP, $CD39^+$, $PD-1^+$, GARP, etc. FOXP3 is critical for Treg differentiation and function, and FOXP3 gene deficiency and mutations, both in scurfy mice and patients with immune dysregulation polyendocrinopathy, enteropathy, X-chromosome linked syndrome (IPEX), result in the breakdown of self-tolerance and the development of autoimmune diseases due to Treg deficiency or lack of function.

The autoimmune responses in type 1 diabetes, Systemic Lupus Erythematosus (SLE), multiple sclerosis, and many others are correlated with a deficiency in Tregs or Treg functions. Data from animal models support the hypothesis that autoimmune responses are facilitated by a failure of Tregs to control the destructive immune response to self, in large part due to the effects of autoreactive $CD4^+$ memory T effector cells. Type 1 diabetes is an autoimmune disease that occurs after the destruction of a majority of the insulin producing $\beta$ cells in the pancreas. The frequency of type 1 diabetes is ~0.3% of the population in the US and its incidence continues to increase in the US, Europe, and in particular Scandinavia (nearly 1%) and is expected to double within the next twenty years.

The cytokine IL-2 plays a major role in the activation and function of both Tregs as well as effector T cells (Teff). A deficiency in IL-2 production or lack of responsiveness preferentially results in a loss of Treg function and an increase in the probability of autoimmunity. Because Tregs constitutively express the high affinity IL-2 receptor at higher levels than Teff, low doses of IL-2 preferentially support the maintenance of Tregs as compared to Teff cells.

With the preferential effect of IL-2 for activating Tregs in vitro and in vivo, the potential for low dose, long-lived IL-2 therapy would seem to have a high prospect for success in autoimmune diseases. A 200 patient, double blind, placebo controlled type 1 diabetes clinical trial with IL-2 (Proleukin®, recombinant human IL-2) is set to begin in late 2013. Recent clinical trials with daily low dose Proleukin ameliorated some of the signs and symptoms of chronic graft-versus-host disease (GVHD) and hepatitis C virus-induced vasculitis (Koreth et al., New Engl J Med 365, 2055-2066 (2011), Saadoun et al., New Engl J Med 365, 2067-2077 (2011)). In both studies low dose Proleukin® induced Tregs and increased the Treg:Teff ratio. However, Proleukin®'s poor PK properties make it suboptimal for maintaining low, consistent levels of IL-2 in man. Other methods being tested in clinical trials are personalized expansion of Tregs ex vivo followed by reinfusion, but this approach is less than ideal and represents a challenging set of quality control issues.

Thus, a new therapeutic approach that re-establishes the natural regulatory T cell (Treg) mediated dominant immune tolerance and severely minimizes any potential stimulatory effects on $CD4^+$ memory T effector cells would greatly enhance the ability to treat patients with autoimmune diseases such as type 1 diabetes, multiple sclerosis, systemic lupus erythematosus, Crohn's disease as well as other autoimmune diseases and immune-based pro-inflammatory diseases such as chronic graft versus host disease, asthma, pulmonary fibrosis, chronic obstructive pulmonary disease, cardiovascular diseases such as atherosclerosis and acute coronary syndrome, and transplant rejection, both solid organ and bone marrow.

WO 2009/135615 describes the use of a previously known IL-2 mutein (IL-2. N88R, BAY50-4798, described in WO 1999/60128) for therapy or prophylaxis of autoimmune disease. It is stated that the IL-2 mutein has an increased activity on Treg cells as compared to wild-type IL-2, while its effect on CD8+ T cells and NK cells is small. No fusion proteins of the IL-2 mutein are described.

WO 2010/85495 describes IL-2 variants that selectively promote activity in Treg cells over non-regulatory T cells, for the treatment of inflammatory disorders. The IL-2 variants described comprise a combination of eight or more amino acid substitutions affecting binding to the different subunits of the IL-2 receptor.

The IL-2 fusion proteins of the present invention preferentially activate human and non-human Tregs with little or no effect on human $CD4^+$ memory T effector cells, tipping the balance toward a higher Treg:Teff ratio and reduce the autoimmune response. They are long-lived, allowing convenient dosing schedules, and devoid of effector functions, reducing potential side effects and impairment of efficacy.

SUMMARY OF THE INVENTION

In one aspect, the invention provides a fusion protein comprising (i) an immunoglobulin molecule, and (ii) two mutant interleukin-2 (IL-2) molecules comprising an amino acid mutation that reduces affinity of the mutant IL-2 molecule to the intermediate affinity IL-2 receptor, as compared to a wild-type IL-2 molecule.

In one embodiment, said immunoglobulin molecule is an IgG-class immunoglobulin molecule, particularly an $IgG_1$-subclass immunoglobulin molecule. In one embodiment, said immunoglobulin molecule is a human immunoglobulin molecule. In one embodiment, said immunoglobulin molecule is capable of specific binding to an antigen. In one embodiment, said immunoglobulin molecule is a monoclonal antibody. In one embodiment, said immunoglobulin molecule is not capable of specific binding to an antigen. In one embodiment, said immunoglobulin molecule comprises a heavy chain variable region sequence based on the human Vh3-23 germline sequence. In a specific embodiment, said immunoglobulin molecule comprises the heavy chain variable region sequence of SEQ ID NO: 9. In one embodiment, said immunoglobulin molecule comprises a light chain variable region sequence based on the human Vk3-20 germline sequence. In a specific embodiment, said immunoglobulin molecule comprises the light chain variable region sequence of SEQ ID NO: 11. In an even more specific embodiment, said immunoglobulin molecule comprises the heavy chain variable region sequence of SEQ ID NO: 9 and the light chain variable region sequence of SEQ ID NO: 11. In one embodiment, said immunoglobulin molecule is not capable of specific binding to an antigen, and comprises a heavy chain variable region sequence based on the human Vh3-23 germline sequence and a light chain variable region sequence based on the human Vk3-20 germline sequence.

In one embodiment, said immunoglobulin molecule comprises a modification reducing binding affinity of the immunoglobulin molecule to an Fc receptor as compared to a corresponding immunoglobulin molecule without said modification. In one embodiment, said Fc receptor is an Fcγ receptor, particularly a human Fcγ receptor. In one embodiment, said Fc receptor is an activating Fc receptor. In one embodiment, said Fc receptor is selected from the group of FcγRIIIa (CD16a), FcγRI (CD64), FcγRIIa (CD32) and FcαRI (CD89). In a specific embodiment, said Fc receptor is FcγRIIIa, particularly human FcγRIIIa. In one embodiment, said modification reduces effector function of the immunoglobulin molecule. In a specific embodiment, said effector function is antibody-dependent cell-mediated cytotoxicity (ADCC). In one embodiment, said modification is in the Fc region, particularly in the CH2 region, of said immunoglobulin molecule. In one embodiment, said immunoglobulin molecule comprises an amino acid substitution at position 329 (EU numbering) of the immunoglobulin heavy chains. In a specific embodiment, said amino acid substitution is P329G. In one embodiment, said immunoglobulin molecule comprises amino acid substitutions at positions 234 and 235 (EU numbering) of the immunoglobulin heavy chains. In a specific embodiment, said amino acid substitutions are L234A and L235A (LALA). In one embodiment, said immunoglobulin molecule comprises amino acid substitutions at positions 234, 235 and 329 (EU numbering) of the immunoglobulin heavy chains. In a particular embodiment, said immunoglobulin molecule comprises the amino acid substitutions L234A, L235A and P329G (EU numbering) in the immunoglobulin heavy chains.

In one embodiment, said mutant IL-2 molecules comprise an amino acid mutation at a position corresponding to residue 88 of human IL-2 (SEQ ID NO: 1). In one embodiment, said amino acid mutation is an amino acid substitution. In a particular embodiment, said amino acid substitution is N88D. In one embodiment, said IL-2 molecules further comprise an amino acid mutation that does not alter the binding affinity of said IL-2 molecules to an IL-2 receptor as compared to naturally occurring, native IL-2. In one embodiment, said IL-2 molecules comprise an amino acid mutation at a position corresponding to residue 125 of human IL-2. In a more specific embodiment, said amino acid mutation is the amino acid substitution C125A. In one embodiment, said mutant IL-2 molecule further comprise an amino acid mutation which eliminates the O-glycosylation site of IL-2 at a position corresponding to residue 3 of human IL-2. In one embodiment said amino acid mutation which eliminates the O-glycosylation site of IL-2 at a position corresponding to residue 3 of human IL-2 is an amino acid substitution selected from the group of T3A, T3G, T3Q, T3E, T3N, T3D, T3R, T3K, and T3P. In a specific embodiment the amino acid mutation which eliminates the O-glycosylation site of IL-2 at a position corresponding to residue 3 of human IL-2 is T3A. In one embodiment, said mutant IL-2 molecules are human IL-2 molecules. In a specific embodiment, said mutant IL-2 molecules comprise a sequence selected from the group of SEQ ID NO: 58, SEQ ID NO: 60, SEQ ID NO: 62 and SEQ ID NO: 64, particularly the sequence of SEQ ID NO: 58. In one embodiment, said mutant IL-2 molecules have a sequence selected from the group of SEQ ID NO: 58, SEQ ID NO: 60, SEQ ID NO: 62 and SEQ ID NO: 64, particularly the sequence of SEQ ID NO: 58. In one embodiment, said mutant IL-2 molecules are each fused at their N-terminal amino acid to the C-terminal amino acid of one of the immunoglobulin heavy chains of said immunoglobulin molecule, optionally through a peptide linker. In one embodiment, said mutant IL-2 molecules are each fused to said immunoglobulin molecule through a peptide linker. In one embodiment, said peptide linker comprises at least 10, particularly at least 15, amino acids. In one embodiment, said peptide linker comprises the amino acid sequence $(G_4S)_3$ (SEQ ID NO: 66).

In a specific embodiment, said fusion protein comprises the polypeptide sequences of SEQ ID NO: 19 and SEQ ID NO: 50. In a specific embodiment, said fusion protein comprises an immunoglobulin light chain of SEQ ID NO: 19 and an immunoglobulin heavy chain-IL-2 fusion polypeptide of SEQ ID NO: 50. In one embodiment, said fusion protein essentially consists of an immunoglobulin molecule, two mutant interleukin-2 (IL-2) molecules comprising an amino acid mutation that reduces affinity of the mutant IL-2 molecule to the intermediate affinity IL-2 receptor, as compared to a wild-type IL-2 molecule, and optionally one or more peptide linker. In one embodiment, said fusion protein essentially consists of two immunoglobulin light chains of SEQ ID NO: 19 and two immunoglobulin heavy chain-IL-2 fusion polypeptides of SEQ ID NO: 50.

In one embodiment, said fusion protein selectively activates regulatory T cells. In one embodiment, said fusion protein selectively activates regulatory T cells over effector T cells, particularly over conventional $CD4^+$ T cells and $CD8^+$ T cells. In one embodiment, said fusion protein selectively activates regulatory T cells over conventional $CD4^-$ memory T cells. In one embodiment, said fusion protein activates regulatory T cells at least 10-fold, at least 100-fold or at least 1000-fold more than conventional $CD4^+$ memory T cells. In one embodiment, said activation is determined by measurement of intracellular STAT, particularly STAT5, phosphorylation levels. In one embodiment, said measurement of intracellular STAT phosphorylation levels is done by flow cytometric analysis.

The invention further provides a polynucleotide encoding the fusion protein of the invention. Further provided is a vector, particularly an expression vector, comprising the polynucleotide of the invention. In another aspect, the invention provides a host cell comprising the polynucleotide or the vector of the invention. The invention also provides a method for producing a fusion protein of the invention, comprising the steps of (i) culturing the host cell of the invention under conditions suitable for expression of the fusion protein, and (i) recovering the fusion protein. Also provided is a fusion protein comprising (i) an immunoglobulin molecule and (ii) two interleukin-2 (IL-2) molecules comprising an amino acid mutation that reduces affinity of the mutant IL-2 molecule to the intermediate affinity IL-2 receptor, as compared to a wild-type IL-2 molecule, produced by said method.

In one aspect, the invention provides a pharmaceutical composition comprising the fusion protein of the invention and a pharmaceutically acceptable carrier. The fusion protein or the pharmaceutical composition of the invention is also provided for use as a medicament, and for use in the treatment or prophylaxis of an autoimmune disease, specifically type 1 diabetes, multiple sclerosis (MS), systemic lupus erythematosus (SLE), inflammatory bowel disease, Crohn's disease or ulcerative colitis, most specifically type 1 diabetes, or graft-versus-host disease or transplant rejection. Further provided is the use of the fusion protein of the invention for the manufacture of a medicament for the treatment of a disease in an individual in need thereof, and a method of treating a disease in an individual, comprising administering to said individual a therapeutically effective amount of a composition comprising the fusion protein of the invention in a pharmaceutically acceptable form. In one embodiment, said disease is an autoimmune disease. In a more specific embodiment, said autoimmune disease is type 1 diabetes, multiple sclerosis (MS), systemic lupus erythematosus (SLE), inflammatory bowel disease, Crohn's disease or ulcerative colitis. In an even more specific embodiment, said autoimmune disease is type 1 diabetes. In another embodiment said disease is transplant rejection or graft-versus-host disease. In one embodiment, said individual is a mammal, particularly a human.

Further provided the fusion protein of the invention for use in selective activation of regulatory T cells in vitro or in vivo. In one embodiment, said activation comprises induction of proliferation of regulatory T cells and/or induction of IL-2 receptor signaling, particularly phosphorylation of STAT5, in regulatory T cells. In one embodiment, said use is in vitro and said fusion protein is used at a concentration of about 10 ng/mL or less, particularly about 1 ng/mL or less. In another embodiment, said use is in vivo and said fusion protein is used at a dose of about 100 μg/kg body weight or less, particularly about 25 μg/kg body weight or less, more particularly about 10 μg/kg body weight or less.

The invention also provides a method for selective activation of regulatory T cells in vitro or in vivo, comprising contacting said regulatory T cells with the fusion protein of the invention. In one embodiment, said activation comprises induction of proliferation of regulatory T cells and/or induction of IL-2 receptor signaling, particularly phosphorylation of STAT5, in regulatory T cells. In one embodiment, said method is in vitro and said fusion protein is used at a concentration of about 10 ng/mL or less, particularly about 1 ng/mL or less. In another embodiment, said method is in vivo and said fusion protein is used at a dose of about 100 μg/kg body weight or less, particularly about 25 μg/kg body weight or less, more particularly about 10 μg/kg body weight or less.

BRIEF DESCRIPTION OF THE DRAWINGS

FIG. 1A: Elution profile of the Protein A affinity chromatography step. FIG. 1B: Elution profile of the size exclusion chromatography step. Yield 4 mg/L. FIG. 1C Analytical capillary electrophoresis SOS (Caliper) of the final product. The following band were observed: non-reduced—7.5% area at 111 kDa, 92.5% area at 174 kDa; reduced—23.6% area at 29 kDa, 23.5% area at 67 kDa, 52.9% area at 82 kDa. The product contains about 7.5% "half IgG". FIG. 1D Analytical size exclusion chromatography of the final product on a TSK-GEL® G3000 SW XL column (91% monomer content).

FIG. 2A-D. Purification of DP47GS IgG-(IL-2)$_2$ fusion protein (see SEQ ID NOs 17, 19). FIG. 2A: Elution profile of the Protein A affinity chromatography step. FIG. 2B: Elution profile of the size exclusion chromatography step. Yield 13 mg/L. FIG. 2C: Analytical capillary electrophoresis SDS (Caliper) of the final product. The following band were observed: non-reduced—2.3% area at 172.5 kDa, 97.7% area at 185 kDa; reduced—18.3% area at 27.3 kDa, 0.6% area at 29.2 kDa, 81.1% area at 78.3 kDa. FIG. 2D: Analytical size exclusion chromatography of the final product on a SUPERDEX® 200 column (100% monomer content).

FIG. 3A Elution profile of the Protein A affinity chromatography step. FIG. 3B: Elution profile of the size exclusion chromatography step. Yield 23.7 mg/L. Collected fractions are boxed. FIG. 3C: Analytical capillary electrophoresis SDS (Caliper) of the final product. The following major bands were observed: non-reduced 100% area at 167.0 kDa; reduced 31.5% area at 28.6 kDa, 31.7% area at 63.5 kDa, 35.3% area at 77.5 kDa. FIG. 3D: Analytical size exclusion chromatography of the final product on a TSKGEL® TSKGEL® G3000 SW XL column (97.3% monomer content).

FIG. 4A: Elution profile of the Protein A affinity chromatography step. FIG. 4B: Elution profile of the size exclusion chromatography step. Yield 32.9 mg/L. Collected fractions are boxed. FIG. 4C: Analytical capillary electrophoresis SDS (Caliper) of the final product. The following major bands were observed: non-reduced—20.7% area at 180.4 kDa, 78.0% area at 184.0 kDa; reduced—16.2% area at 27.3 kDa, 82.7% area at 76.0 kDa. FIG. 4D: Analytical size exclusion chromatography of the final product on a TSKGEL® G3000 SW XL column (98.3% monomer content).

FIG. 5A: Elution profile of the Protein A affinity chromatography step. FIG. 5B: Elution profile of the size exclusion chromatography step. Yield 8.0 mg/L. Collected fractions are boxed. FIG. 5C: Analytical capillary electrophoresis SDS (Caliper) of the final product. The following major bands were observed: non-reduced—10.3% area at 166.0 kDa, 61.4% area at 175.5 kDa, 28.2% area at 181.2 kDa; reduced—16.0% area at 26.1 kDa, 83.1% area at 75.0 kDa. FIG. 5D: Analytical size exclusion chromatography of the final product on a TSKgel G3000 SW XL column (100% monomer content).

FIGS. 6A and 6B: Three regulatory CD4$^+$ T cell (Treg) populations: naive (CD45RA$^+$, CD25$^+$; dotted line), memory (CD45RA$^-$, CD25$^+$; solid line) and activated (CD45RA$^-$, CD25$^{hi}$; dashed line). FIG. 6C and FIG. 6D NKT (dotted line), CD56$^{bright}$ NK cells (dashed line), CD56$^{intermediate}$ NK cells (solid line). Grey: isotype control (IC).

FIG. 11A: total CD3$^+$ CD4$^+$ FoxP3$^+$ Tregs. FIG. 11B: activated Tregs. FIG. 11C: memory Tregs. FIG. 11D: naïve Tregs.

FIG. 15A: memory Tregs, FIG. 15B: naïve Tregs, FIG. 15C: CD56$^{bright}$ NK cells, FIG. 15D total NK cells, FIG. 15 central memory CD4$^+$ T cells, FIG. 15F: effector memory CD4$^+$ T cells, FIG. 15G: naïve CD4$^+$ T cells, FIG. 15H: central memory CD8$^+$ T cells, FIG. 15I: effector memory CD8$^+$ T cells, FIG. 15J: naïve CD8$^+$ T cells, FIG. 15K: Temra [Teff memory RA$^+$] CD8$^+$ T cells, FIG. 15L: NKT cells and CD3$^+$CD4$^-$CD8$^-$CD56$^-$ T cells. All results are shown as the mean±SEM (n=10 donors).

FIG. 17B: for NK cells. The results are shown as the median±the interquartile range; vehicle (n=21), IgG-(IL-2N88D)$_2$ (n=22) and IgG-(IL-2)$_2$ (n=24).

FIG. 20A the flow cytometry gating strategy with FOXP3 (y-axis) and CD45RA (x-axis) used to identify CD4+CD25+ Treg subsets: naïve Tregs (CD45RA+FOXP3+), memory Tregs (CD45RA−FOXP3+), and activated (CD45RA− FOXP3$^{hi}$). FIG. 20B the expression of CD25+ cell surface staining in the Treg subsets prior to stimulation. FIG. 20C pSTAT5a responses for CD4+ CD25+ Treg subsets: activated, memory and naïve for each of the three cynomolgus monkeys (C1-C3).

FIG. 21A the flow cytometry gating strategy used to identify conventional CD4+FOXP3−CD45RA− memory T effector cells with CD45RA on the y-axis and CD25 on the x-axis. FIG. 21B pSTAT5a responses for total CD4+FOXP3− CD45RA− memory T effector cells. FIG. 21C pSTAT5a responses for memory T effector cells that were also CD25−. FIG. 21D pSTAT5a responses for memory T effector cells that were also CD25+.

FIG. 22A-D. Induction of pSTAT5a in cynomolgus peripheral blood T cell subsets in response to DP47GS IgG-(IL-2)$_2$ and DP47GS IgG-(IL-2N88D)$_2$. Two healthy adult donors were assessed for the effects of varying doses (0.03-300 ng/mL) of DP47GS IgG-(IL-2)$_2$ and DP47GS IgG-(IL-2N88D)$_2$ on the induction of STAT5a phosphorylation. The results are shown for CD4+ Treg subsets (A-C): activated (FIG. 22A), memory (FIG. 22C), and naïve (FIG. 22B) Tregs and conventional CD4+ memory T effector cells (FIG. 22D). Similar results were obtained for both monkeys and the results from one donor shown to illustrate the effects of DP47GS IgG-(IL-2)$_2$ and DP47GS IgG-(IL-2N88D)$_2$.

FIG. 23A NOD and NOD.scid mice were injected intravenously (i.v.) with 0.3 mg/kg of DP47GS IgG-IL-2 or 0.3 mg/kg of DP47GS IgG-(IL-2)$_2$. FIG. 23B NOD.scid. IL2Rα$^{−/−}$ mice were injected i.v. with 0.1 mg/kg of DP47GS IgG-IL-2, 0.3 mg/kg of DP47GS IgG-(IL-2)$_2$ or 0.1 mg/kg of DP47GS IgG-(IL-2N88D)$_2$. Human IL-2 was assessed in serum samples at the indicated times by a mAb-based capture assay.

FIG. 24A dose-dependent changes in cell surface CD25 and FIG. 24B dose-dependent changes in intracellular FoxP3 were observed for all four IL2 molecules. The data are represented as the mean±SD, black bars represent the highest dose used and light grey bars the lowest dose.

FIG. 25A DP47GS IgG-IL-2 was injected intravenously (i.v.) as a short bolus at doses of 10, 25, and 100 µg/kg (n=2 per dose). FIG. 25B DP47GS IgG-(IL-2)$_2$ was injected i.v. as a short bolus at doses of 10 and 25 µg/kg (n=2 per dose). Human IL-2 was assessed in serum samples at the indicated times by a mAb-based capture assay.

FIG. 27A time dependent changes in Treg fold increases following dosing with 2 or 6 µg/kg DP47GS IgG-IL-2 (n=4 and 6, respectively). FIG. 27B time dependent changes in Treg absolute counts in blood after dosing with 2 or 6 µg/kg DP47GS IgG-IL-2 (n=4 and 6, respectively). All data are shown as the mean±SD.

FIG. 28A changes in peripheral blood Treg numbers after single dose treatment with 3×10$^4$ to 3×10$^5$ IU/kg Proleukin. FIG. 28B changes in Treg pSTAT5a after single dose treatment with 3×10$^4$ to 3×10$^5$ IU/kg Proleukin. Data are shown as the mean±SD.

FIG. 30A the fold change in Treg pSTAT5a on days 1 and 3, FIG. 30B the fold change in pSTAT5a in conventional $CD4^+CD45^-$ memory T cells, and FIG. 30C the fold change in in naïve T cells pSTAT5a is shown. Data are shown as the mean±SD.

FIG. 31A Treg pSTAT5a before and after treatment with 2 µg/kg of DP47GS IgG-IL-2 (n=4). FIG. 31B Treg pSTAT5a before and after treatment with 6 µg/kg of DP47GS IgG-IL-2 (n=6). Data are shown as the mean±SD.

FIG. 32A % $Ki-67^+$ for Tregs, FIG. 32B % $Ki-67^+$ for conventional $CD4^+CD45^-$ memory/effector T cells, and FIG. 32C % $Ki-67^+$ for naïve $CD4^+CD45RA^+$ T cells are shown. Data are shown as the mean±SD.

FIG. 33A time-dependent changes in Treg absolute numbers after 6 µg/kg DP47 IgG-$(IL-2)_2$. FIG. 33B time dependent changes in Treg pSTAT5a after treatment, FIG. 33C time dependent changes in the fold increase in Tregs, and FIG. 33D comparison of the fold changes in Tregs from DP47Gs IgG-IL-2 treated monkeys (open bars, 2 to 36 µg/kg) versus the DP47GS IgG-$(IL-2)_2$ treated (shaded bar, 6 µg/kg). All data are shown as the mean±SD (n=4 to 6).

FIG. 34A time dependent changes in Treg fold increases following administration of 0.7 and 2 µg/kg DP47GS IgG-$(IL-2)_2$. FIG. 34B time dependent changes in Treg pSTAT5a measured on day 0 before treatment and on days 1-4 after treatment, FIG. 34C time dependent changes in Teff/mem cell pSTAT5a. All data are shown as the mean±SD (n=3 at 0.7 µg/kg and n=8 at 2 µg/kg).

FIG. 37A DP47GS IgG-$(IL-2N88D)_2$ was injected intravenously (iv) in a short bolus at doses of 30 and 100 µg/kg (n=2 per dose). FIG. 37B DP47GS IgG-$(IL-2N88D)_2$ was injected subcutaneously (sc) in 0.2 ml in the lateral dorsum at doses of 30 and 100 µg/kg (n=2 per dose). Human IL-2 was assessed in plasma samples at the indicated times with a monoclonal antibody-based capture assay. FIG. 37B. As a biomarker of IL-2 exposure, soluble CD25 was measured in plasma after injection with IgG-(IL-$2N88D)_2$ at doses of 30 and 100 µg/kg; cynomolgus sCD25 was measured in a human sCD25 mAb-based capture assay known to cross react with cynomolgus sCD25. Results are shown as the mean±SEM (n=4).

FIG. 40A pSTAT5a (MFI, maximal mean fluorescence intensity) before and after treatment with 100 µg/kg of DP47GS IgG-(IL-2N88D)$_2$, n=4. FIG. 40B pSTAT5a before and after treatment with 30 µg/kg of DP47GS IgG-$(IL-2N88D)_2$, n=4. Data are shown as the mean±SEM for the indicated cell subsets.

FIG. 41A CD25 staining (maximal MFI, mean fluorescence intensity) before and after treatment with 100 µg/kg of DP47GS IgG-$(IL-2N88D)_2$, n=4. FIG. 41B CD25 staining before and after treatment with 30 µg/kg of DP47GS IgG-$(IL-2N88D)_2$, n=4. Data are shown as the mean±SEM for the indicated cell subsets.

FIG. 42A Ki-67 staining (% of cells Ki-67$^+$) before and after treatment with 100 μg/kg of DP47GS IgG-(IL-2N88D)$_2$, n=4. FIG. 42B Ki-67 (% of cells Ki-67$^+$) staining before and after treatment with 30 μg/kg of DP47GS IgG-(IL-2N88D)$_2$, n=4. Results are shown as the mean±SEM for the indicated cell subsets.

FIG. 45A results from NOD mice and FIG. 45B C57BL/6 mice. The magnitude of the day four DTH responses are shown as the change in paw weight compared to non-immunized mice (4 paw weight). Data are shown as the mean±SD.

DETAILED DESCRIPTION OF THE INVENTION

Definitions

Figure 1:
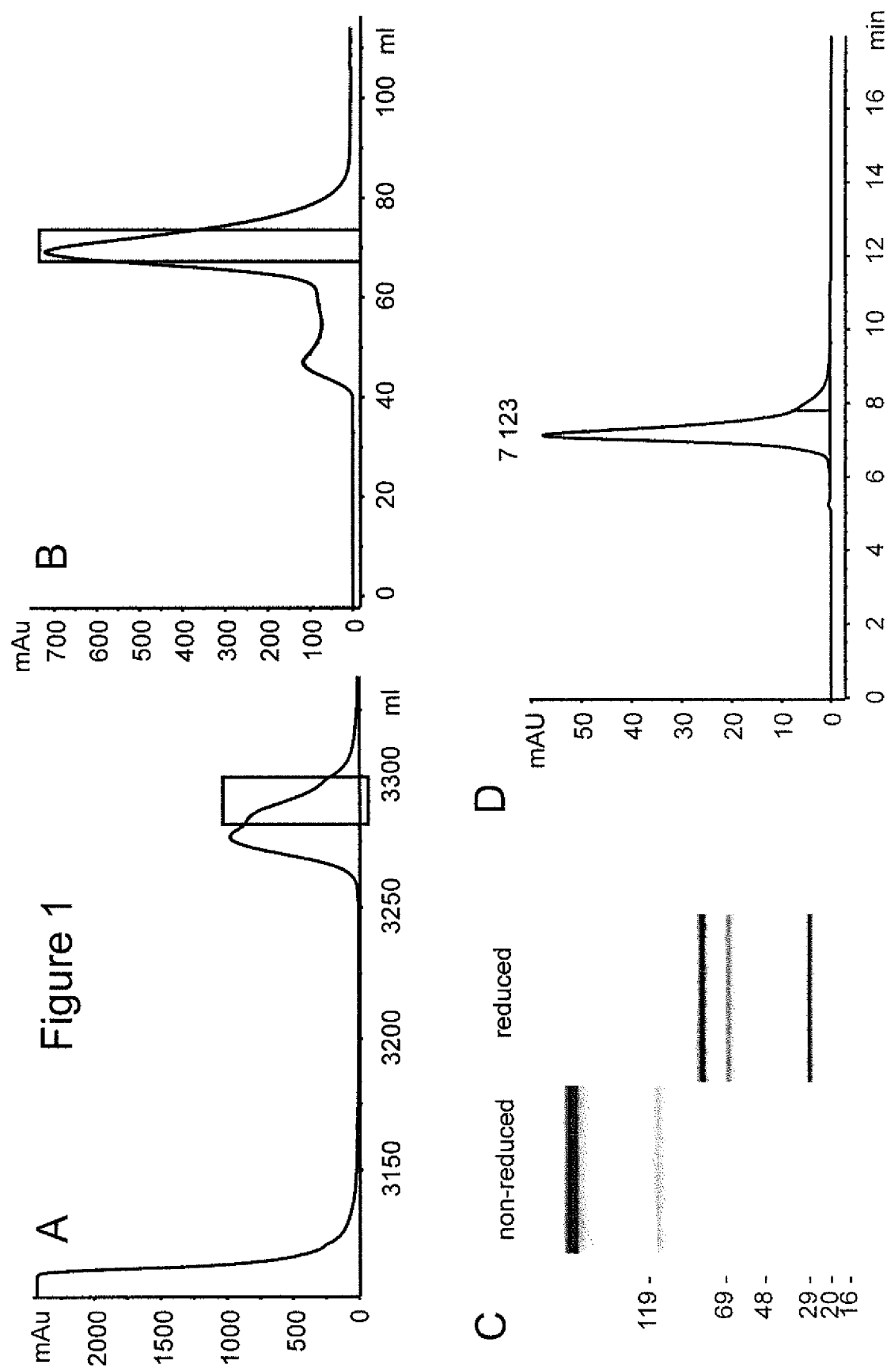
FIG. 1A-1D. Purification of DP47GS IgG-IL-2 fusion protein (see SEQ ID NOs 13, 15, 19).
Figure 3:
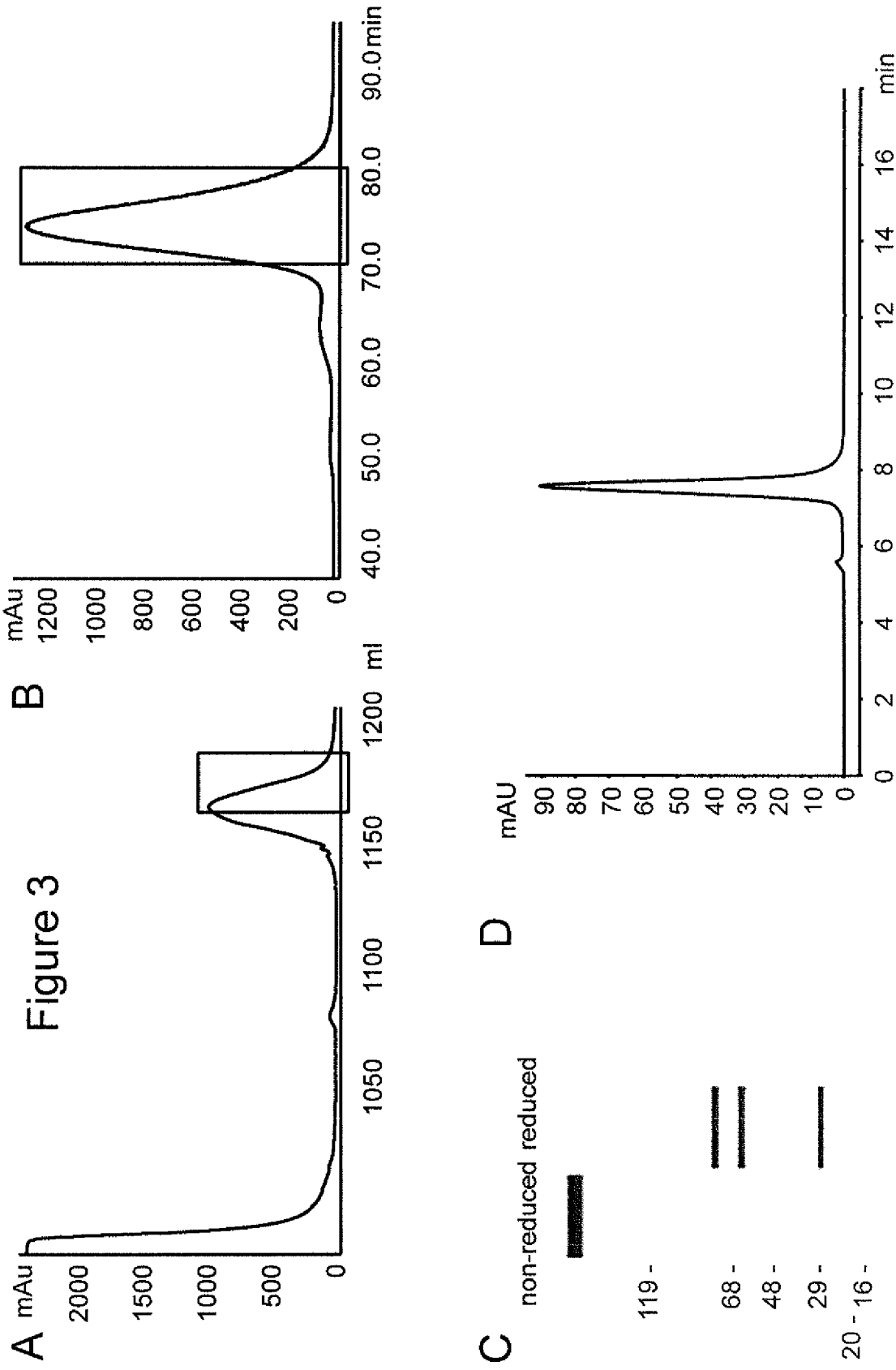
FIG. 3A-D. Purification of DP47GS IgG-IL-2 N88D fusion protein (see SEQ ID NOs 15, 19, 48).

Terms are used herein as generally used in the art, unless otherwise defined in the following. As used herein, the term "fusion protein" refers to a fusion polypeptide molecule comprising an immunoglobulin molecule and an IL-2 molecule, wherein the components of the fusion protein are linked to each other by peptide-bonds, either directly or through peptide linkers. For clarity, the individual peptide chains of the immunoglobulin component of the fusion protein may be linked non-covalently, e.g. by disulfide bonds.

"Fused" refers to components that are linked by peptide bonds, either directly or via one or more peptide linkers.

By "specific binding" is meant that the binding is selective for the antigen and can be discriminated from unwanted or non-specific interactions. The ability of an immunoglobulin to bind to a specific antigen can be measured either through an enzyme-linked immunosorbent assay (ELISA) or other techniques familiar to one of skill in the art, e.g. Surface Plasmon Resonance (SPR) technique (analyzed on a BIAcore instrument) (Liljeblad et al., Glyco J 17, 323-329 (2000)), and traditional binding assays (Heeley, Endocr Res 28, 217-229 (2002)). In one embodiment, the extent of binding of an immunoglobulin to an unrelated protein is less than about 10% of the binding of the immunoglobulin to the antigen as measured, e.g. by SPR. In certain embodiments, an immunoglobulin that binds to the antigen has a dissociation constant ($K_D$) of ≤1 μM, ≤100 nM, ≤10 nM, ≤1 nM, ≤0.1 nM, ≤0.01 nM, or ≤0.001 nM (e.g. 10$^{-8}$ M or less, e.g. from 10$^{-8}$ M to 10$^{-13}$ M, e.g. from 10$^{-9}$ M to 10$^{-13}$ M).

"Affinity" or "binding affinity" refers to the strength of the sum total of non-covalent interactions between a single binding site of a molecule (e.g. an antibody) and its binding partner (e.g. an antigen). Unless indicated otherwise, as used herein, "binding affinity" refers to intrinsic binding affinity which reflects a 1:1 interaction between members of a binding pair (e.g. antibody and antigen). The affinity of a molecule X for its partner Y can generally be represented by the dissociation constant ($K_D$), which is the ratio of dissociation and association rate constants ($k_{off}$ and $k_{on}$, respectively). Thus, equivalent affinities may comprise different rate constants, as long as the ratio of the rate constants remains the same. Affinity can be measured by common methods known in the art, including those described herein. A particular method for measuring affinity is Surface Plasmon Resonance (SPR).

"Reduced binding", for example reduced binding to an Fc receptor or an IL-2 receptor, refers to a decrease in affinity for the respective interaction, as measured for example by SPR. For clarity the term includes also reduction of the affinity to zero (or below the detection limit of the analytic method), i.e. complete abolishment of the interaction. Conversely, "increased binding" refers to an increase in binding affinity for the respective interaction.

As used herein, the term "antigenic determinant" is synonymous with "antigen" and refers to a site (e.g. a contiguous stretch of amino acids or a conformational configuration made up of different regions of non-contiguous amino acids) on a polypeptide macromolecule to which an antibody binds, forming an antibody-antigen complex. Useful antigenic determinants can be found, for example, on the surfaces of cells, free in blood serum, and/or in the extracellular matrix (ECM).

As used herein, the term "single-chain" refers to a molecule comprising amino acid monomers linearly linked by peptide bonds.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$, diabodies, linear antibodies, single-chain antibody molecules (e.g. scFv), and single-domain antibodies.

The term "immunoglobulin molecule" refers to a protein having the structure of a naturally occurring antibody. For example, immunoglobulins of the IgG class are heterotetrameric glycoproteins of about 150,000 daltons, composed of two light chains and two heavy chains that are disulfide-bonded. From N- to C-terminus, each immunoglobulin heavy chain has a variable region (VH), also called a variable heavy domain or a heavy chain variable domain, followed by three constant domains (CH1, CH2, and CH3), also called a heavy chain constant region. Similarly, from N- to C-terminus, each immunoglobulin light chain has a variable region (VL), also called a variable light domain or a light chain variable domain, followed by a constant light (CL) domain, also called a light chain constant region. The heavy chain of an immunoglobulin may be assigned to one of five classes, called α (IgA), δ (IgD), ε (IgE), γ (IgG), or μ (IgM), some of which may be further divided into subclasses, e.g. $\gamma_1$ (IgG$_1$), $\gamma_2$ (IgG$_2$), $\gamma_3$ (IgG$_3$), $\gamma_4$ (IgG$_4$), $\alpha_1$ (IgA$_1$) and $\alpha_2$ (IgA$_2$). The light chain of an immunoglobulin may be assigned to one of two types, called kappa (κ) and lambda (λ), based on the amino acid sequence of its constant domain. An immunoglobulin essentially consists of two Fab molecules and an Fc domain, linked via the immunoglobulin hinge region.

As used herein, "Fab fragment" refers to an immunoglobulin fragment comprising a VL domain and a constant domain of a light chain (CL), and a VH domain and a first constant domain (CH1) of a heavy chain.

The "class" of an antibody or immunoglobulin refers to the type of constant domain or constant region possessed by its heavy chain There are five major classes of immunoglobulins: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called α, δ, ε, γ, and μ, respectively.

The term "variable region" or "variable domain" refers to the domain of an immunoglobulin or antibody heavy or light chain that is generally involved in binding the immunoglobulin or antibody to antigen. However, the immunoglobulin comprised in the fusion protein of the present invention may comprise variable regions which do not confer antigen-binding specificity. The variable domains of the heavy chain and light chain (VH and VL, respectively) of an immunoglobulin or antibody generally have similar structures, with each domain comprising four conserved framework regions (FRs) and three hypervariable regions (HVRs). See, e.g. Kindt et al., Kuby Immunology, 6$^{th}$ ed., W.H. Freeman and Co., page 91 (2007). A single VH or VL domain may be sufficient to confer antigen-binding specificity.

The term "hypervariable region" or "HVR", as used herein, refers to each of the regions of an immunoglobulin or antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the complementarity determining regions (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3) (Chothia and Lesk, J. Mol. Biol. 196, 901-917 (1987)). Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3 (Kabat et al., Sequences of Proteins of Immunological Interest, 5th Ed. Public Health Service, National Institutes of Health, Bethesda, Md. (1991)). With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3 (see Almagro and Fransson, Front. Biosci. 13, 1619-1633 (2008)). Unless otherwise indicated, HVR residues and other residues in the variable domain (e.g. FR residues) are numbered herein according to Kabat et al., supra (referred to as "Kabat numbering").

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

A "human immunoglobulin" is one which possesses an amino acid sequence which corresponds to that of an immunoglobulin produced by a human or a human cell or derived from a non-human source that utilizes human immunoglobulin repertoires or other human immunoglobulin-encoding sequences. This definition of a human immunoglobulin specifically excludes a humanized immunoglobulin comprising non-human antigen-binding residues.

The term "monoclonal antibody" as used herein refers to an antibody obtained from a population of substantially homogeneous antibodies, i.e., the individual antibodies comprising the population are identical and/or bind the same epitope, except for possible variant antibodies, e.g. containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

The term "Fc domain" or "Fc region" herein is used to define a C-terminal region of an immunoglobulin heavy chain that contains at least a portion of the constant region. The term includes native sequence Fc regions and variant Fc regions. An IgG Fc region comprises an IgG CH2 and an IgG CH3 domain. The "CH2 domain" of a human IgG Fc region usually extends from an amino acid residue at about position 231 to an amino acid residue at about position 340. In one embodiment, a carbohydrate chain is attached to the CH2 domain. The CH2 domain herein may be a native sequence CH2 domain or variant CH2 domain. The "CH3 domain" comprises the stretch of residues C-terminal to a CH2 domain in an Fc region (i.e. from an amino acid residue at about position 341 to an amino acid residue at about position 447 of an IgG). The CH3 region herein may be a native sequence CH3 domain or a variant CH3 domain (e.g. a CH3 domain with an introduced "protuberance" ("knob") in one chain thereof and a corresponding introduced "cavity" ("hole") in the other chain thereof; see U.S. Pat. No. 5,821,333, expressly incorporated herein by reference). Such variant CH3 domains may be used to promote heterodimerization of two non-identical immunoglobulin heavy chains as herein described. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, Md., 1991.

The term "effector functions" refers to those biological activities attributable to the Fc region of an immunoglobulin, which vary with the immunoglobulin isotype. Examples of immunoglobulin effector functions include: Clq binding and complement dependent cytotoxicity (CDC), Fc receptor binding, antibody-dependent cell-mediated cytotoxicity (ADCC), antibody-dependent cellular phagocytosis (ADCP), cytokine secretion, immune complex-mediated antigen uptake by antigen presenting cells, down regulation of cell surface receptors (e.g. B cell receptor), and B cell activation.

An "activating Fc receptor" is an Fc receptor that following engagement by an Fc region of an immunoglobulin elicits signaling events that stimulate the receptor-bearing cell to perform effector functions. Activating Fc receptors include FcγRIIIa (CD16a), FcγRI (CD64), FcγRIIa (CD32), and FcαRI (CD89). A particular activating Fc receptor is human FcγRIIIa (see UniProt accession no. P08637 (version 141)).

The term "interleukin-2" or "IL-2" as used herein, refers to any native IL-2 from any vertebrate source, including mammals such as primates (e.g. humans) and rodents (e.g. mice and rats), unless otherwise indicated. The term encompasses unprocessed IL-2 as well as any form of IL-2 that results from processing in the cell. The term also encompasses naturally occurring variants of IL-2, e.g. splice variants or allelic variants. The amino acid sequence of an exemplary human IL-2 is shown in SEQ ID NO: 1. Unprocessed human IL-2 additionally comprises an N-terminal 20 amino acid signal peptide, which is absent in the mature IL-2 molecule.

By a "native IL-2", also termed "wild-type IL-2", is meant a naturally occurring IL-2. The sequence of a native human IL-2 molecule is shown in SEQ ID NO: 1. For the purpose of the present invention, the term wild-type also encompasses forms of IL-2 comprising one or more amino acid mutation that does not alter IL-2 receptor binding compared to the naturally occurring, native IL-2, such as e.g. a substitution of cysteine at a position corresponding to residue 125 of human IL-2 to alanine. In some embodiments wild-type IL-2 for the purpose of the present invention comprises the amino acid substitution C125A (see SEQ ID NO: 3).

The term "CD25" or "IL-2 receptor α" as used herein, refers to any native CD25 from any vertebrate source, including mammals such as primates (e.g. humans) and rodents (e.g., mice and rats), unless otherwise indicated. The term encompasses "full-length", unprocessed CD25 as well as any form of CD25 that results from processing in the cell. The term also encompasses naturally occurring variants of CD25, e.g. splice variants or allelic variants. In certain embodiments CD25 is human CD25. The amino acid sequence of an exemplary human CD25 (with signal sequence, Avi-tag and His-tag) is shown in SEQ ID NO: 25.

The term "high-affinity IL-2 receptor" as used herein refers to the heterotrimeric form of the IL-2 receptor, consisting of the receptor γ-subunit (also known as common cytokine receptor γ-subunit, $\gamma_c$, or CD132), the receptor β-subunit (also known as CD122 or p70) and the receptor α-subunit (also known as CD25 or p55). The term "intermediate-affinity IL-2 receptor" or "IL-2 receptor $\beta_\gamma$" by contrast refers to the IL-2 receptor including only the γ-subunit and the β-subunit, without the α-subunit (for a review see e.g. Olejniczak and Kasprzak, Med Sci Monit 14, RA179-189 (2008)). The amino acid sequences of exemplary human CD122 and CD132 (fused to an Fc region with a His-tag) are shown in SEQ ID NOs 21 and 23, respectively.

By "regulatory T cell" or "Treg cell" is meant a specialized type of $CD4^+$ T cell that can suppress the responses of other T cells (effector T cells). Treg cells are characterized by expression of CD4, the α-subunit of the IL-2 receptor (CD25), and the transcription factor forkhead box P3 (FOXP3) (Sakaguchi, Annu Rev Immunol 22, 531-62 (2004)) and play a critical role in the induction and maintenance of peripheral self-tolerance to antigens, including those expressed by tumors. By "conventional $CD4^+$ T cells" is meant $CD4^+$ T cells other than regulatory T cells. Conventional $CD4^+$ memory T cells are characterized by expression of CD4, CD3, but not FOXP3. "Conventional $CD4^+$ memory T cells" are a subset of conventional $CD4^+$ T cells, further characterized by lack of expression of CD45RA, in contrast to "conventional $CD4^+$ naïve T cells" which do express CD45RA.

By "selective activation of Treg cells" is meant activation of Treg cells essentially without concomitant activation of other T cell subsets (such as $CD4^+$ T helper cells, $CD8^+$ cytotoxic T cells, NK T cells) or natural killer (NK) cells. Methods for identifying and distinguishing these cell types are described in the Examples. Activation may include induction of IL-2 receptor signaling (as measured e.g. by detection of phosphorylated STAT5a), induction of proliferation (as measured e.g. by detection of Ki-67) and/or up-regulation of expression of activation markers (such as e.g. CD25).

The term "peptide linker" refers to a peptide comprising one or more amino acids, typically about 2-20 amino acids. Peptide linkers are known in the art or are described herein. Suitable, non-immunogenic linker peptides include, for example, $(G_4S)_n$, $(SG_4)_n$ or $G_4(SG_4)_n$ peptide linkers. "n" is generally a number between 1 and 10, typically between 2 and 4.

The term "modification" refers to any manipulation of the peptide backbone (e.g. amino acid sequence) or the post-translational modifications (e.g. glycosylation) of a polypeptide.

A "knob-into-hole modification" refers to a modification within the interface between two immunoglobulin heavy chains in the CH3 domain, wherein i) in the CH3 domain of one heavy chain, an amino acid residue is replaced with an amino acid residue having a larger side chain volume, thereby generating a protuberance ("knob") within the interface in the CH3 domain of one heavy chain which is positionable in a cavity ("hole") within the interface in the CH3 domain of the other heavy chain, and ii) in the CH3 domain of the other heavy chain, an amino acid residue is replaced with an amino acid residue having a smaller side chain volume, thereby generating a cavity ("hole") within the interface in the second CH3 domain within which a protuberance ("knob") within the interface in the first CH3 domain is positionable. In one embodiment, the "knob-into-hole modification" comprises the amino acid substitution T366W and optionally the amino acid substitution S354C in one of the antibody heavy chains, and the amino acid substitutions T366S, L368A, Y407V and optionally Y349C in the other one of the antibody heavy chains. The knob-into-hole technology is described e.g. in U.S. Pat. Nos. 5,731,168; 7,695,936; Ridgway et al., Prot Eng 9, 617-621 (1996) and Carter, J Immunol Meth 248, 7-15 (2001). Generally, the method involves introducing a protuberance ("knob") at the interface of a first polypeptide and a corresponding cavity ("hole") in the interface of a second polypeptide, such that the protuberance can be positioned in the cavity so as to promote heterodimer formation and hinder homodimer formation. Protuberances are constructed by replacing small amino acid side chains from the interface of the first polypeptide with larger side chains (e.g. tyrosine or tryptophan). Compensatory cavities of identical or similar size to the protuberances are created in the interface of the second polypeptide by replacing large amino acid side chains with smaller ones (e.g. alanine or threonine). Introduction of two cysteine residues at position S354 and Y349, respectively, results in formation of a disulfide bridge between the two antibody heavy chains in the Fc region, further stabilizing the dimer (Carter, J Immunol Methods 248, 7-15 (2001)).

An amino acid "substitution" refers to the replacement in a polypeptide of one amino acid with another amino acid. In one embodiment, an amino acid is replaced with another amino acid having similar structural and/or chemical properties, e.g. conservative amino acid replacements. "Conservative" amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. Non-conservative substitutions will entail exchanging a member of one of these classes for another class. For example, amino acid substitutions can also result in replacing one amino acid with another amino acid having different structural and/or chemical properties, for example, replacing an amino acid from one group (e.g., polar) with another amino acid from a different group (e.g. basic). Amino acid substitutions can be generated using genetic or chemical methods well known in the art. Genetic methods may include site-directed mutagenesis, PCR, gene synthesis and the like. It is contemplated that methods of altering the side chain group of an amino acid by methods other than genetic engineering, such as chemical modification, may also be useful. Various designations may be used herein to indicate the same amino acid substitution. For example, a substitution from proline at position 329 of the immunoglobulin heavy chain to glycine can be indicated as 329G, G329, $G_{329}$, P329G, or Pro329Gly. "Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary. In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

"Polynucleotide" or "nucleic acid" as used interchangeably herein, refers to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase or by a synthetic reaction. A polynucleotide may comprise modified nucleotides, such as methylated nucleotides and their analogs. A sequence of nucleotides may be interrupted by non-nucleotide components. A polynucleotide may comprise modification(s) made after synthesis, such as conjugation to a label.

By a nucleic acid or polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These alterations of the reference sequence may occur at the 5' or 3' terminal positions of the reference nucleotide sequence or anywhere between those terminal positions, interspersed either individually among residues in the reference sequence or in one or more contiguous groups within the reference sequence. As a practical matter, whether any particular polynucleotide sequence is at least 80%, 85%, 90%, 95%, 96%, 97%, 98% or 99% identical to a nucleotide sequence of the present invention can be determined conventionally using known computer programs, such as the ones discussed above for polypeptides (e.g. ALIGN-2).

The term "vector" as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors".

The terms "host cell", "host cell line", and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein. A host cell is any type of cellular system that can be used to generate the fusion proteins of the present invention. Host cells include cultured cells, e.g. mammalian cultured cells, such as CHO cells, BHK cells, NS0 cells, SP2/0 cells, YO myeloma cells, P3X63 mouse myeloma cells, PER cells, PER.C6 cells or hybridoma cells, yeast cells, insect cells, and plant cells, to name only a few, but also cells comprised within a transgenic animal, transgenic plant or cultured plant or animal tissue.

An "effective amount" of an agent refers to the amount that is necessary to result in a physiological change in the cell or tissue to which it is administered.

A "therapeutically effective amount" of an agent, e.g. a pharmaceutical composition, refers to an amount effective, at dosages and for periods of time necessary, to achieve the desired therapeutic or prophylactic result. A therapeutically effective amount of an agent for example eliminates, decreases, delays, minimizes or prevents adverse effects of a disease.

An "individual" or "subject" is a mammal. Mammals include, but are not limited to, domesticated animals (e.g. cows, sheep, cats, dogs, and horses), primates (e.g. humans and non-human primates such as monkeys), rabbits, and rodents (e.g. mice and rats). Particularly, the individual or subject is a human.

The term "pharmaceutical composition" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical composition, other than an active ingredient, which is nontoxic to a subject. A pharmaceutically acceptable carrier includes, but is not limited to, a buffer, excipient, stabilizer, or preservative.

As used herein, "treatment" (and grammatical variations thereof such as "treat" or "treating") refers to clinical intervention in an attempt to alter the natural course of a disease in the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

"Autoimmune disease" refers to a non-malignant disease or disorder arising from and directed against an individual's own tissues. Examples of autoimmune diseases or disorders include, but are not limited to, inflammatory responses such as inflammatory skin diseases including psoriasis and dermatitis (e.g. atopic dermatitis); responses associated with inflammatory bowel disease (such as Crohn's disease and ulcerative colitis); dermatitis; allergic conditions such as eczema and asthma; rheumatoid arthritis; systemic lupus erythematosus (SLE) (including but not limited to lupus nephritis, cutaneous lupus); diabetes mellitus (e.g. type 1 diabetes mellitus or insulin dependent diabetes mellitus); multiple sclerosis and juvenile onset diabetes.

Fusion Proteins of the Invention

The invention provides novel immunoglobulin-IL-2 fusion proteins with particularly advantageous properties for the use in therapeutic methods as described herein.

In a first aspect, the invention provides a fusion protein comprising (i) an immunoglobulin molecule and (ii) two mutant interleukin-2 (IL-2) molecules comprising an amino acid mutation that reduces affinity of the mutant IL-2 molecule to the intermediate affinity IL-2 receptor, as compared to a wild-type IL-2 molecule.

In one embodiment, said fusion protein essentially consists of an immunoglobulin molecule, two mutant interleukin-2 (IL-2) molecules comprising an amino acid mutation that reduces affinity of the mutant IL-2 molecule to the intermediate affinity IL-2 receptor, as compared to a wild-type IL-2 molecule, and optionally one or more peptide linker.

As shown in the Examples, a fusion protein comprising two IL-2 molecules surprisingly provides for greatly improved efficacy and selectivity in the activation of regulatory T cells, as compared to a corresponding fusion protein comprising a single IL-2 molecule. Moreover, only a fusion protein comprising two (rather than only one) mutant IL-2 molecules with reduced binding to the intermediate affinity IL-2 receptor retains significant stimulatory activity on regulatory T cells.

In one embodiment, said immunoglobulin molecule is an IgG-class immunoglobulin molecule, particularly an $IgG_1$-subclass immunoglobulin molecule. In one embodiment, said immunoglobulin molecule is a human immunoglobulin molecule, i.e. it comprises fully human variable and constant regions. The sequence of an exemplary human IgG₁ constant region is shown in SEQ ID NO: 8. An IgG-class immunoglobulin molecule comprises (i) two immunoglobulin light chains, each comprising from N- to C-terminus a light chain variable domain (VL) and a light chain constant domain (CL), and (ii) two immunoglobulin heavy chains, each comprising from N-terminus to C-terminus a heavy chain variable domain (VH), a heavy chain constant domain (CH) 1, an immunoglobulin hinge region, a CH2 domain and a CH3 domain. The latter two domains form part of the Fc region of the immunoglobulin molecule. The two heavy chains dimerize in the Fc region.

In one embodiment of the fusion protein according to the invention, said two mutant IL-2 molecules are each fused at their N-terminal amino acid to the C-terminal amino acid of one of the immunoglobulin heavy chains of said immunoglobulin molecule, optionally through a peptide linker. Fusion of two (identical) IL-2 molecules to the immunoglobulin heavy chains allows for simple production of the fusion protein, avoiding the formation of undesired side products and obviating the need for modifications promoting heterodimerization of non-identical heavy chains, such as a knob-into-hole modification.

In certain embodiments of the fusion protein according to the invention, said two mutant IL-2 molecules are fused to said immunoglobulin molecule through a peptide linker. In one embodiment, said two mutant IL-2 molecules are each fused to said immunoglobulin molecule through a peptide linker. In one embodiment said two mutant IL-2 molecules are each fused at their N-terminal amino acid to the C-terminal amino acid of one of the immunoglobulin heavy chains of said immunoglobulin molecule through a peptide linker. In one embodiment, each of said mutant IL-2 molecules is fused to said immunoglobulin molecule through a peptide linker having identical amino acid sequence. In one embodiment, said peptide linker comprises at least 10 amino acids. In a particular embodiment, said peptide linker comprises at least 15 amino acids. Without wishing to be bound by theory, a peptide linker of this length may provide the flexibility for optimal binding of the mutant IL-2 molecules to the IL-2 receptor, in particular the high-affinity (heterotrimeric) IL-2 receptor. In a specific embodiment, said peptide linker comprises 15 amino acids. In an even more specific embodiment, said peptide linker comprises the amino acid sequence $(G_4S)_3$ (SEQ ID NO: 66). In one embodiment, said peptide linker is 15 amino acids in length. In one embodiment, said peptide linker has the amino acid sequence (G4S)3 (SEQ ID NO: 66). In one embodiment, said peptide linker consists of 15 amino acids. In one embodiment, said peptide linker consists of the amino acid sequence (G4S)3 (SEQ ID NO: 66).

Fusion of the IL-2 molecules to an immunoglobulin molecule provides for favorable pharmacokinetic properties, including a long serum half-life (due to recycling through binding to FcRn, and molecular size being well above the threshold for renal filtration), as compared to free (unfused) IL-2. Furthermore, the presence of an immunoglobulin molecule also enables simple purification of fusion proteins by e.g. protein A affinity chromatography. Interestingly, as shown in the Examples, a fusion protein comprising two mutant IL-2 molecules with reduced binding to the intermediate affinity IL-2 receptor has a longer serum half-life than a corresponding fusion protein comprising two wild-type IL-2 molecules. Fusion to an immunoglobulin molecule, i.e. a naturally occurring type of molecule, may also minimize toxicity of the fusion protein through the formation of anti-drug antibodies.

While the presence of an immunoglobulin molecule, specifically the Fc region of an immunoglobulin molecule, is favorable for the pharmacokinetic properties of the fusion protein, it may at the same time lead to undesirable targeting of the fusion protein to cells expressing Fc receptors rather than to the preferred IL-2 receptor bearing cells. Moreover, the engagement of Fc receptors may lead to release of (pro-inflammatory) cytokines and undesired activation of various immune cells other than regulatory T cells. Therefore, in certain embodiments, said immunoglobulin molecule comprised in the fusion protein of the invention comprises a modification reducing binding affinity of the immunoglobulin molecule to an Fc receptor, as compared to a corresponding immunoglobulin molecule without said modification. In a specific embodiment, said Fc receptor is an Fcγ receptor, particularly a human Fcγ receptor. Binding affinity to Fc receptors can be easily determined e.g. by ELISA, or by Surface Plasmon Resonance (SPR) using standard instrumentation such as a BIAcore instrument (GE Healthcare) and Fc receptors such as may be obtained by recombinant expression. A specific illustrative and exemplary embodiment for measuring binding affinity is described in the following. According to one embodiment, Binding affinity to an Fc receptor is measured by surface plasmon resonance using a BIACORE® T100 machine (GE Healthcare) at 25° C. with ligand (Fc receptor) immobilized on CM5 chips. Briefly, carboxymethylated dextran biosensor chips (CM5, GE Healthcare) are activated with N-ethyl-N'-(3-dimethylaminopropyl)-carbodiimide hydrochloride (EDC) and N-hydroxysuccinimide (NHS) according to the supplier's instructions. Recombinant ligand is diluted with 10 mM sodium acetate, pH 5.5, to 0.5-30 µg/ml before injection at a flow rate of 10 µl/min to achieve approximately 100-5000 response units (RU) of coupled protein. Following the injection of the ligand, 1 M ethanolamine is injected to block unreacted groups. For kinetics measurements, three- to five-fold serial dilutions of antibody (range between ~0.01 nM to 300 nM) are injected in HBS-EP+ (GE Healthcare, 10 mM HEPES, 150 mM NaCl, 3 mM EDTA, 0.05% Surfactant P20, pH 7.4) at 25° C. at a flow rate of approximately 30-50 µl/min. Association rates ($k_{on}$) and dissociation rates ($k_{off}$) are calculated using a simple one-to-one Langmuir binding model (BIACORE® T100 Evaluation Software version 1.1.1) by simultaneously fitting the association and dissociation sensorgrams. The equilibrium dissociation constant ($K_D$) is calculated as the ratio $k_{off}/k_{on}$. See, e.g., Chen et al., J Mol Biol 293, 865-881 (1999). Alternatively, binding affinity antibodies to Fc receptors may be evaluated using cell lines known to express particular Fc receptors, such as NK cells expressing FcγIIIa receptor.

In one embodiment, the modification comprises one or more amino acid mutation that reduces the binding affinity of the immunoglobulin to an Fc receptor. In one embodiment the amino acid mutation is an amino acid substitution. Typically, the same one or more amino acid mutation is present in each of the two immunoglobulin heavy chains. In one embodiment said amino acid mutation reduces the binding affinity of the immunoglobulin to the Fc receptor by at least 2-fold, at least 5-fold, or at least 10-fold. In embodiments where there is more than one amino acid mutation that reduces the binding affinity of the immunoglobulin to the Fc receptor, the combination of these amino acid mutations may reduce the binding affinity of the immunoglobulin to the Fc receptor by at least 10-fold, at least 20-fold, or even at least 50-fold. In one embodiment said immunoglobulin molecule exhibits less than 20%, particularly less than 10%, more particularly less than 5% of the binding affinity to an Fc receptor as compared to a corresponding immunoglobulin molecule without said modification.

In one embodiment, said Fc receptor is an activating Fc receptor. In a specific embodiment, said Fc receptor is selected from the group of FcγRIIIa (CD16a), FcγRI (CD64), FcγRIIa (CD32) and FcαRI (CD89). In a specific embodiment the Fc receptor is an Fcγ receptor, more specifically an FcγRIIIa, FcγRI or FcγRIIa receptor. Preferably, binding affinity to each of these receptors is reduced. In an even more specific embodiment, said Fc receptor is FcγIIIa, particularly human FcγIIIa. In some embodiments binding affinity to a complement component, specifically binding affinity to C1q, is also reduced. In one embodiment binding affinity to neonatal Fc receptor (FcRn) is not reduced. Substantially similar binding to FcRn, i.e. preservation of the binding affinity of the immunoglobulin molecule to said receptor, is achieved when the immunoglobulin molecule exhibits greater than about 70% of the binding affinity of an unmodified form of the immunoglobulin molecule to FcRn. Immunoglobulin molecules comprised in the fusion proteins of the invention may exhibit greater than about 80% and even greater than about 90% of such affinity.

In one embodiment, said modification reducing binding affinity of the immunoglobulin molecule to an Fc receptor is in the Fc region, particularly the CH2 region, of the immunoglobulin molecule. In one embodiment, said immunoglobulin molecule comprises an amino acid substitution at position 329 (EU numbering) of the immunoglobulin heavy chains. In a more specific embodiment said amino acid substitution is P329A or P329G, particularly P329G. In one embodiment, said immunoglobulin molecule comprises amino acid substitutions at positions 234 and 235 (EU numbering) of the immunoglobulin heavy chains. In a specific embodiment, said amino acid substitutions are L234A and L235A (LALA). In one embodiment said immunoglobulin molecule comprises an amino acid substitution at position 329 (EU numbering) of the antibody heavy chains and a further amino acid substitution at a position selected from position 228, 233, 234, 235, 297 and 331 of the immunoglobulin heavy chains (EU numbering). In a more specific embodiment the further amino acid substitution is S228P, E233P, L234A, L235A, L235E, N297A, N297D or P331S. In a particular embodiment, said immunoglobulin molecule comprises amino acid substitutions at positions P329, L234 and L235 (EU numbering) of the immunoglobulin heavy chains. In a more particular embodiment, said immunoglobulin molecule comprises the amino acid substitutions L234A, L235A and P329G (LALA P329G; EU numbering) in the immunoglobulin heavy chains. This combination of amino acid substitutions particularly efficiently abolishes Fcγ receptor binding of a human IgG-class immunoglobulin, as described in PCT publication no. WO 2012/130831, incorporated herein by reference in its entirety. PCT publication no. WO 2012/130831 also describes methods of preparing such modified immunoglobulin and methods for determining its properties such as Fc receptor binding or effector functions.

Immunoglobulins comprising modifications in the immunoglobulin heavy chains can be prepared by amino acid deletion, substitution, insertion or modification using genetic or chemical methods well known in the art. Genetic methods may include site-specific mutagenesis of the encoding DNA sequence, PCR, gene synthesis, and the like. The correct nucleotide changes can be verified for example by sequencing.

Immunoglobulins or antibodies which comprise modifications reducing Fc receptor binding generally have reduced effector functions, particularly reduced ADCC, as compared to corresponding unmodified immunoglobulins or antibodies. Hence, in one embodiment, said modification reducing binding affinity of the immunoglobulin molecule to an Fc receptor reduces effector function of the immunoglobulin molecule. In a specific embodiment, said effector function is antibody-dependent cell-mediated cytotoxicity (ADCC). In one embodiment, ADCC is reduced to less than 20% of the ADCC induced by a corresponding immunoglobulin molecule without said modification. Effector function of an immunoglobulin or antibody can be measured by methods known in the art. Examples of in vitro assays to assess ADCC activity of a molecule of interest are described in U.S. Pat. No. 5,500,362; Hellstrom et al. Proc Natl Acad Sci USA 83, 7059-7063 (1986) and Hellstrom et al., Proc Natl Acad Sci USA 82, 1499-1502 (1985); U.S. Pat. No. 5,821,337; Bruggemann et al., J Exp Med 166, 1351-1361 (1987). Alternatively, non-radioactive assays methods may be employed (see, for example, ACTI™ non-radioactive cytotoxicity assay for flow cytometry (CellTechnology, Inc. Mountain View, Calif.); and CytoTox 96® non-radioactive cytotoxicity assay (Promega, Madison, Wis.)). Useful effector cells for such assays include peripheral blood mononuclear cells (PBMC) and Natural Killer (NK) cells. Alternatively, or additionally, ADCC activity of the molecule of interest may be assessed in vivo, e.g. in an animal model such as that disclosed in Clynes et al., Proc Natl Acad Sci USA 95, 652-656 (1998). In some embodiments binding of the immunoglobulin molecule to a complement component, specifically to C1q, is also reduced. Accordingly, complement-dependent cytotoxicity (CDC) may also be reduced. C1q binding assays may be carried out to determine whether the immunoglobulin is able to bind C1q and hence has CDC activity. See e.g. C1q and C3c binding ELISA in WO 2006/029879 and WO 2005/100402. To assess complement activation, a CDC assay may be performed (see, for example, Gazzano-Santoro et al., J Immunol Methods 202, 163 (1996); Cragg et al., Blood 101, 1045-1052 (2003); and Cragg and Glennie, Blood 103, 2738-2743 (2004)).

In addition to the immunoglobulin molecules described hereinabove and in PCT publication no. WO 2012/130831, immunoglobulins with reduced Fc receptor binding and/or effector function also include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

$IgG_4$-subclass immunoglobulins exhibit reduced binding affinity to Fc receptors and reduced effector functions as compared to $IgG_1$ immunoglobulins. Hence, in some embodiments, said immunoglobulin molecule comprised in the fusion protein of the invention is an $IgG_4$-subclass immunoglobulin, particularly a human $IgG_4$-subclass immunoglobulin. In one embodiment said $IgG_4$-subclass immunoglobulin comprises amino acid substitutions in the Fc region at position S228 (EU numbering), specifically the amino acid substitution S228P. To further reduce its binding affinity to an Fc receptor and/or its effector function, in one embodiment, said $IgG_4$-subclass immunoglobulin comprises an amino acid substitution at position L235, specifically the amino acid substitution L235E (EU numbering). In another embodiment, said $IgG_4$-subclass immunoglobulin comprises an amino acid substitution at position P329, specifically the amino acid substitution P329G (EU numbering). In a particular embodiment, said $IgG_4$-subclass immunoglobulin comprises amino acid substitutions at positions S228, L235 and P329, specifically amino acid substitutions S228P, L235E and P329G (EU numbering). Such modified IgG$_4$-subclass immunoglobulins and their Fcy receptor binding properties are described in PCT publication no. WO 2012/130831, incorporated herein by reference in its entirety.

In one embodiment, said immunoglobulin molecule is capable of specific binding to an antigen. In one embodiment, said immunoglobulin molecule is a monoclonal antibody. In one embodiment, said immunoglobulin molecule is not capable of specific binding to an antigen, particularly not capable of specific binding to a human antigen. The absence of specific binding of such an immunoglobulin molecule to an antigen (i.e. the absence of any binding that can be discriminated from non-specific interaction) can be determined e.g. by ELISA or surface plasmon resonance as described herein. Such an immunoglobulin molecule is particularly useful e.g. for enhancing the serum half-life of the fusion protein, where targeting to a particular tissue is not desired.

In one embodiment, said immunoglobulin molecule comprises a heavy chain variable region sequence based on the human Vh3-23 germline sequence. In a specific embodiment, said immunoglobulin molecule comprises a heavy chain variable region sequence that is at least 95%, 96%, 97%, 98%, 99% or 100% identical to the sequence of SEQ ID NO: 9. In one embodiment, said immunoglobulin molecule comprises a light chain variable region sequence based on the human Vk3-20 germline sequence. In a specific embodiment, said immunoglobulin molecule comprises a light chain variable region sequence that is at least 95%, 96%, 97%, 98%, 99% or 100% identical to the sequence of SEQ ID NO: 11. In an even more specific embodiment, said immunoglobulin molecule comprises the heavy chain variable region sequence of SEQ ID NO: 9 and the light chain variable region sequence of SEQ ID NO: 11. Immunoglobulin molecules comprising these variable region sequences are not capable of specific, binding to an antigen, particularly a human antigen. They lack binding to normal tissues as well as PBMCs, have no polyreactivity and show no non-specific accumulation in vivo by imaging (data not shown). The variable region sequences are entirely based on human germline sequences, with the exception of the heavy chain CDR 3 wherein a GSG sequence has been introduced to generate a non-binding immunoglobulin.

In one embodiment, said mutant IL-2 molecules comprise an amino acid mutation at a position corresponding to residue 88 of human IL-2 (SEQ ID NO: 1). In one embodiment, said amino acid mutation is an amino acid substitution. In a more specific embodiment, said amino acid substitution is selected from the group of N88D, N88R, N88I, and N88G. In a particular embodiment, said amino acid substitution is N88D. In one embodiment, said mutant IL-2 molecules are human IL-2 molecules. In a specific embodiment, said mutant IL-2 molecules comprise the sequence of SEQ ID NO: 60 (IL-2 N88D). In one embodiment, said mutant IL-2 molecules comprise only one amino acid mutation that reduces affinity of the mutant IL-2 molecule to the intermediate affinity IL-2 receptor, as compared to a wild-type IL-2 molecule. In one embodiment, said mutant IL-2 molecules do not comprise an amino acid mutation that alters affinity of the mutant IL-2 molecule to the high affinity IL-2 receptor, as compared to a wild-type IL-2 molecule. In one embodiment, said mutant IL-2 molecules comprise only a single amino acid mutation that alters affinity of the mutant IL-2 molecule to an IL-2 receptor, as compared to a wild-type IL-2 molecule.

In one embodiment, said mutant IL-2 molecules further comprise an amino acid substitution at a position corresponding to residue 125 of human IL-2. In one embodiment said amino acid substitution is C125A. In a specific embodiment, said mutant IL-2 molecules comprise the sequence of SEQ ID NO: 62 (IL-2 N88D with the amino acid substitution C125A). Alternatively, the cysteine at position 125 may be replaced with another neutral amino acid such as serine, threonine or valine, yielding C125S IL-2, C125T IL-2 or C125V IL-2 respectively, as described in U.S. Pat. No. 4,518,584. As described therein, one may also delete the N-terminal alanine residue of IL-2 yielding such mutants as des-A1 C125S or des-A1 C125A. Alternatively or conjunctively, the IL-2 molecule may include a mutation whereby methionine normally occurring at position 104 of wild-type human IL-2 is replaced by a neutral amino acid such as alanine (see U.S. Pat. No. 5,206,344). Such modifications in human IL-2 may provide additional advantages such as increased expression or stability.

The mutant IL-2 molecules comprised in the fusion protein of the invention may also be unglycosylated IL-2 molecules. For example, elimination of the O-glycosylation site of the IL-2 molecule results in a more homogenous product when the fusion protein is expressed in mammalian cells such as CHO or HEK cells. Thus, in certain embodiments the mutant IL-2 molecules further comprise a modification which eliminates the O-glycosylation site of IL-2 at a position corresponding to residue 3 of human IL-2. In one embodiment said modification which eliminates the O-glycosylation site of IL-2 at a position corresponding to residue 3 of human IL-2 is an amino acid substitution. Exemplary amino acid substitutions include T3A, T3G, T3Q, T3E, T3N, T3D, T3R, T3K, and T3P. In a specific embodiment, said modification is the amino acid substitution T3A. In a specific embodiment, said mutant IL-2 molecules comprise the sequence of SEQ ID NO: 64 (IL-2 T3A N88D).

In a particular embodiment, the mutant IL-2 molecules comprise the amino acid substitutions T3A, N88D and C125A. In a specific embodiment, said mutant IL-2 molecules comprise the sequence of SEQ ID NO: 58 (IL-2 T3A N88D C125A).

In one embodiment, the binding of the fusion protein of the invention to the IL-2 βγ receptor is at least 1.5-fold, preferably at least 2-fold or at least 3-fold reduced as compared to binding of a corresponding fusion protein comprising two wild-type IL-2 molecules to the IL-2 βγ receptor. In one embodiment, the fusion protein of the invention binds to the IL-2 βγ receptor with an affinity constant ($K_D$) at least 2-fold higher than the $K_D$ of a corresponding fusion protein comprising two wild-type IL-2 molecules, when measured by SPR at 25° C. In a specific embodiment, said IL-2 βγ receptor is human IL-2 βγ receptor. In one embodiment, the binding of the fusion protein of the invention to the IL-2 α receptor is about equal to the binding of a corresponding fusion protein comprising two wild-type IL-2 molecules to the IL-2 α receptor. In one embodiment, the fusion protein of the invention binds to the IL-2 α receptor with an affinity constant ($K_D$) about equal to the $K_D$ of a corresponding fusion protein comprising two wild-type IL-2 molecules, when measured by SPR at 25° C. In a specific embodiment, said IL-2 α receptor is human IL-2 α receptor. A method for measuring binding affinity to IL-2 βγ or IL-2 α receptor by SPR is described herein. According to one embodiment, binding affinity ($K_D$) is measured by surface plasmon resonance using a BIACORE® T200 machine (GE Healthcare) at 25° C. with IL-2 receptors immobilized on CM5 or Streptavidin chips. The affinity constant ($K_D$) is calculated as the ratio $k_{off}/k_{on}$. See, e.g., Chen et al., J Mol Biol 293, 865-881 (1999).

In a particular aspect, the invention provides a fusion protein comprising (i) an IgG$_1$-subclass immunoglobulin molecule comprising the amino acid substitutions L234A, L235A and P329G (EU numbering) in the immunoglobulin heavy chains, and (ii) two mutant interleukin-2 (IL-2) molecules comprising the amino acid substitution N88D, each fused at its N-terminal amino acid to the C-terminal amino acid of one of the immunoglobulin heavy chains through a peptide linker. In one embodiment said immunoglobulin molecule and said IL-2 molecules are human. In a specific embodiment, said immunoglobulin molecule comprises the heavy chain variable region sequence of SEQ ID NO: 9 and the light chain variable region sequence of SEQ ID NO: 11. In a further specific embodiment, said IL-2 molecules each comprise the amino acid sequence of SEQ ID NO: 58. In a further embodiment, said peptide linker comprises the amino acid sequence (G$_4$S)$_3$ (SEQ ID NO: 66). In an even more specific embodiment, said fusion protein comprises a polypeptide sequence that is at least about 80%, 85%, 90%, 95%, 96%, 97%, 98%, 99% or 100% identical to the sequence of SEQ ID NO: 50, and a polypeptide sequence that is at least about 80%, 85%, 90%, 95%, 96%, 97%, 98%, 99% or 100% identical to the sequence of SEQ ID NO: 19.

As shown in the Examples, the fusion protein of the invention selectively activates regulatory T cells (i.e. essentially without concomitant activation of other T cell subsets and/or natural killer (NK) cells). Thus, in one aspect the invention provides a fusion protein comprising an immunoglobulin molecule and two mutant IL-2 molecules, wherein said fusion protein selectively activates regulatory T cells over effector T cells and NK cells, particularly over conventional CD4$^+$ T cells, CD8$^+$ T cells and NK cells. In one embodiment, said fusion protein activates regulatory T cells at least 10-fold, at least 100-fold or at least 1000-fold more than effector T cells and NK cells. In one embodiment, said fusion protein selectively activates regulatory T cells over conventional CD4$^+$ memory T cells. In one embodiment, said fusion protein activates regulatory T cells at least 10-fold, at least 100-fold or at least 1000-fold more than conventional CD4$^+$ memory T cells. In one embodiment, said activation is determined by measurement of intracellular STAT, particularly STAT5, phosphorylation levels. In one embodiment, said measurement of intracellular STAT phosphorylation levels is done by flow cytometric analysis. In one embodiment, the EC$_{50}$ value of said fusion protein for induction of IL-2 receptor signaling in regulatory T cells is at least 10-fold, at least 100-fold or at least 1000-fold lower than its EC$_{50}$ value for induction of IL-2 receptor signaling in effector T cells and NK cells. In one embodiment said induction of IL-2 receptor signaling is induction of STAT phosphorylation. In one embodiment, the EC$_{50}$ value of said fusion protein for induction of IL-2 receptor signaling in regulatory T cells is at least 10-fold, at least 100-fold or at least 1000-fold lower than its EC$_{50}$ value for induction of IL-2 receptor signaling in conventional CD4$^+$ memory T cells. In one embodiment said induction of IL-2 receptor signaling is induction of STAT phosphorylation.

In a further aspect, the invention particularly provides the fusion protein for use in selective activation of regulatory T cells in vitro or in vivo. In one embodiment, said use comprises contacting regulatory T cells with said fusion protein in vitro or in vivo. In one embodiment, said use further comprises contacting other (non-regulatory) T cells with said fusion protein. In one embodiment, said use is in vitro and said fusion protein is used at a concentration of about 10 ng/mL or less, particularly about 1 ng/mL or less. In another embodiment, said use is in vivo and said fusion protein is used at a dose of about 100 μg/kg body weight or less, particularly about 25 μg/kg body weight or less, more particularly about 10 μg/kg body weight or less (wherein "body weight" refers to the body weight of the individual to whom the fusion protein is administered).

The invention also provides a method for selective activation of regulatory T cells in vitro or in vivo, comprising contacting said regulatory T cells with the fusion protein of the invention. In one embodiment, said method further comprises contacting other (non-regulatory) T cells with said fusion protein. In one embodiment, said activation comprises induction of proliferation and/or induction of IL-2 receptor signaling. In one embodiment, said method is in vitro and said fusion protein is used at a concentration of about 10 ng/mL or less, particularly about 1 ng/mL or less. In another embodiment, said method is in vivo and said fusion protein is used at a dose of about 100 μg/kg body weight or less, particularly about 25 μg/kg body weight or less, more particularly about 10 μg/kg body weight or less (wherein "body weight" refers to the body weight of the individual to whom the fusion protein is administered).

According to certain embodiments of the fusion protein, use or method described in the preceding paragraphs, said activation comprises induction of proliferation of regulatory T cells and/or induction of IL-2 receptor signaling in regulatory T cells. Induction of proliferation can be measured e.g. by detection of the intracellular proliferation marker Ki-67, as described in the Examples. In one embodiment, proliferation of regulatory T cells activated by the fusion protein of the invention is increased at least about 1.5-fold, at least about 2-fold, or at least about 3-fold, as compared to proliferation of non-activated regulatory T cells. In one embodiment, proliferation of other (non-regulatory) T cells and/or NK cells contacted with the fusion protein of the invention is increased less than about 1.5 fold, less than about 1.2 fold, or less than about 1.1 fold, as compared to proliferation of corresponding cells not contacted with said fusion protein. Induction of IL-2 receptor signaling can be measured e.g. by detection of phosphorylated STAT5, as described in the Examples. In one embodiment, IL-2 receptor signaling in regulatory T cells activated by the fusion protein of the invention is increased at least about 1.5-fold, at least about 2-fold, at least about 3-fold, or at least about 5-fold, as compared to IL-2 receptor signaling in non-activated regulatory T cells. In one embodiment, IL-2 receptor signaling in other (non-regulatory) T cells and/or NK cells contacted with the fusion protein or the invention is increased less than about 1.5 fold, or less than about 1.2 fold, or less than about 1.1 fold, as compared to IL-2 receptor signaling in corresponding cells not contacted with said fusion protein.

Polynucleotides

The invention further provides polynucleotides encoding a fusion as described herein or a fragment thereof.

Polynucleotides of the invention include those that are at least about 80%, 85%, 90%, 95%, 96%, 97%, 98%, 99%, or 100% identical to the sequences set forth in SEQ ID NOs 10, 12, 20, 51, 59, 61, 63 and 65 including functional fragments or variants thereof.

The polynucleotides encoding fusion proteins of the invention may be expressed as a single polynucleotide that encodes the entire fusion protein or as multiple (e.g., two or more) polynucleotides that are co-expressed. Polypeptides encoded by polynucleotides that are co-expressed may associate through, e.g., disulfide bonds or other means to form a functional fusion protein. For example, the light chain portion of an immunoglobulin may be encoded by a separate polynucleotide from the heavy chain portion of the immunoglobulin. When co-expressed, the heavy chain polypeptides will associate with the light chain polypeptides to form the immunoglobulin.

In one embodiment, the present invention is directed to a polynucleotide encoding a fusion protein of an immunoglobulin molecule and two IL-2 molecules, or a fragment thereof, wherein the polynucleotide comprises a sequence that encodes a variable region sequence as shown in SEQ ID NO 9 or 11. In another embodiment, the present invention is directed to a polynucleotide encoding a fusion protein of an immunoglobulin molecule and two IL-2 molecules, or a fragment thereof, wherein the polynucleotide comprises a sequence that encodes a polypeptide sequence as shown in SEQ ID NO 19 or 50. In another embodiment, the invention is further directed to a polynucleotide encoding a fusion protein of an immunoglobulin molecule and two IL-2 molecules, or a fragment thereof, wherein the polynucleotide comprises a sequence that is at least about 80%, 85%, 90%, 95%, 96%, 97%, 98%, or 99% identical to a nucleic acid sequence shown SEQ ID NO 10, 12, 20, 51, 59, 61, 63 or 65. In another embodiment, the invention is directed to a polynucleotide encoding a fusion protein of an immunoglobulin molecule and two IL-2 molecules, or a fragment thereof, wherein the polynucleotide comprises a nucleic acid sequence shown in SEQ ID NO 10, 12, 20, 51, 59, 61, 63 or 65. In another embodiment, the invention is directed to a polynucleotide encoding a fusion protein of an immunoglobulin molecule and two IL-2 molecules, or a fragment thereof, wherein the polynucleotide comprises a sequence that encodes a variable region sequence that is at least about 80%, 85%, 90%, 95%, 96%, 97%, 98%, or 99% identical to the amino acid sequence of SEQ ID NO 9 or 11. In another embodiment, the invention is directed to a polynucleotide encoding a fusion protein of an immunoglobulin molecule and two IL-2 molecules, or a fragment thereof, wherein the polynucleotide comprises a sequence that encodes a polypeptide sequence that is at least 80%, 85%, 90%, 95%, 96%, 97%, 98%, or 99% identical to the amino acid sequence of SEQ ID NO 19 or 50. The invention encompasses a polynucleotide encoding an a fusion protein of an immunoglobulin molecule and two IL-2 molecules, or a fragment thereof, wherein the polynucleotide comprises a sequence that encodes the variable region sequences of SEQ ID NO 9 or 11 with conservative amino acid substitutions. The invention also encompasses a polynucleotide encoding a fusion protein of an immunoglobulin molecule and two IL-2 molecules, or a fragment thereof, wherein the polynucleotide comprises a sequence that encodes the polypeptide sequences of SEQ ID NO 19 or 50 with conservative amino acid substitutions. In certain embodiments the polynucleotide or nucleic acid is DNA. In other embodiments, a polynucleotide of the present invention is RNA, for example, in the form of messenger RNA (mRNA). RNA of the present invention may be single stranded or double stranded.

Recombinant Methods

Fusion proteins of the invention may be obtained, for example, by solid-state peptide synthesis (e.g. Merrifield solid phase synthesis) or recombinant production. For recombinant production one or more polynucleotide encoding the fusion protein (fragment), e.g., as described above, is isolated and inserted into one or more vectors for further cloning and/or expression in a host cell. Such polynucleotide may be readily isolated and sequenced using conventional procedures. In one embodiment a vector, preferably an expression vector, comprising one or more of the polynucleotides of the invention is provided. Methods which are well known to those skilled in the art can be used to construct expression vectors containing the coding sequence of a fusion protein (fragment) along with appropriate transcriptional/translational control signals. These methods include in vitro recombinant DNA techniques, synthetic techniques and in vivo recombination/genetic recombination. See, for example, the techniques described in Maniatis et al., MOLECULAR CLONING: A LABORATORY MANUAL, Cold Spring Harbor Laboratory, N.Y. (1989); and Ausubel et al., CURRENT PROTOCOLS IN MOLECULAR BIOLOGY, Greene Publishing Associates and Wiley Interscience, N.Y. (1989). The expression vector can be part of a plasmid, virus, or may be a nucleic acid fragment. The expression vector includes an expression cassette into which the polynucleotide encoding the fusion protein (fragment) (i.e. the coding region) is cloned in operable association with a promoter and/or other transcription or translation control elements. As used herein, a "coding region" is a portion of nucleic acid which consists of codons translated into amino acids. Although a "stop codon" (TAG, TGA, or TAA) is not translated into an amino acid, it may be considered to be part of a coding region, if present, but any flanking sequences, for example promoters, ribosome binding sites, transcriptional terminators, introns, 5' and 3' untranslated regions, and the like, are not part of a coding region. Two or more coding regions can be present in a single polynucleotide construct, e.g. on a single vector, or in separate polynucleotide constructs, e.g. on separate (different) vectors. Furthermore, any vector may contain a single coding region, or may comprise two or more coding regions, e.g. a vector of the present invention may encode one or more polypeptides, which are post- or co-translationally separated into the final proteins via proteolytic cleavage. In addition, a vector, polynucleotide, or nucleic acid of the invention may encode heterologous coding regions, either fused or unfused to a polynucleotide encoding the fusion protein (fragment) of the invention, or variant or derivative thereof. Heterologous coding regions include without limitation specialized elements or motifs, such as a secretory signal peptide or a heterologous functional domain. An operable association is when a coding region for a gene product, e.g. a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter may be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription. Suitable promoters and other transcription control regions are disclosed herein. A variety of transcription control regions are known to those skilled in the art. These include, without limitation, transcription control regions, which function in vertebrate cells, such as, but not limited to, promoter and enhancer segments from cytomegaloviruses (e.g. the immediate early promoter, in conjunction with intron-A), simian virus 40 (e.g. the early promoter), and retroviruses (such as, e.g. Rous sarcoma virus). Other transcription control regions include those derived from vertebrate genes such as actin, heat shock protein, bovine growth hormone and rabbit â-globin, as well as other sequences capable of controlling gene expression in eukaryotic cells. Additional suitable transcription control regions include tissue-specific promoters and enhancers as well as inducible promoters (e.g. promoters inducible tetracyclins). Similarly, a variety of translation control elements are known to those of ordinary skill in the art. These include, but are not limited to ribosome binding sites, translation initiation and termination codons, and elements derived from viral systems (particularly an internal ribosome entry site, or IRES, also referred to as a CITE sequence). The expression cassette may also include other features such as an origin of replication, and/or chromosome integration elements such as retroviral long terminal repeats (LTRs), or adeno-associated viral (AAV) inverted terminal repeats (ITRs).

Polynucleotide and nucleic acid coding regions of the present invention may be associated with additional coding regions which encode secretory or signal peptides, which direct the secretion of a polypeptide encoded by a polynucleotide of the present invention. For example, if secretion of the fusion is desired, DNA encoding a signal sequence may be placed upstream of the nucleic acid encoding a fusion protein of the invention or a fragment thereof. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the translated polypeptide to produce a secreted or "mature" form of the polypeptide. In certain embodiments, the native signal peptide, e.g. an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, may be used. For example, the wild-type leader sequence may be substituted with the leader sequence of human tissue plasminogen activator (TPA) or mouse β-glucuronidase. The amino acid and nucleotide sequences of exemplary secretory signal peptides are shown in SEQ ID NOs 39-47.

DNA encoding a short protein sequence that could be used to facilitate later purification (e.g. a histidine tag) or assist in labeling the fusion protein may be included within or at the ends of the fusion protein (fragment) encoding polynucleotide.

In a further embodiment, a host cell comprising one or more polynucleotides of the invention is provided. In certain embodiments a host cell comprising one or more vectors of the invention is provided. The polynucleotides and vectors may incorporate any of the features, singly or in combination, described herein in relation to polynucleotides and vectors, respectively. In one such embodiment a host cell comprises (e.g. has been transformed or transfected with) a vector comprising a polynucleotide that encodes (part of) a fusion protein of the invention. As used herein, the term "host cell" refers to any kind of cellular system which can be engineered to generate the fusion proteins of the invention or fragments thereof. Host cells suitable for replicating and for supporting expression of fusion proteins are well known in the art. Such cells may be transfected or transduced as appropriate with the particular expression vector and large quantities of vector containing cells can be grown for seeding large scale fermenters to obtain sufficient quantities of the fusion protein for clinical applications. Suitable host cells include prokaryotic microorganisms, such as *E. coli*, or various eukaryotic cells, such as Chinese hamster ovary cells (CHO), insect cells, or the like. For example, polypeptides may be produced in bacteria in particular when glycosylation is not needed. After expression, the polypeptide may be isolated from the bacterial cell paste in a soluble fraction and can be further purified. In addition to prokaryotes, eukaryotic microbes such as filamentous fungi or yeast are suitable cloning or expression hosts for polypeptide-encoding vectors, including fungi and yeast strains whose glycosylation pathways have been "humanized", resulting in the production of a polypeptide with a partially or fully human glycosylation pattern. See Gerngross, Nat Biotech 22, 1409-1414 (2004), and Li et al., Nat Biotech 24, 210-215 (2006). Suitable host cells for the expression of (glycosylated) polypeptides are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells. Plant cell cultures can also be utilized as hosts. See e.g. U.S. Pat. Nos. 5,959,177, 6,040,498, 6,420,548, 7,125,978, and 6,417,429 (describing PLANTIBODIES™ technology for producing antibodies in transgenic plants). Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293T cells as described, e.g., in Graham et al., J Gen Virol 36, 59 (1977)), baby hamster kidney cells (BHK), mouse sertoli cells (TM4 cells as described, e.g., in Mather, Biol Reprod 23, 243-251 (1980)), monkey kidney cells (CV1), African green monkey kidney cells (VERO-76), human cervical carcinoma cells (HELA), canine kidney cells (MDCK), buffalo rat liver cells (BRL 3A), human lung cells (W138), human liver cells (Rep G2), mouse mammary tumor cells (MMT 060562), TRI cells (as described, e.g., in Mather et al., Annals N.Y. Acad Sci 383, 44-68 (1982)), MRC 5 cells, and FS4 cells. Other useful mammalian host cell lines include Chinese hamster ovary (CHO) cells, including dhfr⁻ CHO cells (Urlaub et al., Proc Natl Acad Sci USA 77, 4216 (1980)); and myeloma cell lines such as Y0, NS0, P3X63 and Sp2/0. For a review of certain mammalian host cell lines suitable for protein production, see, e.g., Yazaki and Wu, Methods in Molecular Biology, Vol. 248 (B. K. C. Lo, ed., Humana Press, Totowa, N.J.), pp. 255-268 (2003). Host cells include cultured cells, e.g., mammalian cultured cells, yeast cells, insect cells, bacterial cells and plant cells, to name only a few, but also cells comprised within a transgenic animal, transgenic plant or cultured plant or animal tissue. In one embodiment, the host cell is a eukaryotic cell, preferably a mammalian cell, such as a Chinese Hamster Ovary (CHO) cell, a human embryonic kidney (HEK) cell or a lymphoid cell (e.g., Y0, NS0, Sp20 cell). Standard technologies are known in the art to express foreign genes in these systems. Cells expressing a polypeptide comprising either the heavy or the light chain of an immunoglobulin, may be engineered so as to also express the other of the immunoglobulin chains such that the expressed product is an immunoglobulin that has both a heavy and a light chain.

In one embodiment, a method of producing a fusion protein according to the invention is provided, wherein the method comprises culturing a host cell comprising a polynucleotide encoding the fusion protein, as provided herein, under conditions suitable for expression of the fusion protein, and recovering the fusion protein from the host cell (or host cell culture medium). In the fusion proteins of the invention, the components (immunoglobulin molecule and IL-2 molecule) are genetically fused to each other. Fusion proteins can be designed such that its components are fused directly to each other or indirectly through a linker sequence. The composition and length of the linker may be determined in accordance with methods well known in the art and may be tested for efficacy. Additional sequences may also be included to incorporate a cleavage site to separate the individual components of the fusion protein if desired, for example an endopeptidase recognition sequence.

In certain embodiments the fusion proteins of the invention comprise at least an immunoglobulin variable region capable of binding to an antigen. Variable regions can form part of and be derived from naturally or non-naturally occurring antibodies and fragments thereof. Methods to produce polyclonal antibodies and monoclonal antibodies are well known in the art (see e.g. Harlow and Lane, "Antibodies, a laboratory manual", Cold Spring Harbor Laboratory, 1988). Non-naturally occurring antibodies can be constructed using solid phase-peptide synthesis, can be produced recombinantly (e.g. as described in U.S. Pat. No. 4,186,567) or can be obtained, for example, by screening combinatorial libraries comprising variable heavy chains and variable light chains (see e.g. U.S. Pat. No. 5,969,108 to McCafferty).

Any animal species of immunoglobulin can be used in the invention. Non-limiting immunoglobulins useful in the present invention can be of murine, primate, or human origin. If the fusion protein is intended for human use, a chimeric form of immunoglobulin may be used wherein the constant regions of the immunoglobulin are from a human. A humanized or fully human form of the immunoglobulin can also be prepared in accordance with methods well known in the art (see e. g. U.S. Pat. No. 5,565,332 to Winter). Humanization may be achieved by various methods including, but not limited to (a) grafting the non-human (e.g., donor antibody) CDRs onto human (e.g. recipient antibody) framework and constant regions with or without retention of critical framework residues (e.g. those that are important for retaining good antigen binding affinity or antibody functions), (b) grafting only the non-human specificity-determining regions (SDRs or a-CDRs; the residues critical for the antibody-antigen interaction) onto human framework and constant regions, or (c) transplanting the entire non-human variable domains, but "cloaking" them with a human-like section by replacement of surface residues. Humanized antibodies and methods of making them are reviewed, e.g., in Almagro and Fransson, Front Biosci 13, 1619-1633 (2008), and are further described, e.g., in Riechmann et al., Nature 332, 323-329 (1988); Queen et al., Proc Natl Acad Sci USA 86, 10029-10033 (1989); U.S. Pat. Nos. 5,821,337, 7,527,791, 6,982,321, and 7,087,409; Jones et al., Nature 321, 522-525 (1986); Morrison et al., Proc Natl Acad Sci 81, 6851-6855 (1984); Morrison and Oi, Adv Immunol 44, 65-92 (1988); Verhoeyen et al., Science 239, 1534-1536 (1988); Padlan, Molec Immun 31(3), 169-217 (1994); Kashmiri et al., Methods 36, 25-34 (2005) (describing SDR (a-CDR) grafting); Padlan, Mol Immunol 28, 489-498 (1991) (describing "resurfacing"); Dall'Acqua et al., Methods 36, 43-60 (2005) (describing "FR shuffling"); and Osbourn et al., Methods 36, 61-68 (2005) and Klimka et al., Br J Cancer 83, 252-260 (2000) (describing the "guided selection" approach to FR shuffling). Particular immunoglobulins according to the invention are human immunoglobulins. Human antibodies and human variable regions can be produced using various techniques known in the art. Human antibodies are described generally in van Dijk and van de Winkel, Curr Opin Pharmacol 5, 368-74 (2001) and Lonberg, Curr Opin Immunol 20, 450-459 (2008). Human variable regions can form part of and be derived from human monoclonal antibodies made by the hybridoma method (see e.g. Monoclonal Antibody Production Techniques and Applications, pp. 51-63 (Marcel Dekker, Inc., New York, 1987)). Human antibodies and human variable regions may also be prepared by administering an immunogen to a transgenic animal that has been modified to produce intact human antibodies or intact antibodies with human variable regions in response to antigenic challenge (see e.g. Lonberg, Nat Biotech 23, 1117-1125 (2005). Human antibodies and human variable regions may also be generated by isolating Fv clone variable region sequences selected from human-derived phage display libraries (see e.g., Hoogenboom et al. in Methods in Molecular Biology 178, 1-37 (O'Brien et al., ed., Human Press, Totowa, N.J., 2001); and McCafferty et al., Nature 348, 552-554; Clackson et al., Nature 352, 624-628 (1991)). Phage typically display antibody fragments, either as single-chain Fv (scFv) fragments or as Fab fragments.

In certain embodiments, the immunoglobulins comprised in the fusion proteins of the present invention are engineered to have enhanced binding affinity according to, for example, the methods disclosed in PCT publication WO 2012/020006 (see Examples relating to affinity maturation) or U.S. Pat. Appl. Publ. No. 2004/0132066, the entire contents of which are hereby incorporated by reference. The ability of the fusion proteins of the invention to bind to a specific antigenic determinant can be measured either through an enzyme-linked immunosorbent assay (ELISA) or other techniques familiar to one of skill in the art, e.g. surface plasmon resonance technique (Liljeblad, et al., Glyco J 17, 323-329 (2000)), and traditional binding assays (Heeley, Endocr Res 28, 217-229 (2002)). Competition assays may be used to identify an antibody that competes with a reference antibody for binding to a particular antigen. In certain embodiments, such a competing antibody binds to the same epitope (e.g. a linear or a conformational epitope) that is bound by the reference antibody. Detailed exemplary methods for mapping an epitope to which an antibody binds are provided in Morris (1996) "Epitope Mapping Protocols", in Methods in Molecular Biology vol. 66 (Humana Press, Totowa, N.J.). In an exemplary competition assay, immobilized antigen is incubated in a solution comprising a first labeled antibody that binds to the antigen and a second unlabeled antibody that is being tested for its ability to compete with the first antibody for binding to the antigen. The second antibody may be present in a hybridoma supernatant. As a control, immobilized antigen is incubated in a solution comprising the first labeled antibody but not the second unlabeled antibody. After incubation under conditions permissive for binding of the first antibody to the antigen, excess unbound antibody is removed, and the amount of label associated with immobilized antigen is measured. If the amount of label associated with immobilized antigen is substantially reduced in the test sample relative to the control sample, then that indicates that the second antibody is competing with the first antibody for binding to the antigen. See Harlow and Lane (1988) Antibodies: A Laboratory Manual ch. 14 (Cold Spring Harbor Laboratory, Cold Spring Harbor, N.Y.).

Figure 4:
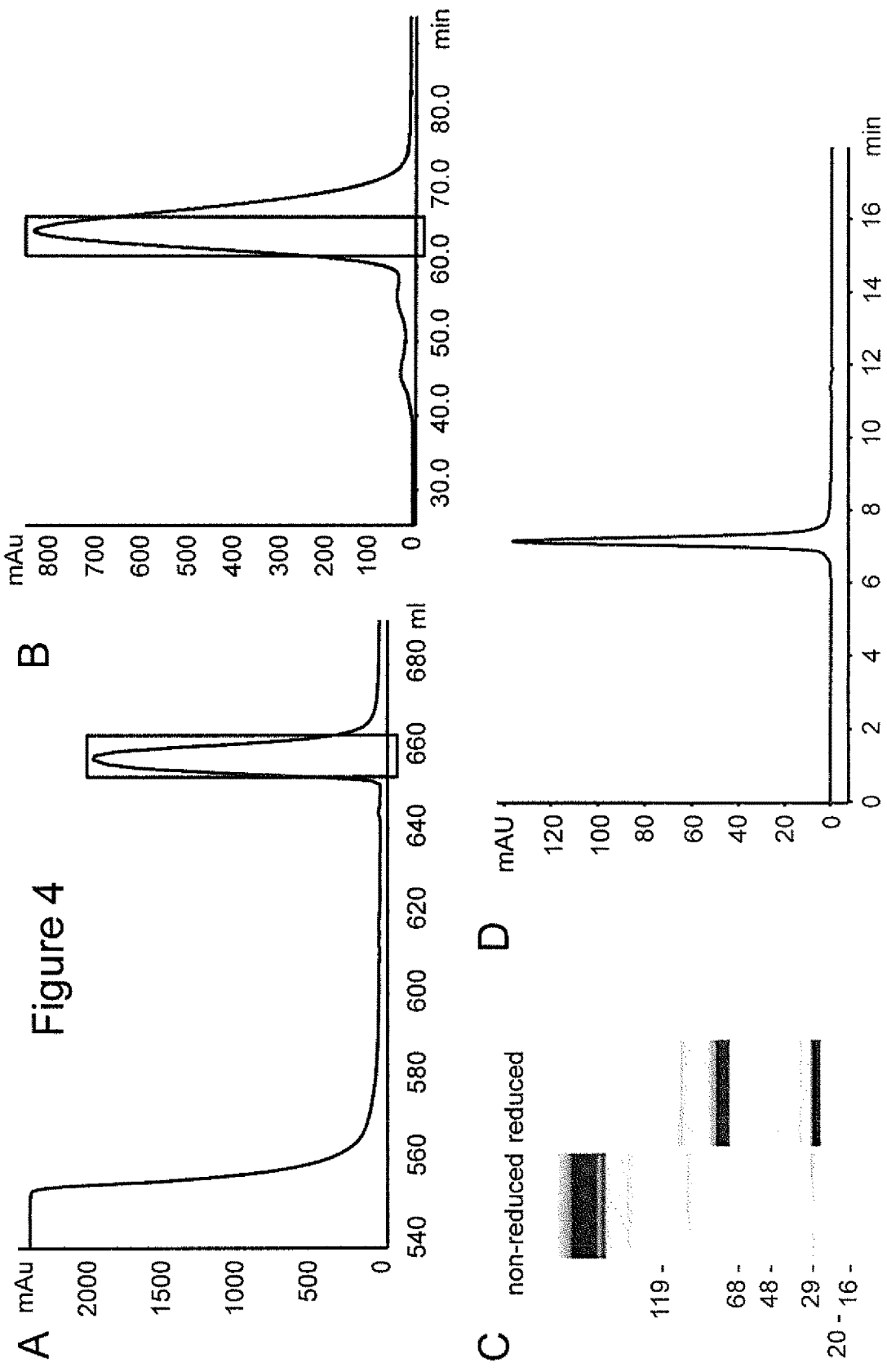
FIG. 4A-D. Purification of DP47GS IgG-(IL-2 N88D)$_2$ fusion protein (see SEQ ID NOs 19 and 50).
Figure 5:
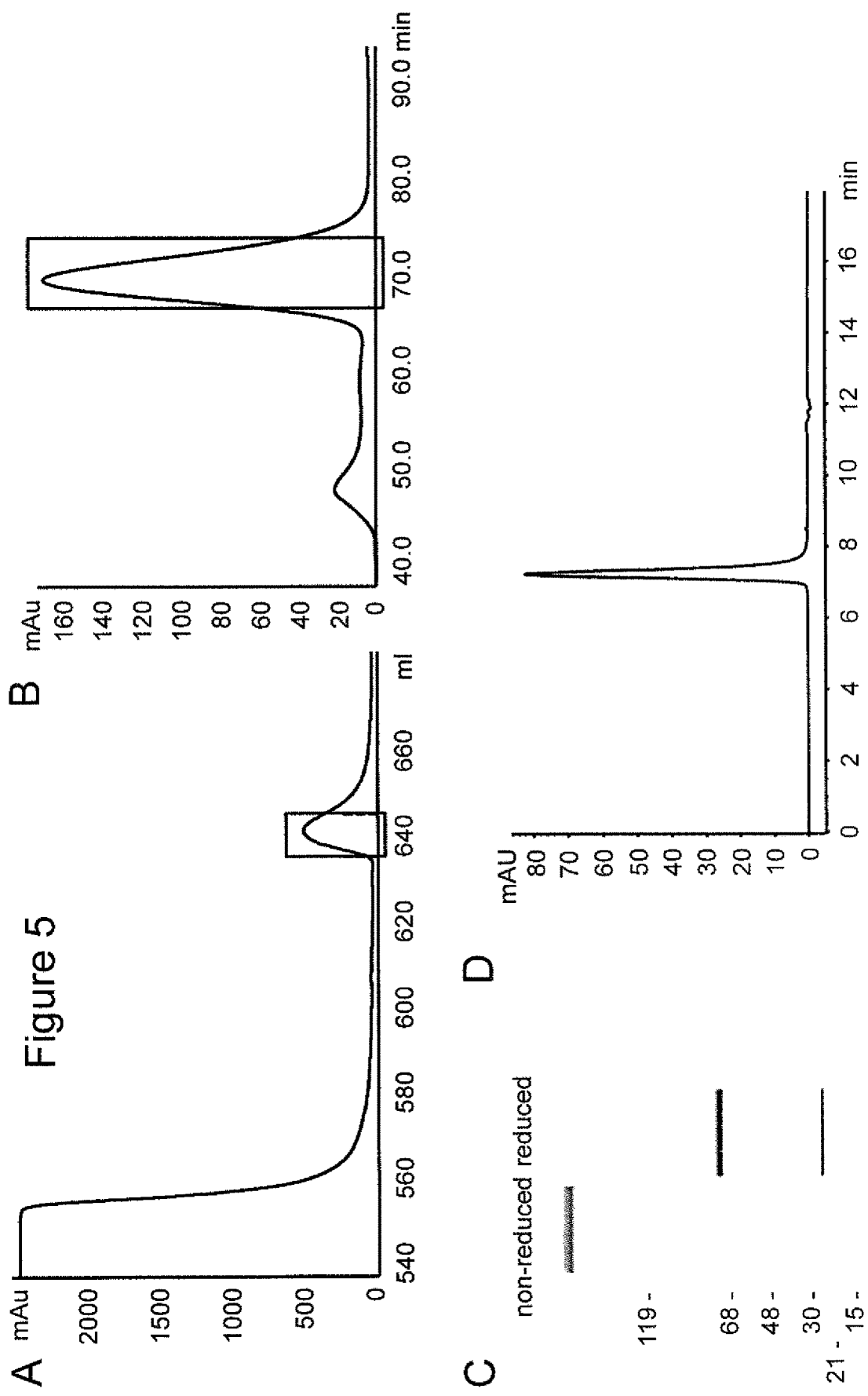
FIG. 5A-D. Purification of DP47GS IgG-(IL-2 E95A)$_2$ fusion protein (see SEQ ID NOs 19 and 52).

Fusion proteins prepared as described herein may be purified by art-known techniques such as high performance liquid chromatography, ion exchange chromatography, gel electrophoresis, affinity chromatography, size exclusion chromatography, and the like. The actual conditions used to purify a particular protein will depend, in part, on factors such as net charge, hydrophobicity, hydrophilicity etc., and will be apparent to those having skill in the art. For affinity chromatography purification an antibody, ligand, receptor or antigen can be used to which the fusion protein binds. For example, for affinity chromatography purification of fusion proteins of the invention, a matrix with protein A or protein G may be used. Sequential Protein A or G affinity chromatography and size exclusion chromatography can be used to isolate a fusion protein essentially as described in the Examples. The purity of the fusion protein can be determined by any of a variety of well-known analytical methods including gel electrophoresis, high pressure liquid chromatography, and the like. For example, the fusion proteins expressed as described in the Examples were shown to be intact and properly assembled as demonstrated by reducing and non-reducing SDS-PAGE (see e.g. FIG. 4).

Compositions, Formulations, and Routes of Administration

In a further aspect, the invention provides pharmaceutical compositions comprising any of the fusion proteins provided herein, e.g., for use in any of the below therapeutic methods. In one embodiment, a pharmaceutical composition comprises any of the fusion proteins provided herein and a pharmaceutically acceptable carrier. In another embodiment, a pharmaceutical composition comprises any of the fusion proteins provided herein and at least one additional therapeutic agent, e.g. as described below.

Further provided is a method of producing a fusion protein of the invention in a form suitable for administration in vivo, the method comprising (a) obtaining a fusion protein according to the invention, and (b) formulating the fusion protein with at least one pharmaceutically acceptable carrier, whereby a preparation of fusion protein is formulated for administration in vivo.

Pharmaceutical compositions of the present invention comprise a therapeutically effective amount of one or more fusion protein dissolved or dispersed in a pharmaceutically acceptable carrier. The phrases "pharmaceutical or pharmacologically acceptable" refers to molecular entities and compositions that are generally non-toxic to recipients at the dosages and concentrations employed, i.e. do not produce an adverse, allergic or other untoward reaction when administered to an animal, such as, for example, a human, as appropriate. The preparation of a pharmaceutical composition that contains at least one fusion protein and optionally an additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards or corresponding authorities in other countries. Preferred compositions are lyophilized formulations or aqueous solutions. As used herein, "pharmaceutically acceptable carrier" includes any and all solvents, buffers, dispersion media, coatings, surfactants, antioxidants, preservatives (e.g. antibacterial agents, antifungal agents), isotonic agents, absorption delaying agents, salts, preservatives, antioxidants, proteins, drugs, drug stabilizers, polymers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

The composition may comprise different types of carriers depending on whether it is to be administered in solid, liquid or aerosol form, and whether it need to be sterile for such routes of administration as injection. Fusion proteins of the present invention (and any additional therapeutic agent) can be administered by any method or any combination of methods as would be known to one of ordinary skill in the art (see, for example, Remington's Pharmaceutical Sciences, 18th Ed. Mack Printing Company, 1990, incorporated herein by reference). Parenteral administration, in particular intravenous injection, is most commonly used for administering polypeptide molecules such as the fusion proteins of the invention.

Parenteral compositions include those designed for administration by injection, e.g. subcutaneous, intradermal, intralesional, intravenous, intraarterial, intramuscular, intrathecal or intraperitoneal injection. For injection, the fusion proteins of the invention may be formulated in aqueous solutions, preferably in physiologically compatible buffers such as Hanks' solution, Ringer's solution, or physiological saline buffer. The solution may contain formulatory agents such as suspending, stabilizing and/or dispersing agents. Alternatively, the fusion proteins may be in powder form for constitution with a suitable vehicle, e.g., sterile pyrogen-free water, before use. Sterile injectable solutions are prepared by incorporating the fusion proteins of the invention in the required amount in the appropriate solvent with various of the other ingredients enumerated below, as required. Sterility may be readily accomplished, e.g., by filtration through sterile filtration membranes. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein. Suitable pharmaceutically acceptable carriers include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Aqueous injection suspensions may contain compounds which increase the viscosity of the suspension, such as sodium carboxymethyl cellulose, sorbitol, dextran, or the like. Optionally, the suspension may also contain suitable stabilizers or agents which increase the solubility of the compounds to allow for the preparation of highly concentrated solutions. Additionally, suspensions of the active compounds may be prepared as appropriate oily injection suspensions. Suitable lipophilic solvents or vehicles include fatty oils such as sesame oil, or synthetic fatty acid esters, such as ethyl cleats or triglycerides, or liposomes.

Pharmaceutical compositions comprising the fusion proteins of the invention may be manufactured by means of conventional mixing, dissolving, emulsifying, encapsulating, entrapping or lyophilizing processes. Pharmaceutical compositions may be formulated in conventional manner using one or more physiologically acceptable carriers, diluents, excipients or auxiliaries which facilitate processing of the proteins into preparations that can be used pharmaceutically. Proper formulation is dependent upon the route of administration chosen.

The fusion proteins may be formulated into a composition in a free acid or base, neutral or salt form. Pharmaceutically acceptable salts are salts that substantially retain the biological activity of the free acid or base. These include the acid addition salts, e.g. those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Pharmaceutical salts tend to be more soluble in aqueous and other protic solvents than are the corresponding free base forms.

Therapeutic Methods and Compositions

Any of the fusion proteins provided herein may be used in therapeutic methods.

For use in therapeutic methods, fusion proteins of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

In one aspect, fusion proteins of the invention for use as a medicament are provided. In further aspects, fusion proteins of the invention for use in treating a disease are provided. In certain embodiments, fusion proteins of the invention for use in a method of treatment are provided. In one embodiment, the invention provides a fusion protein as described herein for use in the treatment of a disease in an individual in need thereof. In certain embodiments, the invention provides a fusion protein for use in a method of treating an individual having a disease comprising administering to the individual a therapeutically effective amount of the fusion protein. In certain embodiments the disease to be treated is an autoimmune disease. Exemplary autoimmune diseases include type 1 diabetes, psoriasis, asthma, rheumatoid arthritis, inflammatory bowel disease, Crohn's disease, ulcerative colitis, systemic lupus erythematosus (SLE) and multiple sclerosis. In one embodiment, the disease is transplant rejection or graft-versus-host disease. In a particular embodiment the disease is selected from the group of type 1 diabetes, inflammatory bowel disease, Crohn's disease, ulcerative colitis, SLE, and multiple sclerosis. In a more particular embodiment, the disease is type 1 diabetes. In another particular embodiment, the disease is inflammatory bowel disease. In another particular embodiment, the disease is multiple sclerosis. In further embodiments, the disease is asthma, pulmonary fibrosis or obstructive pulmonary disease. In still further embodiments, the disease is a cardiovascular disease, particularly atherosclerosis and acute coronary syndrome. In further embodiments, the disease is an allergic condition, particularly a food allergy. In certain embodiments the method further comprises administering to the individual a therapeutically effective amount of at least one additional therapeutic agent, e.g. an immunosuppressive agent if the disease to be treated is an autoimmune disease. An "individual" according to any of the above embodiments is a mammal, preferably a human.

In a further aspect, the invention provides for the use of a fusion protein of the invention in the manufacture or preparation of a medicament for the treatment of a disease in an individual in need thereof. In one embodiment, the medicament is for use in a method of treating a disease comprising administering to an individual having the disease a therapeutically effective amount of the medicament. In certain embodiments the disease to be treated is an autoimmune disease.

In one embodiment, the disease is transplant rejection or graft-versus-host disease. In a particular embodiment the disease is selected from the group of type 1 diabetes, inflammatory bowel disease, Crohn's disease, ulcerative colitis, SLE, and multiple sclerosis. In a more particular embodiment, the disease is type 1 diabetes. In another particular embodiment, the disease is inflammatory bowel disease. In another particular embodiment, the disease is multiple sclerosis. In further embodiments, the disease is asthma, pulmonary fibrosis or obstructive pulmonary disease. In still further embodiments, the disease is a cardiovascular disease, particularly atherosclerosis and acute coronary syndrome. In further embodiments, the disease is an allergic condition, particularly a food allergy. In one embodiment, the method further comprises administering to the individual a therapeutically effective amount of at least one additional therapeutic agent, e.g., an immunosuppressive agent if the disease to be treated is an autoimmune disease. An "individual" according to any of the above embodiments may be a mammal, preferably a human.

In a further aspect, the invention provides a method for treating a disease in an individual, comprising administering to said individual a therapeutically effective amount of a fusion protein of the invention. In one embodiment a composition is administered to said individual, comprising a fusion protein of the invention in a pharmaceutically acceptable form. In certain embodiments the disease to be treated is an autoimmune disease. In one embodiment, the disease is transplant rejection or graft-versus-host disease. In a particular embodiment the disease is selected from the group of type 1 diabetes, inflammatory bowel disease, Crohn's disease, ulcerative colitis, SLE, and multiple sclerosis. In a more particular embodiment, the disease is type 1 diabetes. In another particular embodiment, the disease is inflammatory bowel disease. In another particular embodiment, the disease is multiple sclerosis. In further embodiments, the disease is asthma, pulmonary fibrosis or obstructive pulmonary disease. In further embodiments, the disease is an allergic condition, particularly a food allergy. In still further embodiments, the disease is a cardiovascular disease, particularly atherosclerosis and acute coronary syndrome. In certain embodiments the method further comprises administering to the individual a therapeutically effective amount of at least one additional therapeutic agent, e.g. an immunosuppressive agent if the disease to be treated is an autoimmune disease. An "individual" according to any of the above embodiments may be a mammal, preferably a human.

In some embodiments, an effective amount of a fusion protein of the invention is administered to a cell. In other embodiments, a therapeutically effective amount of a fusion protein of the invention is administered to an individual for the treatment of disease.

For the prevention or treatment of disease, the appropriate dosage of a fusion protein of the invention (when used alone or in combination with one or more other additional therapeutic agents) will depend on the type of disease to be treated, the route of administration, the body weight of the patient, the type of fusion protein, the severity and course of the disease, whether the fusion protein is administered for preventive or therapeutic purposes, previous or concurrent therapeutic interventions, the patient's clinical history and response to the fusion protein, and the discretion of the attending physician. The practitioner responsible for administration will, in any event, determine the concentration of active ingredient(s) in a composition and appropriate dose(s) for the individual subject. Various dosing schedules including but not limited to single or multiple administrations over various time-points, bolus administration, and pulse infusion are contemplated herein.

The fusion protein is suitably administered to the patient at one time or over a series of treatments. Depending on the type and severity of the disease, about 1 µg/kg to 15 mg/kg (e.g. 0.1 mg/kg-10 mg/kg) of fusion protein can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the fusion protein would be in the range from about 0.005 mg/kg to about 10 mg/kg. In other non-limiting examples, a dose may also comprise from about 1 µg/kg body weight, about 5 µg/kg body weight, about 10 µg/kg body weight, about 50 µg/kg body weight, about 100 µg/kg body weight, about 200 µg/kg body weight, about 350 µg/kg body weight, about 500 µg/kg body weight, about 1 mg/kg body weight, about 5 mg/kg body weight, about 10 mg/kg body weight, about 50 mg/kg body weight, about 100 mg/kg body weight, about 200 mg/kg body weight, about 350 mg/kg body weight, about 500 mg/kg body weight, to about 1000 mg/kg body weight or more per administration, and any range derivable therein. In non-limiting examples of a derivable range from the numbers listed herein, a range of about 5 mg/kg body weight to about 100 mg/kg body weight, about 5 µg/kg body weight to about 500 mg/kg body weight etc., can be administered, based on the numbers described above. Thus, one or more doses of about 0.5 mg/kg, 2.0 mg/kg, 5.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the fusion protein). An initial higher loading dose, followed by one or more lower doses may be administered. However, other dosage regimens may be useful. The progress of this therapy is easily monitored by conventional techniques and assays.

The fusion proteins of the invention will generally be used in an amount effective to achieve the intended purpose. For use to treat or prevent a disease condition, the fusion proteins of the invention, or pharmaceutical compositions thereof, are administered or applied in a therapeutically effective amount. Determination of a therapeutically effective amount is well within the capabilities of those skilled in the art, especially in light of the detailed disclosure provided herein.

For systemic administration, a therapeutically effective dose can be estimated initially from in vitro assays, such as cell culture assays. A dose can then be formulated in animal models to achieve a circulating concentration range that includes the $IC_{50}$ as determined in cell culture. Such information can be used to more accurately determine useful doses in humans.

Initial dosages can also be estimated from in vivo data, e.g., animal models, using techniques that are well known in the art. One having ordinary skill in the art could readily optimize administration to humans based on animal data.

Dosage amount and interval may be adjusted individually to provide plasma levels of the fusion proteins which are sufficient to maintain therapeutic effect. Usual patient dosages for administration by injection range from about 0.1 to 50 mg/kg/day, typically from about 0.5 to 1 mg/kg/day. Therapeutically effective plasma levels may be achieved by administering multiple doses each day. Levels in plasma may be measured, for example, by HPLC.

In cases of local administration or selective uptake, the effective local concentration of the fusion protein may not be related to plasma concentration. One having skill in the art will be able to optimize therapeutically effective local dosages without undue experimentation.

A therapeutically effective dose of the fusion proteins described herein will generally provide therapeutic benefit without causing substantial toxicity. Toxicity and therapeutic efficacy of a fusion protein can be determined by standard pharmaceutical procedures in cell culture or experimental animals. Cell culture assays and animal studies can be used to determine the $LD_{50}$ (the dose lethal to 50% of a population) and the $ED_{50}$ (the dose therapeutically effective in 50% of a population). The dose ratio between toxic and therapeutic effects is the therapeutic index, which can be expressed as the ratio $LD_{50}/ED_{50}$. Fusion proteins that exhibit large therapeutic indices are preferred. In one embodiment, the fusion protein according to the present invention exhibits a high therapeutic index. The data obtained from cell culture assays and animal studies can be used in formulating a range of dosages suitable for use in humans. The dosage lies preferably within a range of circulating concentrations that include the $ED_{50}$ with little or no toxicity. The dosage may vary within this range depending upon a variety of factors, e.g., the dosage form employed, the route of administration utilized, the condition of the subject, and the like. The exact formulation, route of administration and dosage can be chosen by the individual physician in view of the patient's condition (see, e.g., Fingl et al., 1975, in The Pharmacological Basis of Therapeutics, Ch. 1, p. 1, incorporated herein by reference in its entirety).

The attending physician for patients treated with fusion proteins of the invention would know how and when to terminate, interrupt, or adjust administration due to toxicity, organ dysfunction, and the like. Conversely, the attending physician would also know to adjust treatment to higher levels if the clinical response were not adequate (precluding toxicity). The magnitude of an administered dose in the management of the disorder of interest will vary with the severity of the condition to be treated, with the route of administration, and the like. The severity of the condition may, for example, be evaluated, in part, by standard prognostic evaluation methods. Further, the dose and perhaps dose frequency will also vary according to the age, body weight, and response of the individual patient.

Other Agents and Treatments

The fusion proteins of the invention may be administered in combination with one or more other agents in therapy. For instance, a fusion protein of the invention may be co-administered with at least one additional therapeutic agent. The term "therapeutic agent" encompasses any agent administered to treat a symptom or disease in an individual in need of such treatment. Such additional therapeutic agent may comprise any active ingredients suitable for the particular indication being treated, preferably those with complementary activities that do not adversely affect each other. In certain embodiments, an additional therapeutic agent is an immunosuppressive agent.

Such other agents are suitably present in combination in amounts that are effective for the purpose intended. The effective amount of such other agents depends on the amount of fusion protein used, the type of disorder or treatment, and other factors discussed above. The fusion proteins are generally used in the same dosages and with administration routes as described herein, or about from 1 to 99% of the dosages described herein, or in any dosage and by any route that is empirically/clinically determined to be appropriate.

Such combination therapies noted above encompass combined administration (where two or more therapeutic agents are included in the same or separate compositions), and separate administration, in which case, administration of the fusion protein of the invention can occur prior to, simultaneously, and/or following, administration of the additional therapeutic agent and/or adjuvant.

Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is a fusion protein of the invention. The label or package insert indicates that the composition is used for treating the condition of choice. Moreover, the article of manufacture may comprise (a) a first container with a composition contained therein, wherein the composition comprises a fusion protein of the invention; and (b) a second container with a composition contained therein, wherein the composition comprises a further therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

EXAMPLES

The following are examples of methods and compositions of the invention. It is understood that various other embodiments may be practiced, given the general description provided above.

Recombinant DNA Techniques

Standard methods were used to manipulate DNA as described in Sambrook et al., Molecular cloning: A laboratory manual; Cold Spring Harbor Laboratory Press, Cold Spring Harbor, N.Y., 1989. The molecular biological reagents were used according to the manufacturer's instructions. General information regarding the nucleotide sequences of human immunoglobulin light and heavy chains is given in: Kabat, E. A. et al., (1991) Sequences of Proteins of Immunological Interest, Fifth Ed., NIH Publication No 91-3242.

DNA Sequencing

DNA sequences were determined by double strand sequencing.

Gene Synthesis

Desired gene segments where required were either generated by PCR using appropriate templates or were synthesized by Geneart AG (Regensburg, Germany) from synthetic oligonucleotides and PCR products by automated gene synthesis. In cases where no exact gene sequence was available, oligonucleotide primers were designed based on sequences from closest homologues and the genes were isolated by RT-PCR from RNA originating from the appropriate tissue. The gene segments flanked by singular restriction endonuclease cleavage sites were cloned into standard cloning/sequencing vectors. The plasmid DNA was purified from transformed bacteria and concentration determined by UV spectroscopy. The DNA sequence of the subcloned gene fragments was confirmed by DNA sequencing. Gene segments were designed with suitable restriction sites to allow sub-cloning into the respective expression vectors. All constructs were designed with a 5'-end DNA sequence coding for a leader peptide which targets proteins for secretion in eukaryotic cells. SEQ ID NOs 39-47 give exemplary leader peptides and polynucleotide sequences encoding them.

Preparation of IL-2R βγ Subunit-Fc Fusions and IL-2R α Subunit Fc Fusion

To study IL-2 receptor binding affinity, a tool was generated that allowed for the expression of a heterodimeric IL-2 receptor. The β-subunit of the IL-2 receptor was fused to an Fc molecule that was engineered to heterodimerize (Fc(hole)) (see SEQ ID NOs 21 and 22 (human), SEQ ID NOs 27 and 28 (mouse) and SEQ ID NOs 33 and 34 (cynomolgus)) using the "knobs-into-holes" technology (Merchant et al., Nat Biotech. 16, 677-681 (1998)). The γ-subunit of the IL-2 receptor was then fused to the Fc(knob) variant (see SEQ ID NOs 23 and 24 (human), SEQ ID NOs 29 and 30 (mouse) and SEQ ID NOs 35 and 36 (cynomolgus)), which heterodimerized with Fc(hole). This heterodimeric Pc-fusion protein was then used as a substrate for analyzing the IL-2/IL-2 receptor interaction. The IL-2R α-subunit was expressed as monomeric chain with an AcTev cleavage site and an Avi His tag (SEQ ID NOs 25 and 26 (human), SEQ ID NOs 31 and 32 (mouse) and SEQ ID NOs 37 and 38 (cynomolgus)). The respective IL-2R subunits were transiently expressed in HEK EBNA 293 cells with serum for the IL-2R βγ subunit construct and without serum for the α-subunit construct. The IL-2R βγ subunit construct was purified on protein A (GE Healthcare), followed by size exclusion chromatography (GE Healthcare, SUPERDEX®200 filtration media). The IL-2R α-subunit was purified via His tag on a NiNTA column (Qiagen) followed by size exclusion chromatography (GE Healthcare, SUPERDEX®75 filtration media). Amino acid and corresponding nucleotide sequences of various receptor constructs are given in SEQ ID NOs 21-38.

Preparation of Fusion Proteins

The DNA sequences were generated by gene synthesis and/or classical molecular biology techniques and subcloned into mammalian expression vectors under the control of an MPSV promoter and upstream of a synthetic polyA site, each vector carrying an EBV OriP sequence. Fusion proteins as applied in the examples below were produced by co-transfecting exponentially growing HEK293-EBNA cells with the mammalian expression vectors using calcium phosphate-transfection. Alternatively, HEK293 cells growing in suspension were transfected with the respective expression vectors by polyethylenimine (PEI). Alternatively, stably transfected CHO cell pools or CHO cell clones were used for production in serum-free media. Subsequently, the fusion proteins were purified from the supernatant. Briefly, fusion proteins were purified by one affinity step with protein A (HITRAP® ProtA column, GE Healthcare) equilibrated in 20 mM sodium phosphate, 20 mM sodium citrate pH 7.5. After loading of the supernatant, the column was first washed with 20 mM sodium phosphate, 20 mM sodium citrate, pH 7.5 and subsequently washed with 13.3 mM sodium phosphate, 20 mM sodium citrate, 500 mM sodium chloride, pH 5.45. The fusion protein was eluted with 20 mM sodium citrate, 100 mM sodium chloride, 100 mM glycine, pH 3 or 10 mM sodium citrate pH 3.0. Fractions were neutralized with 0.5 M $Na_2HPO_4$ pH 8.0 (1:10), pooled and purified by size exclusion chromatography (HILOAD®16/60 SUPERDEX®200 gel filtration media, GE Healthcare or HILOAD®26/60 SUPERDEX®200 gel filtration media, GE Healthcare) in final formulation buffer: 20 mM histidine, 140 mM NaCl pH 6.0. The protein concentration of purified protein samples was determined by measuring the optical density (OD) at 280 nm, using the molar extinction coefficient calculated on the basis of the amino acid sequence. Molecular weight was also determined on the basis of the amino acid sequence. Purity and molecular weight of fusion proteins were analyzed by SDS-PAGE in the presence and absence of a reducing agent (5 mM 1,4-dithiothreitol) and stained with Coomassie blue (SimpleBlue™ SafeStain, Invitrogen). The NUPAGE® Pre-Cast gel system (Invitrogen) was used according to the manufacturer's instructions (4-20% Tris-glycine gels or 3-12% Bis-Tris). Alternatively, purity and molecular weight of molecules were analyzed by CE-SDS analyses in the presence and absence of a reducing agent, using the Caliper LABCHIP® GXII system (Caliper Lifescience) according to the manufacturer's instructions. The aggregate content of fusion protein samples was analyzed using a SUPERDEX®200 10/300GL analytical size-exclusion column (GE Healthcare) in 2 mM MOPS, 150 mM NaCl, 0.02% $NaN_3$, pH 7.3 running buffer at 25° C. Alternatively, the aggregate content of antibody samples was analyzed using a TSK-GEL® G3000 SW XL analytical size-exclusion column (Tosoh) in 25 mM $K_2HPO_4$, 125 mM NaCl, 200 mM L-arginine monohydrocloride, 0.02% (w/v) $NaN_3$, pH 6.7 running buffer at 25° C.

Results of the purification and characterization of the DP47GS IgG-IL-2, DP47GS IgG-(IL-2)$_2$, DP47GS IgG-IL-2 N88D, DP47GS IgG-(IL-2 N88D)$_2$ and DP47GS IgG-(IL-2 E95A)$_2$ constructs are shown in FIGS. 1, 2, 3, 4 and 5, respectively.

Affinity to IL-2 Receptors

The affinity of the fusion proteins was determined by surface plasmon resonance (SPR) on a Biacore T200 (GE Healthcare) for the human, murine and cynomolgus IL-2R βγ heterodimer using recombinant IL-2R βγ heterodimer under the following conditions: ligands: biotinylated human, murine and cynomolgus IL-2R βγ knob γ hole heterodimer immobilized on SA chip (immobilization levels were 194, 114 and 116 RU, respectively), analytes: DP47GS IgG-IL-2 (see SEQ ID NOs 13, 15 and 19), DP47GS IgG-(IL-2)$_2$ (see SEQ ID NOs 17 and 19), DP47GS IgG-IL-2 N88D (see SEQ ID NOs 15, 19 and 48), DP47GS IgG-(IL-2 N88D)$_2$ (see SEQ ID NOs 19 and 50), and DP47GS IgG-(IL-2 E95A)$_2$ (see SEQ ID NOs 19 and 52), temperature: 25° C., buffer: HBS-EP, analyte concentration: 100 nM down to 1.2 nM (1:3 dilutions), flow rate: 30 μl/min, association: 120 s, dissociation: 600 s for the 2 highest concentrations and 120 s for the lower concentrations, regeneration: 60 s 3M $MgCl_2$, fitting: 1:1 Langmuir binding model, RI≠0, Rmax=local, Affinities were determined based on the kinetic rate constants $k_{on}$ and $k_{off}$. The affinity of the fusion proteins was also determined for the human, murine and cynomolgus IL-2R α-subunit using recombinant monomeric IL-2R α-subunit under the following conditions: ligands: human, murine and cynomolgus IL-2R α-subunit immobilized on a CM5 chip via amine coupling (immobilization levels were 240, 245 and 220 RU, respectively), analytes: DP47GS IgG-IL-2 (see SEQ ID NOs 13, 15 and 19), DP47GS IgG-(IL-2)$_2$ (see SEQ ID NOs 17 and 19), DP47GS IgG-IL-2 N88D (see SEQ ID NOs 15, 19 and 48), DP47GS IgG-(IL-2 N88D)$_2$ (see SEQ ID NOs 19 and 50), and DP47GS IgG-(IL-2 E95A)$_2$ (see SEQ ID NOs 19 and 52), temperature: 25° C., buffer: HBS-EP, analyte concentration 300 nM down to 0.41 nM (1:3 dilutions), flow rate: 30 μl/min, association: 120 s, dissociation: 180 s, regeneration: 10 mM glycine pH 1.5 for 60 s. Affinities were determined by steady state analysis.

Results of the affinity measurements based on kinetics for the IL-2R βγ heterodimer and steady state for the IL-2R α-subunit are given in Table 1.

TABLE 1

Binding of fusion proteins to IL-2R βγ and IL-2R α.

| $K_D$ in nM | Hu IL-2R βγ | Cy IL-2R βγ | Mu IL-2R βγ | Hu IL-2R α | Cy IL-2R α | Mu IL-2R α |
|---|---|---|---|---|---|---|
| DP47GS IgG-IL-2 | 0.15 | 0.60 | 0.85 | 51 | 81 | 112 |
| DP47GS IgG-(IL-2)$_2$ | 0.11 | 0.17 | 0.37 | 20 | 31 | 26 |

TABLE 1-continued

Binding of fusion proteins to IL-2R βγ and IL-2R α.

| $K_D$ in nM | Hu IL-2R βγ | Cy IL-2R βγ | Mu IL-2R βγ | Hu IL-2R α | Cy IL-2R α | Mu IL-2R α |
|---|---|---|---|---|---|---|
| DP47GS IgG-IL-2 N88D | 0.93 | 1.3 | 2.4 | 18 | 31 | 48 |
| DP47GS IgG-(IL-2 N88D)$_2$ | 0.24 | 0.57 | 2.1 | 22 | 30 | 25 |
| DP47GS IgG-(IL-2 E95A)$_2$ | 0.16 | 0.29 | 0.36 | 24 | 32 | 26 |

The human DP47GS IgG-IL-2 fusions and mutants thereof not only bind to the 3 different human IL-2 receptor chains α, β and γ but also to the respective receptor chains from cynomolgus monkey and mouse, although the affinities, on average, tend to be slightly lower for the latter two species. Affinities of these cytokine fusions to the human and cynomolgus a chains are comparable, to the murine a chain there is a ~2-fold affinity difference compared to the human a chain observed for the molecules carrying only one cytokine portion. For the molecules with two cytokine portions, most likely due to avidity, this difference does not exist. The affinities of DP47GS IgG-IL-2 and DP47GS IgG-IL-2 N88D to the α chains should in theory be equal as the N88D mutation should not affect the interface to the α chain. N88 is positioned in the interface to the IL-2 receptor β chain and mutagenesis to D leads to decreased affinity as can be observed comparing binding of DP47GS IgG-IL-2 and DP47GS IgG-IL-2 N88D to IL-2R βγ of all three species (0.15 nM, 0.60 nM and 0.85 nM vs. 0.93 nM, 1.3 nM and 2.4 nM, respectively). For DP47GS IgG-(IL-2 N88D)$_2$ carrying two mutated IL-2 cytokines, at least towards the human IL-2R βγ, this difference is less pronounced, most likely due to avidity. DP47GS IgG-(IL-2)$_2$ and DP47GS IgG-(IL-2 E95A)$_2$ exhibit very similar avidities in binding to IL-2R βγ of all three species. Although E95 is also positioned in the interface to the IL-2 receptor β chain, mutagenesis to A, at least when two of these mutants are fused to the IgG, does not lead to a significant decrease in avidity.

Expression of IL-2 Receptors on Immune Cells

The high-affinity trimeric IL-2 receptor is composed of the α (IL-2RA, CD25), β (IL-2RB, CD122) and γ (IL-2RG, CD132) chains and has a $K_D$ of ~10 pM. CD25 alone has only a low affinity ($K_D$~10 nM) for IL-2. The IL-2RB/IL-2RG dimer, which is expressed on some cell types in the absence of IL-2RA, also binds IL-2 but with an intermediate affinity ($K_D$~1 nM). Signaling via the IL-2 receptor is mediated by the IL-2RB and IL-2RG chains. From crystal structure analyses, IL-2RA does not seem to contact either IL-2RB or IL-2RG. It has been proposed that the basis of the cooperativity of the trimeric receptor is an entropy reduction when CD25 captures IL-2 at the cell surface for presentation to IL-2RB and IL-2RG, or alternatively a CD25-induced alteration in IL-2 conformation occurs, thus stabilizing the complex. In FOXP3$^+$ regulatory CD4$^+$ T cells, there is a large stoichiometric excess of IL-2RA as compared to the β and γ chains of the receptor supporting the hypothesis that dimers, or even larger complexes, of the α chain aid in the binding of IL-2. There is also evidence that CD25 on one cell can present IL-2 to IL-2RB/IL-2RG dimers on another cell, in a high-affinity, intercellular interaction emphasizing the unique relationship amongst the three chains composing the high affinity IL-2 receptor.

Figure 6:
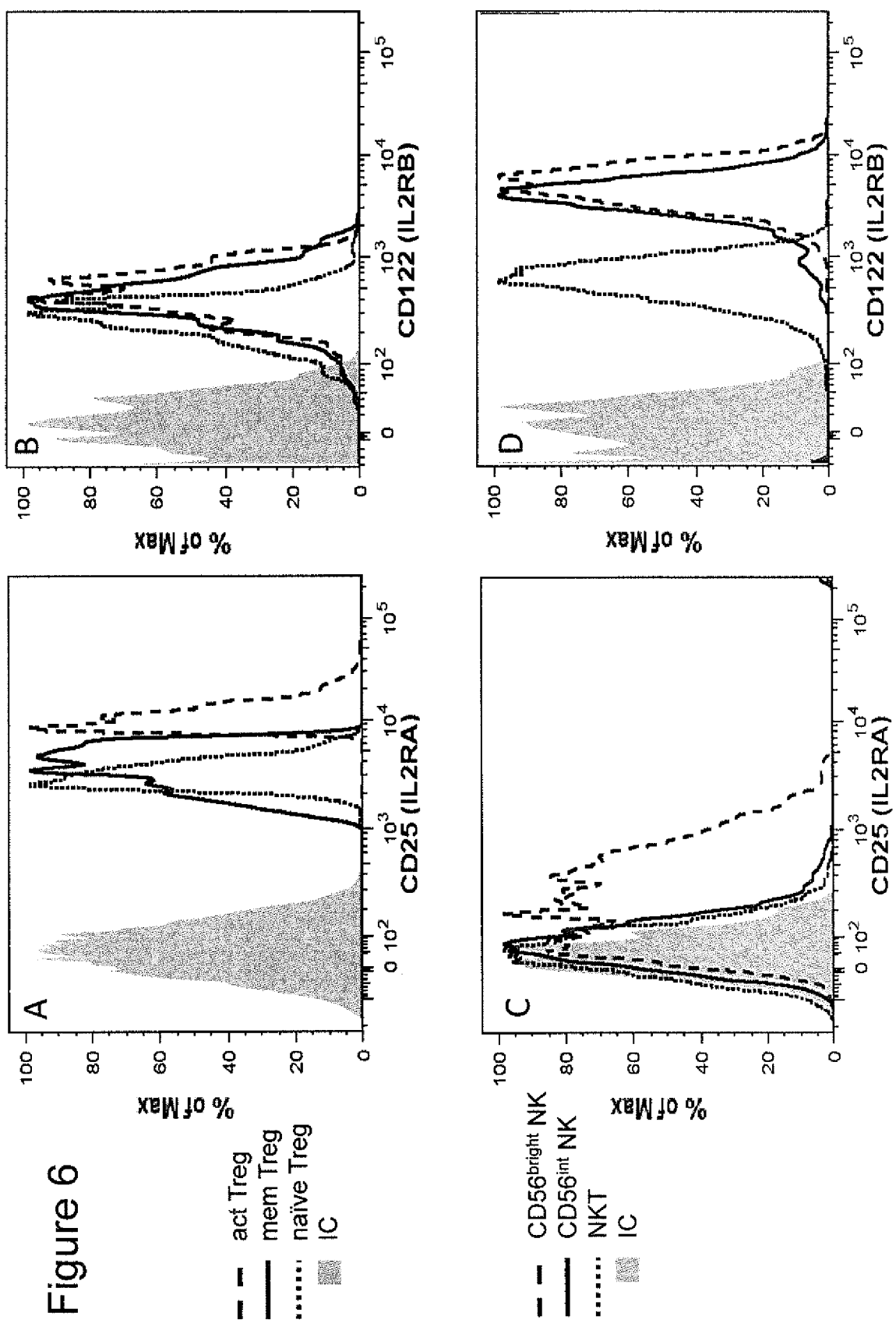
FIG. 6A-D. CD25 (IL-2RA) and CD122 (IL-2RB) expression on CD4$^+$ Treg subsets, NK cell subsets and NKT cells. Cell surface markers were used to define CD4$^+$ Treg subsets, NKT cells and NK cells. In order to optimize staining for CD25 and CD122, intracellular FOXP3 staining was not performed.
Figure 7:
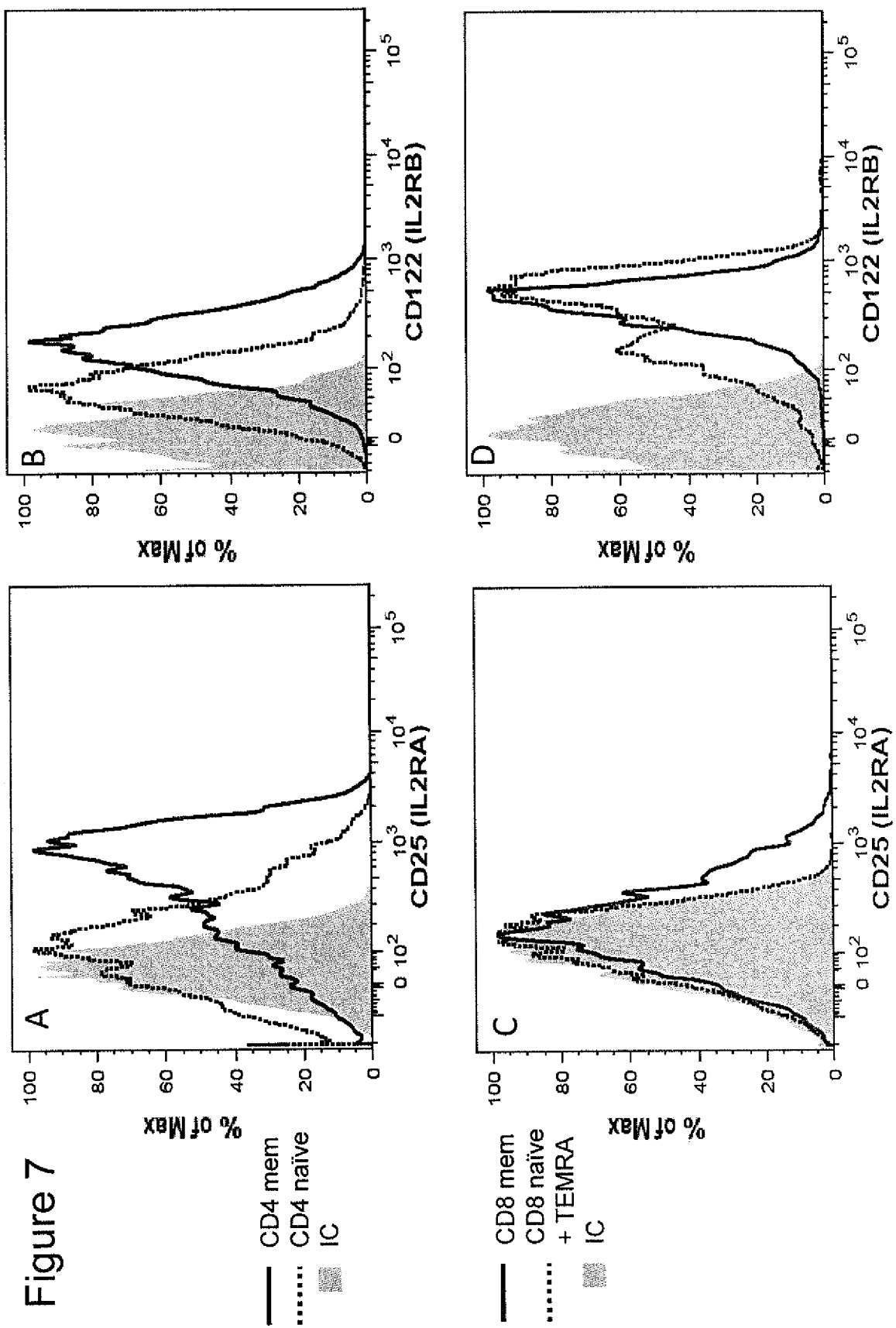
FIG. 7A-D. CD25 (IL-2RA) and CD122 (IL-2RB) expression on CD4$^+$ and CD8$^+$ conventional T cell subsets. Cell surface markers were used to define naïve (CD45RA$^+$; dotted line) and memory (CD45RA$^-$; solid line) conventional CD4$^+$ T cells FIGS. 7A and 7B, memory conventional CD8$^+$ T cells (CD45RA$^-$; solid line) and CD45RA$^+$CD8 T cells (a combination of the naïve and TEMRA subsets; TEMRA refers to effector memory cells that have reverted to expressing CD45RA; dotted line) FIGS. 7C and 7D. Grey: isotype control (IC).

CD25 (IL-2RA) and CD122 (IL-2RB) expression on CD4$^+$ Treg subsets, NK cell subsets and NKT cells, as well as on CD4$^+$ and CD8$^+$ conventional T cell subsets was determined by FACS (FIGS. 6 and 7). Cell surface markers were used to define CD4$^+$ Treg subsets, NKT cells and NK cells (FIG. 6). In order to optimize staining for CD25 and CD122, intracellular FoxP3 staining was not performed. Briefly, using 150 µl of blood donated by a healthy volunteer, fluorescent antibodies were incubated for 45 min at room temperature in the dark (vortexed at the beginning and after 20 min). Red blood cells were lysed with BD lysis buffer (BD FACS Lysing Solution, 349202) for 9 minutes and the remaining cells were washed (2 ml of PBS+0.1% BSA) and fixed (1% PFA). Cells were analysed on an LSRFortessa™ cell analyser (Becton Dickinson) and data analysed using FloJo software (TreeStar). Treg subsets were identified using antibodies specific for TCRαβ-FITC (IP26, BioLegend), CD4-Alexa Fluor® 700 (RPA-T4, BioLegend), CD127-PE/CY7 (ebioRDR5, Ebioscience), CD45RA-Pacific Blue (HI100, BioLegend), CD25-APC (2A3, M-A251, BD Biosciences) and CD122-PE (TU27, BioLegend). NK and NKT cells were stained in a separate tube with antibodies specific for TCRαβ-FITC, CD4-Alexa Fluor® 700, CD8-PE/CY7 (HTT8a, BioLegend), CD56-Pacific Blue (HCD56, BioLegend), CD25-APC and CD122-PE. Following the gating of lymphocytes based on FSC/SSC and excluding doublets, naïve Tregs were identified as TCRαβ$^+$CD4$^-$CD127$^-$ CD25$^+$CD45RA$^+$, memory Tregs were identified as TCRαβ$^+$CD4$^-$CD127$^-$CD25$^+$CD45RA$^-$ and activated Tregs were identified as TCRαβ$^+$CD4$^+$CD127$^-$ CD25$^{high}$CD45RA$^-$. NK cells were identified as TCRαβ$^-$ CD56$^{-/dim}$ and activated NK cells identified as TCRαβ$^-$ CD56$^{high}$. NKT cells were identified as TCRαβ$^+$CD56$^+$. Isotype controls (IC) conjugated to APC and PE were used in order to estimate background fluorescence for CD25 and CD122, respectively.

Similarly, cell surface markers were used to define naïve and memory conventional CD4$^+$ T cells (FIGS. 7A and 7B), memory conventional CD8$^+$ T cells and CD45RA$^+$ CD8 T cells (a combination of the naïve and TEMRA subsets; TEMRA refers to effector memory T cells that have reverted to expressing CD45RA) (FIGS. 7C and 7D). Staining and analysis was performed as described above. Using the same tube described above to characterize CD4$^+$ Tregs, CD4$^+$ conventional naïve T cells were identified as TCRαβ$^+$CD4$^+$ CD127$^+$CD25$^{-/+}$CD45RA$^+$ and CD4$^+$ conventional memory T cells were identified as TCRαβ$^+$CD4$^+$CD127$^+$ CD25$^{-/+}$CD45RA$^-$. CD8 T cells were defined using TCRαβ-FITC, CD8-Alexa Fluor® 700 (HTT8a, BioLegend), CD28-PE/CY7 (CD28.2, BioLegend), CD45RA-Pacific Blue, CD25-APC and CD122-PE. CD8$^+$ memory T cells were identified as TCRαβ$^+$CD8$^+$CD45RA$^-$. CD8$^+$ naïve and TEMRA cells were identified as TCRαβ$^+$CD8$^+$ CD45RA$^+$. CD28 was not used to distinguish CD8$^+$ naïve T cells from CD8$^+$ TEMRA T cells since the CD28 marker was not included in the pSTAT5a analysis described below (see FIG. 8). In some tests (FIG. 15), additional subsets were defined as follows: central memory CD4$^+$ T cells (TCαβ$^+$ CD4$^+$CD56$^-$FOXP3$^-$CD45RA$^-$CD127$^+$CD25$^{-/+}$), effector memory CD4$^+$ T cells (TCRαβ$^+$CD4$^+$CD56$^-$FOXP3$^-$ CD45RA$^-$CD127$^-$CD25$^{-/+}$), central memory CD8$^+$ T cells (TCRαβ$^+$CD8$^+$CD56$^-$FOXP3$^-$CD45RA$^-$CD127$^+$ CD25$^{-/+}$), effector memory CD8$^+$ T cells (TCRαβ$^+$CD8$^+$ CD56⁻FOXP3⁻CD45RA⁻CD127⁻CD25⁻/⁺), and TEMRA CD8⁺ cells (TCRαβ⁺CD8⁺CD56⁻FOXP3⁻CD45RA⁺ CD127⁻CD25⁻/⁺).

In FIGS. 6 and 7, the cell-specific expression of IL-2RA and IL-2RB is shown for subsets of T cells, NK cells and NK T cells in human peripheral blood (IL-2RG has essentially ubiquitous expression on hematopoietic cells since it partners with a large number of cytokine receptors). The highest level of IL-2RA is present on the three regulatory CD4⁺ T cell (Treg) populations: naïve (CD45RA⁺CD25⁺), memory (CD45RA⁻CD25⁺) and activated (CD45RA⁻CD25$^{hi}$) (FIG. 6A). On average, conventional memory CD4⁺ T cells express approximately 10-fold less CD25 than Tregs (FIG. 7A). The expression of CD25 on naïve CD4⁺ T cells varies significantly amongst donors but is always lower than that observed on memory CD4⁺ T cells (FIG. 7A). Expression of CD25 on NK, NKT and CD8 T cells is very low or not detectable except for CD56$^{bright}$ NK cells (FIGS. 6C and 7C). The CD56$^{bright}$ NK and CD56⁺ NK cells express the highest level of IL-2RB (FIG. 6D), approximately 10-fold more than any of the T cell subsets, including NKT cells (FIGS. 6B, 6D, 7B, 7D).

Induction of pSTAT5a in Human Peripheral Blood Cell Subsets

Following IL-2-induced oligomerization of the trimeric IL-2R, the JAK1 and JAK3 cytoplasmic protein tyrosine kinases, that are associated with the intracellular domains of IL-2RB and IL-2RG respectively, become activated. These kinases phosphorylate certain IL-2RB tyrosine residues that act as docking sites for STAT5a and STAT5b that are in turn phosphorylated. The IL-2-induced activation of several signaling pathways eventually results in the transcription of target genes that contribute to the various functions associated with the IL-2/IL-2R pathway. Since various cell types express different levels of the IL-2 receptor IL-2RA and IL-2RB molecules (FIGS. 6 and 7), we measured pSTAT5a levels within individual cells by polychromatic flow cytometry in order to understand the integrated signaling response to IL-2 mediated by various combinations of the high and intermediate affinity receptors.

The effects of various doses of DP47GS IgG-IL-2, DP47GS IgG-(IL-2)₂, DP47GS IgG-(IL-2E95A)₂, DP47GS IgG-IL-2N88D and DP47GS IgG-(IL-2N88D)₂ on the induction of STAT5a phosphorylation were assessed in human CD4⁺ Treg subsets, naïve and memory conventional CD4⁺ T cells, memory conventional CD8⁺ T cells, CD45RA⁺ CD8 T cells, NKT cells and NK cells (FIG. 8-14 and Table 2 and 3). All subsets were characterized in a single tube for each dose. Briefly, blood from a healthy human adult volunteer was collected into heparinized tubes. Various concentrations of DP47GS IgG-IL-2 fusion proteins were added to 500 µl of blood and incubated at 37° C. After 30 minutes the blood was lysed and fixed using pre-warmed lyse/fix buffer (Becton Dickinson #558049) for 10 minutes at 37° C., washed 2× with PBS containing 0.2% BSA followed by permeabilization with −20° C. pre-cooled methanol (Sigma, Biotech grade #494437) for 20 minutes on ice. The cells were then extensively washed 4× with PBS containing 0.2% BSA before FACS staining was performed using a panel of fluorescent antibodies to distinguish different lymphocyte and NK cell subpopulations and pSTAT5a status. The antibodies utilized were anti-CD4-Alexa Fluor® 700 (clone RPA-T4), CD3-PerCP/Cy5.5 (UCHT1), CD45RA-PE/Cy7 (HI100), CD8-Brilliant Violet 605 (RPA-T8), CD56-Brilliant Violet 421 (HCD56), FOXP3-PE (259D) (all from BioLegend), CD25-APC (clones M-A251 & 2A3) and pSTAT5a-Alexa Fluor® 488 (pY694) (Becton Dickinson). Samples were acquired using an LSRFortessa™ cell analyzer (Becton Dickinson) and data analysed using FlowJo software (FlowJo, LLC). After gating on lymphocytes and excluding doublets, Tregs were defined as CD3⁺CD4⁺FOXP3⁺ and subdivided as CD45⁻FOXP3$^{hi}$ (activated Treg), CD3⁺CD4⁺CD45RA⁻FOXP3⁺ (memory Treg) and CD3⁺CD4⁺CD45⁺FOXP3⁺ (naïve Treg). Conventional CD4⁺ T cells were defined as CD3⁺CD4⁺CD45RA⁺ (naïve) and CD3⁺CD4⁺CD45RA⁻ (memory). CD8 T cells were defined as CD3⁺CD8⁺CD45RA⁻ (memory) and CD3⁺CD8⁺ CD45RA⁺. NKT cells were defined as CD3⁺CD56⁺ and NK cells were defined as CD3⁻CD56$^{bright}$ (activated NK cells) or CD3⁻CD56⁺ (NK cells). Intracellular pSTAT5a levels were quantified in all cell subsets at all doses.

Figure 8:
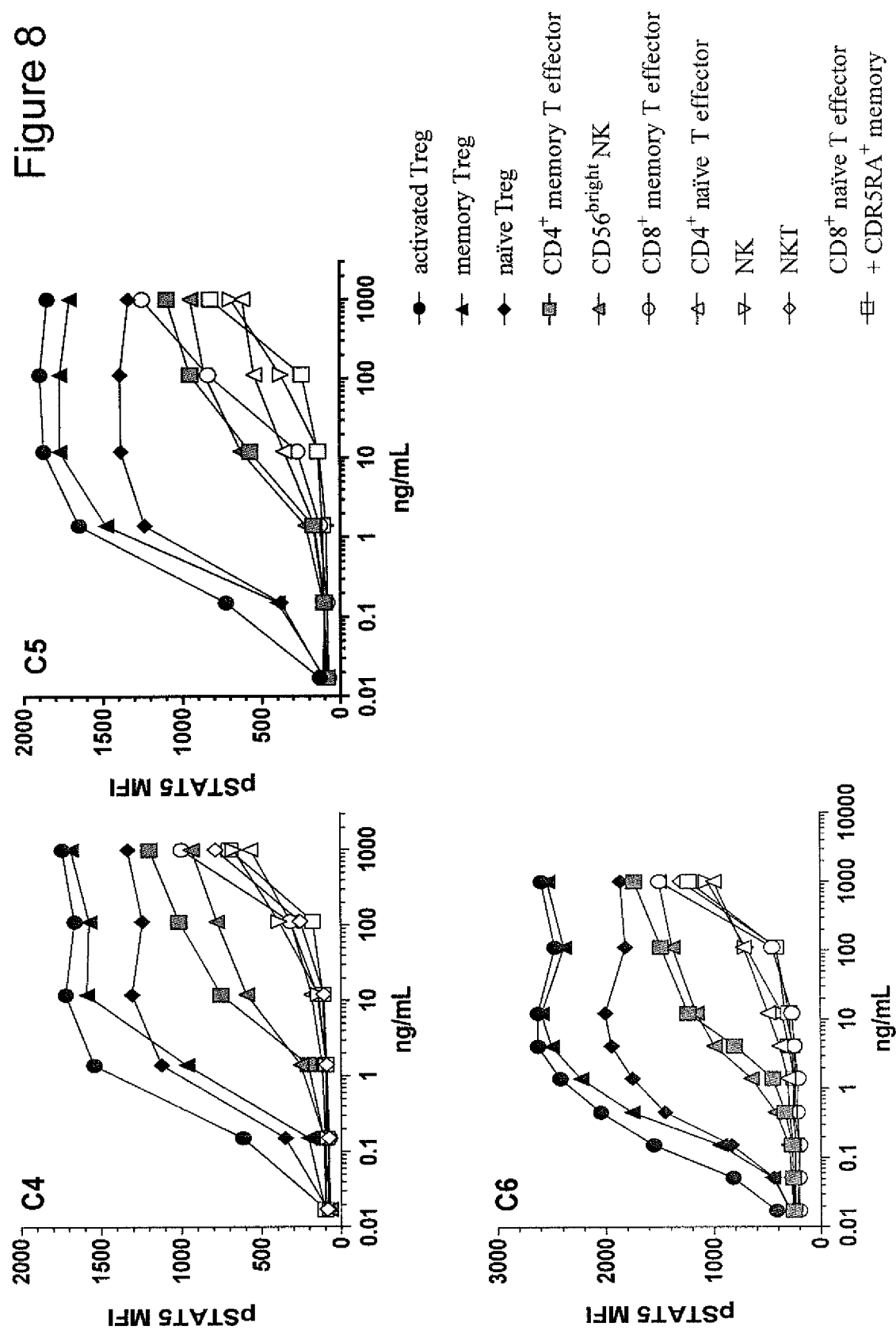
FIG. 8 C4, C5, and C6. Induction of pSTAT5a in human peripheral blood cell subsets in response to DP47GS IgG-IL-2. Three different human donors (C4 to C6) were assessed at separate times for the effects of various doses of DP47GS IgG-IL-2 on the induction of STAT5a phosphorylation. The results for donor C4 are shown in FIG. 8 C4. The results for donor C5 are shown in FIG. 8 C5. The results for donor C6 are shown in FIG. 8 C6. The results are shown for CD4$^+$ Treg subsets: activated, memory and naive Tregs; conventional CD4$^+$ memory T effector cells; CD56$^{bright}$ NK cells; CD8$^+$ memory T effector cells; CD4$^+$ naive T effector cells; NK cells; NKT cells; and CD8$^+$ naive T effector+CD45RA$^+$ memory cells.

FIG. 8 shows the dose response of the DP47GS IgG-IL-2 immunoconjugate on T cells, NK cells and NK T cells in human peripheral blood from three individual donors each tested on different days. The hierarchy of responsiveness to DP47GS IgG-IL-2 was the same in all three donors and the same as that observed when recombinant human IL-2 (Proleukin®) was used (data not shown). All three Treg populations, activated (CD45RA⁻CD25$^{hi}$), memory (CD45RA⁻CD25⁺), and naïve (CD45RA⁺CD25⁺) increased pSTAT5a levels at the 0.1 ng/ml concentration of DP47GS IgG-IL-2 whereas other cell populations required either greater than 1 ng/ml (CD56$^{bright}$ NK and memory CD4⁺ T cells) or 10-100 ng/ml (memory CD8⁺ T cells, CD56⁺ NK cells, naïve CD4⁺ T cells, NKT cells and CD45RA⁺ CD8 T cells) of DP47 IgG-IL-2 to produce detectable increases in pSTAT5a. Also see FIG. 11 for more detailed dose responses by the Treg populations that display their high sensitivity for DP47GS IgG-IL-2. It is notable that the high expression of IL-2RB on NK cells with intermediate levels of CD56 (FIG. 6D) as compared to IL-2RB expression on T cell subsets is not sufficient to allow Treg-like IL-2 sensitivity. Overall, activated, memory and naive Treg subsets showed the greatest sensitivity to DP47GS IgG-IL-2, while CD56$^{bright}$ NK cells and CD4⁺ conventional memory T effector cells were 20-50 fold less sensitive. Amongst the other cell subsets analyzed for pSTAT5a increases, CD8⁺ memory T effector cells, CD4⁺ naïve T effector cells, NKT cells, "resting" NK cells (positive, not bright staining for CD56), and CD8⁺ naïve T effector+CD45RA⁺ memory cells were relatively insensitive to the IgG-IL-2 immunoconjugate.

Figure 9:
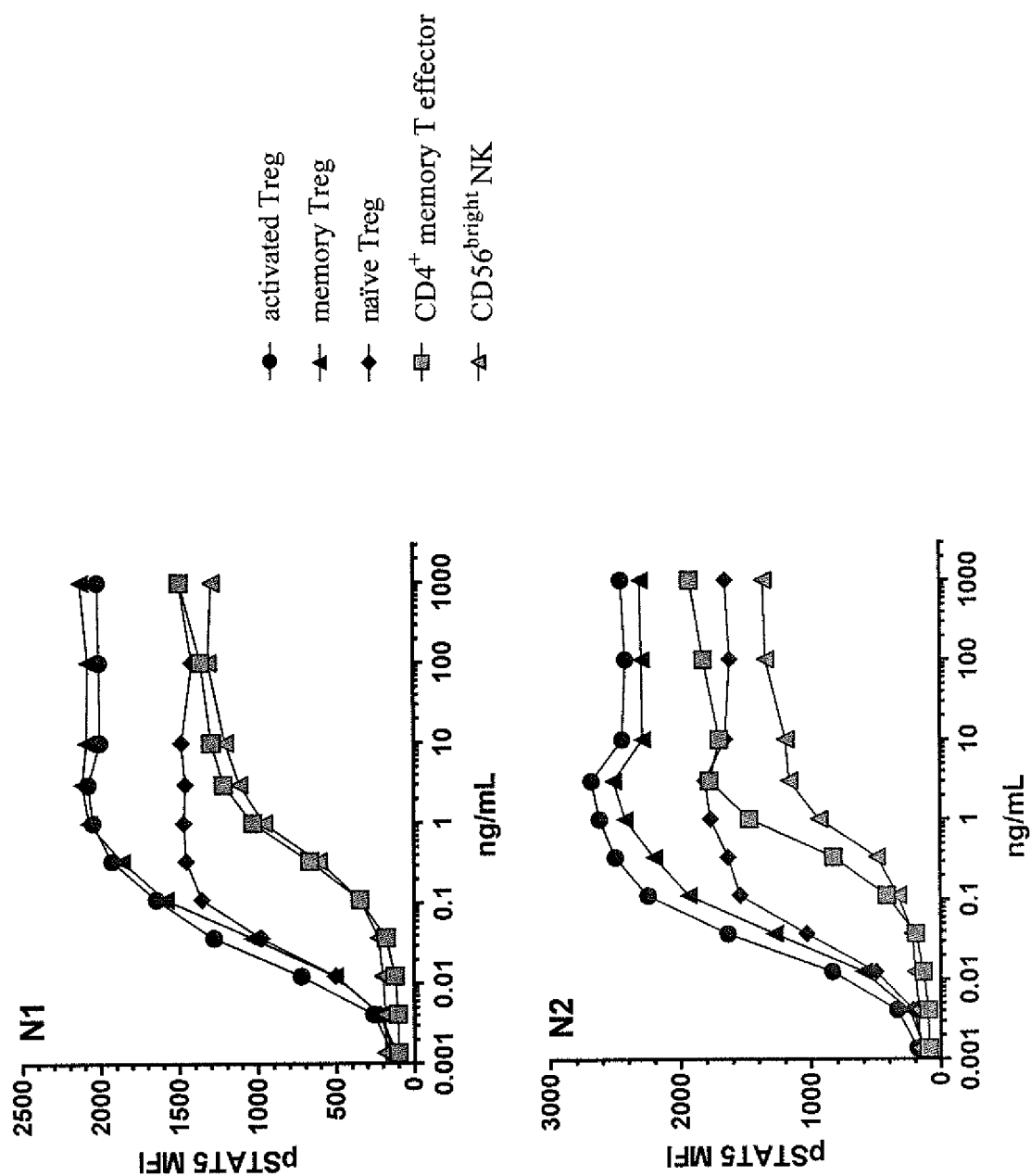
FIG. 9 N1, N2, C4, C5, and C6. Induction of pSTAT5a in human peripheral blood cell subsets in response to DP47GS IgG-(IL-2)$_2$. Five different human donors (N1, N2, C4-C6) were assessed at separate times for the effects of various doses of DP47GS IgG-(IL-2)$_2$ immunoconjugate on the induction of STAT5a phosphorylation. The results for donor N1 are shown in FIG. 9 N1. The results for donor N2 are shown in FIG. 9 N2. The results for donor C4 are shown in FIG. 9 C4. The results for donor C5 are shown in FIG. 9 C5. The results for donor C6 are shown in FIG. 9 C6. The results are shown for CD4$^+$ Treg subsets: activated, memory and naive Tregs; conventional CD4$^+$ memory T effector cells; CD56$^{bright}$ NK cells; CD8$^+$ memory T effector cells; CD4$^+$ naive T effector cells; NK cells; NKT cells; and CD8$^+$ naive T effector+CD45RA$^+$ memory cells.
Figure 9:
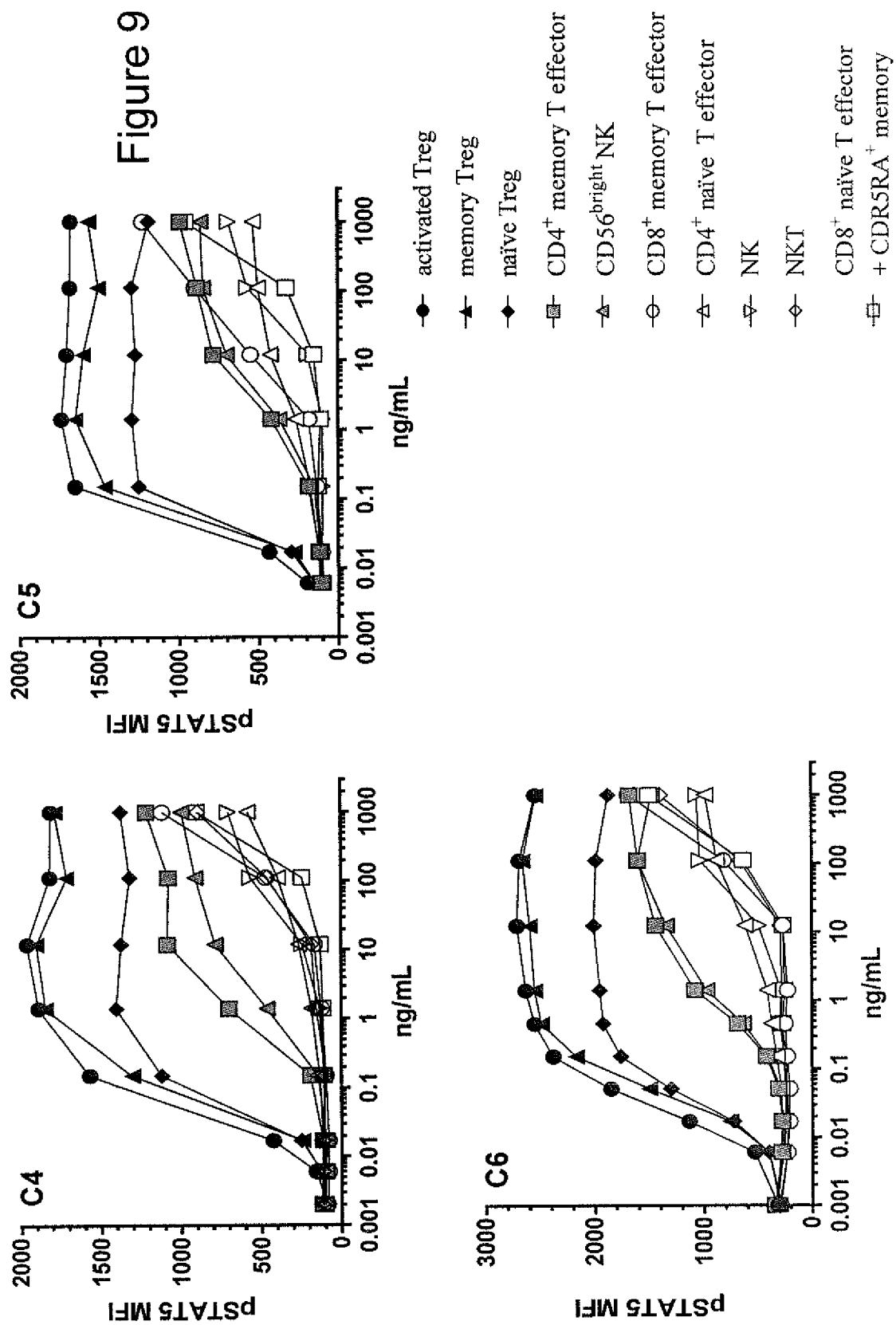

FIG. 9 shows the dose response of DP47GS IgG-(IL-2)₂ on T cells, NK cells and NK T cells in human peripheral blood from five individual donors each tested on different days. As observed for DP47GS IgG-IL-2 (FIG. 8), the three Treg subsets were the cells most sensitive to DP47GS IgG-(IL-2)₂ induced pSTAT5a (FIGS. 9 and 11) and similar hierarchical dose responses were found for the other cell subsets in all five donors.

Figure 10:
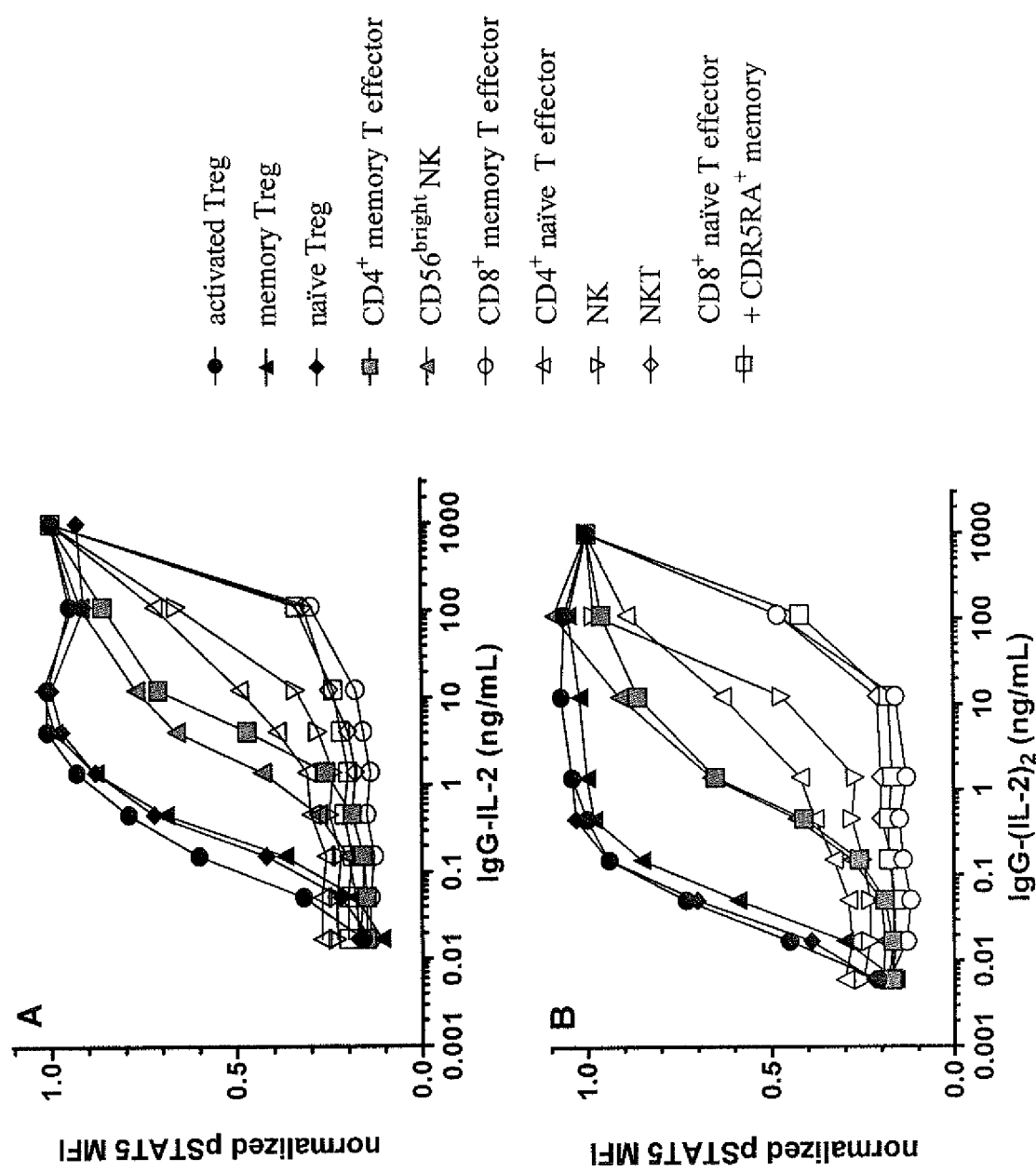
FIGS. 10A and 10B. Induction of pSTAT5a in human peripheral blood cell subsets: comparison of DP47GS IgG-IL-2 and DP47GS IgG-(IL-2)$_2$. The results for each cell subset were normalized to the maximum observed effect from each subset and the approximate EC50 for Tregs are presented in Table 2. normalized results for DP47GS IgG-IL-2, normalized results for DP47GS IgG-(IL-2)$_2$.

To more readily compare DP47GS IgG-IL-2 and DP47GS IgG-(IL-2)₂, the pSTAT5a values were normalized (FIG. 10). To normalize MFI values, unstimulated pSTAT5a MFI values specific for each gated subset were subtracted from all stimulated MFI values for that cell subset. The resulting values were divided by the highest pSTAT5a MFI value obtained by that subset in the dose response. The $EC_{50}$s were estimated based on the amount of IL-2 fusion protein required to reach 50% of the maximal pSTAT5a MFI observed for that subset. As shown in FIG. 10, the DP47GS IgG-(IL2)₂ immunoconjugate produced a more potent induction of pSTAT5a in cells constitutively expressing CD25, potentially as a consequence of increased avidity of the immunoconjugate for the high affinity IL-2 receptor. The $EC_{50}$ for pSTAT5a activation was observed to be 5-9 fold lower in Treg when directly comparing DP47GS IgG-(IL-2)$_2$ to DP47GS IgG-IL-2. Table 2 summarizes representative EC$_{50}$ values and fold-differences for pSTAT5a activation by DP47GS IgG-IL-2 vs. DP47GS IgG-(IL-2)$_2$ in the different cell subsets.

TABLE 2

EC$_{50}$ values and fold differences for pSTAT5a activation by DP47GS IgG-IL-2 vs. DP47GS IgG-(IL-2)$_2$ in different cell subsets.

| T cell | IgG-IL-2 | IgG-(IL-2)$_2$ | Fold change |
| --- | --- | --- | --- |
| activated Treg | 0.10 ng/mL | 0.020 ng/mL | 5 |
| memory Treg | 0.22 ng/mL | 0.033 ng/mL | 7 |
| naïve Treg | 0.20 ng/mL | 0.023 ng/mL | 9 |
| CD56$^{bright}$ NK | 2.0 ng/mL | 0.63 ng/mL | 3 |
| CD4$^+$ memory Teff | 5 ng/mL | 0.7 ng/mL | 7 |
| NK cells | 35 ng/mL | 10 ng/mL | 4 |

Figure 11:
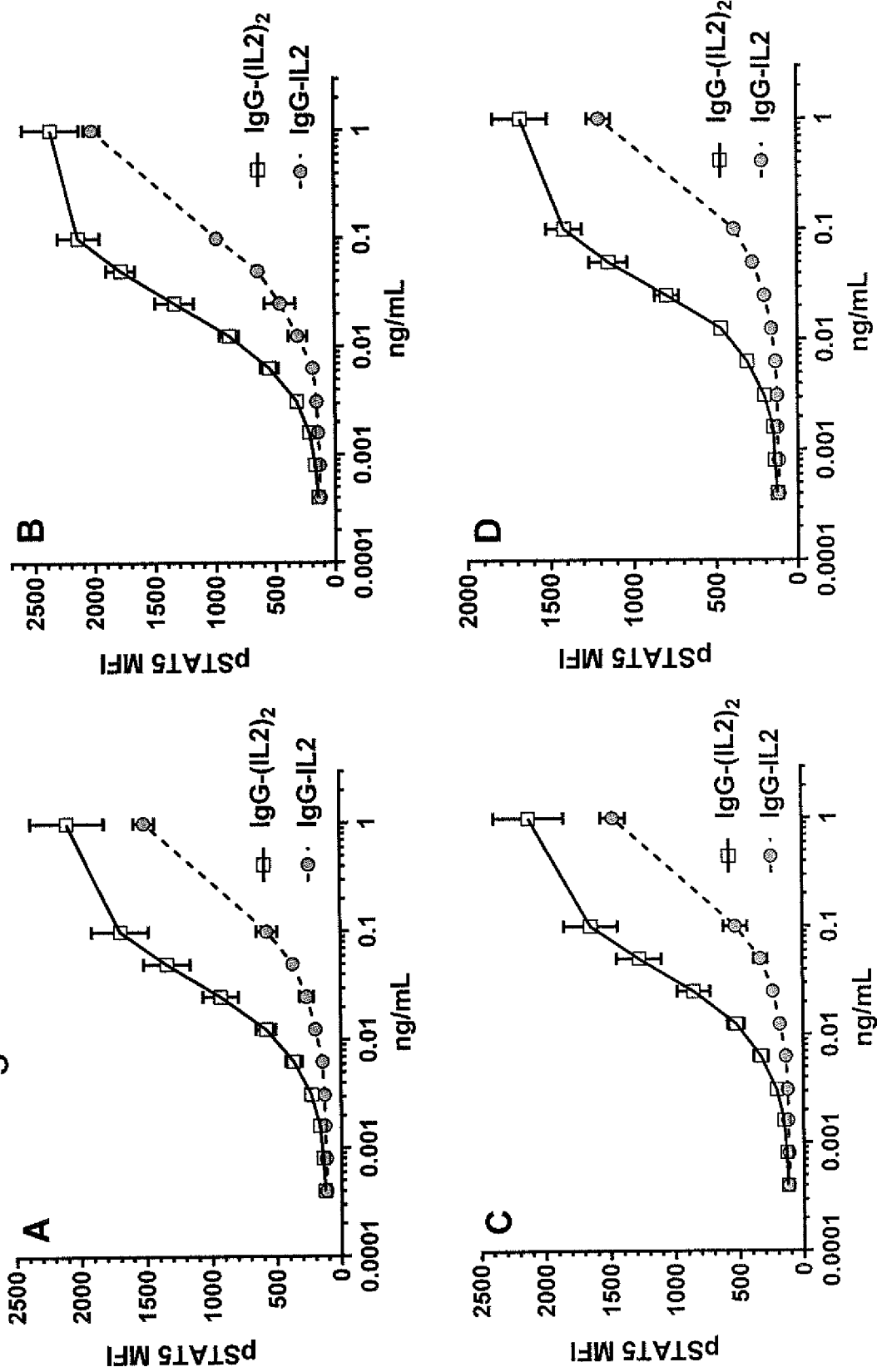
FIG. 11A-D. Detailed examination of Treg subset sensitivity in three donors comparing DP47GS IgG-IL-2 and DP47GS IgG-(IL-2)$_2$. Graphs represent the mean±SD of the pSTAT5a MFI for the three donors.

Even at extremely limiting concentrations, DP47GS IgG-(IL-2)$_2$ produced higher levels of pSTAT5a as compared to DP47GS IgG-IL-2 (FIG. 11). For this experiment, blood from three healthy volunteers was tested individually on the same day for responses to a 2-fold titration of DP47 IgG-IL-2 and DP47 IgG-(IL-2)$_2$ at limiting concentrations of IL-2. Graphs in FIG. 11 represent the mean±SD of the pSTAT5a MFI for the three donors. In addition to the three Treg subsets examined individually (FIG. 11B-D), a gate was applied to assess pSTAT5a in total CD3$^+$CD4$^+$ FoxP3$^+$ Tregs (FIG. 11A). The results clearly indicate a 5-10-fold increase in potency for DP47GS IgG-(IL-2)$_2$ activation of Tregs despite only a 2-fold increase in IL-2 per molecule of IgG. Polychromatic flow cytometry was performed as described above (see FIG. 8).

CD4$^+$ conventional memory T effector cells also responded to lower (7-fold) concentrations of DP47GS IgG-(IL-2)$_2$ as compared to DP47GS IgG-IL-2. While the EC$_{50}$ values were lower for CD56$^{bright}$ NK cells and CD56$^+$ NK cells when comparing DP47GS IgG-(IL-2)$_2$ to DP47 IgG-IL-2, the lowering was only 3-fold and 4-fold, respectively. This is likely due to the reliance of these cells on the intermediate affinity IL-2 receptor for IL-2-mediated signaling. This differential shift in the ED$_{50}$ for Tregs versus NK cells increases the preference for Treg activation several fold.

Figure 12:
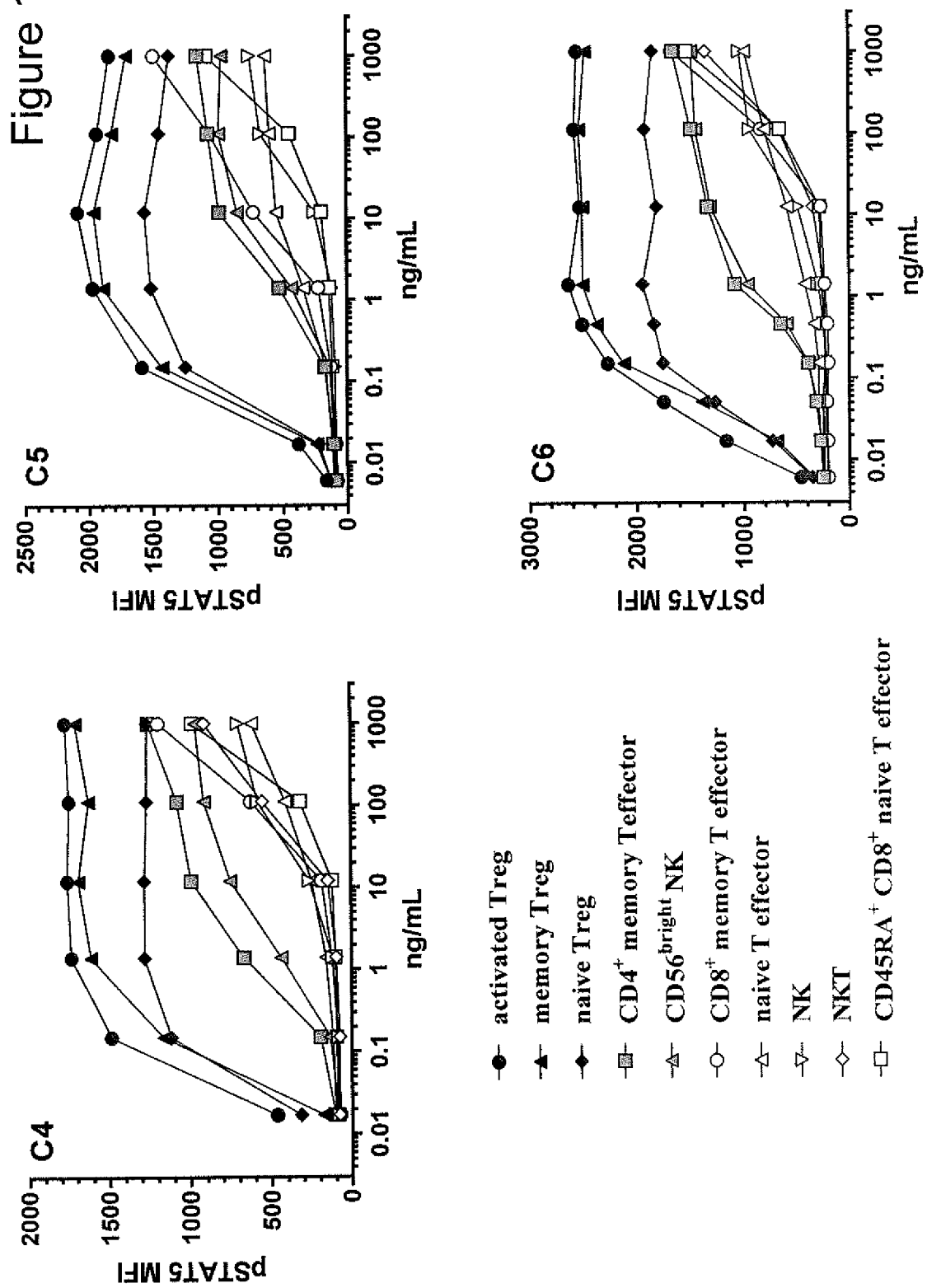
FIG. 12 C4, C5, and C6. Induction of pSTAT5a in human peripheral blood cell subsets in response to DP47GS IgG-(IL-2E95A)$_2$. Three different human donors (C4 to C6) were assessed at separate times for the effects of various doses of DP47GS IgG-(IL-2E95A)$_2$ on the induction of STAT5a phosphorylation. The results for donor C4 are shown in FIG. 12 C4. The results for donor C5 are shown in FIG. 12 C5. The results for donor C6 are shown in FIG. 12 C6. The results are shown for CD4$^+$ Treg subsets: activated, memory and naive Tregs; conventional CD4$^+$ memory T effector cells; CD56$^{bright}$ NK cells; CD8$^+$ memory T effector cells; CD4$^+$ naive T effector cells; NK cells; NKT cells; and CD8$^+$CD45RA$^+$ naive T effector cells.

FIG. 12 shows the dose response of the DP47GS IgG-(IL-2E95A)$_2$ on T cells, NK cells and NK T cells in human peripheral blood from three individual donors each tested on different days. The IL-2E95A molecule was designed and predicted to reduce the IL-2Rβγ binding activity but in fact exhibited similar binding properties to the IL-2Rβγ receptor as did wild type IL-2. The hierarchy of responsiveness to DP47GS IgG-(IL-2E95A)$_2$ was the same in all three donors and the same as that observed in the same donors with the wild type IL-2 immunoconjugate DP47GS IgG-(IL-2)$_2$. All three Treg populations, activated (CD45RA$^-$CD25$^{hi}$), memory (CD45RA$^-$CD25$^+$), and naïve (CD45RA$^+$CD25$^+$) increased pSTAT5a levels at less than 0.1 ng/ml concentrations of DP47GS IgG-(IL-2E95A)$_2$ whereas other cell populations required either 1 ng/ml (CD56$^{bright}$ NK and CD4$^+$ conventional memory T effector cells) or 10-100 ng/ml (memory CD8$^+$ T cells, CD56$^+$ NK cells, naïve CD4$^+$ T cells, NKT cells and CD45RA$^+$CD8$^-$ T cells) of DP47 IgG-(IL-2E95A)$_2$ to produce detectable increases in pSTAT5a. It is notable that the high expression of IL-2RB on NK cells with intermediate levels of CD56 (FIG. 6D) as compared to IL-2RB expression on T cell subsets is not sufficient to allow Treg-like IL-2 sensitivity. Overall, activated, memory and naive Treg subsets showed the greatest sensitivity to DP47GS IgG-(IL-2E95A)$_2$, while CD56$^{bright}$ NK cells and CD4$^+$ conventional memory T effector cells were 20-50 fold less sensitive. Amongst the other cell subsets analyzed for pSTAT5a increases, CD8$^+$ memory T effector cells, CD4$^+$ naïve T effector cells, NKT cells, "resting" NK cells (positive, not bright staining for CD56), and CD8$^+$ CD45RA$^+$ naïve T effector cells were relatively insensitive to the IgG-(IL-2E95A)$_2$ immunoconjugate.

Figure 13:
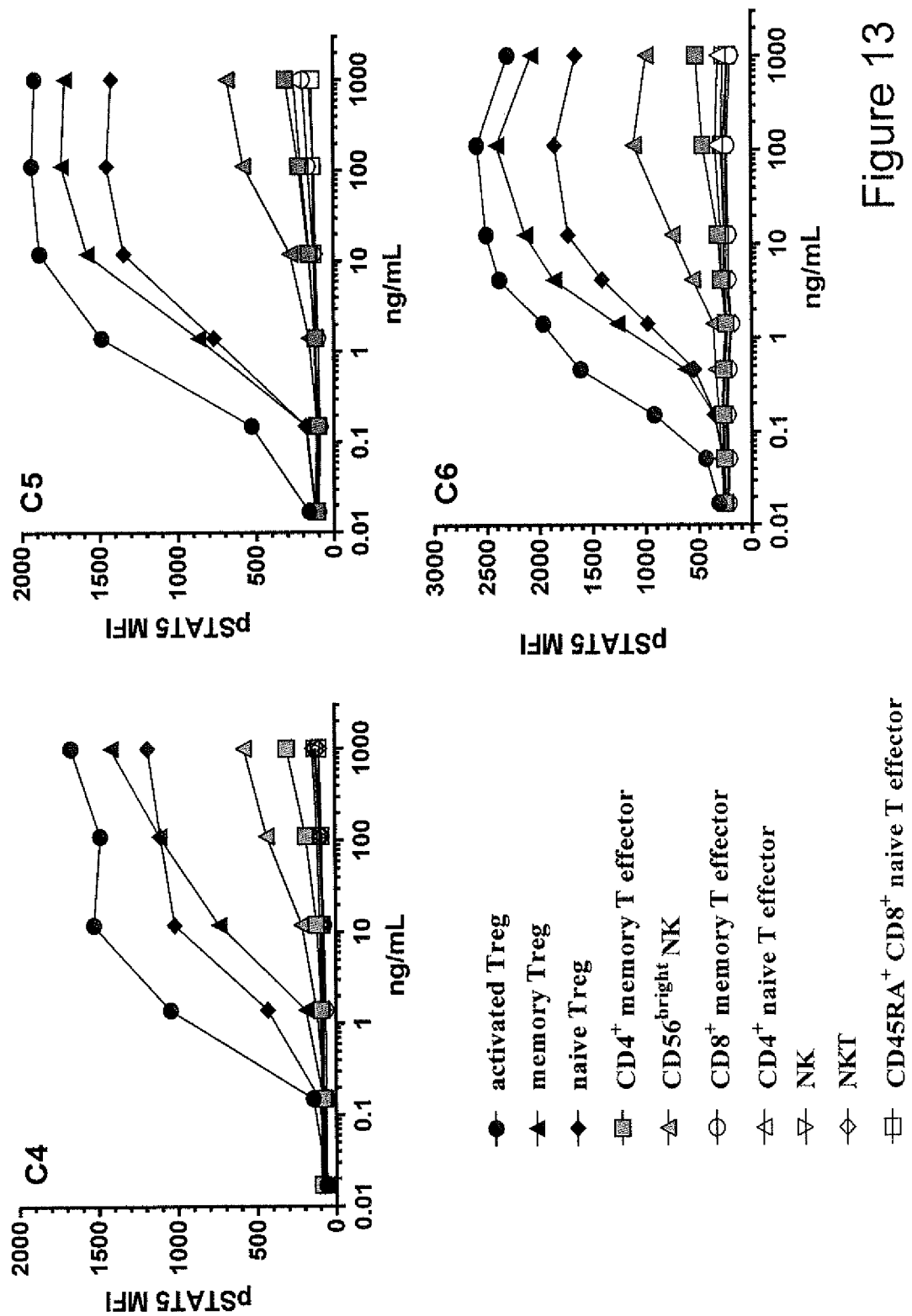
FIG. 13 C4, C5, C6, N1, N2, and N3. Induction of pSTAT5a in human peripheral blood cell subsets in response to DP47GS IgG-(IL-2N88D)$_2$. Five different human donors (C4, C5, C6, N1, N2) were assessed at separate times for the effects of various doses of DP47GS IgG-(IL-2N88D)$_2$ on the induction of STAT5a phosphorylation. The results for donor C4 are shown in FIG. 13 C4. The results for donor C5 are shown in FIG. 13 C5. The results for donor C6 are shown in FIG. 13 C6. The results for donor N1 are shown in FIG. 13 N1. The results for donor N2 are shown in FIG. 13 N2. The results for donor N3 are shown in FIG. 13 N3. The results are shown for CD4$^+$ Treg subsets: activated, memory and naive Tregs; conventional CD4$^+$ memory T effector cells; CD56$^{bright}$ NK cells; CD8$^+$ memory T effector cells; CD4$^+$ naive T effector cells; NK cells; NKT cells; and CD8$^+$CD45RA$^+$ naive T effector cells.
Figure 13:
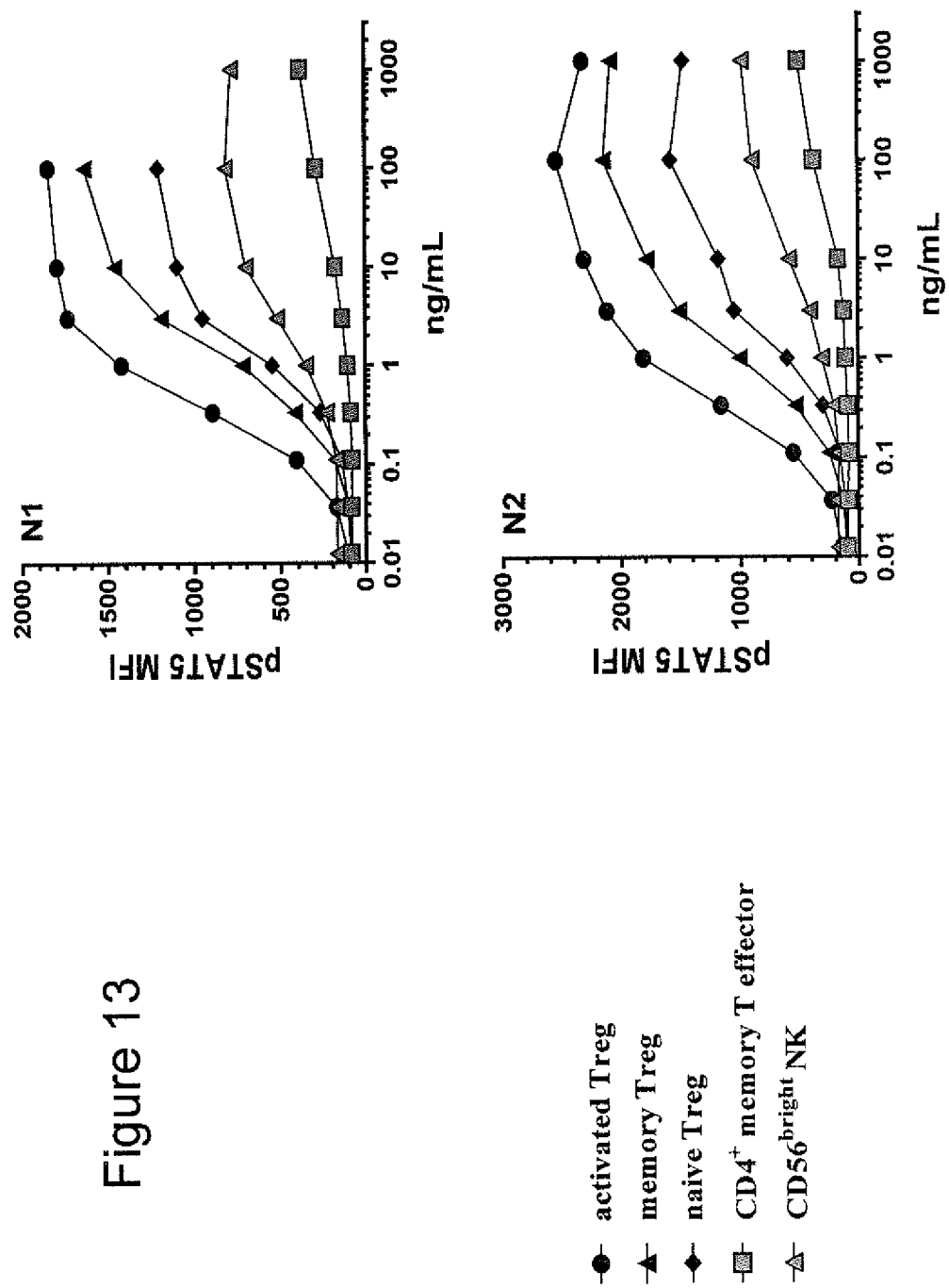

FIG. 13 shows the dose response of DP47GS IgG-(IL-2N88D)$_2$ on T cells, NK cells and NK T cells in human peripheral blood from five individual donors each tested on different days. The IL-2N88D molecule was designed to reduce the IL2Rβγ binding activity and unlike the E95A point mutation, it had 6.2-fold less binding affinity to IL2Rβγ by Biacore analysis (Table 1, K$_D$ 0.15 nM versus 0.93 nM). As observed for all of the IL-2 immunoconjugates to date, the three Treg subsets were the cells most sensitive to pSTAT5a activation by DP47GS IgG-(IL-2N88D)$_2$ and similar hierarchical dose responses were found for the other cell subsets in all five donors. Of particular note was the lack of responsiveness of the CD4$^+$ memory T effector cells when stimulated with DP47GS IgG-(IL-2N88D)$_2$; even at doses of 1000 ng/ml it had little effect stimulating this important autoimmune cell population.

In this example, a uniquely designed IL-2 single point mutation, N88D, dramatically reduced stimulatory activity on the desired cell population, the CD4$^+$ memory T effector cells, all while maintaining the Treg stimulatory effects required for a novel and improved therapeutic entity.

Figure 14:
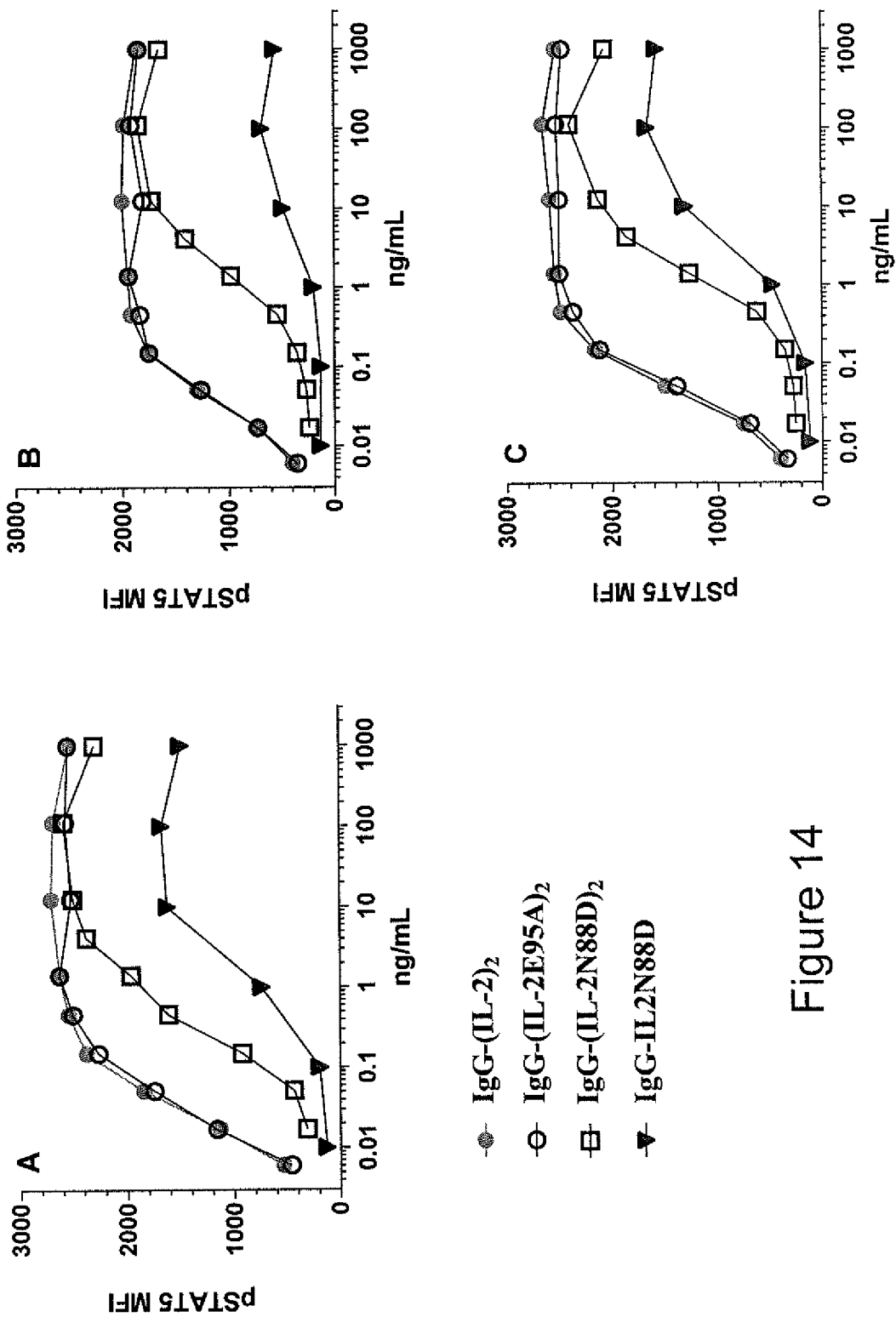
FIG. 14A-E. Induction of pSTAT5a in human peripheral blood cell subsets: comparison of DP47GS IgG-IL-2, DP47GS IgG-(IL-2)$_2$, DP47GS IgG-(IL-2E95A)$_2$, DP47GS IgG-(IL-2 N88D)$_2$, and DP47GS IgG-IL-2N88D. The results are shown for CD4$^+$ Treg subsets (A-C): activated (A), memory (C) and naïve (B) Tregs; conventional CD4$^+$ memory T effector cells (D); CD56$^{bright}$ NK cells (E).
Figure 14:
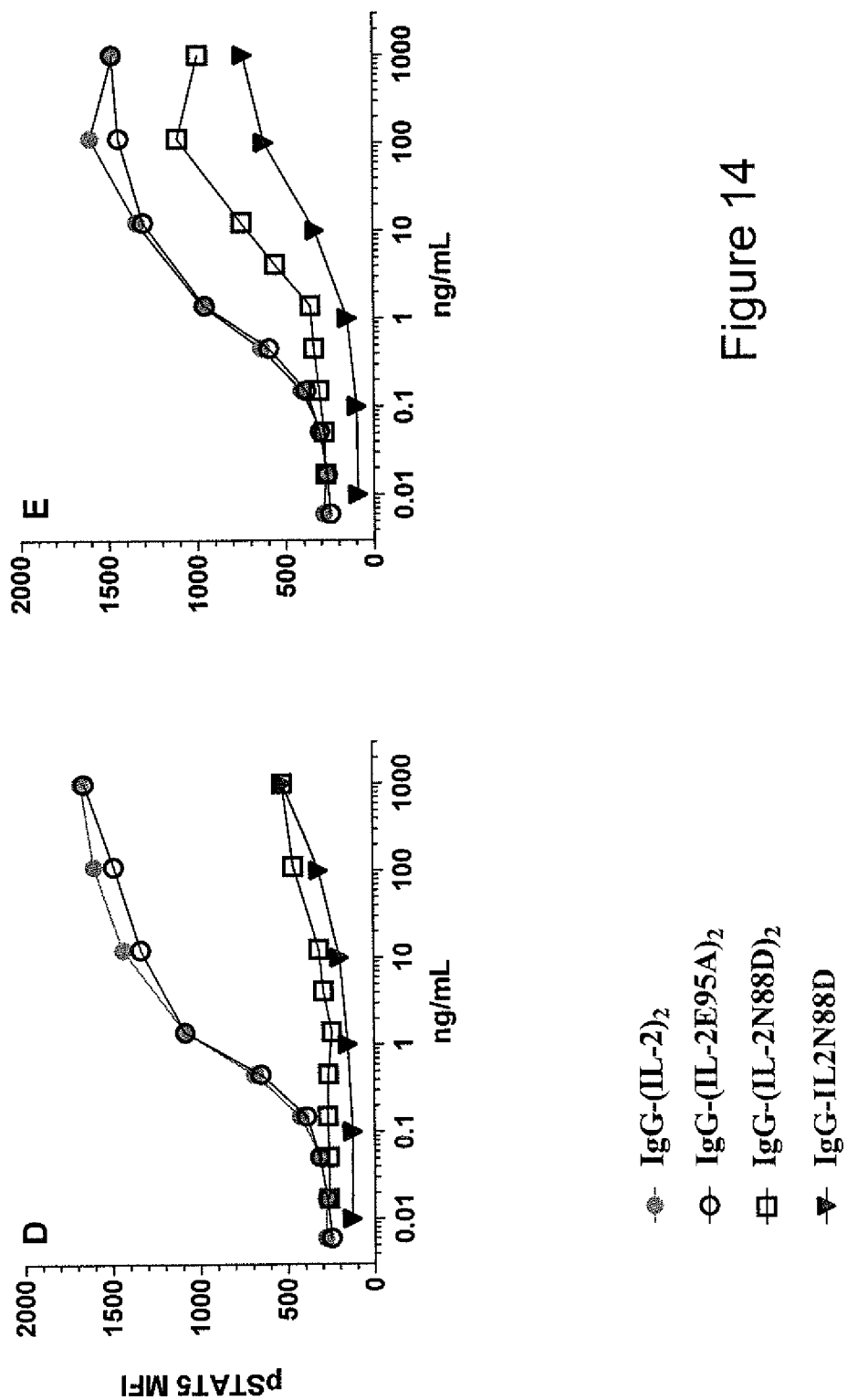

To compare wild type IL-2 DP47GS IgG-(IL-2)$_2$ with the E95A and N88D IL-2 point mutation immunoconjugates, the pSTAT5a values were plotted versus each other for each of the cell types being tested (FIG. 14). DPS47GS IgG-(IL-2E95A)$_2$ showed identical activity as its wild type counterpart DP47GS IgG-(IL-2)$_2$ stimulating each of the human cell populations with superimposable dose response curves. In contrast, the reduced IL2Rβγ binding molecules, DP47GS IgG-IL-2N88D and DP47GS IgG-(IL-2N88D2)$_2$, had little effect on CD4$^+$ memory T effector cells and only the bivalent conjugate DP47GS IgG-(IL-2N88D)$_2$ retained significant stimulatory activity on the different Treg populations.

Figure 15:
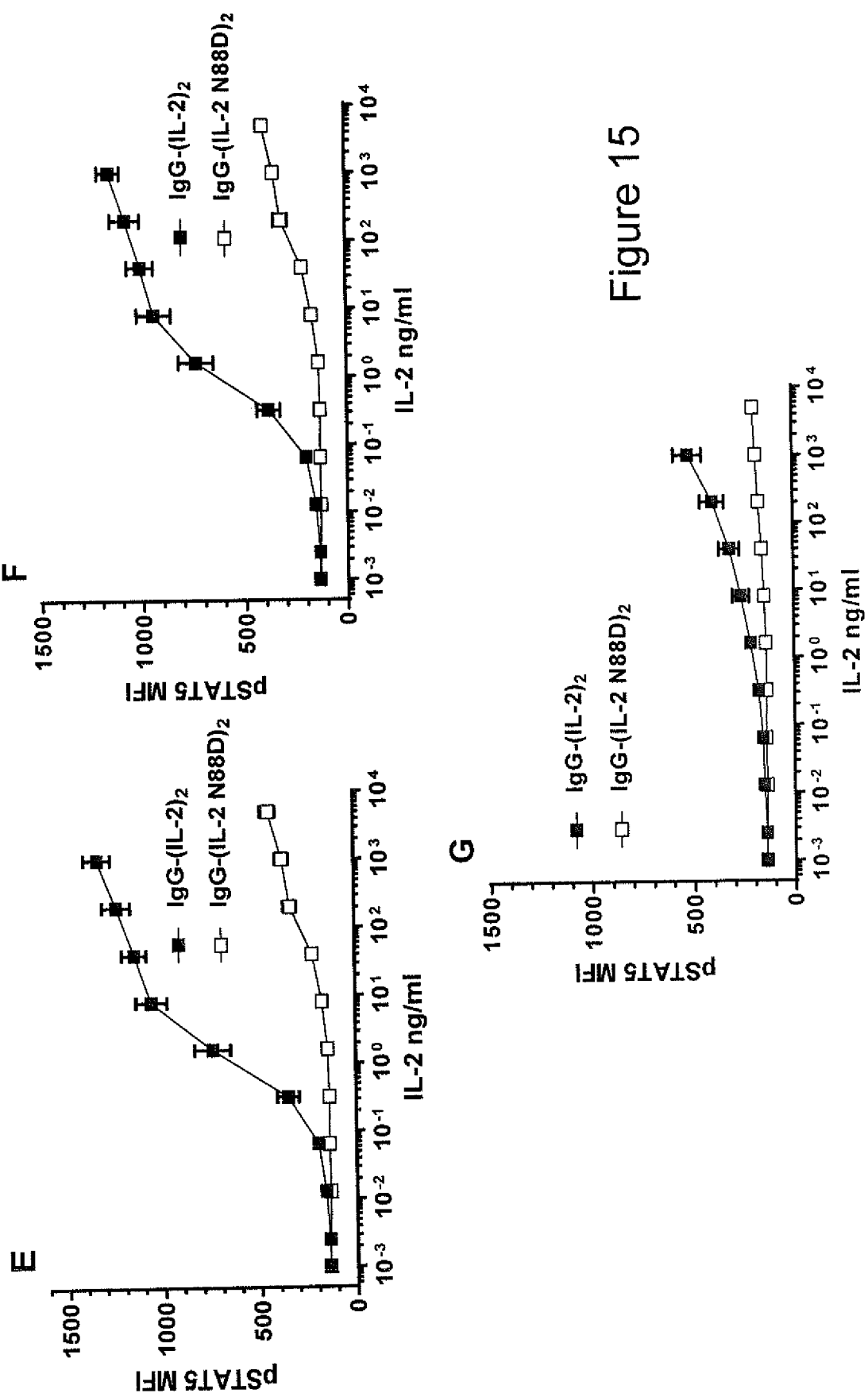
FIG. 15A-L. Induction of pSTAT5a in human peripheral blood cell subsets in response to both DP47GS IgG-(IL-2N88D)$_2$ and DP47GS IgG-(IL-2)$_2$. Ten different human donors were assessed on separate days for the effects of a wide (6 log) dose range of DP47GS IgG-(IL-2N88D)$_2$ and DP47GS IgG-(IL-2)$_2$ on the induction of STAT5a phosphorylation. The results are shown for the following cell subsets.
Figure 15:
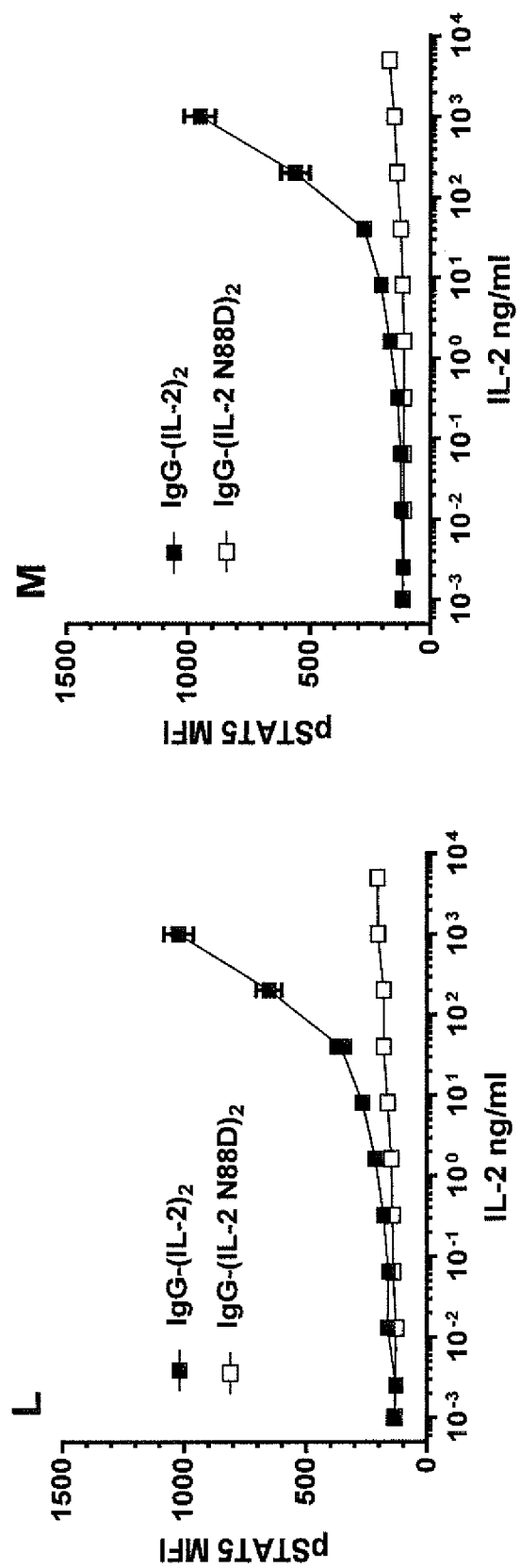

The results in FIG. 15 show the whole blood pSTAT5a responses collected from an additional ten human blood donors. On separate days, each donor was tested comparing a wide (≥6 log)) titration range of DP47GS IgG-(IL-2)$_2$ and DP47GS IgG-(IL-2N88D)$_2$. As seen previously with DP47GS IgG-(IL-2)$_2$ (FIG. 9), memory Tregs and naïve Tregs were the cells most sensitive to DP47GS IgG-(IL-2)$_2$ and DP47GS IgG-(IL-2N88D)$_2$ induced pSTAT5a (FIG. 15A, B); while each fusion protein stimulated maximal pSTAT5a responses they differed in the concentrations needed for the inflection point of activation as well as the maximal dose for activation. CD56$^{bright}$ NK cells presented as a cell subset less sensitive than Tregs to DP47GS IgG-(IL-2N88D)$_2$ compared to the wild type IL-2 fusion proteins (FIG. 15C); the inflection point of activation was higher and in this case never achieved a maximal effect even at the highest dose tested (5000 ng/ml). Unlike DP47GS IgG-(IL-2)$_2$, NK cells were unresponsive to DP47GS IgG-(IL-2N88D)$_2$ (FIG. 15D). Both central memory CD4$^+$ T cells (FIG. 15E) and effector memory CD4$^+$ T cells (FIG. 15F) were relatively unresponsive to DP47GS IgG-(IL-2N88D)$_2$ with an inflection point of activation 1000-fold higher than DP47GS IgG-(IL-2)$_2$ and inducing only partial responses at the highest dose tested (5000 ng/ml). While DP47GS IgG-(IL-2)$_2$ induced varying degrees of activation, DP47GS IgG-(IL-2N88D)$_2$ had no effect on the following cell subsets: naïve CD4$^+$ T cells (FIG. 15G), central memory CD8$^+$ T cells (FIG. 15H), effector memory CD8$^+$ T cells (FIG. 15G), naïve CD8$^+$ T cells (FIG. 15J), effector memory CD45RA$^+$CD8$^+$ T cells (FIG. 15K), NKT cells (FIG. 15L) and CD3$^+$CD4$^-$CD8$^-$CD56$^-$ T cells (FIG. 15M).

EC$_{50}$ values are shown in Table 3 and were based on the amount of the IL-2 fusion proteins required to reach 50% of the maximal pSTAT5a response observed for that cell subset. DP47GS IgG-(IL-2E95A)$_2$ like its wild type IL-2 counterpart DP47GS IgG-(IL-2)$_2$ produced the most potent induction of pSTAT5a in Tregs, the cells that constitutively express the high affinity receptor CD25 (IL2Rα), potentially as a consequence of its increased avidity for the high affinity IL-2 receptor. The dose responses to DP47GS IgG-(IL-2E95A)$_2$ and DP47GS IgG-(IL-2)$_2$ were superimposable. The EC$_{50}$ for pSTAT5a activation in Tregs was 6 to 7-fold lower with DP47GS IgG-(IL-2E95A)$_2$ and DP47GS IgG-(IL-2)$_2$ compared to monovalent DP47GS IgG-IL-2. Likewise, the EC$_{50}$ for Treg activation was 7 to 10-fold lower with monovalent DP47GS IgG-IL-2 compared to bivalent DP47GS IgG-(IL-2N88D)$_2$. And lastly, the EC$_{50}$ for Treg activation was 36 to 61-fold lower with bivalent DP47GS IgG-(IL-2)$_2$ compared to bivalent DP47GS IgG-(IL-2N88D)$_2$.

The most significant immunologic advantage that DP47GS IgG-(IL-2N88D)$_2$ has for treating autoimmune disorders is best illustrated in Table 3 demonstrating the dramatic margin of specificity that DP47GS IgG-(IL-2N88D)$_2$ has for Treg activation versus CD4$^+$ memory T effector cells (>320-fold to >500-fold). In comparison, the margin of specificity for Tregs versus CD4$^+$ memory T effector cells is substantially less for DP47GS IgG-(IL-2)$_2$ (13 to 14-fold) and DP47GS IgG-IL-2 (10 to 16-fold).

TABLE 3

EC$_{50}$ values and fold specificity differences for pSTAT5a activation by DP47GS IgG-(IL-2E95A)$_2$, DP47GS IgG-IL-2, and DP47GS IgG-(IL-2N88D)$_2$ in different cell subsets.

| Human cell subset | IgG-IL-2 ED$_{50}$ (pM) | IgG-(IL-2)$_2$ ED$_{50}$ (pM) | IgG-(IL-2N88D)$_2$ ED$_{50}$ (pM) |
|---|---|---|---|
| memory Treg | 2.2 | 0.31 | 11.4 |
| naïve Treg | 1.8 | 0.29 | 17.7 |
| CD4$^+$ memory T effector | 29 | 4 | >5700 |
| Fold specificity of: | | | |
| memory Tregs vs. CD4$^+$ memory Teff | 10 | 13 | >500 |
| naïve Tregs vs. CD4$^+$ memory Teff | 16 | 14 | >320 |

Figure 16:
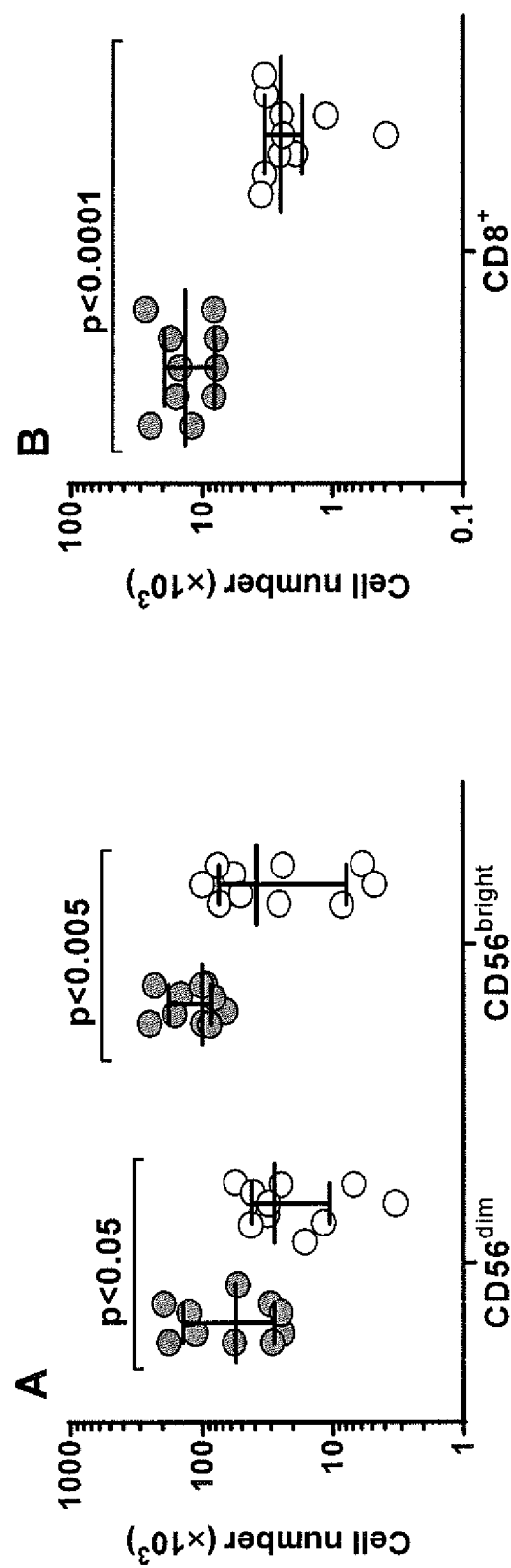
FIG. 16A-B. Comparison of the in vitro effects of DP47GS IgG-(IL-2N88D)$_2$ and DP47GS IgG-(IL-2)$_2$ on human NK cells and CD8$^+$ T cells. PBMC from normal human donors (n=10) were cultured at 5×10$^6$ cells/U-bottom well with 50 ng/ml of DP47GS IgG-(IL-2N88D)$_2$ (open symbols) or DP47GS IgG-(IL-2)$_2$ (gray shaded symbols) for 6 days at which time cell numbers were quantified by flow cytometry. The effects on NK cells were quantified on CD56$^{dim}$ and CD56$^{bright}$ NK cells FIG. 16A. The effects on CD8$^+$ T cells are shown in FIG. 16B. Results are shown as the median±interquartile range, statistical differences were determined using a Mann-Whitney U test.

Differential effects of IL-2 fusion proteins on human NK cells and CM$^+$ T cells in vitro Fresh human peripheral blood mononuclear cells (PBMC) were cultured in vitro without further stimulation other than the IL-2, conditions known to favor the survival and growth of NK cells and CD8$^+$ T cells. Human NK cells can be subdivided into those which express little or no detectable CD56 (termed CD56$^{-/dim}$) and an "activated" subset which expresses high levels of CD56 (termed CD56$^{bright}$); the majority of NK cells in blood are CD56$^{-/dim}$ with a minority classified as CD56$^{bright}$. "Activated" NK cells that are CD56$^{bright}$ are thought to be precursors of NK cells which lack CD56 expression (i.e. CD56$^{-/dim}$). After six days in vitro with DP47GS IgG-(IL-2)$_2$ and DP47GS IgG-(IL-2N88D)$_2$ (each at 0, 5, 50 and 500 ng/ml) differences were detected in the growth and survival of NK CD56$^{-/dim}$ cells, NK CD56$^{bright}$ cells and CD8$^+$ T cells. Significant differences in cell numbers were seen between stimuli with DP47GS IgG-(IL-2)$_2$ stimulating the greatest increases in CD56$^{bright}$ cells (a median of 101×10$^3$ versus 38×10$^3$, p<0.005) (FIG. 16A) and also in CD8$^+$ T cells (a median of 13.6×10$^3$ cells versus 2.5×10$^3$ cells, p<0.0001) (FIG. 16B).

Effects of IL-2 Fusion Proteins in Humanized Mice

Figure 17:
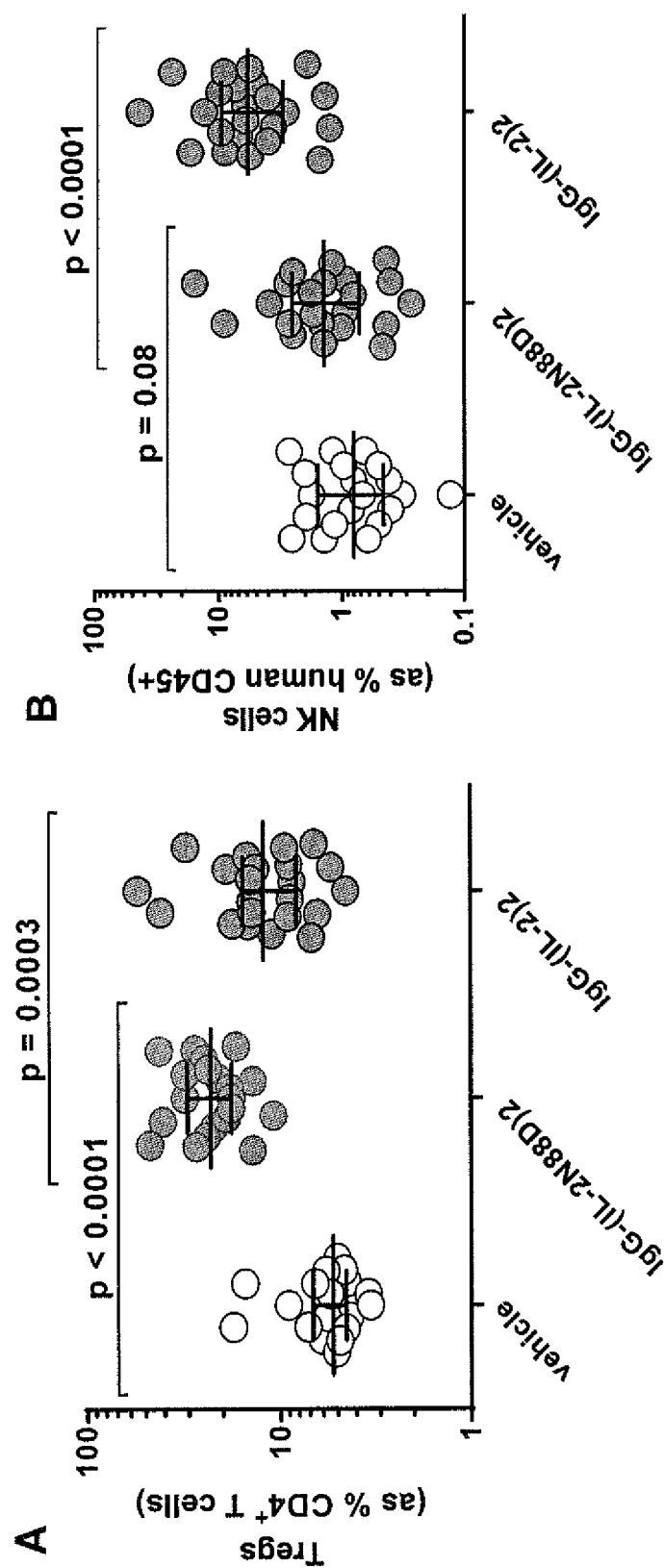
FIG. 17A-B. Comparison of the in vivo effects of DP47GS IgG-(IL-2N88D)$_2$ and DP47GS IgG-(IL-2)$_2$ on CD34$^+$ stem cell humanized mice. Ten to 12 weeks after CD34$^+$ stem cell engraftment, mice were treated twice weekly with vehicle (DP47GS IgG, no IL-2), DP47GS IgG-(IL-2N88D)$_2$ or DP47GS IgG-(IL-2)$_2$. Maximal increases of human Tregs and NK cells in blood were seen after 3 treatments and the results are shown in FIG. 17A: for Tregs

Humanised mice were constructed using lightly irradiated newborn NOD.Prkdc$^{scid}$ IL2rg$^{null}$ (NSG) mice as the immunocompromised host and engrafting them with human fetal liver CD34$^+$ stem cells injected IP. At 8 to 10 weeks of age, blood from each mouse was tested to assure that human engraftment had occurred. Comparing Proleukin and DP47GS IgG-(IL-2)$_2$ we found that the primary cells affected in vivo were NK cells and Tregs; following DP47GS IgG-(IL-2)$_2$ treatment there was a substantial increase in both NK cells and Tregs with NK cells responding proportionally greater. The in vivo effects of Proleukin were similar but the effects on NK cells and Tregs within a group were less consistent and the extent of increases reduced compared to DP47GS IgG-(IL-2)$_2$. Humanized mice were also able to differentiate the in vivo effects of the IL-2 fusion proteins. Wild type DP47GS IgG-(IL-2)$_2$ increased both Tregs (FIG. 17A) and NK cells (FIG. 17B) whilst DP47GS IgG-(IL-2N88D)$_2$ had no effect on NK (FIG. 17B) cells but increased Tregs to a significantly greater extent (FIG. 17A) than wild type IgG-(IL-2)$_2$.

Figure 18:
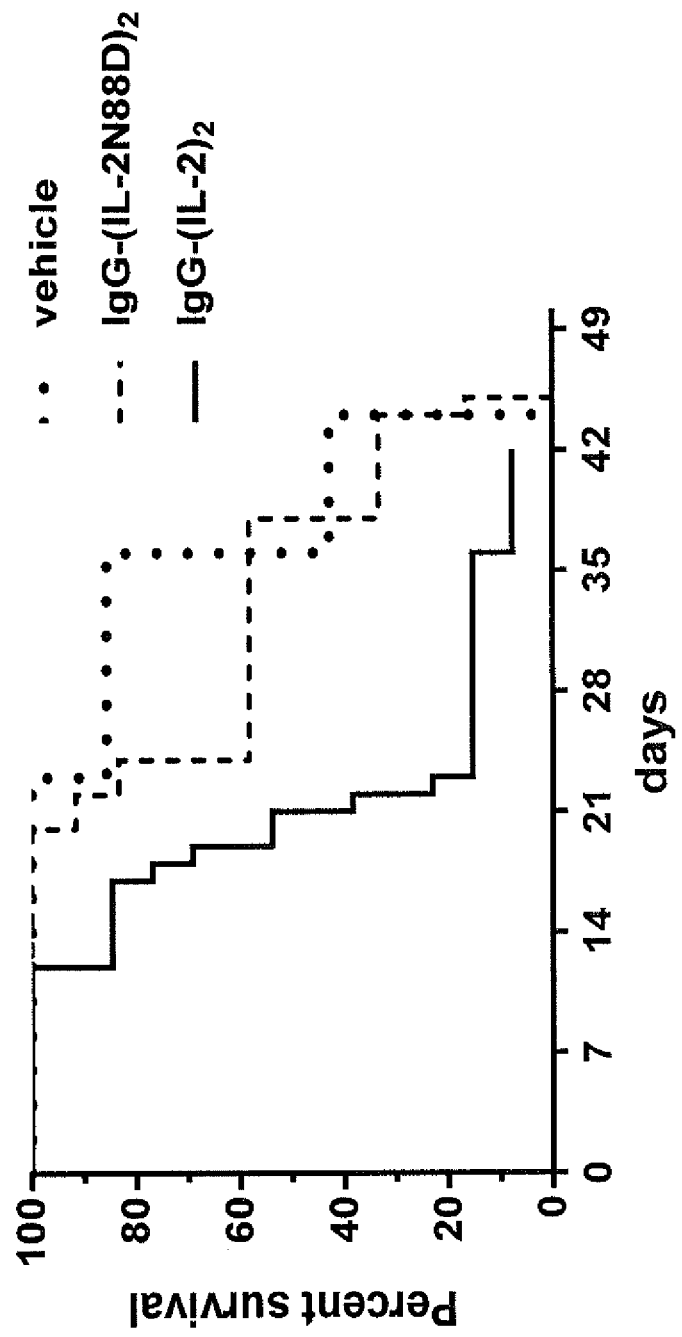
FIG. 18. Comparison of the in vivo effects of DP47GS IgG-(IL-2N88D)$_2$ and DP47GS IgG-(IL-2)$_2$ on the survival of CD34$^+$ stem cell humanized mice. Ten to 12 weeks after CD34$^+$ stem cell engraftment, mice were treated twice weekly with vehicle (DP47GS IgG, no IL-2), DP47GS IgG-(IL-2N88D)$_2$ or DP47GS IgG-(IL-2)$_2$ until the severity of the human xenogeneic graft versus host response reached a predetermined stage (≥15% weight loss) requiring their removal from the study. The results are plotted as a Kaplan-Meier survival curve from GraphPad Prism for vehicle (n=7), DP47GS IgG-(IL-2N88D)$_2$(n=12) and DP47GS I$_g$G-(IL-2)$_2$ (n=13).

A long-term consequence of humanizing NSG mice is their shorter survival time due to a human xenogeneic graft versus host response that results in weight loss and multisystem organ failure. Twice weekly administration of vehicle had no effect and resulted in a median survival of 36 days after treatment initiation (FIG. 18). Similar to vehicle, treatment with DP47GS IgG-(IL-2N88D)$_2$ resulted in a median survival of 37 days. In contrast, twice weekly treatment with DP47GS IgG-(IL-2)$_2$ shortened this group's median survival time to 21 days (FIG. 18, p<0.0037 compared to DP47GS IgG-(IL-2N88D)$_2$).

Figure 19:
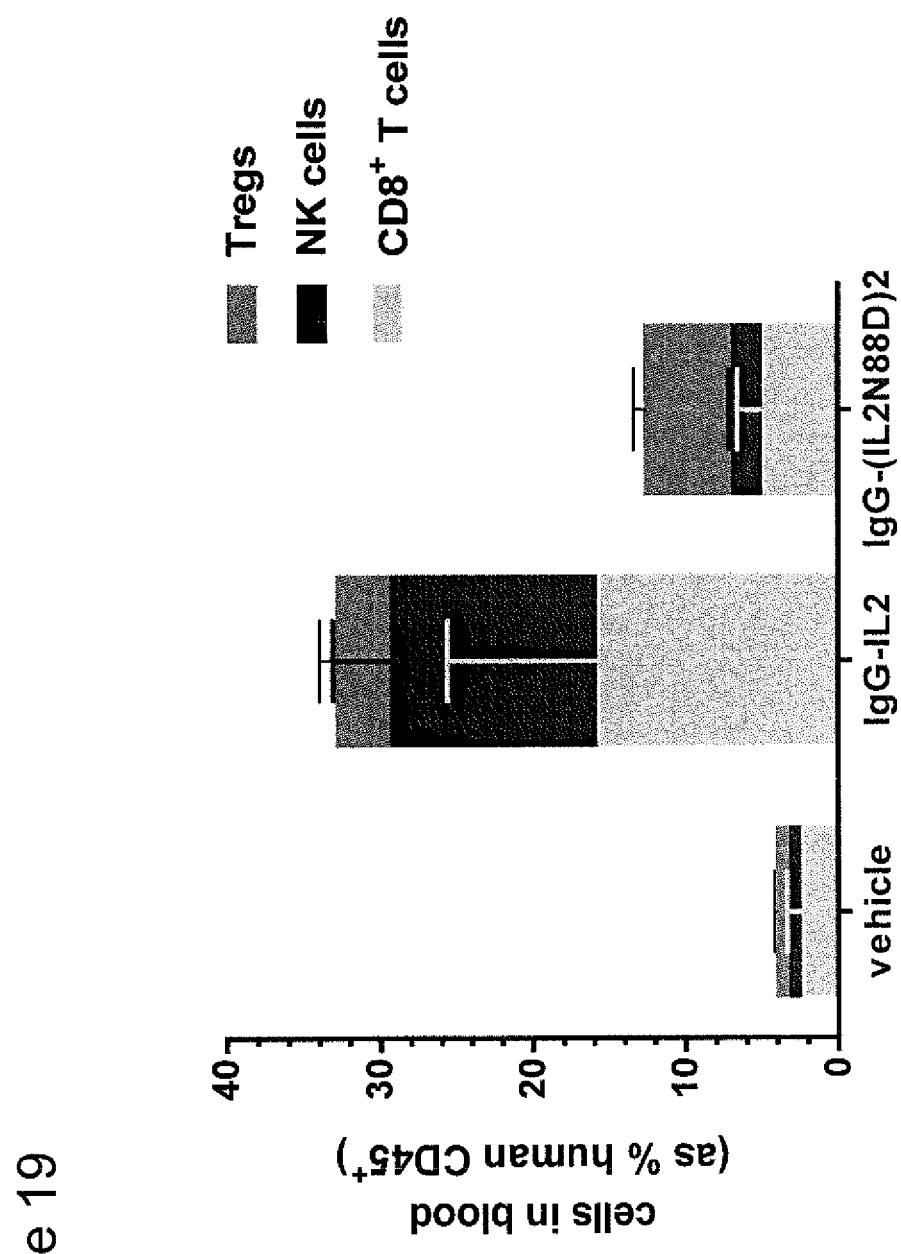
FIG. 19. Comparison of the in vivo effects of DP47GS IgG-(IL-2N88D)$_2$ and DP47GS IgG-(IL-2)$_2$ on Tregs, NK cells and CD8+ T cells in CD34+ stem cell humanized mice. Ten to 12 weeks after CD34+ stem cell engraftment, mice were treated twice weekly with either vehicle (DP47GS IgG, no IL-2), DP47GS IgG-(IL-2N88D)$_2$ or DP47GS IgG-(IL-2)$_2$ until the severity of the human xenogeneic graft versus host response reached a predetermined stage (≥15% weight loss) requiring their removal from the study at which time blood was assessed for individual human cell subsets. Shown are the human Tregs, NK cells and CD8+ cells in blood as the % of human CD45+ cells. Results are shown as the mean±the SEM for vehicle (n=6), DP47GS IgG-(IL-2N88D)$_2$ (n=9) or DP47GS IgG-(IL-2)$_2$ (n=9).

When a predetermined severity of the graft versus host response dictated an end to the in-life portion for each mouse (weight loss ≥15%), the human cell composition was assessed in blood. With a life-threatening graft versus host response underway, striking differences in the treatment arms were seen in the final composition of Tregs, NK cells and CD8$^+$ T cells in blood (FIG. 19). In vehicle treated mice, human Tregs accounted for less than 1% of the total human CD45$^+$ cells and NK and CD8$^+$ T cells comprised ~3% of the human CD45$^+$ cells in blood. Treatment with DP47GS IgG-(IL-2N88D)$_2$ increased NK and CD8$^+$ T cells to 2% and 5%, respectively, while Tregs increased to 6%. In contrast, wild type DP47GS IgG-(IL-2)$_2$ treatment increased the fraction of NK cells and CD8$^+$ T cells to 30% of the total human CD45$^+$ cells and Tregs to 3.5%, perhaps explaining the significant reduction in survival times in this group compared to DP47GS IgG-(IL-2N88D)$_2$ treated mice.

Induction of pSTAT5a in Cynomolgus Peripheral Blood Cell Subsets

As observed in human peripheral blood, there is a preferential and similar dose-dependent induction of pSTAT5a in Treg subsets in cynomolgus peripheral blood stimulated with IL-2 (Proleukin) (data not shown). In a direct comparison of the ability of DP47GS IgG-(IL-2)$_2$ and DP47GS IgG-IL-2 to induce pSTAT5a in the three Treg subsets, 2- to 8-fold less DP47GS IgG-(IL-2)$_2$ was required to reach 50% of the maximal level of pSTAT5a than for DP47GS IgG-IL-2. Table 4 summarizes the EC$_{50}$ values for pSTAT5a activation by DP47GS IgG-IL-2 versus DP47GS IgG-(IL- 2)$_2$ in the different cynomolgus Treg subsets, results that are strikingly similar to those seen with human peripheral blood (Table 3).

Similar to human whole blood, cell surface and intracellular markers were used to identify regulatory T cell subsets and conventional T cells in whole blood from normal healthy cynomolgus monkeys. Blood samples were collected on the same day from three healthy cynomolgus monkeys in sodium heparin tubes and various concentrations of DP47GS IgG-IL-2 or DP47GS IgG-(IL-2)$_2$ were added to 500 µl of blood and incubated at 37° C. After 10 min at 37° C., samples were lysed and fixed with pre-warmed BD Lyse/Fix buffer (BD Biosciences). After washing, cells were permeabilized with 1 mL methanol for 30 min on ice. Samples were washed 3 times and stained with a panel of FOXP3-Alexa Fluor® 647 (clone: 259D, BioLegend), CD4-V500 (clone: L200, BD Biosciences), CD45RA-V450 (clone: 5H9, BD Biosciences), CD25-PE (clone: 4E3, eBioscience), pSTAT5a-Alexa Fluor® 488 (clone: 47, BD Biosciences), and Ki-67-PerCP-Cy5.5 (clone: B56, BD Biosciences) for 1 hour at 4° C. All the samples were acquired by an LSRFortessa™ cell analyzer (Becton Dickinson) and then analyzed with FlowJo software (FlowJo, LLC).

TABLE 4

Induction of pSTAT5a in cynomolgus peripheral blood Treg subsets in response to DP47GS IgG-IL-2 and DP47GS IgG-(IL-2)$_2$.

| T cell | IgG-IL-2 | IgG-(IL-2)$_2$ | Fold change |
|---|---|---|---|
| activated Treg | 0.07 ng/mL | 0.02 ng/mL | 4 |
| memory Treg | 0.21 ng/mL | 0.025 ng/mL | 8 |
| naïve Treg | 0.04 ng/mL | 0.02 ng/mL | 2 |

In a further experiment, similar to the pSTAT5a assays with human blood, fresh heparinized blood from normal healthy adult cynomolgus monkeys was stimulated in vitro with PBS as a vehicle control, DP47GS IgG-(IL-2)$_2$ and DP47GS IgG-(IL-2N88D)$_2$ and the effects on STAT5a phosphorylation in Treg subsets and conventional CD4$^+$ memory T effector cells were examined. A 20 ng/mL stimulation dose was chosen based on maximal human Treg responses at ≤1 ng/mL and near maximal responses of conventional CD4$^+$ memory T effector cells in that dose range (results in FIG. 9).

The experimental conditions were as described above. Blood samples were collected on the same day from three healthy cynomolgus monkeys (donors C1, C2, C3) in sodium heparin tubes and 20 ng/mL of DP47GS IgG-(IL-2)$_2$ or DP47GS IgG-(IL-2N88D)$_2$ was added to 500 µl of blood and incubated at 37° C. for 20 min before lysis and analysis.

Figure 20:
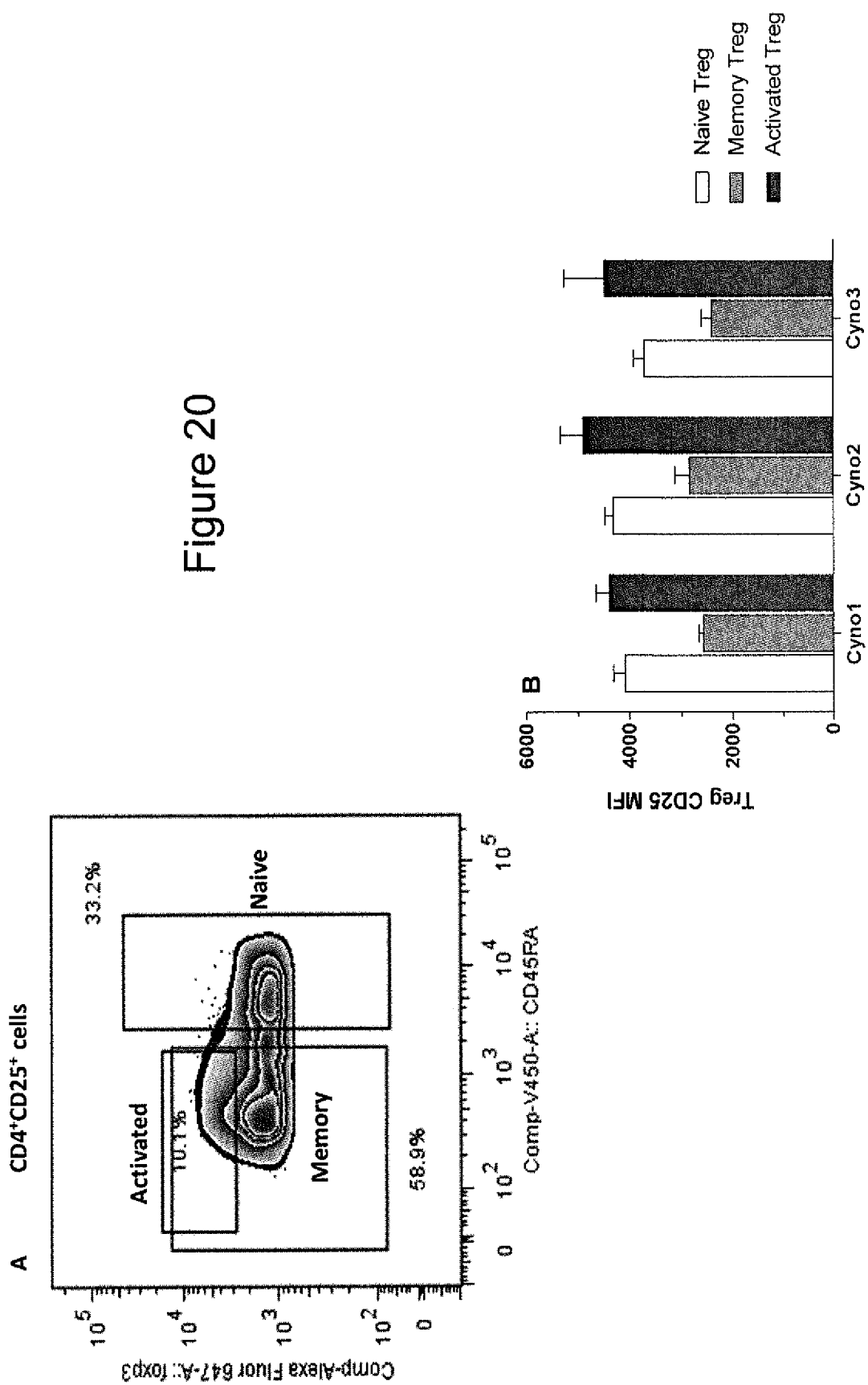
FIG. 20A-C. Induction of Treg pSTAT5a in cynomolgus monkey blood in response to DP47GS IgG-(IL-2)$_2$ and DP47GS IgG-(IL-2N88D)$_2$. Three normal healthy donors (C1-C3) were assessed at the same time for the effects of a maximal dose (20 ng/mL) of DP47GS IgG-(IL-2)$_2$ and DP47GS IgG-(IL-2N88D)$_2$ on the induction of STAT5a phosphorylation in Tregs.
Figure 20:
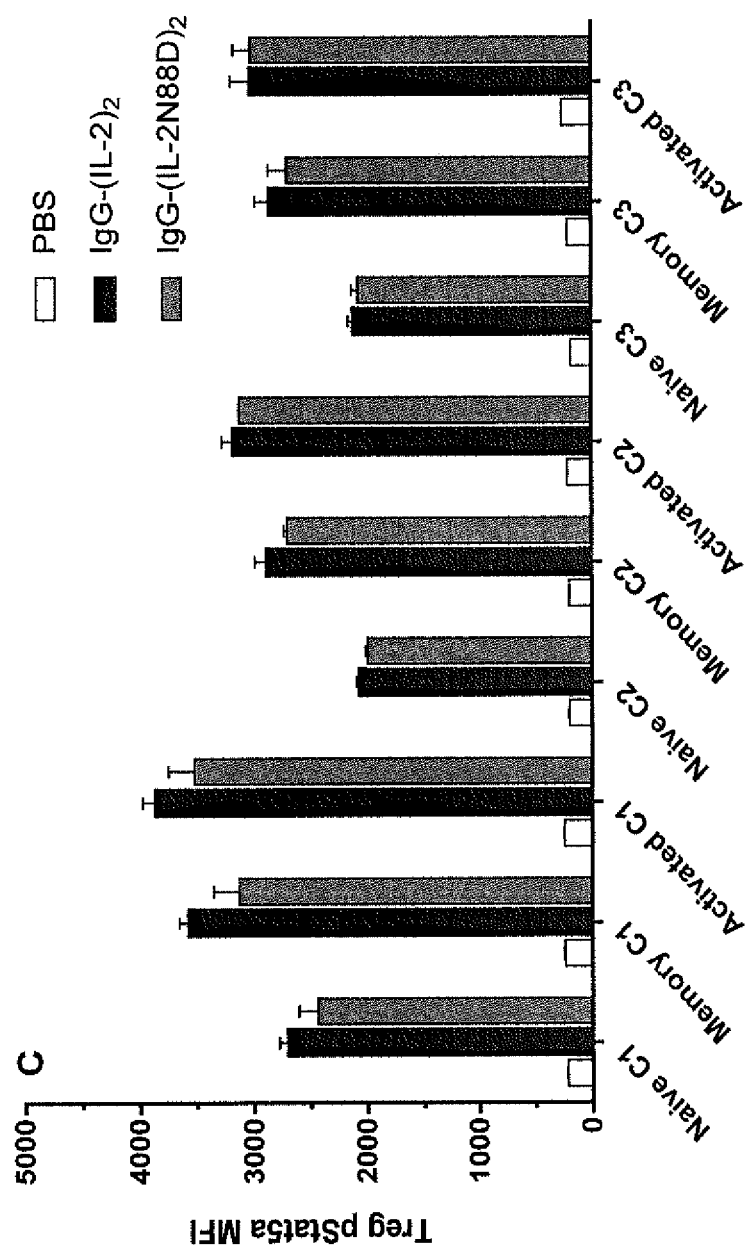

The flow cytometry gating strategy for dividing cynomolgus CD4$^+$CD25$^+$ Tregs into naïve (FOXP3$^+$CD45RA$^+$), memory (FOXP3$^+$CD45RA$^-$), and activated (FOXP3$^{hi}$ CD45RA$^-$) subsets for analysis is shown in FIG. 20A. As in humans the three subsets of CD4$^+$CD25$^+$FOXP3$^+$ Tregs from each donor expressed high levels of the high affinity IL-2 receptor CD25 (FIG. 20B). Following in vitro stimulation with 20 ng/mL of both DP47GS IgG-(IL-2)$_2$ and DP47GS IgG-(IL-2N88D)$_2$, Tregs from all three donors produced significant STAT5a phosphorylation (FIG. 20C). Similarly to humans cynomolgus activated and memory Tregs showed a greater potential for pSTAT5a induction as compared to naïve Tregs.

Figure 21:
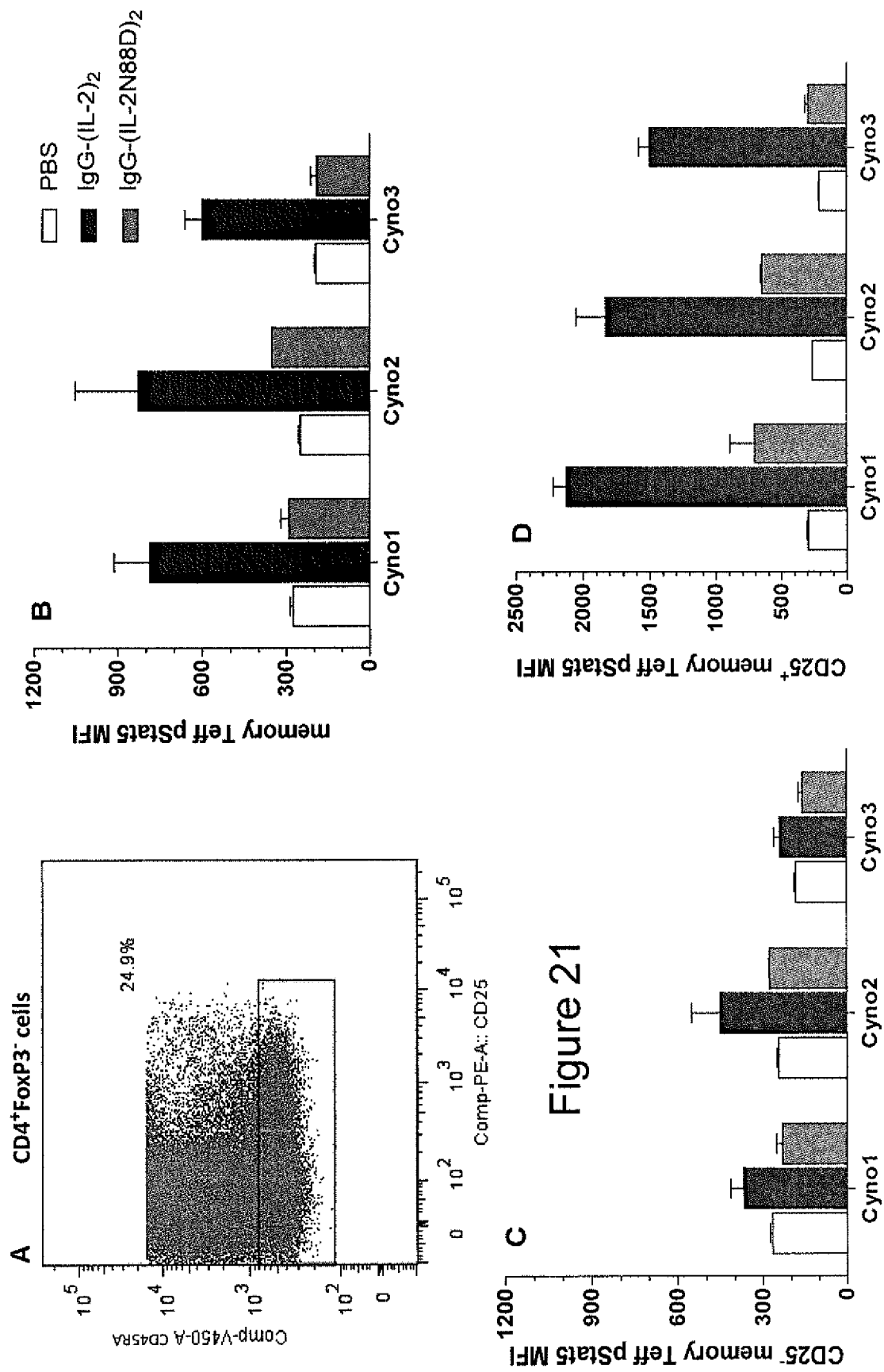
FIG. 21A-D. Activation of conventional CD4+ memory T effector cell pSTAT5a in cynomolgus blood in response to DP47GS IgG-(IL-2)$_2$ or DP47GS IgG-(IL-2N88D)$_2$. Using the same 20 ng/mL stimulated blood samples from the three monkey donors described in FIG. 11, the induction of pSTAT5a in conventional CD4+ memory T effector cells was examined.

Human conventional CD4$^+$ memory T effector cells, while not as sensitive as Tregs, are able to be stimulated with IL-2 with an estimated ED$_{90}$ of 20 ng/mL for DP47GS IgG-(IL-2)$_2$ using pSTAT5a as the biomarker of activation (FIG. 14). Cynomolgus conventional CD4$^+$ memory T effector cells can similarly be identified in blood as CD4$^+$ FOXP3$^-$CD45RA$^-$ cells with the majority of cells being CD25$^-$ and a smaller subset being CD25$^+$ (FIG. 21A). When taken as a whole population, cynomolgus memory Teff cells from all three donors responded to 20 ng/mL DP47GS IgG-(IL-2)$_2$ with increases in pSTAT5A while 20 ng/mL DP47GS IgG-(IL-2N88D)$_2$ had little (cyno 2) or no effect (cynos 1 and 3) on pSTAT5a (FIG. 21B). When memory Teff cells were further subdivided into CD25$^-$ and CD25$^+$ subsets, the response to DP47GS IgG-(IL-2)$_2$ primarily was found to reside in the CD25$^+$ subset (FIG. 21D) with little response in the CD25$^-$ subset (FIG. 21C). In contrast, DP47GS IgG-(IL-2N88D)$_2$ was without effect on the CD25$^-$ memory Teff cells (FIG. 21C) and had 70-80% less stimulatory activity on the CD25$^+$ subset (FIG. 21D).

Additional studies in fresh normal cynomolgus blood directly compared varying concentrations of DP47GS IgG-(IL-2)$_2$ and DP47GS IgG-(IL-2N88D)$_2$ in a dose response fashion for their ability to stimulate pSTAT5a in different T cell subsets, i.e. activated, naïve, and memory Tregs and CD4$^+$ memory T effector cells. Both DP47GS IgG-(IL-2)$_2$ and DP47GS IgG-(IL-2N88D)$_2$ stimulated Tregs in a dose dependent manner with the wild type bivalent IL-2 fusion protein ~10-fold more potent than the bivalent IL-2N88D fusion protein in each of the Treg subsets (FIG. 22A-C). In contrast a dramatic difference between the two molecules was seen when CD4$^+$ memory T effector cells were assessed for pSTAT5a induction (FIG. 22D). DP47GS IgG-(IL-2)$_2$ presented with an ~EC90 at 300 ng/mL while DP47GS IgG-(IL-2N88D)$_2$ was virtually without effect at that high dose. The EC$_{50}$ values for cynomolgus pSTAT5a stimulation are shown in Table 5 as well as the relative fold specificities for stimulating Tregs versus CD4$^+$ memory T effector cells. These results in cynomolgus whole blood are quite similar to the results using human whole blood (FIG. 14 and Table 3) and suggest that studies in the cynomolgus may have a high predictive value for human clinical trials.

TABLE 5

EC$_{50}$ values and fold specificity differences for pSTAT5a activation by DP47GS IgG-(IL-2)$_2$ and DP47GS IgG-(IL-2N88D)$_2$ in cynomolgus T cell subsets.

| Cyno Tregs | IgG-(IL-2)$_2$ (ng/mL) | IgG-(IL-2 N88D)$_2$ (ng/mL) |
|---|---|---|
| activated Treg | 0.1 | 0.7 |
| memory Treg | 0.1 | 1.1 |
| naïve Treg | 0.06 | 0.8 |
| CD4$^+$ memory T effector | 1.2 | >1,000 |
| Fold Specificity of: | | |
| act Tregs vs. CD4$^+$ memory Teff | 12 | >1,400 |
| mem Tregs vs. CD4$^+$ memory Teff | 12 | >900 |
| naive Tregs vs. CD4$^+$ memory Teff | 20 | >1,200 |

Pharmacokinetic Properties in Mice

Figure 23:
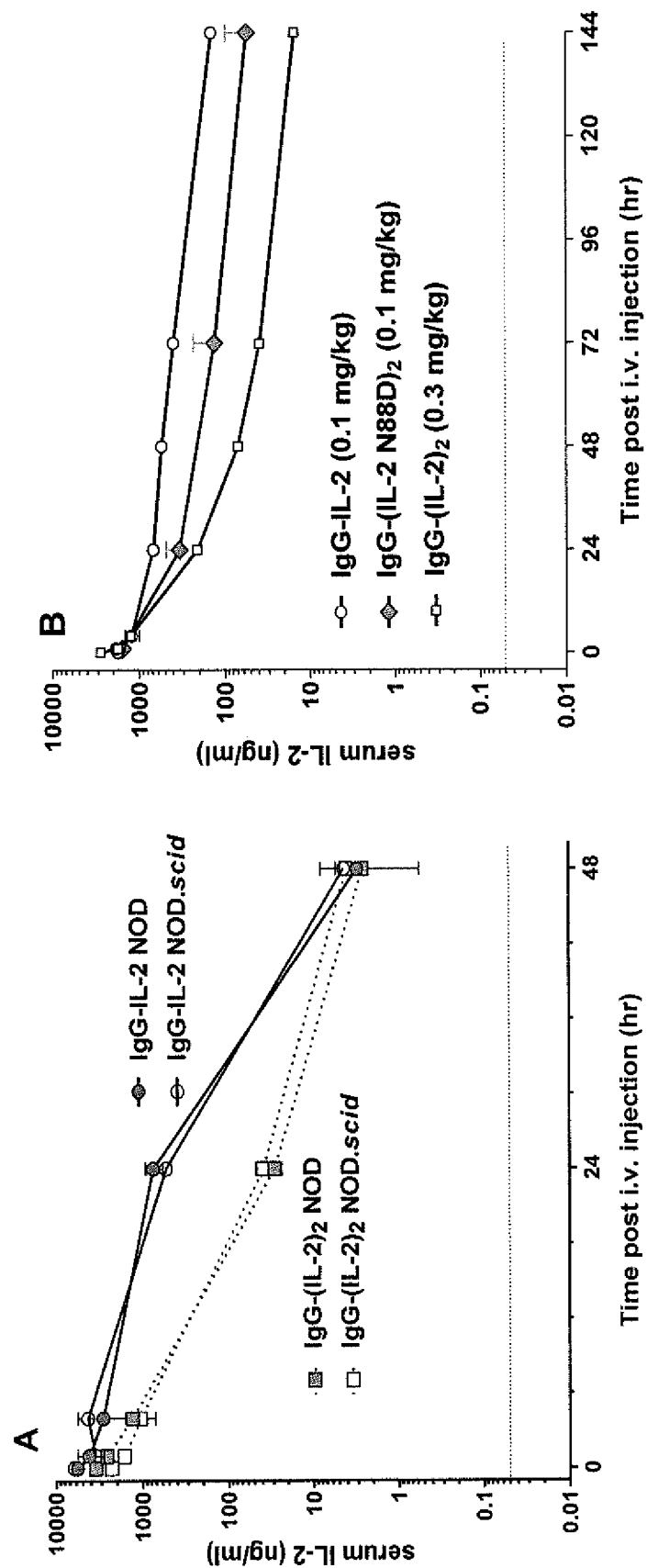
FIG. 23A-B. In mice, DP47GS IgG-IL-2 has superior pharmacokinetic (PK) properties compared to DP47GS IgG-(IL-2)$_2$ while DP47GS IgG-(IL-2N88D)$_2$ is intermediate.

Prior to performing functional studies in mice, the pharmacokinetic (PK) properties of wild type and N88D monovalent and bivalent IL-2 immunoconjugates were evaluated in NOD, NOD.scid, and NOD.scid.IL2ra$^{-/-}$ mice (FIG. 23).

NOD and NOD.scid mice (n=3) were injected intravenously (i.v.) with 0.3 mg/kg per mouse of DP47GS IgG-IL-2 or DP47GS IgG-(IL-2)$_2$ in PBS containing 0.5% mouse serum and bled at various times after injection, ranging from 2 minutes to 168 hours (FIG. 23A). Human IL-2 was assessed in the mouse serum samples using mouse anti-human IL-2 mAb (BD Pharmingen, #555051, clone 5344.111) to coat 96-well plates in order to capture the IL-2. Human IL-2 was then detected using biotinylated mouse anti-human IL-2 mAb (BD Pharmingen, #555040, clone B33-2). IL-2 binding was visualized and quantified using Europium-conjugated streptavidin. Over the first 24 hours DP47GS IgG-(IL-2)$_2$ was cleared more rapidly than DP47GS IgG-IL-2 in both NOD and NOD.scid mice. By 48 hours the serum levels of each were at similar concentrations and all were below the limit of detection at 72 hours. The limit of IL-2 detection was 0.05 ng/mL and is indicated by the dotted line. The surprisingly rapid clearance of both the monovalent and bivalent IgG-IL-2 immunoconjugates in mice without an adaptive immune system suggested that a non-hematopoietic IL-2 compartment or "sink" exists in mice and might be driving the rapid in vivo clearance of the IL-2 immunoconjugates.

To test this hypothesis, we performed PK studies in NOD.scid mice that also lacked the high affinity IL-2 receptor, IL2Rα (CD25), i.e. NOD.scid.Il2ra$^{-/-}$ mice (FIG. 23B). In NOD.scid. Il2ra$^{-/-}$ mice, DP47GS IgG-(IL-2)$_2$, despite being given at a three-fold higher dose (0.3 mg/kg), was cleared more rapidly over the first 24 to 48 hours than 0.1 mg/kg DP47GS IgG-IL-2 and 0.1 mg/kg DP47GS IgG-(IL-2N88D)$_2$. However, after 48 hours, blood levels of each conjugate displayed a slow steady elimination phase with readily detectable IL-2 in blood out to 6 days. Interestingly in these high affinity IL-2 receptor deficient mice, the DP47GS IgG-(IL-2N88D)$_2$ molecule had an initial 24 hour distribution phase slightly quicker than IgG-IL-2 but thereafter displayed an elimination phase similar to the wild type monovalent immunoconjugate out to six days, the last time they were tested. These data for DP47GS IgG-(IL-2N88D)$_2$ are particularly relevant since PK results in the NOD.scid.Il2ra$^{-/-}$ mice seem to closely predict PK results in nonhuman primates.

FOXP3 and CD25 Increase in Mouse Tregs after Treatment with IL-2

Figure 24:
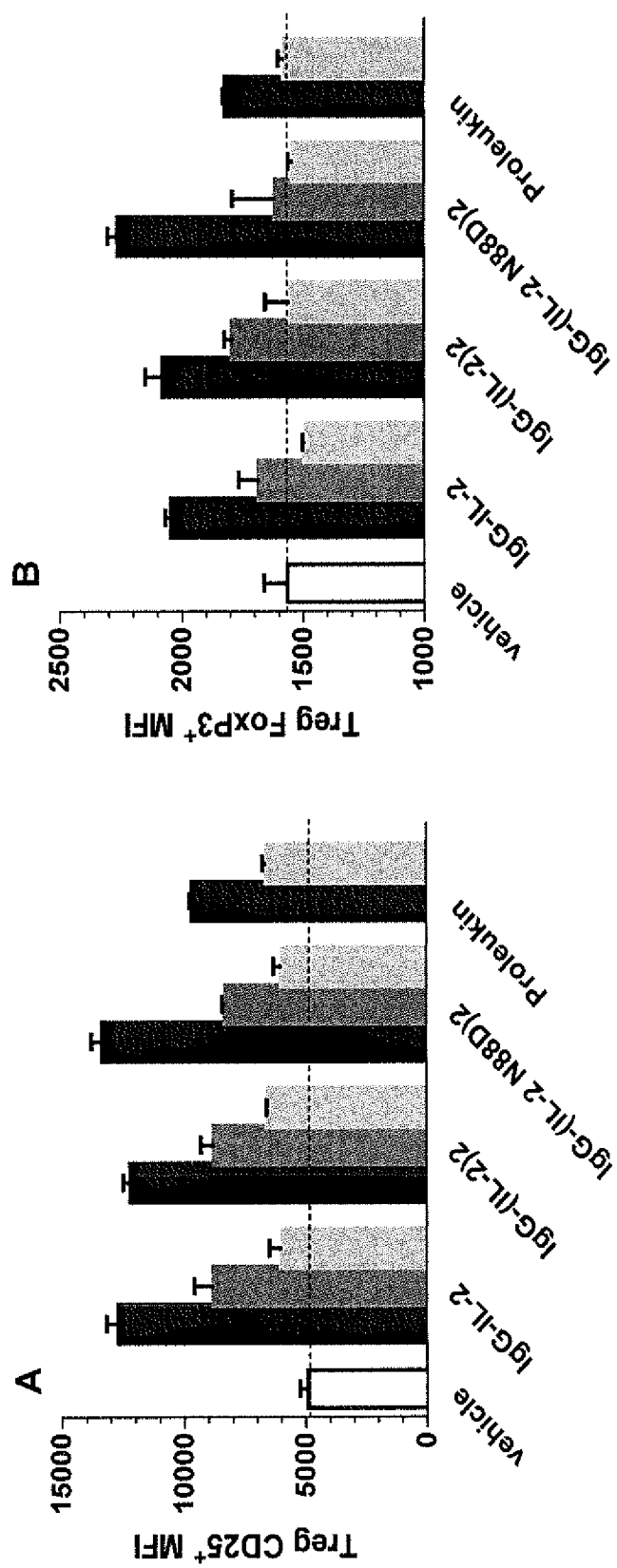
FIG. 24A-B. Both CD25 and FoxP3 increase in murine Tregs after treatment with Proleukin®, DP47GS IgG-IL-2, DP47GS IgG-(IL-2)$_2$, and DP47GS IgG-(IL-2N88D)$_2$. BALB/c mice were treated with Proleukin® (20,000 and 100,000 IU/mouse, n=3), DP47GS IgG-IL-2, DP47GS IgG-(IL-2)$_2$, or DP47GS IgG-(IL-2N88D)$_2$ (60, 300, or 1,500 IU/mouse, n=3), vehicle treated mice were included as unstimulated controls (n=4). Twenty-four hours after treatment, splenic Tregs were assessed for CD25 and FOXP3 levels.

To compare the abilities of different molecular forms and configurations of human IL-2 to stimulate FoxP3$^+$ Tregs in vivo, mice were injected subcutaneously with vehicle, Proleukin (recombinant human IL-2), DP47GS IgG-IL-2, DP47GS IgG-(IL-2)$_2$, or DP47GS IgG-(IL-2N88D)$_2$ and Tregs were assessed for changes in expression of cell surface CD25 and intracellular FOXP3 at a previously determined optimal time of 24 hours (FIG. 24). Young healthy BALB/c mice (n=3/treatment group, n=4/vehicle cohorts) were injected subcutaneously with Proleukin (20,000 or 100,000 IU/mouse), DP47GS IgG-IL-2 (60, 300, or 1500 IU/mouse), DP47GS IgG-(IL-2)$_2$ (60, 300, or 1500 IU/mouse), or DP47GS IgG-(IL-2N88D)$_2$ (60, 300, or 1500 IU/mouse). Doses were delivered in a vehicle comprised of 100 μl sterile PBS pH 7.2 containing 0.5% sterile-filtered mouse serum. After 24 hours, mice were euthanized and spleens excised. A single cell suspension of splenocytes was generated in 1 ml L-15 media and stored on ice, until further processing. A filtered aliquot of the single cell suspension, 40 μl, was transferred to FACS tubes and washed with 2 ml FACS buffer (600×g, 5 min). Samples were then incubated with fluorochrome-conjugated antibodies directed against cell surface antigens: CD4 (clone RM4-5, fluorochrome A700), CD25 (eBio7D4, Af488), CD44 (IM7, e605), CD62L (MEL-14, PE), ICOS (C398.4A, PE/Cy7), CD103 (2E7, APC). Staining was performed for 30 min, at 4° C. in 100 μl FACS buffer (PBS pH 7.2+0.2% BSA). Following cell surface staining, samples were washed with 4 ml FACS buffer (600×g, 5 min) before intracellular staining (according to the eBioscience intracellular staining protocol). Briefly, samples were resuspended in 200 μl fixation/permeabilisation buffer (eBioscience #00-5521) and incubated for 1 h, 4° C. 1 ml of 1× permeabilisation buffer (eBioscience #00-8333) was added to samples before 3 ml FACS buffer and washing (600×g, 5 min). Intracellular antigens, Ki-67 (B56, PerCP Cy5.5) and FOXP3 (FJK-16S, e450), were stained in 100 μl 1× permeabilisation buffer for 1 h, 4° C. Samples were washed with 4 ml FACS buffer (600×g, 5 min—twice) and data acquired on a BD Fortessa™ Analyzer and analyzed using FlowJo software (FlowJo, LLC). Tregs were defined as CD4$^+$FOXP3$^+$ from singlets within the lymphocyte gate; from this population, CD25 and FOXP3 mean fluorescence intensity (MFI) were calculated for all samples.

As shown in FIG. 24, the three IL-2 immunoconjugates were equipotent at stimulating the expression of CD25 (24A) and FoxP3 (24B) in mouse Tregs and showed consistent dose dependent responses across the range of 60, 300, and 1500 IU/mouse doses. In every case, 1500 IU of each immunoconjugate (black bars) was significantly more effective than 100,000 IU of Proleukin (black bars). In most cases, 300 IU of the immunoconjugates (dark grey bars) were equivalent to 100,000 IU of Proleukin, and 60 IU of the immunoconjugates (light grey bars) were equivalent to 20,000 IU of Proleukin (light grey bars). In all treatment groups the data are shown as the mean±SD.

Pharmacokinetic Properties in Cynomolgus Monkeys

Figure 25:
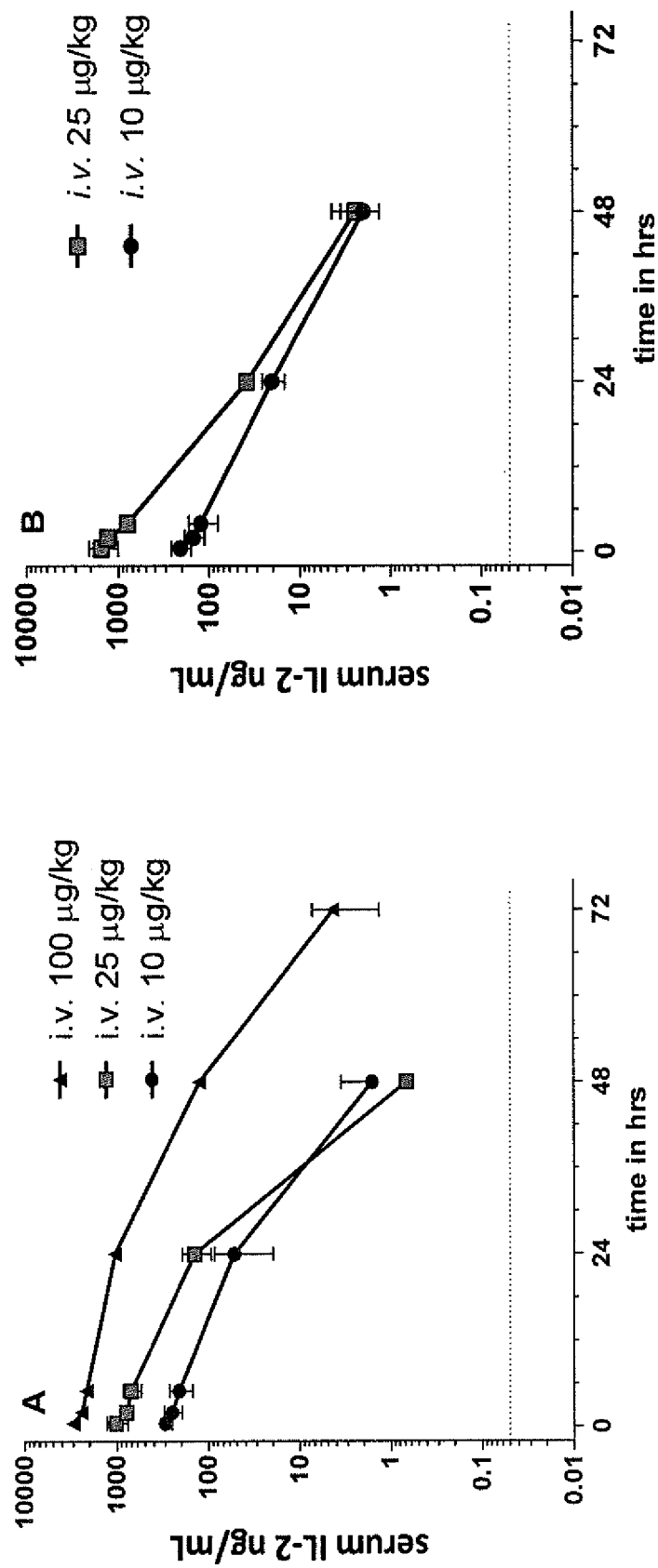
FIG. 25A-B. The PK properties of DP47GS IgG-IL-2 and DP47GS IgG-(IL-2)$_2$ were assessed in normal healthy adult biologic-naïve cynomolgus monkeys.

Prior to performing functional studies in nonhuman primates, the pharmacokinetic (PK) properties of IL-2 immunoconjugates were evaluated in biologic-naïve healthy adult cynomolgus monkeys (FIG. 25). Monkeys (n=2/dose) were injected intravenously (i.v.) with a short bolus of sterile DP47GS IgG-IL-2 or DP47GS IgG-(IL-2)$_2$ in PBS containing 0.5% cynomolgus serum and bled at various times after injection, ranging from 30 minutes to 72 hours. Human IL-2 was assessed in the cynomolgus serum samples using mouse anti-human IL-2 mAb (BD Pharmingen, Catalog #555051, clone 5344.111) to coat 96-well plates in order to capture the human IL-2. Human IL-2 was then detected using biotinylated mouse anti-human IL-2 mAb (BD Pharmingen, Catalog #555040, clone B33-2). IL-2 binding was visualized and quantified using Europium-conjugated streptavidin. The level of detection using cynomolgus serum in the assay was 0.05 ng/mL of IL-2 (dotted line in the figures). Cynomolgus serum taken prior to treatment had no detectable IL-2 (therefore □ 0.05 ng/mL).

IL-2 was detected in cynomolgus serum from 30 minutes to 48 hours after i.v. injection with all doses of DP47GS IgG-IL-2 (FIG. 25A) and DP47GS IgG-(IL-2)$_2$ (FIG. 25B). By 72 hours, serum levels of IL-2 were below the limit of detection (0.05 ng/mL, dotted line) for all animals treated with 10 and 25 μg/kg of DP47GS IgG-IL-2 or DP47GS IgG-(IL-2)$_2$. After doses of 100 μg/kg of DP47GS IgG-IL-2 detectable serum IL-2 was still present at 72 hours.

Induction of Treg Number in Cynomolgus Monkeys

Figure 26:
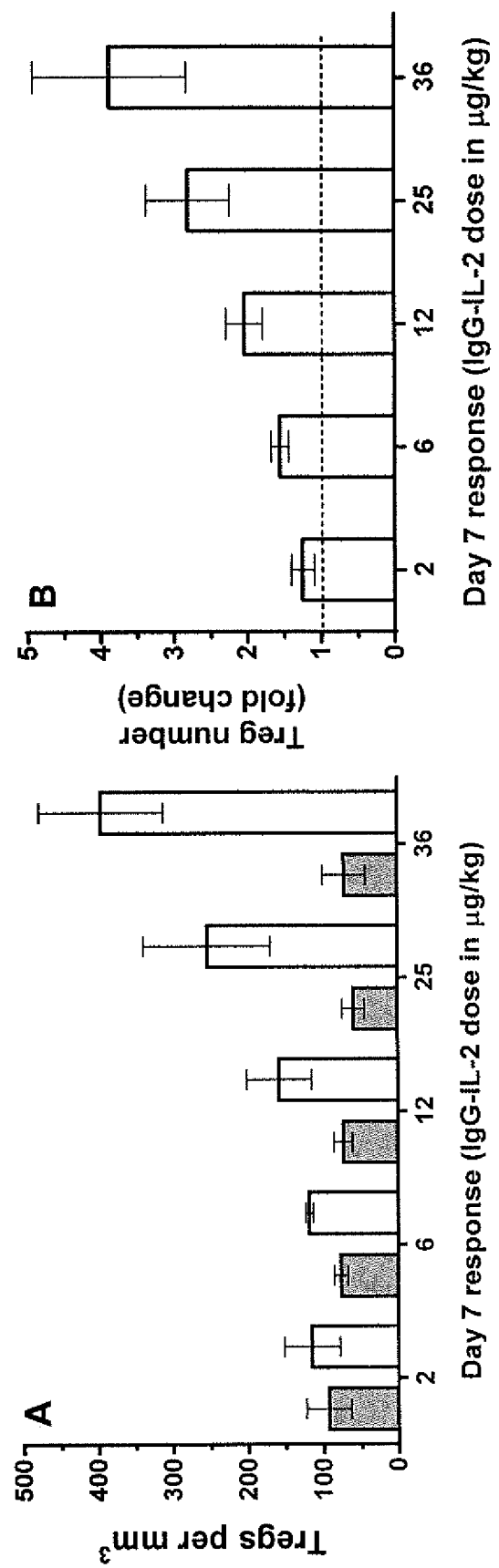
FIG. 26A-B. DP47GS IgG-IL2 has a dose dependent effect in cynomolgus monkeys increasing regulatory T cells. The changes in whole blood CD4+CD25+FOXP3+ regulatory T cells (Tregs) on day 7 post treatment are shown as FIG. 26A the absolute cell number of Tregs per mm$^3$ of whole blood and FIG. 26B the fold change in Tregs. All data are represented as the mean±SD. Open bars: DP47GS IgG-IL-2 (n=6); shaded bars: vehicle (n=3).

Cynomolgus animals treated in vivo with DP47GS IgG-IL-2 had dose-dependent increases in the absolute number of Tregs as well as the fold increase above baseline 7 days post dosing (FIGS. 26A and 26B, respectively). Normal healthy cynomolgus monkeys of both sexes at ages ranging from 3 to 6 years were used in all tests and no animal was used more than once. While under anesthesia, various doses of DP47GS IgG-IL-2 (n=4-6) or vehicle (n=3) were injected SC on the lateral dorsum. Individual doses of DP47GS IgG-IL-2 were based on body weight and formulated for injection in a vehicle of sterile PBS pH 7.2 containing 0.5% sterile normal cynomolgus serum. Blood samples were collected at various times post treatment and tested for hematological changes (CBC and Differential) with an Advia Automated Hematology Analyzer as well as cell surface and intracellular markers detailed above (experimental procedures for Table 4). The changes in whole blood CD4$^+$CD25$^+$FOXP3$^+$, regulatory T cells on day 7 post treatment are shown in FIG. 26 as the absolute cell number per mm$^3$ of whole blood (FIG. 26A) and the fold change in Tregs (FIG. 26B); all data are represented as the mean±SD. At the higher doses of 25 µg/kg and 36 µg/kg DP47GS IgG-IL-2, average Treg increases of nearly 3-fold (range of 111-255%, n=6) and 4-fold (range of 110-470%, n=6), respectively, were observed. Further reduction of the SC dose of DP47GS IgG-IL-2 (12, 6, and 2 µg/kg) continued to produce correspondingly reduced changes in Treg number and fold change. Without wishing to be bound by theory, the ~2-fold increase in Tregs (ranging from 67-133%, n=6) with the 12 µg/kg DP47GS IgG-IL2 dose may represent the desirable increase in Tregs for some autoimmune and inflammatory diseases. There is a large range in the numbers of Tregs in humans (20-90 Tregs per mm$^3$ of blood; 4 to 10% of CD4$^+$ T cells) and it is reasonable to assume that an increase of Tregs induced by IL-2 within an individual will result in an overall increase in functional suppression.

Figure 27:
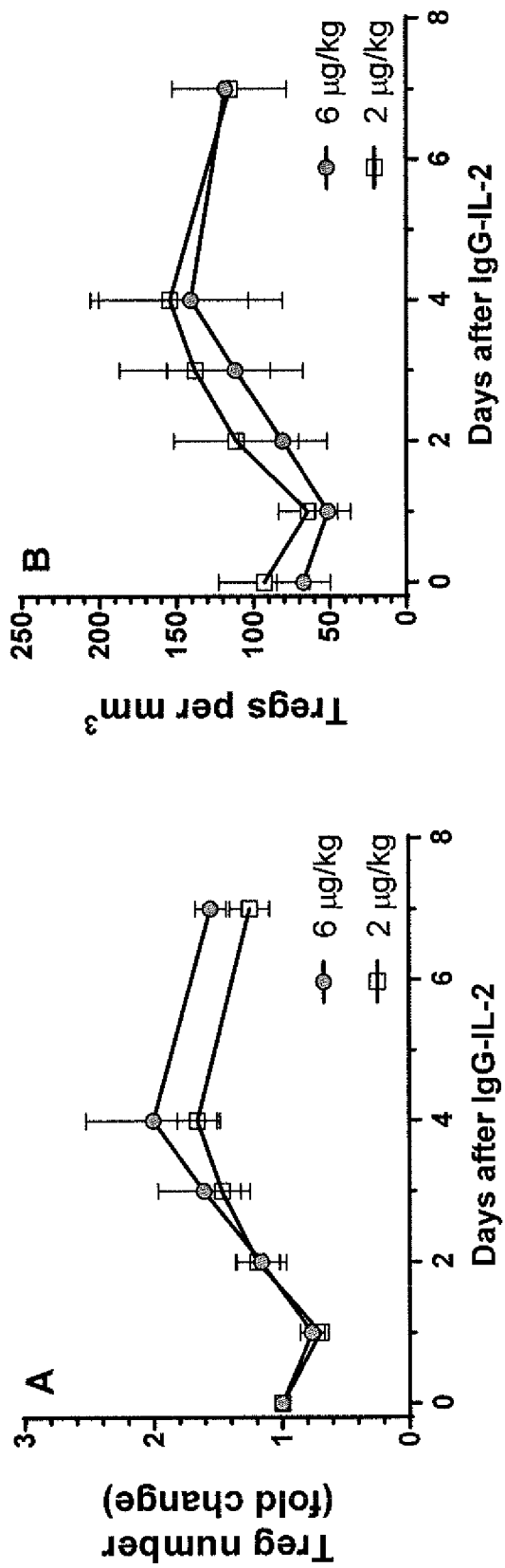
FIG. 27A-B. Time and low dose effects of DP47GS IgG-IL-2 on Tregs in cynomolgus monkeys.

When the lower doses of DP47GS IgG-IL-2 were evaluated (2-6 µg/kg), more frequent blood samples were collected to identify optimal times for detecting changes in Tregs subsequent to DP47GS IgG-IL-2 administration (FIG. 27). While changes in Tregs were present at 7 days, maximal stimulation occurred on day 4, sooner than was measured with the higher doses of DP47GS IgG-IL-2 (day 7, FIG. 26).

Figure 28:
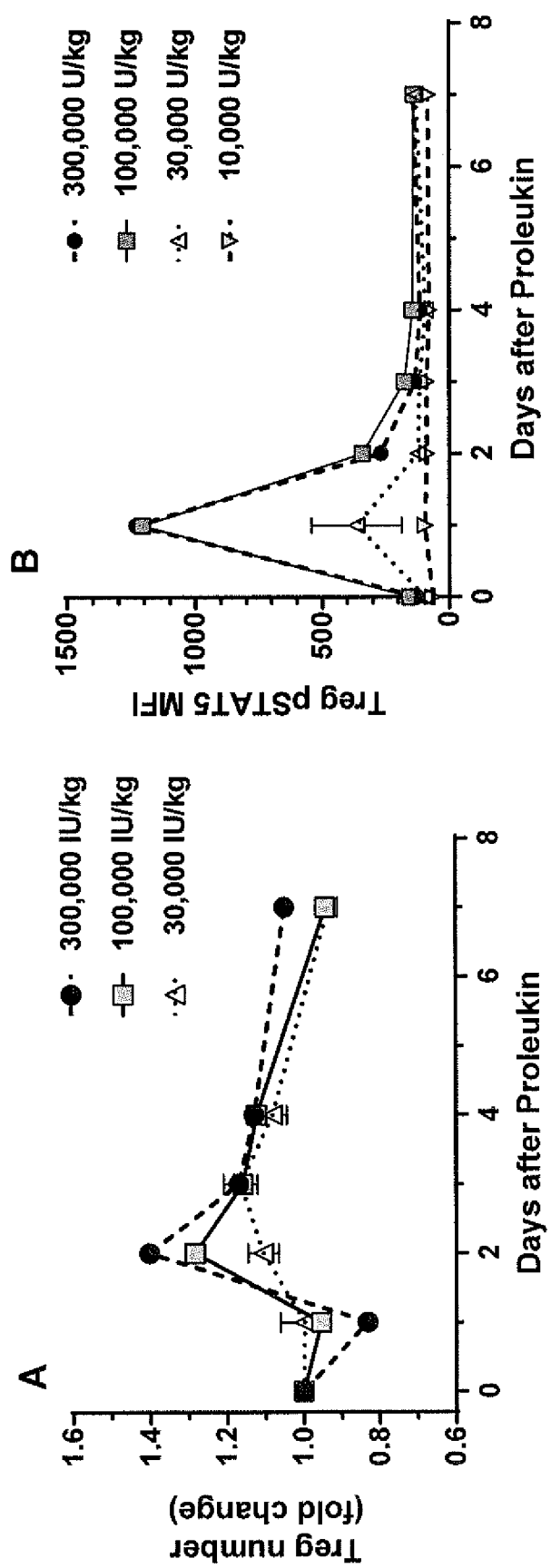
FIG. 28A-B. Single dose Proleukin stimulates a transient dose dependent Treg response in cynomolgus monkeys.

Proleukin and DP47GS IgG-IL-2 are comparable in vitro in human and cynomolgus whole blood assays when compared directly by the units of IL-2 activity used to stimulate pSTAT5a in Tregs and other IL-2 responsive cells (data not shown). With the known short half-life of Proleukin in humans, a single dose study was done in cynomolgus monkeys to assess in vivo Treg induction and activation. Proleukin produced a dose and time dependent change in Tregs measured by fold change in absolute numbers as well as pSTAT5a activation. While the increase in Treg numbers was nominal (FIG. 28A: 10-40%), the Proleukin®-induced increase in Treg pSTAT5a was substantial and dose dependent one day after treatment (FIG. 28B) but of short in vivo duration returning to normal by day 2 to 3.

Figure 29:
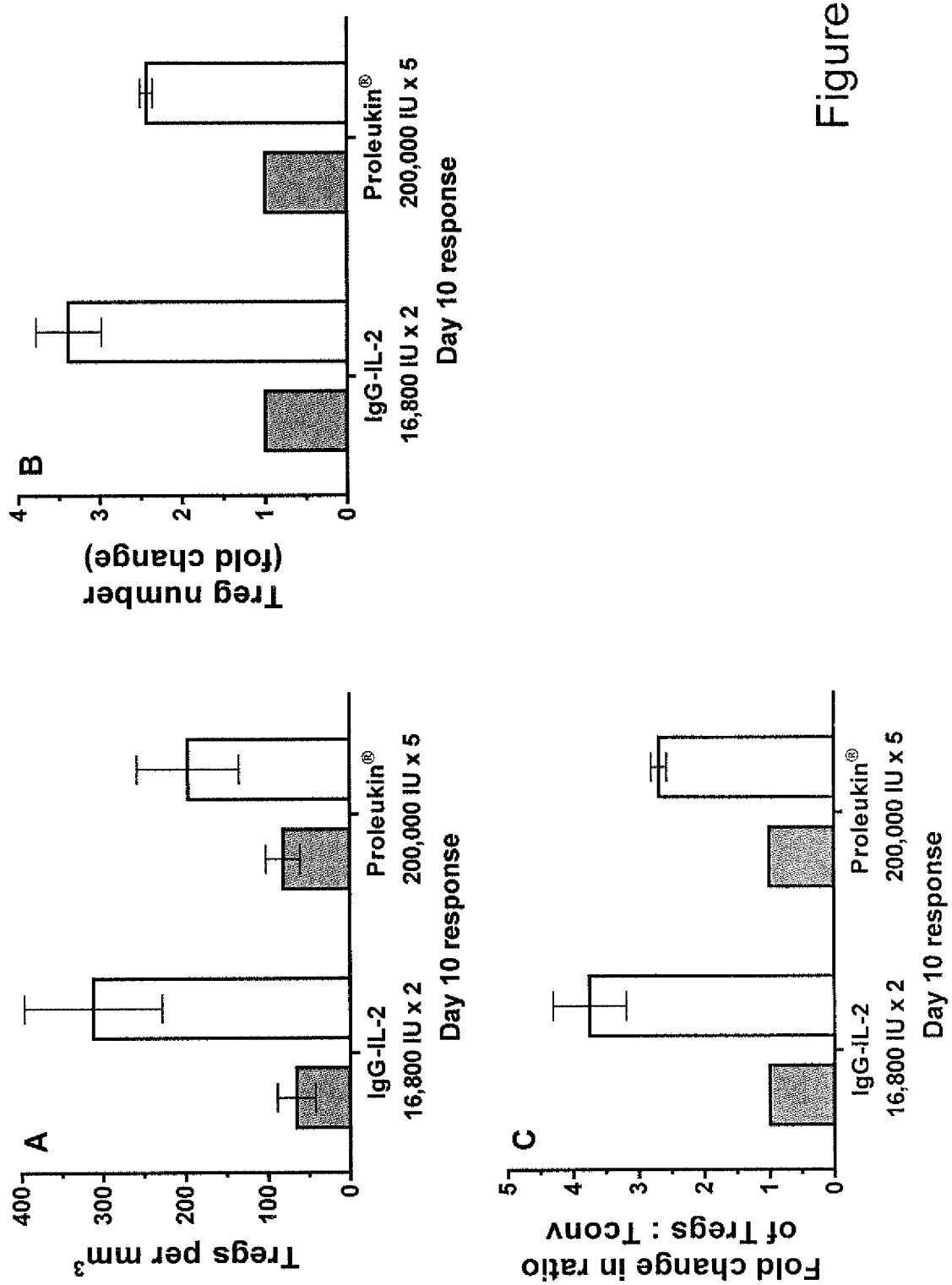
FIG. 29A-C. Low dose DP47GS IgG-IL-2 is more effective than high dose Proleukin® in Treg induction in cynomolgus monkeys. Normal healthy cynomolgus monkeys (groups of n=5) were treated with low dose DP47GS IgG-IL-2 or high dose Proleukin and the change in regulatory T cells tested at day 10. On days 0 and 7, DP47GS IgG-IL-2 was given SC at a dose of 16,800 IU/kg (12 µg/kg). Proleukin treatment (200,000 IU/kg) was given SC 3 times per week (MWF) for a total of 5 doses. The results are shown as mean±SD for FIG. 29A the change in total Tregs per mm$^3$ blood, FIG. 29B the fold increase in Tregs, and FIG. 29C the change in the ratio of Tregs to conventional CD4+FOXP3− cells. Open bars depict IL-2 treatment and shaded bars the vehicle control.

A comparison of the ability of DP47GS IgG-IL-2 to induce an increase in Tregs in vivo in cynomolgus monkeys with that of Proleukin is shown in FIG. 29. Normal healthy cynomolgus monkeys (groups of n=5) were treated with low doses of DP47GS IgG-IL-2 or high doses of Proleukin and the change in regulatory T cells tested at day 10. On days 0 and 7, DP47 IgG-IL-2 was given SC at a dose of 16,800 IU/kg (the 12 µg/kg dose shown in FIG. 26). Based on published work where Proleukin was given to type 1 diabetes patients (4.5×10$^6$ IU/person, 3 times/week) and shown to increase Tregs and the single dose data in FIG. 28, Proleukin was given SC 3 times per week (M/W/F) for a total of 5 doses each at 200,000 IU/kg (the cynomolgus equivalent of 4.5×10$^6$ IU/person). The results are shown in FIG. 29 as mean±SD for the change in total Tregs per mm$^3$ blood (FIG. 29A), the fold increase in number of Tregs (FIG. 29B), and the change in the ratio of Tregs to conventional CD4$^+$ FOXP3$^-$ cells (FIG. 29C).

Although nearly 30-fold less DP47GS IgG-IL-2 activity was administered over the 10 day period, DP47GS IgG-IL-2 induced a larger increase in the number of Tregs than Proleukin (FIG. 29A, p=0.06). The fold increase of Treg numbers above baseline (FIG. 29B) and the increase of Tregs relative to conventional CD4 T cells (FIG. 29C) were also larger (p=0.0011 and p=0.016, respectively) in monkeys dosed with DP47GS IgG-IL-2 as compared to Proleukin. In humans the ratio of CD4$^+$ regulatory T cells (usually defined as FOXP3$^+$ and a combination of surface markers) to non-regulatory CD4 T cells (referred to as conventional or effector cells) is often used to define the functional levels of Tregs in patients through time.

In Vivo Response of Cynomolgus Peripheral Blood Cell Subsets to Low Dose DP47GS IgG-IL-2 Treatment The in vivo cellular specificity of low dose IL-2 treatment is a critical parameter. We have determined that in vivo cell activation induced by DP47GS IgG-IL-2 or Proleukin can be sensitively monitored by measuring pSTAT5a levels ex vivo in blood taken at various times after dosing cynomolgus monkeys or mice. The in vivo response of all cell populations that can be monitored in vitro (FIGS. 8-10) can also be examined ex vivo.

Figure 30:
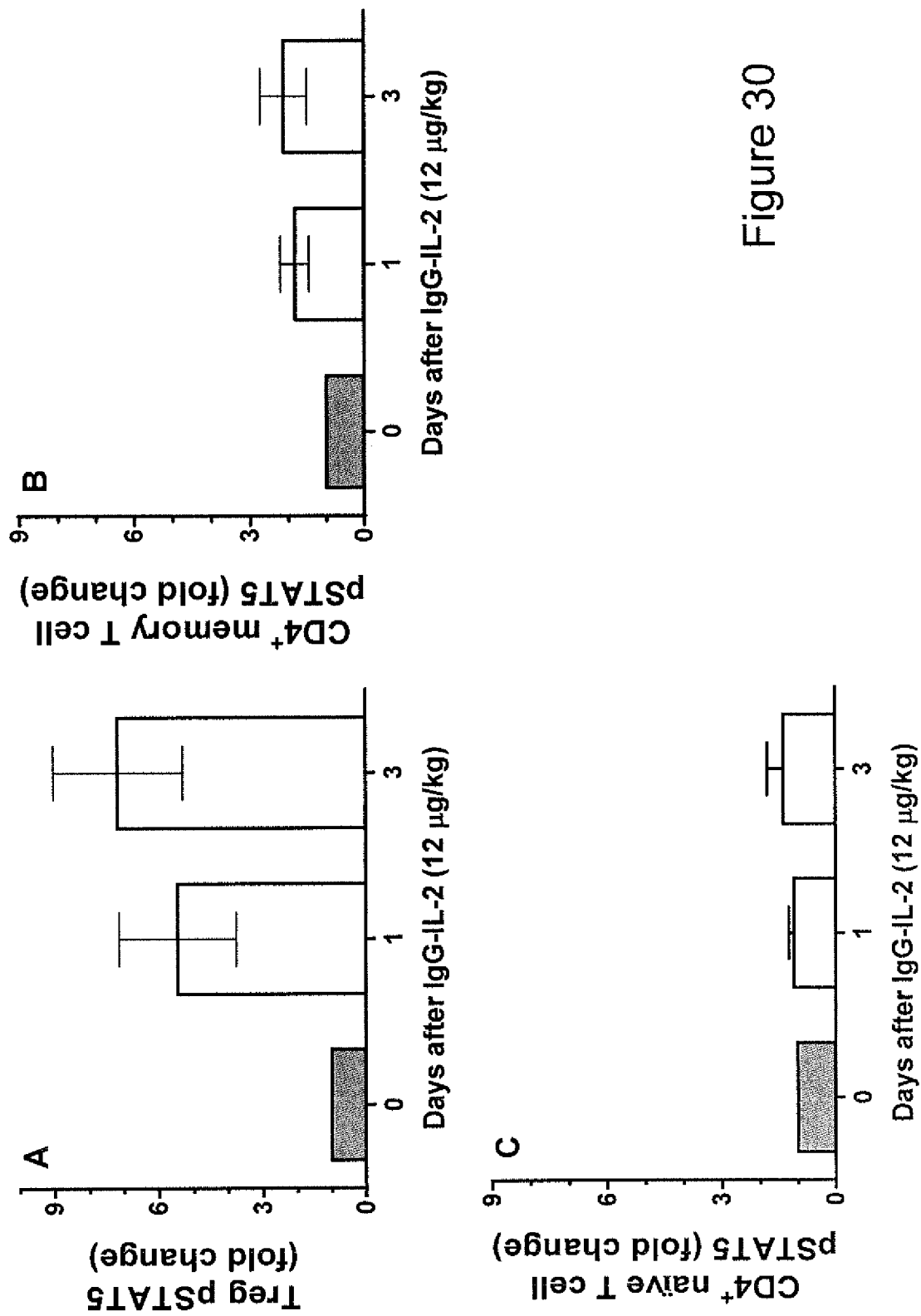
FIG. 30A-C. Ex vivo whole blood phosphorylated STAT5 as a sensitive biomarker for DP47GS IgG-IL-2 Treg activation in vivo. One and 3 days after in vivo administration of a single low dose of DP47GS IgG-IL-2 (12 µg/kg) to healthy cynomolgus monkeys (n=5), whole blood was collected and tested immediately without stimulation for phosphorylated STAT5 (pSTAT5a). Each monkey was bled on day 0 before treatment and the amount of pSTAT5a was measured (shaded bars) and used individually to assess the fold-changes post treatment (open bars).

One and 3 days after in vivo administration of a single low dose of DP47GS IgG-IL-2 (12 µg/kg) to healthy cynomolgus monkeys (n=5), whole blood was collected and tested for STAT5a phosphorylation as described above (experimental procedures to Table 4). Each monkey was bled on day 0 before treatment and the amount of STAT5a phosphorylation was measured and used individually to assess fold-changes post treatment. The fold change in pSTAT5a in Tregs on days 1 and 3 is shown in FIG. 30A, the fold change in pSTAT5a in conventional CD4$^+$CD45RA$^-$ memory T effector cells in FIG. 30B, and the fold change in pSTAT5a in conventional CD4$^+$CD45RA$^+$ naïve T effector cells is in FIG. 30C. The results clearly show that cynomolgus blood obtained one and three days after a single low dose (12 µg/kg) of DP47GS IgG-IL-2 showed preferential pSTAT5a increases in Treg cells as compared to memory and naïve CD4$^+$ T cells (FIG. 30A-C). Single low dose DP47GS IgG-IL-2 was clearly superior to single high dose Proleukin (FIG. 28B) in producing a sustained in vivo Treg state of activation.

Figure 31:
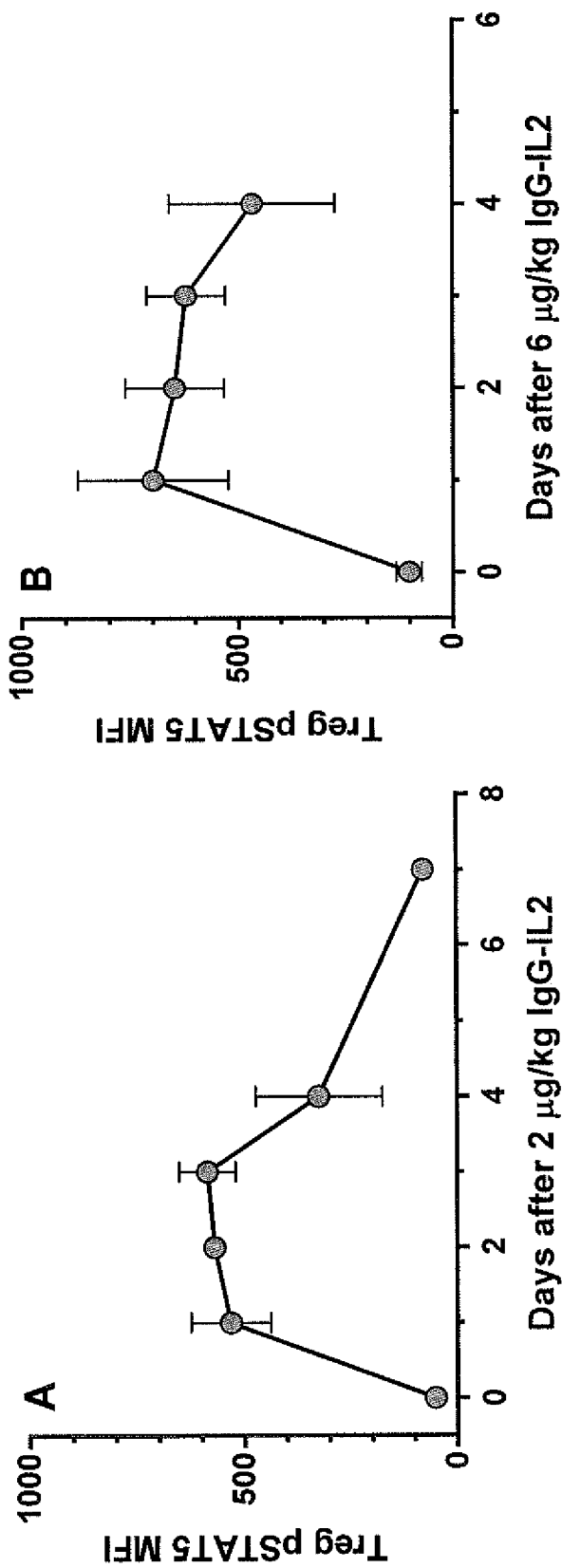
FIG. 31A-B. Ex vivo whole blood pSTAT5a as a sensitive biomarker for low dose DP47GS IgG-IL-2 Treg activation in vivo. From one to seven days after in vivo administration of a single low dose of DP47GS IgG-IL-2 to healthy cynomolgus monkeys, whole blood was collected and tested immediately without stimulation for pSTAT5a. Each monkey was bled on day 0 before treatment for unstimulated levels of pSTAT5a and compared to changes in pSTAT5a post-treatment.
Figure 32:
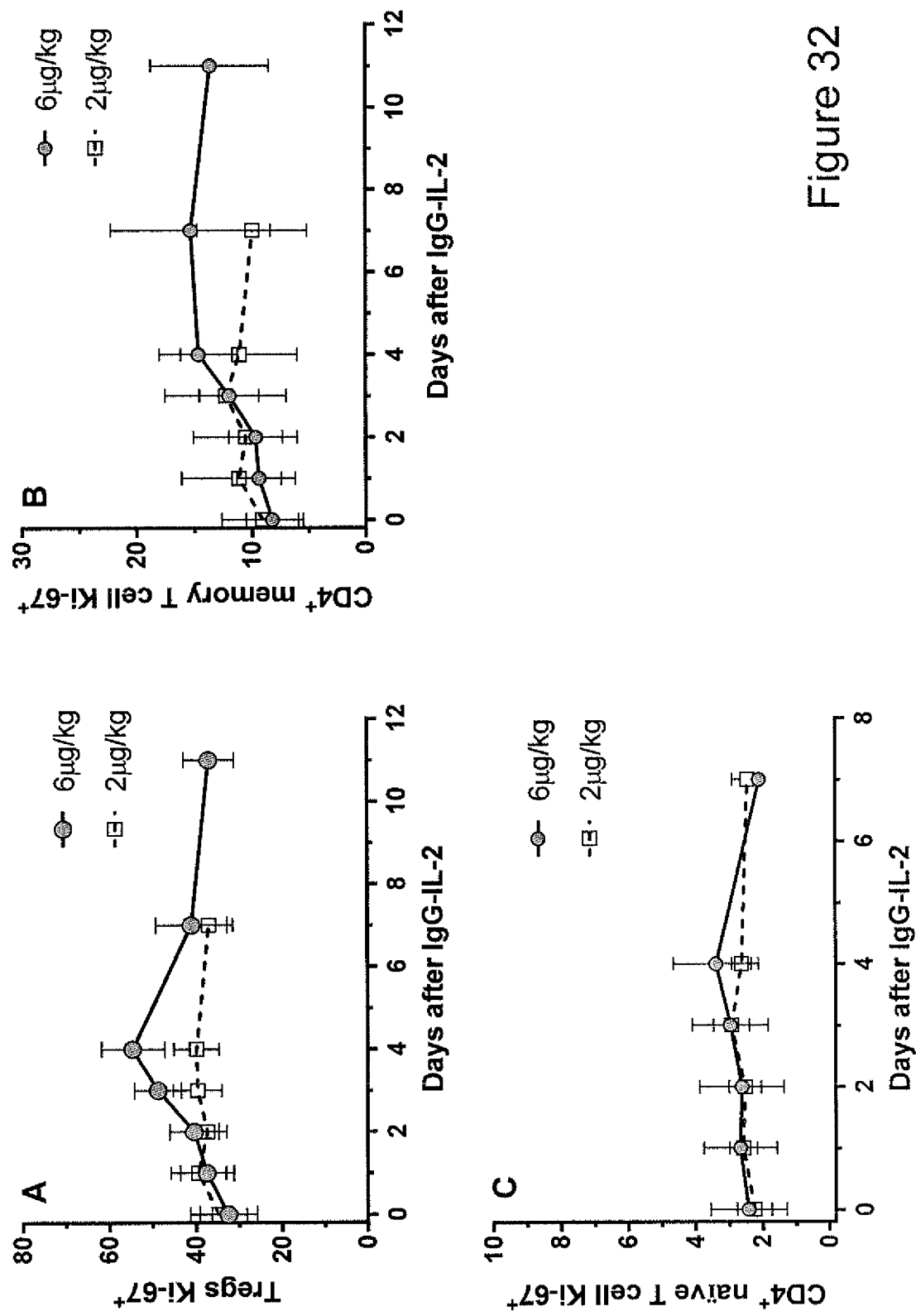
FIG. 32A-C Ex vivo cynomolgus whole blood Ki-67 serves as a marker for DP47GS IgG-IL-2 induced T cell proliferation in vivo. The cynomolgus monkeys treated with 2 and 6 µg/kg of DP47GS IgG-IL-2 as described in FIG. 14 were also monitored ex vivo for changes in the intracellular marker Ki-67 to assess the extent of proliferation in vivo. The normal steady state percentage of cells in cell cycle ($Ki-67^+$) were quantified on day 0 prior to treatment and then monitored daily for the next 7 to 11 days.

The initial studies using phosphorylation of STAT5a as an in vivo biomarker of Treg activation saw maximal pSTAT5a only at 1 day with single dose Proleukin (FIG. 28B) and 1 and 3 days with low dose (12 µg/kg) DP47GS IgG-IL-2 (FIG. 30A). Further titration of DP47GS IgG-IL-2 combined with additional sampling times showed that in vivo pSTAT5a signals could be maintained for 4 days before dropping back to normal at 7 days (FIGS. 31A, 31B). The MFI (mean fluorescence intensity) of the pSTAT5a signals for both the 2 µg/kg (31A, n=4) and 6 µg/kg (31B, n=6) dose suggested that less than maximal pSTAT5a signaling occurred (see FIG. 33B). Even these very low doses of DP47GS IgG-IL-2 provided sustained in vivo signaling of Tregs and were superior to Proleukin (FIG. 28B). These results support our hypothesis that very low levels of long-lived IL-2, i.e. DP47GS IgG-IL-2 but not Proleukin, can stimulate Tregs for extended periods of time in vivo thereby reducing the frequency of treatment needed to re-establish dominant self-tolerance and improve disease outcomes. The increase in Treg cells in peripheral blood after low dose IL-2 treatment could reflect a change in the distribution of the cells in the body rather than an actual increase of the cells. To substantiate that Treg increases in vivo are at least in part due to the induction of cell division by IL-2 treatment, the intracellular marker of proliferation Ki-67 was assessed. Ki-67 is a protein that can be detected in the nucleus during $G_1$, S, $G_2$, and mitosis but is absent from resting cells that are in the $G_0$ phase of the cell cycle. The cynomolgus monkeys treated with 2 and 6 µg/kg DP47GS IgG-IL-2 described above (FIG. 31) were also monitored for ex vivo changes in the intracellular marker Ki-67 as described (experimental procedures to Table 4) to assess the extent of proliferation in vivo. The percentage of cells that were in cell cycle (Ki-67$^+$) on day 0 was compared to the percentage of cells Ki-67$^+$ at 1 to 11 days post treatment. Ki-67$^+$ Tregs are shown in FIG. 32A, conventional CD4$^+$CDRA45$^-$ memory T effector cells are in FIG. 32B, and conventional CD4$^+$CD45RA$^+$ naïve T effector cells are in FIG. 32C. Cynomolgus blood cells obtained one to seven days after a single low dose of DP47GS IgG-IL-2 (6 µg/kg) showed preferential Ki-67 increases in Tregs compared to conventional CD4$^+$ naïve T effector cells (FIG. 32A versus 32C). Unlike naïve T effector cells, DP47GS IgG-IL-2 (6 µg/kg) was able to stimulate proliferation of conventional memory CD4$^+$ T effector cells (FIG. 32B). At the lowest dose of DP47GS IgG-IL-2 (2 µg/kg), there was minimal activation into cell cycle and proliferation compared to the 6 µg/kg dose.

In human and cynomolgus whole blood assays the in vitro activity of bivalent DP47GS IgG-(IL-2)$_2$ was in aggregate, approximately 6-fold more potent on Tregs than monovalent DP47GS IgG-IL-2 (Tables 2 and 4). Hence, the first dose into cynomolgus monkeys was 6-fold less than the highest dose of DP47GS IgG-IL-2 tested (36 µg/kg). DP47GS IgG-(IL-2)$_2$ administered at 6 µg/kg (n=4) produced large increases in circulating Tregs (FIG. 33A) that remained well above normal 14 days after treatment, significant and prolonged pSTAT5a in Tregs that returned to normal at 1 week (FIG. 33B), and nearly a 3 fold increase in the number of Tregs (FIG. 33C). The fold changes induced by DP47GS IgG-IL-2 (from FIG. 26, open bars) were compared to the 6 µg/kg dose of bivalent DP47GS IgG-(IL-2)$_2$ (shaded bar) (FIG. 33D). Similar to the human and cynomolgus whole blood assays, DP47GS IgG-(IL-2)$_2$ exhibited enhanced in vivo potency beyond its 2 fold increase in IL-2 per molecule of IgG.

Figure 34:
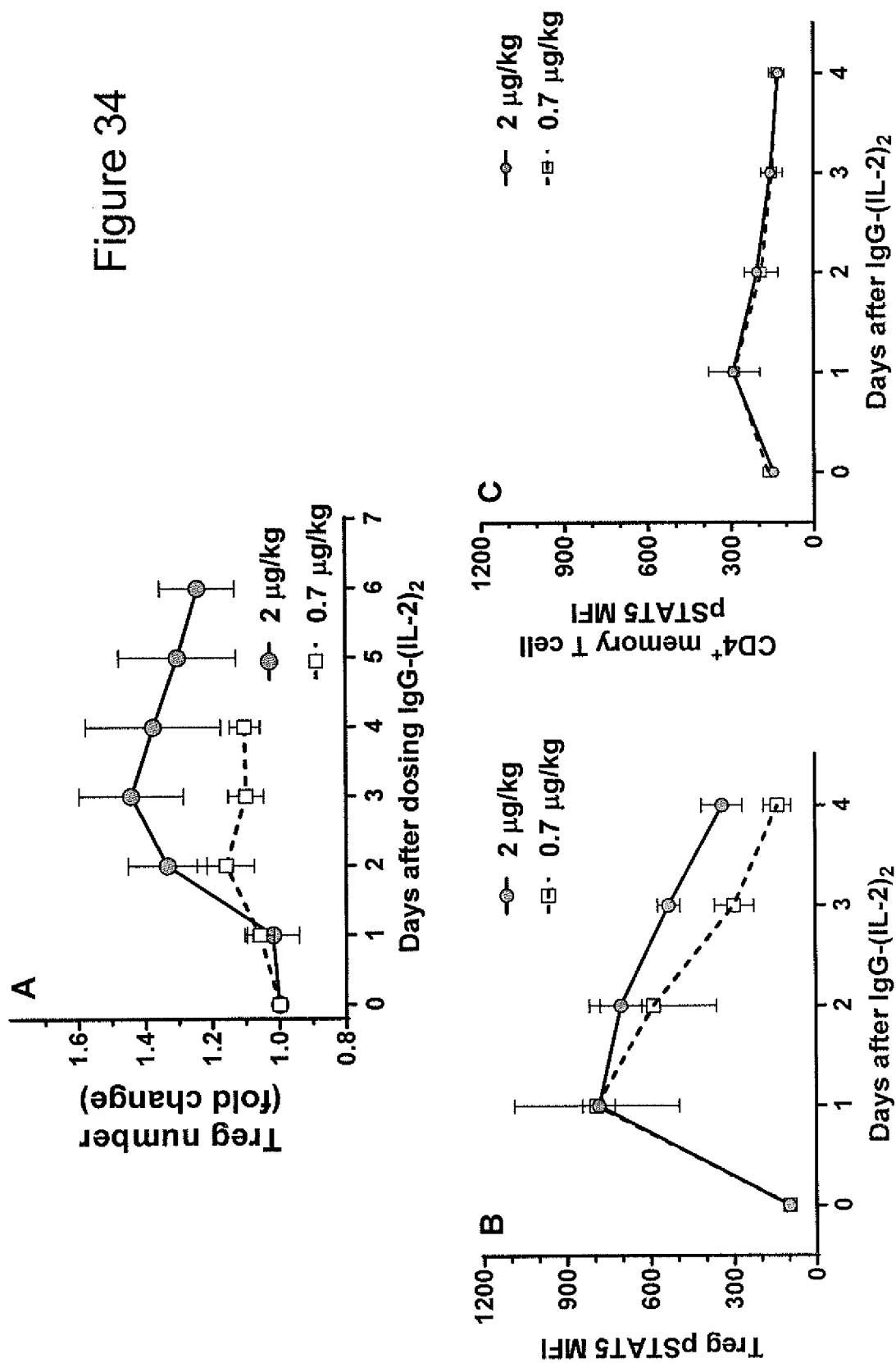
FIG. 34A-C. Time and dose dependent effects of very low dose DP47GS IgG-$(IL-2)_2$ on Tregs in naïve healthy cynomolgus monkeys.

Additional doses of bivalent DP47GS IgG-(IL-2)$_2$ were given to cynomolgus monkeys to assess its in vivo effects at very low doses (2 and 0.7 µg/kg) (FIG. 34). While 2 µg/kg produced moderate fold changes (mean of 46%, ranging from 20 to 70%, n=8), the 0.7 µg/kg dose had little effect on T cell numbers (mean increase of 16%, n=3) (FIG. 34A). Both low doses stimulated pSTAT5a increases in Treg (FIG. 34B, n=3 each) while having little effect on Teff/mem cell pSTAT5a (FIG. 34C, n=3 each).

Figure 35:
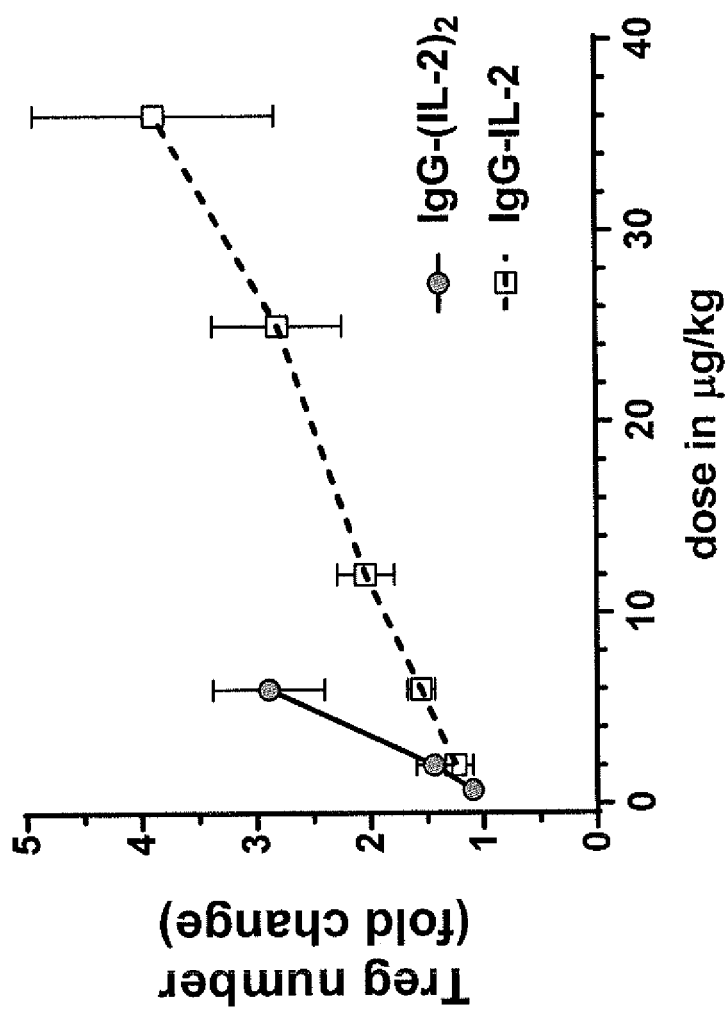
FIG. 35. Dose dependent comparison of DP47GS IgG-IL-2 versus DP47GS IgG-$(IL-2)_2$ and their ability to increase whole blood cynomolgus Tregs. All data are presented as the mean±SD (n=3 to 6).

The overarching effects of monovalent and bivalent wild type IL-2 fusion protein therapy and its ability to increase Tregs in cynomolgus monkeys are presented in FIG. 35. Both forms of long-lived IgG-IL-2 are potent inducers of Tregs which can be followed in vivo with pSTAT5a as a biomarker of activation and in this figure as the fold increase in the numbers of circulating Tregs. DP47GS IgG-(IL-2)$_2$ with its enhanced potency achieved by doubling the IL-2 molecules at the C-terminus of IgG has a dose dependent superiority over DP47GS IgG-IL-2.

DNA Demethylation of FOXP3 and CTLA-4 in Cynomolgus T Cell Subsets.

Functionally active Tregs are able to produce the immunosuppressive cytokines CTLA-4, IL-10 and TGFβ and require the stable expression of the transcription factor FOXP3. Expression of FOXP3 in human and cynomolgus Tregs depends on demethylation of the ten CpG DNA methylation sites in the Treg specific demethylated region (TSDR) within the FOXP3 locus. Likewise, expression and production of CTLA-4 relies on demethylation of the seven CpG DNA methylation sites in the human and cynomolgus CTLA-4 locus. Accordingly we assessed the demethylation status of both FOXP3 and CTLA-4 in various CD4$^+$ T cell subsets before and after treatment with DP47GS IgG-IL-2 (n=4, 25 µg/kg s.c.) and DP47GS IgG-(IL-2)$_2$ (n=4, 6 µg/kg s.c.) given at doses and times previously shown to significantly increase the number of Tregs in blood. Only biologic-naïve adult male cynomolgus monkeys were used in the study and their weights ranged from 9.1 to 10.9 kg. Treatments were administered 3 weeks after the initial baseline blood collection and post-treatment blood was collected 4-5 days later. PBMCs from 30 mL of heparinized blood were sorted using a FACSAria™ (Becton Dickinson) into the relevant CD4$^+$ subsets including Tregs (CD4$^+$CD25$^+$CD127$^{low}$), memory T effectors (CD4$^+$CD45RA$^-$), naïve T effectors (CD4$^+$CD45RA$^+$), and CD4$^+$CD25$^-$CD127$^-$ cells.

Sorted cell subsets were frozen in aliquots of 100,000 cells and stored as dry pellets at –80° C. to allow processing of all samples together. Cell pellets were thawed and DNA was extracted and bisulfite treated in a single step using Epitect Fast Lyse All kit (Qiagen) following the manufacturer's instructions. 5 ng (in 2 µl) of bisulfite DNA was used in a 20 µl first round duplex PCR containing 10 µl Multiplex PCR kit (Qiagen), 6 µl water, 0.5 µl FOXP3 forward primer tgtaaaacgacggccagtTTTAGAAGTTGTATGGGGGATGTT (SEQ ID NO: 54), 0.5 µl FOXP3 reverse primer caggaaacagctatgaccAAAATATCTACCCTCTTCTCTTCCTC (SEQ ID NO: 55), 0.5 µl CTLA-4 forward primer tgtaaaacgacggccagtGGGTTTGGTTATGAAGGAGTA TGA (SEQ ID NO: 56) and 0.5 µl CTLA-4 reverse primer caggaaacagctatgaccTTCACT TAATTTCCACTAAAAATACCC (SEQ ID NO: 57). First round PCR cycling was 95° C. for 15 minutes followed by 20 cycles of 95° C. for 30 seconds, 60° C. for 90 seconds and 72° C. for 60 seconds, followed by 10 minutes at 72° C. PCR product was purified using AMPure XP beads (Becton Coulter) according to manufacturer's instructions, and eluted in 20 µl of water. A second round PCR was performed that added a unique index sequence to the beginning of each sample, through a 15 µl PCR containing 7.5 µl of Multiplex PCR kit (Qiagen), 6.5 µl of first round PCR product and 1 µl of index primer. Second round PCR cycling conditions were 95° C. for 15 minutes followed by 7 cycles of 95° C. for 30 seconds, 54° C. for 90 seconds and 72° C. for 60 seconds, followed by 5 minutes at 72° C. The PCR products were purified using AMPure XP beads and eluted in 15 µl of water, and 4 µl was used to quantify the amount of PCR product using a Shimadzu MultiNA. Equal molar concentration of each sample was pooled, to make the sequencing library which was quantified using Kapa Illumina library quantification kit. The library was sequenced using an Illumina MiSeq with v3 reagents and 2×300 bp paired end run. The sequenced data was demultiplexed using a bespoke python script and the Cutadapt program was used to remove sequencing adaptors. Forward and reverse reads were merged using FLASH and the sequence of each methylation site was extracted.

Figure 33:
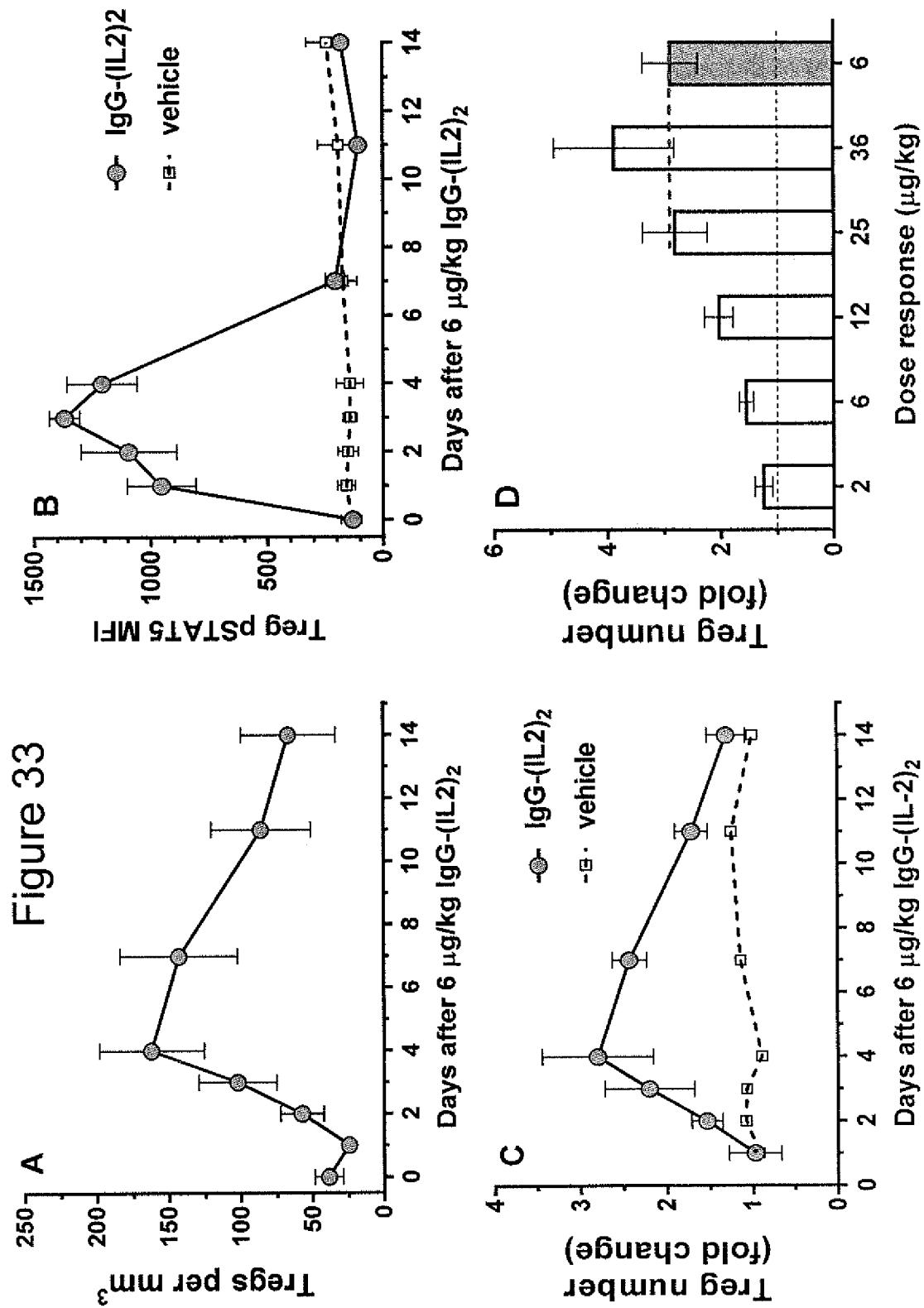
FIG. 33A-D. Time and low dose effects of DP47GS IgG-$(IL-2)_2$ on Tregs in naïve healthy cynomolgus monkeys.
Figure 36:
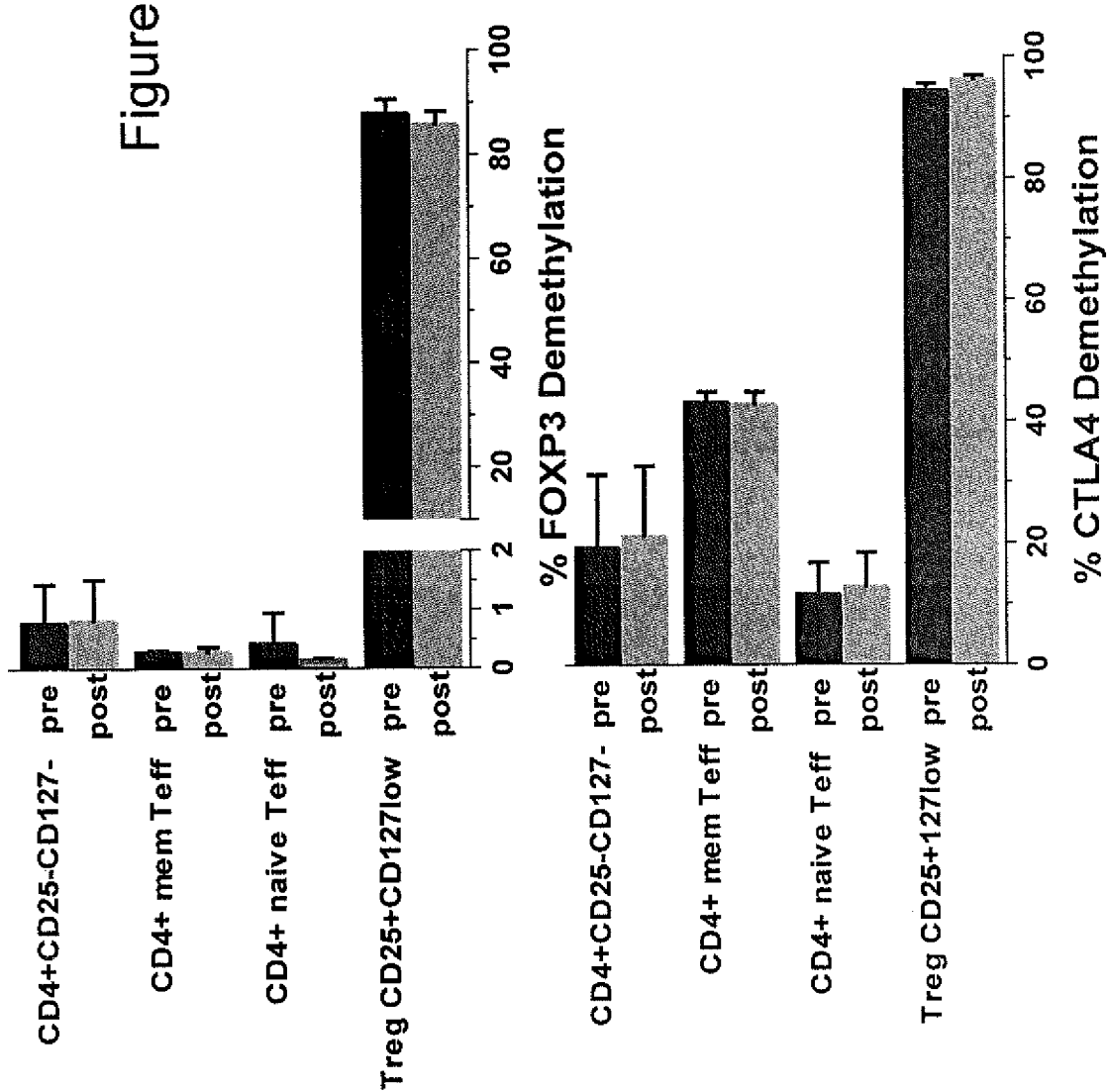
FIG. 36. Next generation sequencing (NGS) was used to analyze T cell subset-specific DNA demethylation for the transcription factor FOXP3 and the immunosuppressive molecule CTLA-4. Blood from adult biologic naïve cynomolgus monkeys were analyzed before and after treatment with an optimal dose of DP47GS IgG-IL-2 (25 µg/kg, n=4) and DP47GS IgG-$(IL-2)_2$ (6 µg/kg, n=4). $CD4^+$ T cell subsets were sorted with a BD FACSAria from whole blood PBMCs and 100,000 cells per subset were used for gene specific DNA demethylation. Similar results were seen with both treatments and data from the DP47GS IgG-$(IL-2)_2$ treated monkeys are shown for FOXP3 in the top panel and for CTLA-4 in the bottom panel (n=4, mean±SD).

Treatment of cynomolgus monkeys with both DP47GS IgG-IL-2 and DP47GS IgG-(IL-2)$_2$ induced substantially increased numbers of Tregs in blood in all animals treated, similar to what was seen before using the same treatment protocol (FIGS. 33 and 35). Importantly the rapid and dramatic increase in Tregs following treatment with both DP47GS IgG-IL-2 and DP47GS IgG-(IL-2)$_2$ did not adversely affect or reduce the demethylation status of FOXP3 (FIG. 36, top panel) or CTLA-4 (FIG. 36, bottom panel). Similar results were seen for both molecules and the data with DP47GS IgG-(IL-2)$_2$ are shown in FIG. 36. That the demethylation status of both FOXP3 and CTLA-4 was unaffected and not reduced by treatment indicates that all of the Tregs maintained their natural mature functional immunosuppressive phenotype despite the substantial increases in absolute numbers. These Treg FOXP3 and CTLA-4 demethylation results in nonhuman primates suggest that treatment with low doses of long-lived IgG-(IL-2)$_2$-like molecules in man should be capable of increasing the numbers of fully functional mature Tregs that in turn will correct the immunoregulatory imbalances present in human autoimmune diseases as well as other chronic immune-mediated chronic inflammatory diseases.

Pharmacokinetics of DP47GS IgG-(IL-2N88D)$_2$ in Cynomolgus Monkeys

Figure 37:
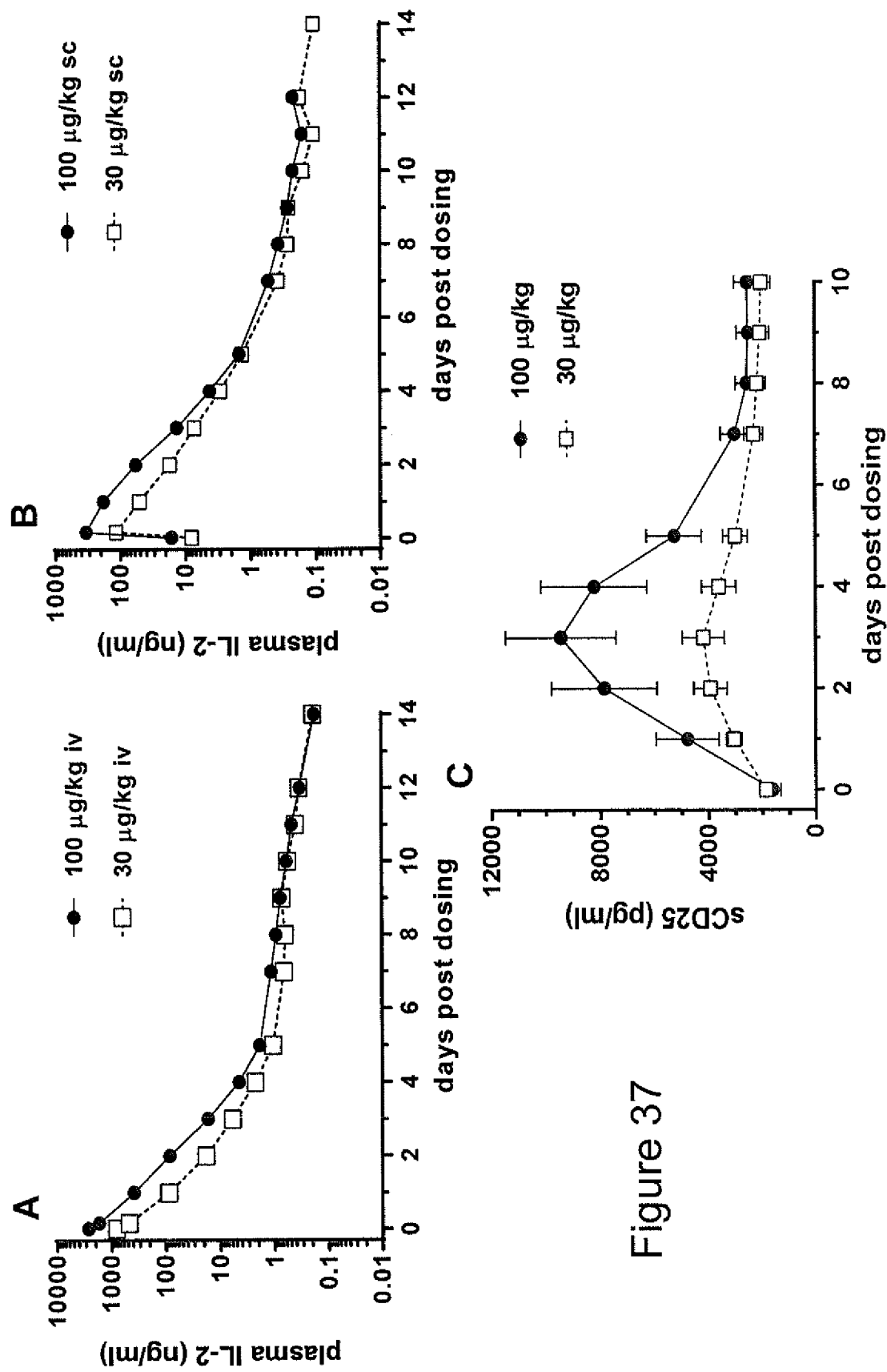
FIG. 37A-C. The PK properties of DP47GS IgG-(IL-$2N88D)_2$ were assessed in normal healthy biologic-naïve cynomolgus monkeys.

The PK properties of DP47GS IgG-(IL-2N88D)$_2$ were evaluated in biologic-naïve cynomolgus monkeys (FIG. 37). Monkeys (n=2/dose) were injected intravenously (iv) and subcutaneously (sc) with 30 or 100 µg/kg of sterile DP47GS IgG-(IL-2N88D)$_2$ in PBS containing 0.5% cynomolgus serum and bled at various times after injection, ranging from 30 minutes to 14 days. Human IL-2 was assessed in the cynomolgus plasma samples as described previously. The level of detection using cynomolgus plasma in the assay was 0.05 ng/mL of IL-2. Cynomolgus plasma taken prior to treatment had no detectable IL-2 (therefore ☐ 0.05 ng/mL).

Unlike the PK of the wild type fusion proteins (FIG. 25) where blood levels could only be detected out to 48 to 72 hours, DP47GS IgG-(IL-2N88D)$_2$ was detected in cynomolgus plasma from all animals at all time points out to 14 days with iv (FIG. 37A) and sc (FIG. 37B) routes of administration. Plasma levels were dose proportional for the first two to three days and displayed an extended half-life compared to the wild type IL-2 fusion molecules.

As a biomarker of IL-2 exposure in vivo, plasma levels of soluble CD25 (sCD25, IL-2RA) were measured (FIG. 37C). Monoclonal antibody reagents for human sCD25 known to cross react with cynomolgus sCD25 were used in a sandwich immunoassay using capture (MAB623, R&D Systems) and biotinylated detection (BAF223, R&D Systems) antibodies using Eu$^{++}$-conjugated streptavidin to detect bound sCD25. Increases in sCD25 after DP47GS IgG-(IL-2N88D)$_2$ administration were dose-dependent and present between 1 to 7 days, returning to normal levels by day 8.

The Induction of Tregs in Cynomolgus Monkeys with DP47GS IgG-(IL-2N88D)$_2$

The previously described tests in cynomolgus treated in vivo with wild type DP47GS IgG-IL-2 and DP47GS IgG-(IL-2)$_2$ presented dose-dependent increases of 2 to 4-fold in the absolute number of Tregs (FIGS. 26 and 33, respectively) that were reflective of their in vitro activities in human whole blood assays, i.e. 6 to 9-fold in vitro differences (Tables 2 and 3). With its loss of in vitro potency in human whole blood (Table 3), in vivo doses of 30 and 100 µg/kg were chosen for DP47GS IgG-(IL-2N88D)$_2$. Similar to previous tests, DP47GS IgG-(IL-2N88D)$_2$ was injected by an iv or sc route with individual doses based on body weight and formulated for injection in a vehicle of sterile PBS pH 7.2 containing 0.5% sterile normal cynomolgus serum per dose and route of injection). Blood samples were collected before treatment (days −4 and −5), immediately before treatment (day 0) and at various times post-treatment (day 1-14) and tested for hematological changes (CBC and Differential) as well as the cell surface and intracellular markers previously described.

Figure 38:
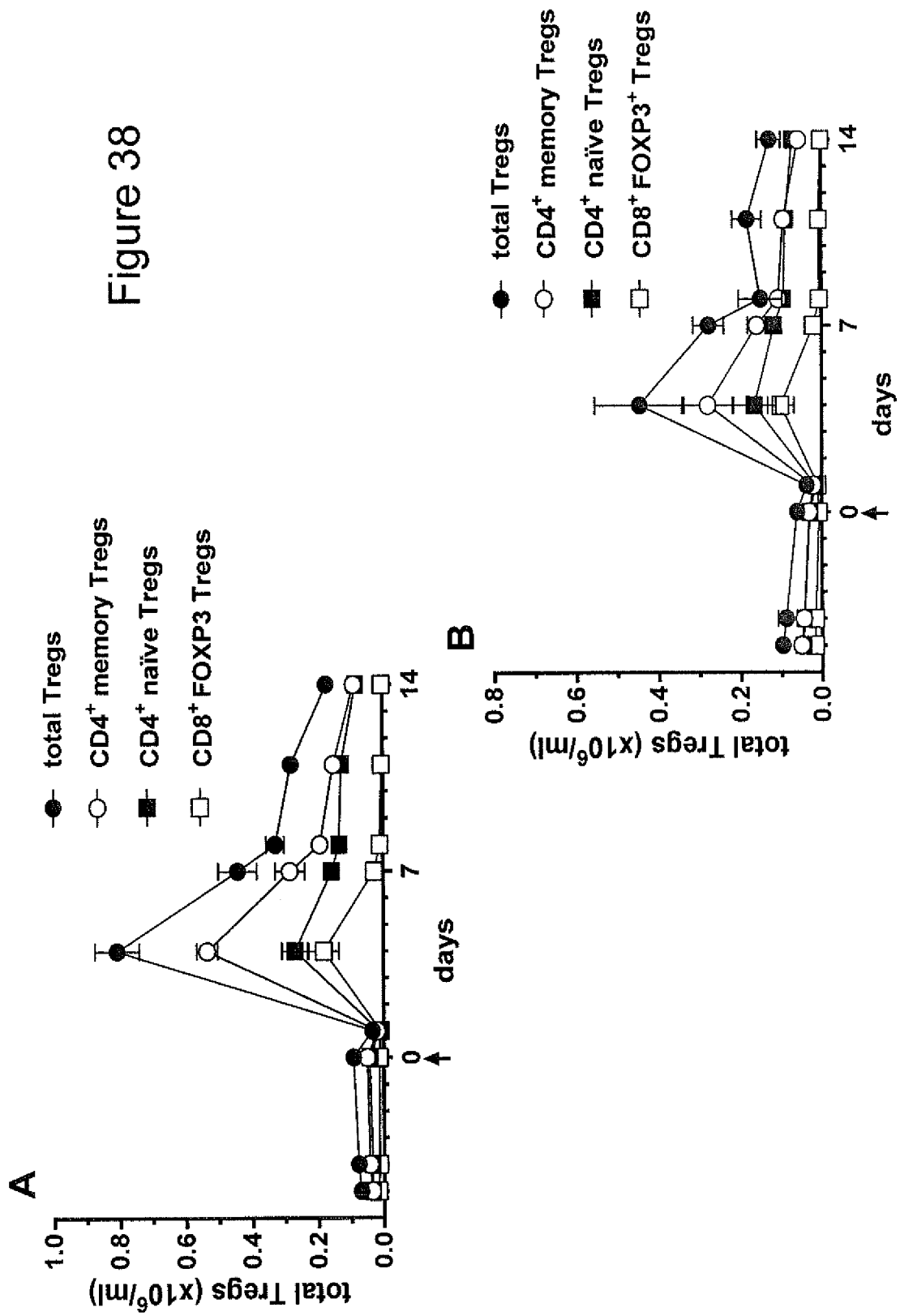
FIG. 38A-D. In vivo time and dose-dependent effects of DP47GS IgG-$(IL-2N88D)_2$ on Tregs in naïve healthy cynomolgus monkeys. Time-dependent changes in the absolute number ($\times 10^6$/ml blood) of total Tregs, $CD4^+$ memory Tregs, $CD4^+$ naïve Tregs and $CD8^+FOXP3^+$ Tregs following injection with FIG. 38A 100 µg/kg DP47 IgG-$(IL-2N88D)_2$ or FIG. 38B 30 µg/kg DP47 IgG-$(IL-2N88D)_2$. Time-dependent changes in Tregs as the % of $CD4^+$ or $CD8^+$ T cells for total Tregs, $CD4^+$ memory Tregs, $CD4^+$ naïve Tregs and $CD8^+FOXP3^+$ Tregs following injection with 100 µg/kg DP47 IgG-$(IL-2N88D)_2$ FIG. 38C or 30 µg/kg DP47 IgG-$(IL-2N88D)_2$ FIG. 38D. Results are shown as the mean±SEM (n=4).

The increases in total CD4$^+$ Tregs, CD4$^+$ memory Tregs, CD4$^+$ naïve Tregs and CD8$^+$ FOXP3$^+$ Tregs are shown as time-dependent responses as either the absolute cell number/ml of blood (FIGS. 38A and 38B) or as the % of total CD4$^+$ or CD8$^+$ T cells (FIGS. 38C and 38D).

Total CD4$^+$ Tregs increased in number after 100 µg/kg from 90,000/ml to 810,000/ml (9-fold) and from 4.2% to 26% of total CD4$^+$ T cells (6.2-fold) and were still elevated at 14 days. At 30 µg/kg, total CD4$^+$ Tregs increased from 62,000/ml to 447,000/ml (7.2-fold) and from 4.5% to 16.7% of total CD4$^+$ cells (3.7-fold).

Memory Tregs increased in number at 100 µg/kg from 42,000/ml to 536,000/ml (12.8-fold) and from 2% to 17.4% of total CD4$^+$ T cells (8.7-fold). At 30 µg/kg, memory Tregs increased from 51,000/ml to 280,000/ml (5.5-fold) and from 2.3% to 10.5% of total CD4$^+$ T cells (4.6-fold).

Naïve Tregs increased in number at 100 µg/kg from 35,000/ml to 272,000/ml (7.8-fold) and from 2% to 8.6% of total CD4$^+$ T cells (4.3-fold). At 30 µg/kg, naive Tregs increased from 46,000/ml to 166,000/ml (3.6-fold) and from 2.2% to 6.2% of total CD4+ T cells (2.8-fold).

Figure 39:
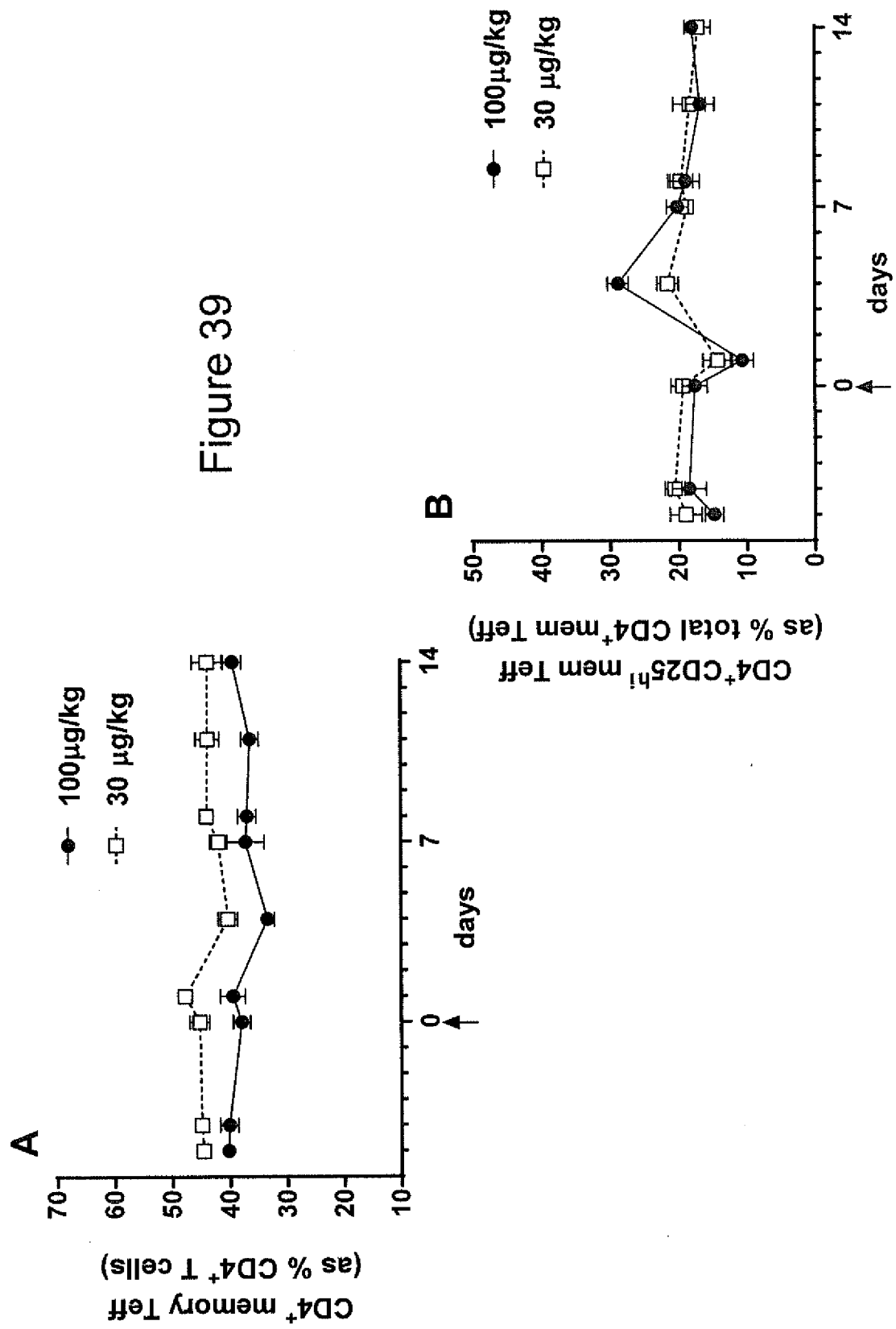
FIG. 39A-B. In vivo time and dose-dependent effects of DP47GS IgG-$(IL-2N88D)_2$ on lymphocytes in naïve healthy cynomolgus monkeys. Time-dependent changes in $CD4^+$ memory T effectors are shown as the % of total $CD4^+$ T cells following injection with 100 µg/kg DP47 IgG-$(IL-2N88D)_2$ or 30 µg/kg DP47 IgG-$(IL-2N88D)_2$ FIG. 39A. Time-dependent changes in $CD4^+CD25^{hi}$ memory T effectors are shown as the % of $CD4^+$ memory T effectors following injection with 100 µg/kg DP47 IgG-$(IL-2N88D)_2$ or 30 µg/kg DP47 IgG-$(IL-2N88D)_2$ FIG. 39B. Results are shown as the mean±SEM (n=4).

After the administration of 100 µg/kg of DP47GS IgG-(IL-2N88D)$_2$, CD8$^+$FOXP3$^+$ Tregs increased from a rare cell type at 16,000/ml to 183,000/ml (11.4-fold) and from 0.7% to 7.8% of total CD8$^+$ T cells (11.1-fold). At the 30 µg/kg dose of DP47GS IgG-(IL-2N88D)$_2$, total CD8$^+$ Tregs increased from 17,000/ml to 101,000/ml (5.9-fold) and from 0.5% to 4.3% of total CD8$^+$ T cells (8.6-fold). There were no treatment-related increases in CD4$^+$ memory Teff cells after 100 µg/kg or 30 µg/kg of DP47GS IgG-(IL-2N88D)$_2$ (FIG. 39A); in fact the percentages decreased on day 4 likely due to the large increase in CD4$^+$ Tregs at that time. CD4$^+$ CD25$^{hi}$ memory Teff cells were unchanged after 30 µg/kg of DP47GS IgG-(IL-2N88D)$_2$ but were elevated 1.6-fold on day 4 with a return to baseline at 7-10 days (FIG. 39B).

Induction of pSTAT5a, CD25 and Ki-67 in Cynomolgus with DP47GS IgG-(IL-2N88D)$_2$ As described earlier, the in vivo cellular specificity of IL-2 treatment is a critical parameter and we demonstrated that in vivo cell subset activation could be monitored by measuring ex vivo pSTAT5a, cell surface CD25 and intracellular Ki-67 in blood taken at various times after dosing.

Figure 40:
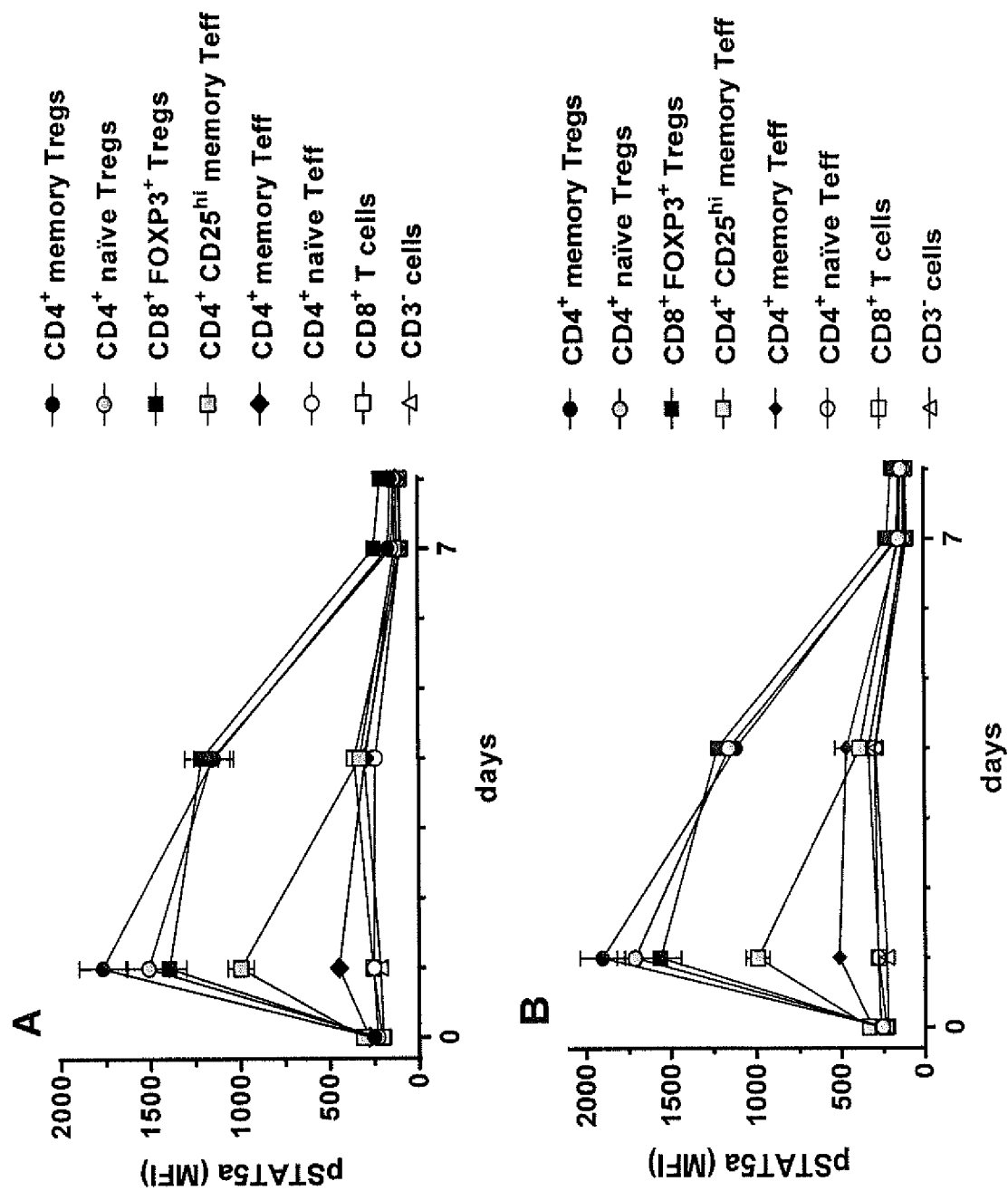
FIG. 40A-B. Ex vivo whole blood pSTAT5a is a sensitive biomarker for IL-2 activation in vivo. From 1 to 11 days after in vivo administration of a single dose of DP47GS IgG-$(IL-2N88D)_2$ to cynomolgus monkeys, whole blood was collected and tested immediately without stimulation for pSTAT5a. Each monkey was bled on day 0 before treatment for unstimulated levels of pSTAT5a and compared to changes in pSTAT5a post-treatment.

The results in FIGS. 40A and 40B show the preferential pSTAT5a induction and prolonged pSTAT5a signaling responses of CD4$^+$ and CD8$^+$ Tregs following treatment with DP47GS IgG-(IL-2N88D)$_2$; maximal responses were maintained from day 1 to day 4 by both 100 µg/kg and 30 µg/kg, returning to baseline at 7 days. CD4$^+$CD25$^{hi}$ memory Teff responded with ~half-maximal responses on day 1 and returned to normal by day 4. All other cell types tested showed little or no induction of pSTAT5a after treatment.

Figure 41:
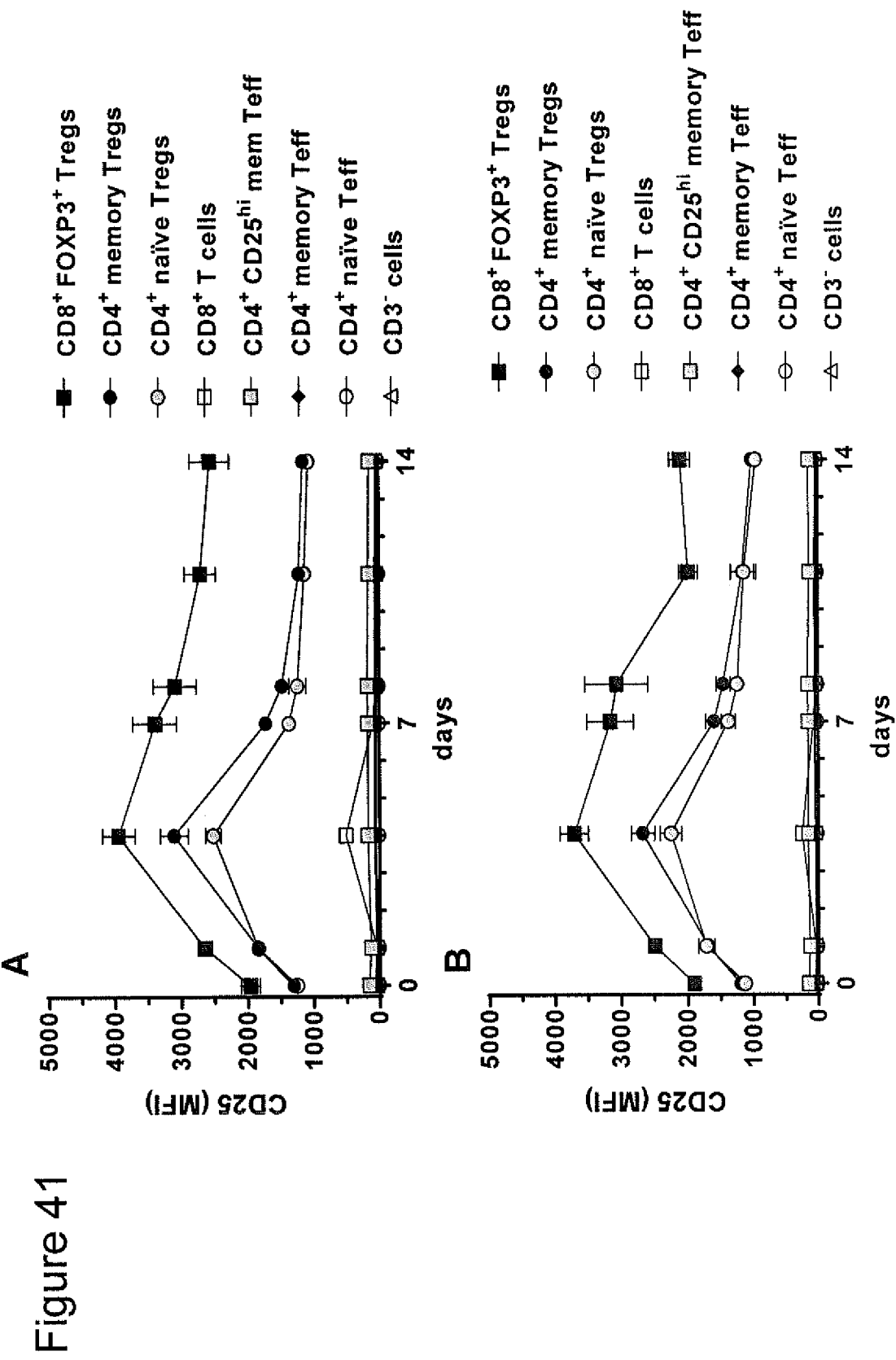
FIG. 41A-B. Ex vivo whole blood cell surface CD25 staining is a sensitive biomarker for IL-2 activation in vivo. From 1 to 14 days after in vivo administration of single doses of DP47GS IgG-$(IL-2N88D)_2$ to cynomolgus monkeys, whole blood was collected and tested immediately without stimulation for surface CD25 on the indicated cell types. Each monkey was bled on day 0 before treatment for unstimulated levels of CD25 and compared to changes in CD25 post-treatment.

An increase in cell surface CD25 is a consequence of IL-2 activation and is a sensitive biomarker of in vivo activation. Shortly after treatment with both 100 µg/kg and 30 µg/kg of DP47GS IgG-(IL-2N88D)$_2$, CD25 was preferentially increased in CD4$^+$ memory and naïve Tregs as well as CD8$^+$FOXP3$^+$ Tregs (FIG. 41A, 41B). The CD25 responses of CD4$^+$ memory and naïve Tregs peaked on day 4 and returned to baseline by 7 days while the CD25 elevations in CD8$^+$FOXP3$^+$ Tregs were sustained through 10-14 days.

Figure 42:
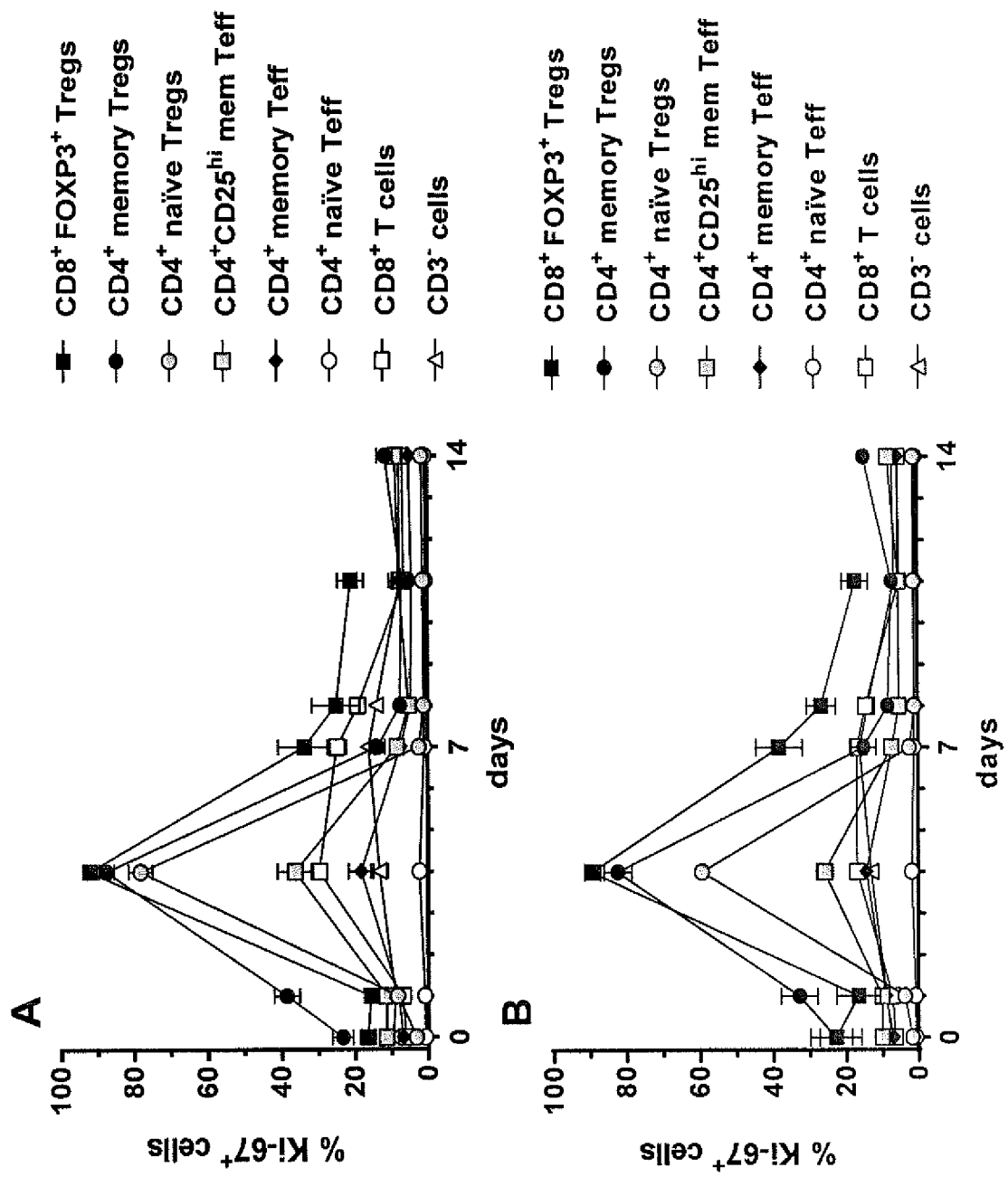
FIG. 42A-B. Ex vivo whole blood intracellular Ki-67 staining is a sensitive biomarker for cell proliferation after IL-2 activation in vivo. From 1 to 14 days after in vivo administration of a single dose of DP47GS IgG-(IL-2N88D)$_2$ to cynomolgus monkeys, whole blood was collected and tested immediately without stimulation for intracellular Ki-67 on the indicated cell types. Each monkey was bled on day 0 before treatment for unstimulated levels of Ki-67$^+$ cells and compared to changes in the % Ki-67$^+$ cells post-treatment.

In tests with wild type IL-2 fusion proteins we showed that Ki-67 was a sensitive intracellular marker for cells that have begun to proliferate in vivo and was a sensitive biomarker for IL-2 induced activation in cynomolgus monkeys. The responses to 100 µg/kg of DP47GS IgG-(IL-2N88D)$_2$ showed 80-90% of the CD4$^+$ and CD8$^+$ Tregs became Ki-67$^+$ (FIG. 42A) while 60-90% became Ki-67$^+$ after 30 μg/kg (FIG. 42B). As shown, the other cell subsets tested were less responsive compared to Tregs.

Figure 43:
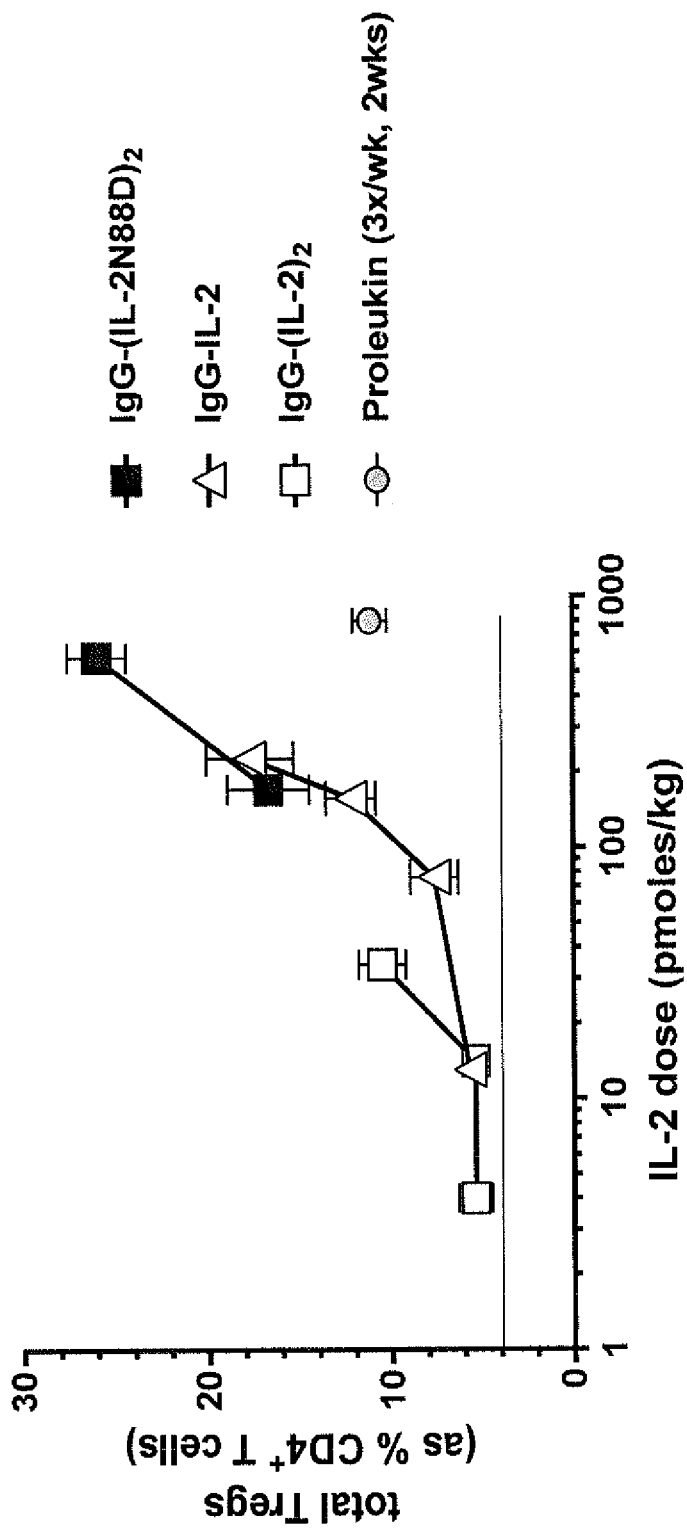
FIG. 43. A comparison summary of the in vivo effects of IL-2 on cynomolgus Tregs. The maximal increase in total Tregs as the % of CD4$^+$ T cells is shown for Proleukin, IgG-IL-2, IgG-(IL-2)$_2$ and IgG-(IL-2N88D)$_2$; for comparison, all in vivo doses were converted to pmoles/kg. Proleukin was given 3 times per week (MWF) for 2 weeks and the IL-2 fusion proteins were administered as a single injection. Results are shown as the mean±SEM; Proleukin (n=5), IgG-IL-2 (n=6), IgG-(IL-2)$_2$ (n=6) and IgG-(IL-2N88D)$_2$ (n=4).

To capture the penultimate in vivo effects of increasing Treg numbers with the novel engineered IL-2 molecules, all cynomolgus doses were converted to pmoles/kg allowing direct comparisons regardless of molecular weight; dose-dependent responses were compared head-to-head as the maximal increases in CD4$^+$ Tregs as the % of total CD4$^+$ T cells (FIG. 43). Despite its loss of in vitro potency compared to the wild type fusion proteins, DP47GS IgG-(IL-2N88D)$_2$ induced unexpectedly large increases in cynomolgus Tregs, perhaps in part due to its increase in systemic exposure following both iv and sc administration.

Eosinophilia as a Consequence of In Vivo IL-2 Administration

Figure 44:
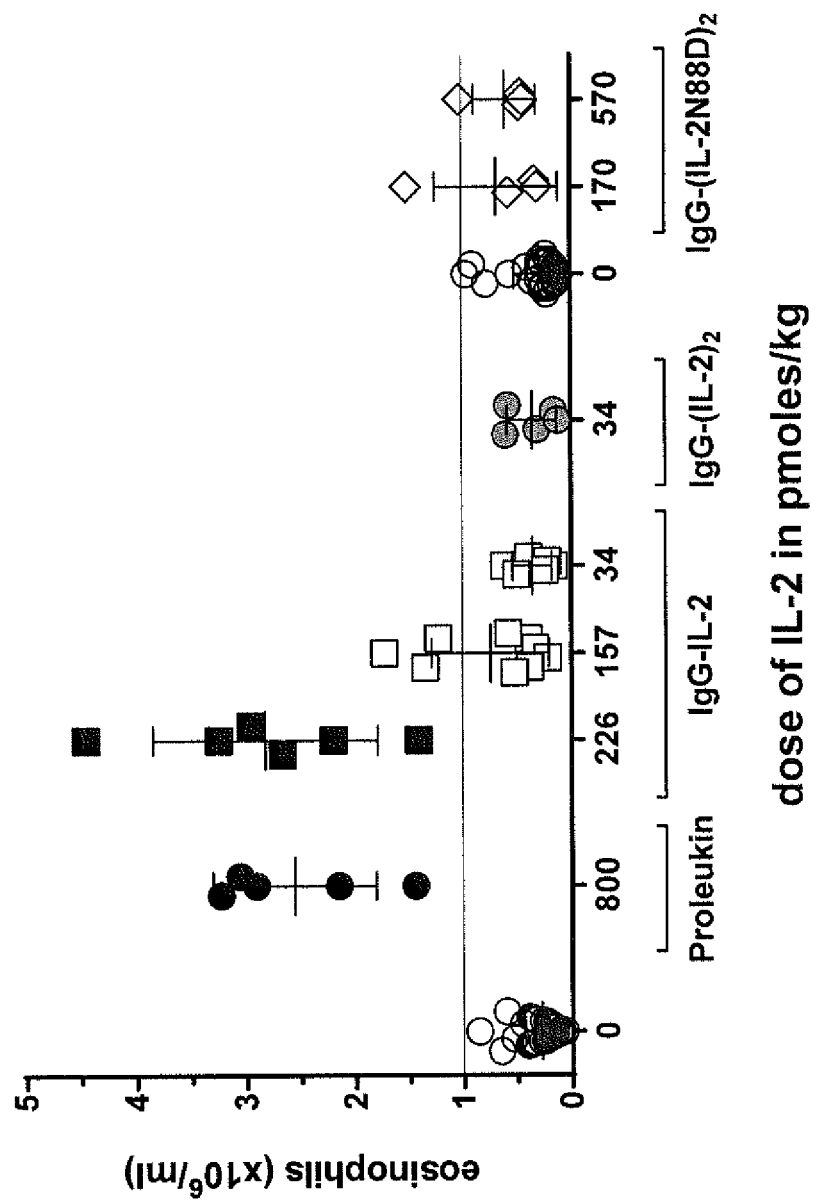
FIG. 44. High dose IL-2 induces eosinophilia in cynomolgus monkeys. Changes in blood eosinophil counts were monitored in all tests with Proleukin or the immunoconjugates of IL-2. Eosinophilia was detected 7 to 14 days after treatment with high dose Proleukin (2×10$^5$ IU/kg 3 times per week for 2 weeks) or the higher doses of DP47GS IgG-IL-2 but not with DP47GS IgG-(IL-2)$_2$ or DP47GS IgG-(IL-2N88D)$_2$. Baseline eosinophil counts are the open circles shown as a "0" for the dose of IL-2 and were done twice, once for the wild type IL-2 molecule testing and once for the DP47GS IgG-(IL-2N88D)$_2$ testing. Data are shown as the mean±SD.

Proleukin in humans stimulates an eosinophilia when given daily at doses of 1×10$^6$ to 4.5×10$^6$ IU/person. In cynomolgus monkeys similar increases in eosinophils were seen in 100% of the animals after repeated treatment with high dose Proleukin or single 226 pmoles/kg doses of DP47GS IgG-IL-2 (FIG. 44). The results in FIG. 44 represent every animal tested (colony baselines were taken for animals prior to testing: n=44 and n=30) and for the various IL-2 treatment groups (n=5-9) regardless if eosinophil numbers were normal or elevated. In striking contrast to the effects of Proleukin and DP47GS IgG-IL-2 was the virtual lack of effect on eosinophils with DP47GS IgG-(IL-2N88D)$_2$ at in vivo doses of 170 and 570 pmoles/kg (30 and 100 μg/kg, respectively). This lack of inducing a systemic eosinophilia by DP47GS IgG-(IL-2N88D)$_2$ is striking in light of the extent of Treg expansion induced by these different treatments (compared in FIG. 43).

In Vivo Treatment with DP47GS IgG-IL-2 Suppresses Immune Responses In Mice

Figure 45:
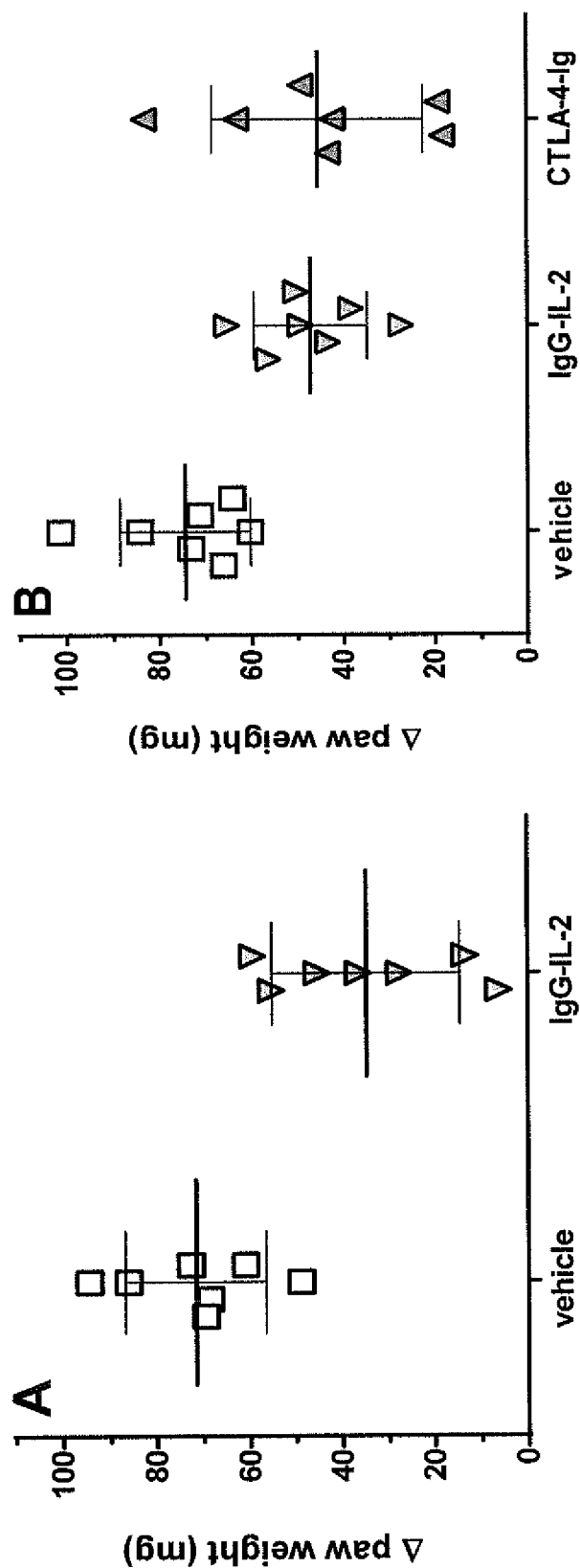
FIG. 45A-B. In vivo treatment with DP47GS IgG-IL-2 suppresses murine sheep red blood cell delayed type hypersensitivity (DTH). All data are shown for individual mice treated with vehicle (100% response), IgG-IL-2 (4,000 IU/mouse), or mouse CTLA-4-Ig as a positive control (200 μg/mouse).
Figure 46:
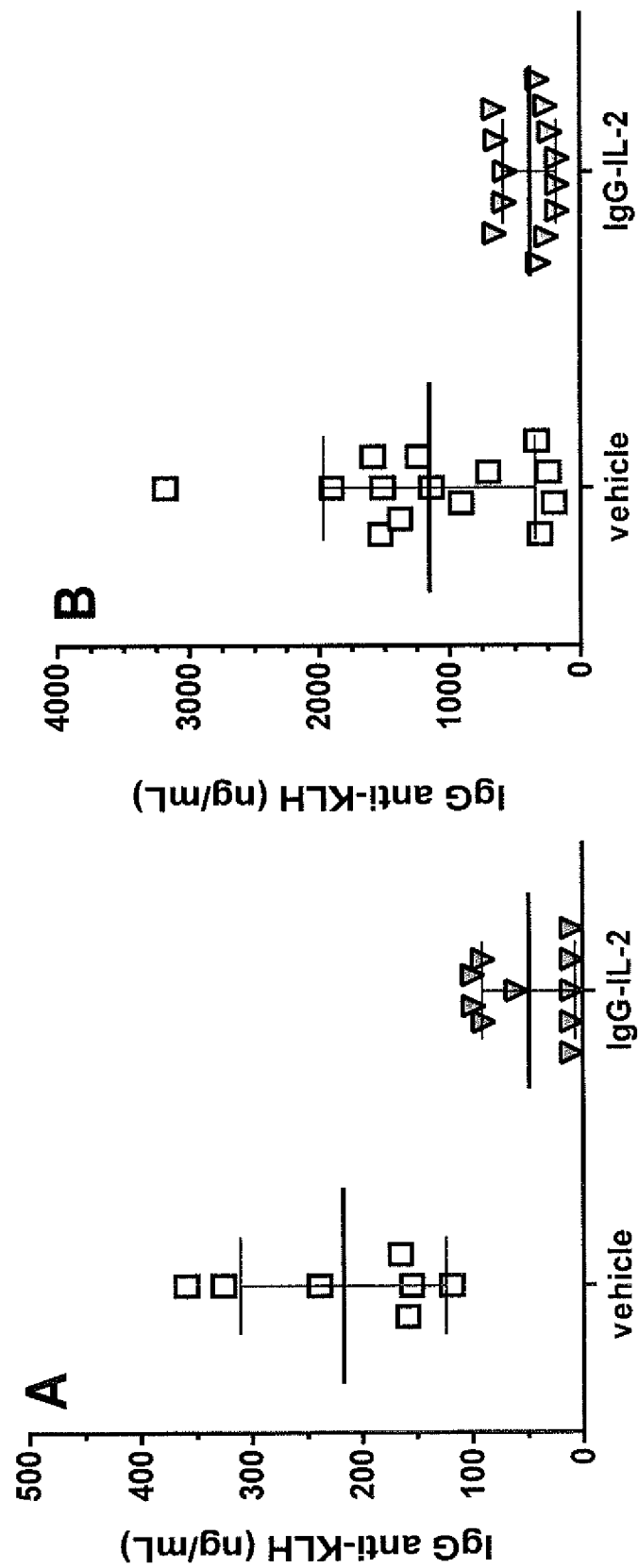
FIG. 46A-B. In vivo treatment with DP47GS IgG-IL-2 (4,000 IU/mouse) suppresses the murine IgG antibody responses to KLH in FIG. 46A C57BL/6 mice 21 days after immunization and FIG. 46B NOD mice seven days after immunization. Data are shown as the mean±SD.

In preliminary studies we observed that a 4000 IU DP47GS IgG-IL-2 dose activated mouse FOXP3$^+$ regulatory T cells in vivo; this dose was then used to assess its ability to suppress classic T dependent immune responses in mice, i.e. delayed type hypersensitivity (FIG. 45) and an IgG anti-KLH response (FIG. 46).

NOD mice and C57BL/6 mice (n=7) were immunized IV with sheep red blood cells (srbc) and challenged 3 days later with a bolus of srbc in a single hind foot to induce a delayed type hypersensitivity (DTH) response. One day after challenge, mice were euthanized with $CO_2$ and the paws excised and weighed. The magnitude of the DTH response is shown as the change in paw weight compared to non-immunized mice (Δ paw weight). DP47GS IgG-IL-2 was given SC at 4000 IU per mouse 3 days before and on the day of srbc immunization and the vehicle was sterile PBS pH 7.2. Statistical significance was derived from the Mann Whitney test in GraphPad Prism.

Dosing DP47GS IgG-IL-2 three days before and on the day of sheep red blood cell immunization suppressed the subsequent delayed type hypersensitivity response to a sheep blood cell challenge by 51% in NOD mice (FIG. 45A; p=0.0023) and 38% in C57BL/6 mice (FIG. 45B; p=0.002). Mouse CTLA-4-Ig as a positive control immunosuppressant inhibited the DTH response to a similar level as DP47GS IgG-IL-2.

DP47GS IgG-IL-2 was also able to suppress KLH-specific IgG responses in C57BL/6 (78% inhibition, p=0.0007, FIG. 46A) and NOD (67% inhibition, p=0.004, FIG. 46B) mice. For this experiment, healthy young C57BL/6 mice (n=7-10) and NOD mice (n=13-14) were immunized IP with 100 μg of human vaccine grade KLH without adjuvant as recommended by the manufacturer (Stellar). DP47GS IgG-IL-2 treatment consisted of 1 (NOD) or 2 (C57BL/6) weekly treatments with 4000 IU per mouse SC initiated on the day of immunization. Seven days (NOD) and 21 days (C57BL/6) after immunization, blood was collected and serum KLH-specific IgG responses were measured by ELISA.

The ability of DP47GS IgG-IL-2 to suppress immune responses in vivo supports the hypothesis that the regulatory T cell activation induced by low dose IL-2 produces functional regulatory T cells that mediate a reduction in the immune response.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

The invention claimed is:

1. A fusion protein comprising:
   (i) an immunoglobulin molecule comprising human immunoglobulin constant domains and the amino acid substitutions L234A, L235A, and P329G (EU numbering) in the immunoglobulin heavy chains, wherein said immunoglobulin molecule is not capable of specific binding to an antigen; and
   (ii) two mutant interleukin-2 (IL-2) molecules comprising an amino acid mutation that reduces affinity of the mutant IL-2 molecule to the intermediate affinity IL-2 receptor, as compared to a wild-type IL-2 molecule, wherein the two mutant IL-2 molecules are the same and comprise the amino acid sequence selected from the group consisting of SEQ ID NO:58, SEQ ID NO:60, SEQ ID NO:62 and SEQ ID NO:64, and wherein the two mutant IL-2 molecules is each fused at the N-terminus to the C-terminus of an immunoglobulin heavy chain of said immunoglobulin molecule, optionally through a peptide linker.

2. The fusion protein of claim 1, wherein said immunoglobulin molecule is an 19G-class immunoglobulin molecule or an IgG$_1$-subclass immunoglobulin molecule.

3. The fusion protein of claim 1, wherein said immunoglobulin molecule comprises a heavy chain variable region sequence that is at least 95% identical to SEQ ID NO: 9.

4. The fusion protein of claim 1, wherein said immunoglobulin molecule comprises the heavy chain variable region sequence of SEQ ID NO: 9.

5. The fusion protein of claim 1, wherein said immunoglobulin molecule comprises a light chain variable region sequence that is at least 95% identical to SEQ ID NO: 11.

6. The fusion protein of claim 1, wherein said immunoglobulin molecule comprises the light chain variable region sequence of SEQ ID NO: 11.

7. The fusion protein of claim 1, wherein said mutant IL-2 molecules are each fused to said immunoglobulin molecule heavy chain through a peptide linker.

8. The fusion protein of claim 7, wherein said peptide linker comprises at least 10 or at least 15, amino acids.

9. The fusion protein of claim 7, wherein said peptide linker comprises the amino acid sequence (G$_4$S)$_3$ (SEQ ID NO: 66).

10. The fusion protein of claim 1, wherein the fusion protein comprises the polypeptide sequences of SEQ ID NO: 19 and SEQ ID NO: 50.

11. The fusion protein of claim 1, wherein said fusion protein selectively activates regulatory T cells.

12. A fusion protein produced by the method comprising the steps of (i) culturing the host cell that comprises a polynucleotide encoding the fusion protein of claim 1, or a vector comprising a polynucleotide encoding the fusion protein of claim 1, under conditions suitable for expression of the fusion protein, and (ii) recovering the fusion protein.

13. A pharmaceutical composition comprising the fusion protein of claim 1 or 12 and a pharmaceutically acceptable carrier.

14. The fusion protein of claim 1, wherein the two mutant IL-2 molecules each comprises the amino acid sequence of SEQ ID NO:58.

15. The fusion protein of claim 14, wherein said immunoglobulin molecule is an IgG-class immunoglobulin molecule or an IgG$_1$-subclass immunoglobulin molecule.

16. The fusion protein of claim 14, wherein said immunoglobulin molecule comprises the heavy chain variable region sequence of SEQ ID NO: 9.

17. The fusion protein of claim 14, wherein said immunoglobulin molecule comprises the light chain variable region sequence of SEQ ID NO: 11.

18. The fusion protein of claim 14, wherein the fusion protein comprises the polypeptide sequences of SEQ ID NO: 19 and SEQ ID NO: 50.

19. The fusion protein of claim 14, wherein said mutant IL-2 molecules are each fused to the immunoglobulin heavy chain through a peptide linker.

20. The fusion protein of claim 19, wherein said peptide linker comprises at least 10 or at least 15, amino acids.

21. The fusion protein of claim 19, wherein said peptide linker comprises the amino acid sequence (G4S)3 (SEQ ID NO: 66).

22. A fusion protein produced by the method comprising the steps of (i) culturing the host cell that comprises a polynucleotide encoding the fusion protein of claim 14, or a vector comprising a polynucleotide encoding the fusion protein of claim 14, under conditions suitable for expression of the fusion protein, and (ii) recovering the fusion protein.

23. A pharmaceutical composition comprising the fusion protein of claim 14 or 22 and a pharmaceutically acceptable carrier.

24. The fusion protein of claim 1, wherein said immunoglobulin molecule comprises a modification reducing binding affinity of the immunoglobulin molecule to an Fc receptor as compared to a corresponding immunoglobulin molecule without said modification.

25. The fusion protein of claim 24, wherein said Fc receptor is a human Fcγ receptor.

26. The fusion protein of claim 24, wherein said Fc receptor is an activating Fc receptor.

27. The fusion protein of claim 24, wherein said Fc receptor is selected from the group of FcγRIIIa (CD16a), FcγRI (CD64), FcγRIIa (CD32) and FcαRI (CD89).

28. The fusion protein of claim 24, wherein said Fc receptor is human FcγRIIIa.

* * * * *

SEQUENCE LISTING

```
<160> NUMBER OF SEQ ID NOS: 66

<210> SEQ ID NO 1
<211> LENGTH: 133
<212> TYPE: PRT
<213> ORGANISM: Homo sapiens

<400> SEQUENCE: 1

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
```

```
                85                  90                  95
Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 2
<211> LENGTH: 399
<212> TYPE: DNA
<213> ORGANISM: Artificial Sequence
<220> FEATURE:
<223> OTHER INFORMATION: Wild-type human IL-2

<400> SEQUENCE: 2
gcacctactt caagttctac aaagaaaaca cagctacaac tggagcattt actgctggat      60
ttacagatga ttttgaatgg aattaataat tacaagaatc ccaaactcac caggatgctc    120
acatttaagt tttacatgcc caagaaggcc acagaactga acatcttca gtgtctagaa     180 gaagaactca aacctctgga ggaagtgcta aatttagctc aaagcaaaaa ctttcactta    240
agacccaggg acttaatcag caatatcaac gtaatagttc tggaactaaa gggatctgaa    300
acaacattca tgtgtgaata tgctgatgag acagcaacca ttgtagaatt tctgaacaga    360
tggattacct tttgtcaaag catcatctca acactgact                           399

<210> SEQ ID NO 3
<211> LENGTH: 133
<212> TYPE: PRT
<213> ORGANISM: Artificial Sequence
<220> FEATURE:
<223> OTHER INFORMATION: Wild-type human IL-2 (C125A)

<400> SEQUENCE: 3

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125

Ile Ser Thr Leu Thr
        130

<210> SEQ ID NO 4
<211> LENGTH: 399
<212> TYPE: DNA
<213> ORGANISM: Artificial Sequence
<220> FEATURE:
<223> OTHER INFORMATION: Wild-type human IL-2 (C125A) (1)
```

<400> SEQUENCE: 4

```
gctcctacat cctccagcac caagaaaacc cagctccagc tggaacatct cctgctggat      60
ctgcagatga tcctgaacgg catcaacaac tacaagaacc ccaagctgac ccggatgctg     120
accttcaagt tctacatgcc caagaaggcc accgagctga acatctgca gtgcctggaa      180 gaggaactga agcctctgga agaggtgctg aacctggccc agtccaagaa cttccacctg     240
aggcctcggg acctgatctc caacatcaac gtgatcgtgc tggaactgaa gggctccgag     300
acaaccttca tgtgcgagta cgccgacgag acagctacca tcgtggaatt tctgaaccgg     360
tggatcacct tcgcccagtc catcatctcc accctgacc                            399
```

<210> SEQ ID NO 5
<211> LENGTH: 399
<212> TYPE: DNA
<213> ORGANISM: Artificial Sequence
<220> FEATURE:
<223> OTHER INFORMATION: Wild-type human IL-2 (C125A) (2)

<400> SEQUENCE: 5

```
gcacctactt caagttctac aaagaaaaca cagctacaac tggagcattt actgctggat      60
ttacagatga ttttgaatgg aattaataat tacaagaatc ccaaactcac caggatgctc     120
acatttaagt tttacatgcc caagaaggcc acagaactga acatcttca gtgtctagaa      180 gaagaactca aacctctgga ggaagtgcta aatttagctc aaagcaaaaa ctttcactta     240
agacccaggg acttaatcag caatatcaac gtaatagttc tggaactaaa gggatctgaa     300
acaacattca tgtgtgaata tgctgatgag acagcaacca ttgtagaatt tctgaacaga     360
tggattacct ttgcccaaag catcatctca acactgact                            399
```

<210> SEQ ID NO 6
<211> LENGTH: 399
<212> TYPE: DNA
<213> ORGANISM: Artificial Sequence
<220> FEATURE:
<223> OTHER INFORMATION: Wild-type human IL-2 (C125A) (3)

<400> SEQUENCE: 6

```
gctcctacta gcagctccac caagaaaacc cagctccagc tggaacatct gctgctggat      60
ctgcagatga tcctgaacgg catcaacaac tacaagaacc ccaagctgac ccggatgctg     120
accttcaagt tctacatgcc caagaaggcc accgaactga acatctgca gtgcctggaa      180 gaggaactga agcctctgga agaggtgctg aacctggccc agagcaagaa cttccacctg     240 aggcccagg acctgatcag caacatcaac gtgatcgtgc tggaactgaa gggcagcgag     300
acaaccttca tgtgcgagta cgccgacgag acagccacca tcgtggaatt tctgaaccgg     360
tggatcacct tcgcccagag catcatcagc accctgaca                            399
```

<210> SEQ ID NO 7
<211> LENGTH: 399
<212> TYPE: DNA
<213> ORGANISM: Artificial Sequence
<220> FEATURE:
<223> OTHER INFORMATION: Wild-type IL-2 (C125A) (4)

<400> SEQUENCE: 7

```
gcacctactt caagttctac aaagaaaaca cagctacaac tggagcattt actgctggat      60
ttacagatga ttttgaatgg aattaataat tacaagaatc ccaaactcac caggatgctc     120
```

-continued

```
acatttaagt tttacatgcc caagaaggcc acagaactga acatcttca gtgtctagaa    180 gaagaactca aacctctgga ggaagtgcta aatttagctc aaagcaaaaa ctttcactta    240
agacccaggg acttaatcag caatatcaac gtaatagttc tggaactaaa gggatctgaa    300
acaacattca tgtgtgaata tgctgatgag acagcaacca ttgtagaatt tctgaacaga    360
tggattacct ttgcccaaag catcatctca acactgact                          399
```

<210> SEQ ID NO 8
<211> LENGTH: 227
<212> TYPE: PRT
<213> ORGANISM: Homo sapiens

<400> SEQUENCE: 8

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 9
<211> LENGTH: 115
<212> TYPE: PRT
<213> ORGANISM: Artificial Sequence
<220> FEATURE:
<223> OTHER INFORMATION: DP47GS VH

<400> SEQUENCE: 9

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gly Ser Gly Phe Asp Tyr Trp Gly Gln Gly Thr Leu Val Thr
            100                 105                 110

Val Ser Ser
        115

<210> SEQ ID NO 10
<211> LENGTH: 345
<212> TYPE: DNA
<213> ORGANISM: Artificial Sequence
<220> FEATURE:
<223> OTHER INFORMATION: DP47GS VH

<400> SEQUENCE: 10
gaggtgcaat tgttggagtc tgggggaggc ttggtacagc ctgggggtc cctgagactc        60 tcctgtgcag cctccggatt cacctttagc agttatgcca tgagctgggt ccgccaggct      120
ccagggaagg ggctggagtg ggtctcagct attagtggta gtggtggtag cacatactac      180
gcagactccg tgaagggccg gttcaccatc tccagagaca attccaagaa cacgctgtat      240
ctgcagatga acagcctgag agccgaggac acggccgtat attactgtgc gaaaggcagc      300
ggatttgact actggggcca aggaaccctg gtcaccgtct cgagt                      345

<210> SEQ ID NO 11
<211> LENGTH: 108
<212> TYPE: PRT
<213> ORGANISM: Artificial Sequence
<220> FEATURE:
<223> OTHER INFORMATION: DP47GS VL

<400> SEQUENCE: 11

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Leu Thr Phe Gly Gln Gly Thr Lys Val Glu Ile Lys
            100                 105

<210> SEQ ID NO 12
<211> LENGTH: 324
<212> TYPE: DNA
<213> ORGANISM: Artificial Sequence
<220> FEATURE:
<223> OTHER INFORMATION: DP47GS VL

<400> SEQUENCE: 12

```
gaaatcgtgt taacgcagtc tccaggcacc ctgtctttgt ctccagggga aagagccacc      60
ctctcttgca gggccagtca gagtgttagc agcagctact tagcctggta ccagcagaaa     120
cctggccagg ctcccaggct cctcatctat ggagcatcca gcagggccac tggcatccca     180
gacaggttca gtggcagtgg atccgggaca gacttcactc tcaccatcag cagactggag     240
cctgaagatt ttgcagtgta ttactgtcag cagtatggta gctcaccgct gacgttcggc     300
caggggacca agtggaaat caaa                                              324
```

<210> SEQ ID NO 13
<211> LENGTH: 592
<212> TYPE: PRT
<213> ORGANISM: Artificial Sequence
<220> FEATURE:
<223> OTHER INFORMATION: DP47GS HC(Fc knob,P329G LALA)-IL2

<400> SEQUENCE: 13

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ser Gly Phe Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
```

```
            290                 295                 300
Thr Val Leu His Gln Asp Trp Leu Asn Gly Lys Glu Tyr Lys Cys Lys
305                 310                 315                 320

Val Ser Asn Lys Ala Leu Gly Ala Pro Ile Glu Lys Thr Ile Ser Lys
                325                 330                 335

Ala Lys Gly Gln Pro Arg Glu Pro Gln Val Tyr Thr Leu Pro Pro Cys
                340                 345                 350

Arg Asp Glu Leu Thr Lys Asn Gln Val Ser Leu Trp Cys Leu Val Lys
            355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
                420                 425                 430

His Tyr Thr Gln Lys Ser Leu Ser Leu Ser Pro Gly Gly Gly Gly Gly
            435                 440                 445

Ser Gly Gly Gly Gly Ser Gly Gly Gly Gly Ser Ala Pro Thr Ser Ser
    450                 455                 460

Ser Thr Lys Lys Thr Gln Leu Gln Leu Glu His Leu Leu Leu Asp Leu
465                 470                 475                 480

Gln Met Ile Leu Asn Gly Ile Asn Asn Tyr Lys Asn Pro Lys Leu Thr
                485                 490                 495

Arg Met Leu Thr Phe Lys Phe Tyr Met Pro Lys Lys Ala Thr Glu Leu
                500                 505                 510

Lys His Leu Gln Cys Leu Glu Glu Glu Leu Lys Pro Leu Glu Glu Val
            515                 520                 525

Leu Asn Leu Ala Gln Ser Lys Asn Phe His Leu Arg Pro Arg Asp Leu
530                 535                 540

Ile Ser Asn Ile Asn Val Ile Val Leu Glu Leu Lys Gly Ser Glu Thr
545                 550                 555                 560

Thr Phe Met Cys Glu Tyr Ala Asp Glu Thr Ala Thr Ile Val Glu Phe
                565                 570                 575

Leu Asn Arg Trp Ile Thr Phe Ala Gln Ser Ile Ile Ser Thr Leu Thr
            580                 585                 590

<210> SEQ ID NO 14
<211> LENGTH: 1776
<212> TYPE: DNA
<213> ORGANISM: Artificial Sequence
<220> FEATURE:
<223> OTHER INFORMATION: DP47GS HC(Fc knob,P329G LALA)-IL2

<400> SEQUENCE: 14
gaggtgcaat tgttggagtc tgggggaggc ttggtacagc ctggggggtc cctgagactc      60
tcctgtgcag cctccggatt cacctttagc agttatgcca tgagctgggt ccgccaggct     120
ccagggaagg gctgagtg gtctcagct attagtggta gtggtggtag cacatactac       180
gcagactccg tgaagggccg gttcaccatc tccagagaca attccaagaa cacgctgtat     240
ctgcagatga acagcctgag agccgaggac acggccgtat attactgtgc gaaaggcagc     300
ggatttgact actggggcca aggaaccctg gtcaccgtct cgagtgctag caccaagggc     360
ccatcggtct tccccctggc accctcctcc aagagcacct ctgggggcac agcggccctg     420
```

-continued

```
ggctgcctgg tcaaggacta cttccccgaa ccggtgacgg tgtcgtggaa ctcaggcgcc    480
ctgaccagcg gcgtgcacac cttcccggct gtcctacagt cctcaggact ctactccctc    540
agcagcgtgg tgaccgtgcc ctccagcagc ttgggcaccc agacctacat ctgcaacgtg    600
aatcacaagc ccagcaacac caaggtggac aagaaagttg agcccaaatc ttgtgacaaa    660
actcacacat gcccaccgtg cccagcacct gaagctgcag ggggaccgtc agtcttcctc    720
ttccccccaa aacccaagga caccctcatg atctcccgga cccctgaggt cacatgcgtg    780
gtggtggacg tgagccacga agaccctgag gtcaagttca actggtacgt ggacggcgtg    840
gaggtgcata atgccaagac aaagccgcgg gaggagcagt acaacagcac gtaccgtgtg    900
gtcagcgtcc tcaccgtcct gcaccaggac tggctgaatg gcaaggagta caagtgcaag    960
gtctccaaca agccctcggc gcccccatcg agaaaaacca tctccaaagc caagggcag    1020 ccccgagaac cacaggtgta caccctgccc ccatgccggg atgagctgac caagaaccag    1080
gtcagcctgt ggtgcctggt caaaggcttc tatcccagcg acatcgccgt ggagtgggag    1140
agcaatgggc agccggagaa caactacaag accacgcctc ccgtgctgga ctccgacggc    1200
tccttcttcc tctacagcaa gctcaccgtg gacaagagca ggtggcagca ggggaacgtc    1260
ttctcatgct ccgtgatgca tgaggctctg cacaaccact acacgcagaa gagcctctcc    1320
ctgtctccgg gtggcggcgg aggctccgga ggcggaggtt ctggaggcgg aggctccgca    1380
cctacttcaa gttctacaaa gaaaacacag ctacaactgg agcatttact gctggattta    1440
cagatgattt tgaatggaat taataattac aagaatccca aactcaccag gatgctcaca    1500
tttaagtttt acatgcccaa gaaggccaca gaactgaaac atcttcagtg tctagaagaa    1560
gaactcaaac tctggagga agtgctaaat ttagctcaaa gcaaaaactt tcacttaaga    1620
cccagggact taatcagcaa tatcaacgta atagttctgg aactaagggg atctgaaaca    1680
acattcatgt gtgaatatgc tgatgagaca gcaaccattg tagaatttct gaacagatgg    1740
attacctttg cccaaagcat catctcaaca ctgact                              1776
```

<210> SEQ ID NO 15
<211> LENGTH: 445
<212> TYPE: PRT
<213> ORGANISM: Artificial Sequence
<220> FEATURE:
<223> OTHER INFORMATION: DP47GS HC(Fc hole, P329G LALA)

<400> SEQUENCE: 15

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ser Gly Phe Asp Tyr Trp Gly Gln Gly Thr Leu Val Thr
            100                 105                 110

Val Ser Ser Ala Ser Thr Lys Gly Pro Ser Val Phe Pro Leu Ala Pro

```
                115                 120                 125
Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Gly Ala Pro Ile Glu Lys Thr Ile Ser Lys
                325                 330                 335

Ala Lys Gly Gln Pro Arg Glu Pro Gln Val Cys Thr Leu Pro Pro Ser
            340                 345                 350

Arg Asp Glu Leu Thr Lys Asn Gln Val Ser Leu Ser Cys Ala Val Lys
        355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Val Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 16
<211> LENGTH: 1335
<212> TYPE: DNA
<213> ORGANISM: Artificial Sequence
<220> FEATURE:
<223> OTHER INFORMATION: DP47GS HC(Fc hole, P329G LALA)

<400> SEQUENCE: 16
gaggtgcaat tgttggagtc tgggggaggc ttggtacagc ctggggggtc cctgagactc      60
tcctgtgcag cctccggatt cacctttagc agttatgcca tgagctgggt ccgccaggct     120
ccagggaagg gctgagtg gtctcagct attagtggta gtggtggtag cacatactac        180
gcagactccg tgaagggccg gttcaccatc tccagagaca attccaagaa cacgctgtat     240
```

```
ctgcagatga acagcctgag agccgaggac acggccgtat attactgtgc gaaaggcagc    300
ggatttgact actggggcca aggaaccctg gtcaccgtct cgagtgctag caccaagggc    360
ccctccgtgt tccccctggc ccccagcagc aagagcacca gcggcggcac agccgctctg    420
ggctgcctgg tcaaggacta cttccccgag cccgtgaccg tgtcctggaa cagcggagcc    480
ctgacctccg gcgtgcacac cttccccgcc gtgctgcaga gttctggcct gtatagcctg    540
agcagcgtgg tcaccgtgcc ttctagcagc ctgggcaccc agacctacat ctgcaacgtg    600
aaccacaagc ccagcaacac caaggtggac aagaaggtgg agcccaagag ctgcgacaaa    660
actcacacat gcccaccgtg cccagcacct gaagctgcag ggggaccgtc agtcttcctc    720
ttccccccaa aacccaagga caccctcatg atctcccgga cccctgaggt cacatgcgtg    780
gtggtggacg tgagccacga agaccctgag gtcaagttca actggtacgt ggacggcgtg    840
gaggtgcata atgccaagac aaagccgcgg gaggagcagt acaacagcac gtaccgtgtg    900
gtcagcgtcc tcaccgtcct gcaccaggac tggctgaatg gcaaggagta caagtgcaag    960
gtctccaaca aagccctcgg cgccccatc gagaaaacca tctccaaagc caaagggcag   1020
ccccgagaac acaggtgtg cacctgcc ccatcccggg atgagctgac caagaaccag   1080
gtcagcctct cgtgcgcagt caaaggcttc tatcccagcg acatcgccgt ggagtgggag   1140
agcaatgggc agccggagaa caactacaag accacgcctc ccgtgctgga ctccgacggc   1200
tccttcttcc tcgtgagcaa gctcaccgtg gacaagagca ggtggcagca ggggaacgtc   1260
ttctcatgct ccgtgatgca tgaggctctg cacaaccact acacgcagaa gagcctctcc   1320
ctgtctccgg gtaaa                                                    1335
```

<210> SEQ ID NO 17
<211> LENGTH: 592
<212> TYPE: PRT
<213> ORGANISM: Artificial Sequence
<220> FEATURE:
<223> OTHER INFORMATION: DP47GS HC (Fc wt, P329G LALA)-IL2

<400> SEQUENCE: 17

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ser Gly Phe Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160
```

-continued

```
Leu Thr Ser Gly Val His Thr Phe Pro Ala Val Leu Gln Ser Ser Gly
            165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
            195                 200                 205

Val Asp Lys Lys Val Glu Pro Lys Ser Cys Asp Lys Thr His Thr Cys
210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
            275                 280                 285

Pro Arg Glu Glu Gln Tyr Asn Ser Thr Tyr Arg Val Val Ser Val Leu
            290                 295                 300

Thr Val Leu His Gln Asp Trp Leu Asn Gly Lys Glu Tyr Lys Cys Lys
305                 310                 315                 320

Val Ser Asn Lys Ala Leu Gly Ala Pro Ile Glu Lys Thr Ile Ser Lys
            325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
            405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Gly Gly Gly Gly
            435                 440                 445

Ser Gly Gly Gly Gly Ser Gly Gly Gly Gly Ser Ala Pro Thr Ser Ser
            450                 455                 460

Ser Thr Lys Lys Thr Gln Leu Gln Leu Glu His Leu Leu Leu Asp Leu
465                 470                 475                 480

Gln Met Ile Leu Asn Gly Ile Asn Asn Tyr Lys Asn Pro Lys Leu Thr
            485                 490                 495

Arg Met Leu Thr Phe Lys Phe Tyr Met Pro Lys Lys Ala Thr Glu Leu
            500                 505                 510

Lys His Leu Gln Cys Leu Glu Glu Glu Leu Lys Pro Leu Glu Glu Val
            515                 520                 525

Leu Asn Leu Ala Gln Ser Lys Asn Phe His Leu Arg Pro Arg Asp Leu
            530                 535                 540

Ile Ser Asn Ile Asn Val Ile Val Leu Glu Leu Lys Gly Ser Glu Thr
545                 550                 555                 560

Thr Phe Met Cys Glu Tyr Ala Asp Glu Thr Ala Thr Ile Val Glu Phe
            565                 570                 575

Leu Asn Arg Trp Ile Thr Phe Ala Gln Ser Ile Ile Ser Thr Leu Thr
```

<210> SEQ ID NO 18
<211> LENGTH: 1776
<212> TYPE: DNA
<213> ORGANISM: Artificial Sequence
<220> FEATURE:
<223> OTHER INFORMATION: DP47GS HC (Fc wt, P329G LALA)-IL2

<400> SEQUENCE: 18

```
gaggtgcaat tgttggagtc tgggggaggc ttggtacagc ctggggggtc cctgagactc        60
tcctgtgcag cctccggatt cacctttagc agttatgcca tgagctgggt ccgccaggct       120
ccagggaagg ggctggagtg gtctcagct attagtggta gtggtggtag cacatactac       180
gcagactccg tgaagggccg gttcaccatc tccagagaca attccaagaa cacgctgtat       240
ctgcagatga acagcctgag agccgaggac acggccgtat attactgtgc gaaaggcagc       300
ggatttgact actggggcca aggaaccctg gtcaccgtct cgagtgctag caccaagggc       360
ccatcggtct tccccctggc accctcctcc aagagcacct ctgggggcac agcggccctg       420
ggctgcctgg tcaaggacta cttccccgaa ccggtgacgg tgtcgtggaa ctcaggcgcc       480
ctgaccagcg gcgtgcacac cttcccggct gtcctacagt cctcaggact ctactccctc       540
agcagcgtgg tgaccgtgcc ctccagcagc ttgggcaccc agacctacat ctgcaacgtg       600
aatcacaagc ccagcaacac caaggtggac aagaaagttg agcccaaatc ttgtgacaaa       660
actcacacat gcccaccgtg cccagcacct gaagctgcag gggaccgtc agtcttcctc       720
ttccccccaa aacccaagga caccctcatg atctcccgga cccctgaggt cacatgcgtg       780
gtggtggacg tgagccacga agaccctgag gtcaagttca actggtacgt ggacggcgtg       840
gaggtgcata atgccaagac aaagccgcgg gaggagcagt acaacagcac gtaccgtgtg       900
gtcagcgtcc tcaccgtcct gcaccaggac tggctgaatg gcaaggagta caagtgcaag       960
gtctccaaca agccctcgg cgcccccatc gagaaaacca tctccaaagc caagggcag      1020
ccccgagaac acaggtgta caccctgccc ccatcccggg atgagctgac caagaaccag      1080
gtcagcctga cctgcctggt caaaggcttc tatcccagcg acatcgccgt ggagtgggag      1140
agcaatgggc agccggagaa caactacaag accacgcctc ccgtgctgga ctccgacggc      1200
tccttcttcc tctacagcaa gctcaccgtg gacaagagca ggtggcagca ggggaacgtc      1260
ttctcatgct ccgtgatgca tgaggctctg cacaaccact acacgcagaa gagcctctcc      1320
ctgtctccgg gtggcggcgg aggctccgga ggcggaggtt ctggaggcgg aggctccgca      1380
cctacttcaa gttctacaaa gaaaacacag ctacaactgg agcatttact gctggattta      1440
cagatgattt tgaatggaat taataattac aagaatccca aactcaccag gatgctcaca      1500
tttaagtttt acatgcccaa gaaggccaca gaactgaaac atcttcagtg tctagaagaa      1560
gaactcaaac ctctggagga agtgctaaat ttagctcaaa gcaaaaactt tcacttaaga      1620
cccagggact aatcagcaa tatcaacgta atagttctgg aactaaaggg atctgaaaca      1680
acattcatgt gtgaatatgc tgatgagaca gcaaccattg tagaatttct gaacagatgg      1740
attacctttg cccaaagcat catctcaaca ctgact                                1776
```

<210> SEQ ID NO 19
<211> LENGTH: 215
<212> TYPE: PRT
<213> ORGANISM: Artificial Sequence
<220> FEATURE:
<223> OTHER INFORMATION: DP47GS LC

<400> SEQUENCE: 19

| Glu | Ile | Val | Leu | Thr | Gln | Ser | Pro | Gly | Thr | Leu | Ser | Leu | Ser | Pro | Gly |
|---|---|---|---|---|---|---|---|---|---|---|---|---|---|---|---|
| 1 | | | | 5 | | | | | 10 | | | | | 15 | |

| Glu | Arg | Ala | Thr | Leu | Ser | Cys | Arg | Ala | Ser | Gln | Ser | Val | Ser | Ser |
|---|---|---|---|---|---|---|---|---|---|---|---|---|---|---|
| | | | 20 | | | | | 25 | | | | | 30 | |

| Tyr | Leu | Ala | Trp | Tyr | Gln | Gln | Lys | Pro | Gly | Gln | Ala | Pro | Arg | Leu | Leu |
|---|---|---|---|---|---|---|---|---|---|---|---|---|---|---|---|
| | | 35 | | | | | 40 | | | | | 45 | | | |

| Ile | Tyr | Gly | Ala | Ser | Ser | Arg | Ala | Thr | Gly | Ile | Pro | Asp | Arg | Phe | Ser |
|---|---|---|---|---|---|---|---|---|---|---|---|---|---|---|---|
| | 50 | | | | | 55 | | | | | 60 | | | | |

| Gly | Ser | Gly | Ser | Gly | Thr | Asp | Phe | Thr | Leu | Thr | Ile | Ser | Arg | Leu | Glu |
|---|---|---|---|---|---|---|---|---|---|---|---|---|---|---|---|
| 65 | | | | | 70 | | | | | 75 | | | | | 80 |

| Pro | Glu | Asp | Phe | Ala | Val | Tyr | Tyr | Cys | Gln | Gln | Tyr | Gly | Ser | Ser | Pro |
|---|---|---|---|---|---|---|---|---|---|---|---|---|---|---|---|
| | | | | 85 | | | | | 90 | | | | | 95 | |

| Leu | Thr | Phe | Gly | Gln | Gly | Thr | Lys | Val | Glu | Ile | Lys | Arg | Thr | Val | Ala |
|---|---|---|---|---|---|---|---|---|---|---|---|---|---|---|---|
| | | | 100 | | | | | 105 | | | | | 110 | | |

| Ala | Pro | Ser | Val | Phe | Ile | Phe | Pro | Pro | Ser | Asp | Glu | Gln | Leu | Lys | Ser |
|---|---|---|---|---|---|---|---|---|---|---|---|---|---|---|---|
| | | 115 | | | | | 120 | | | | | 125 | | | |

| Gly | Thr | Ala | Ser | Val | Val | Cys | Leu | Leu | Asn | Asn | Phe | Tyr | Pro | Arg | Glu |
|---|---|---|---|---|---|---|---|---|---|---|---|---|---|---|---|
| | 130 | | | | | 135 | | | | | 140 | | | | |

| Ala | Lys | Val | Gln | Trp | Lys | Val | Asp | Asn | Ala | Leu | Gln | Ser | Gly | Asn | Ser |
|---|---|---|---|---|---|---|---|---|---|---|---|---|---|---|---|
| 145 | | | | | 150 | | | | | 155 | | | | | 160 |

| Gln | Glu | Ser | Val | Thr | Glu | Gln | Asp | Ser | Lys | Asp | Ser | Thr | Tyr | Ser | Leu |
|---|---|---|---|---|---|---|---|---|---|---|---|---|---|---|---|
| | | | | 165 | | | | | 170 | | | | | 175 | |

| Ser | Ser | Thr | Leu | Thr | Leu | Ser | Lys | Ala | Asp | Tyr | Glu | Lys | His | Lys | Val |
|---|---|---|---|---|---|---|---|---|---|---|---|---|---|---|---|
| | | | 180 | | | | | 185 | | | | | 190 | | |

| Tyr | Ala | Cys | Glu | Val | Thr | His | Gln | Gly | Leu | Ser | Ser | Pro | Val | Thr | Lys |
|---|---|---|---|---|---|---|---|---|---|---|---|---|---|---|---|
| | | 195 | | | | | 200 | | | | | 205 | | | |

| Ser | Phe | Asn | Arg | Gly | Glu | Cys |
|---|---|---|---|---|---|---|
| 210 | | | | | 215 | |

<210> SEQ ID NO 20
<211> LENGTH: 645
<212> TYPE: DNA
<213> ORGANISM: Artificial Sequence
<220> FEATURE:
<223> OTHER INFORMATION: DP47GS LC

<400> SEQUENCE: 20

```
gaaatcgtgt taacgcagtc tccaggcacc ctgtctttgt ctccagggga aagagccacc      60
ctctcttgca gggccagtca gagtgttagc agcagctact tagcctggta ccagcagaaa     120
cctggccagg ctcccaggct cctcatctat ggagcatcca gcagggccac tggcatccca     180
gacaggttca gtggcagtgg atccgggaca gacttcactc tcaccatcag cagactggag     240
cctgaagatt ttgcagtgta ttactgtcag cagtatggta gctcaccgct gacgttcggc     300
caggggacca agtggaaat caaacgtacg gtggctgcac catctgtctt catcttcccg     360
ccatctgatg agcagttgaa atctggaact gcctctgttg tgtgcctgct gaataacttc     420
tatcccagag aggccaaagt acagtggaag gtggataacg ccctccaatc gggtaactcc     480
caggagagtg tcacagagca ggacagcaag gacagcacct acagcctcag cagcaccctg     540
acgctgagca agcagactac gagaaacac aaagtctacg cctgcgaagt cacccatcag     600
ggcctgagct cgcccgtcac aaagagcttc aacaggggag agtgt                      645
```

<210> SEQ ID NO 21

<211> LENGTH: 466
<212> TYPE: PRT
<213> ORGANISM: Artificial Sequence
<220> FEATURE:
<223> OTHER INFORMATION: Human IL-2R-beta-Fc(hole) fusion protein

<400> SEQUENCE: 21

```
Met Asp Met Arg Val Pro Ala Gln Leu Leu Gly Leu Leu Leu Leu Trp
1               5                   10                  15

Phe Pro Gly Ala Arg Cys Ala Val Asn Gly Thr Ser Gln Phe Thr Cys
            20                  25                  30

Phe Tyr Asn Ser Arg Ala Asn Ile Ser Cys Val Trp Ser Gln Asp Gly
        35                  40                  45

Ala Leu Gln Asp Thr Ser Cys Gln Val His Ala Trp Pro Asp Arg Arg
    50                  55                  60

Arg Trp Asn Gln Thr Cys Glu Leu Leu Pro Val Ser Gln Ala Ser Trp
65                  70                  75                  80

Ala Cys Asn Leu Ile Leu Gly Ala Pro Asp Ser Gln Lys Leu Thr Thr
                85                  90                  95

Val Asp Ile Val Thr Leu Arg Val Leu Cys Arg Glu Gly Val Arg Trp
            100                 105                 110

Arg Val Met Ala Ile Gln Asp Phe Lys Pro Phe Glu Asn Leu Arg Leu
        115                 120                 125

Met Ala Pro Ile Ser Leu Gln Val Val His Val Glu Thr His Arg Cys
    130                 135                 140

Asn Ile Ser Trp Glu Ile Ser Gln Ala Ser His Tyr Phe Glu Arg His
145                 150                 155                 160

Leu Glu Phe Glu Ala Arg Thr Leu Ser Pro Gly His Thr Trp Glu Glu
                165                 170                 175

Ala Pro Leu Leu Thr Leu Lys Gln Lys Gln Glu Trp Ile Cys Leu Glu
            180                 185                 190

Thr Leu Thr Pro Asp Thr Gln Tyr Glu Phe Gln Val Arg Val Lys Pro
        195                 200                 205

Leu Gln Gly Glu Phe Thr Thr Trp Ser Pro Trp Ser Gln Pro Leu Ala
    210                 215                 220

Phe Arg Thr Lys Pro Ala Ala Leu Gly Lys Asp Thr Gly Ala Gln Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Lys Phe Asn Trp Tyr Val Asp Gly Val Glu Val His
    290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
            340                 345                 350

Lys Thr Ile Ser Lys Ala Lys Gly Gln Pro Arg Glu Pro Gln Val Cys
        355                 360                 365

Thr Leu Pro Pro Ser Arg Asp Glu Leu Thr Lys Asn Gln Val Ser Leu
    370                 375                 380
```

| Ser | Cys | Ala | Val | Lys | Gly | Phe | Tyr | Pro | Ser | Asp | Ile | Ala | Val | Glu | Trp |
| 385 | | | | 390 | | | | | 395 | | | | | 400 | |

| Glu | Ser | Asn | Gly | Gln | Pro | Glu | Asn | Asn | Tyr | Lys | Thr | Thr | Pro | Pro | Val |
| | | | | 405 | | | | | 410 | | | | | 415 | |

| Leu | Asp | Ser | Asp | Gly | Ser | Phe | Phe | Leu | Val | Ser | Lys | Leu | Thr | Val | Asp |
| | | | 420 | | | | | 425 | | | | | 430 | | |

| Lys | Ser | Arg | Trp | Gln | Gln | Gly | Asn | Val | Phe | Ser | Cys | Ser | Val | Met | His |
| | | | 435 | | | | | 440 | | | | | 445 | | |

| Glu | Ala | Leu | His | Asn | His | Tyr | Thr | Gln | Lys | Ser | Leu | Ser | Leu | Ser | Pro |
| | | | 450 | | | | | 455 | | | | | 460 | | |

| Gly | Lys |
| 465 | |

<210> SEQ ID NO 22
<211> LENGTH: 1401
<212> TYPE: DNA
<213> ORGANISM: Artificial Sequence
<220> FEATURE:
<223> OTHER INFORMATION: Human IL-2R-beta-Fc(hole) fusion protein

<400> SEQUENCE: 22

```
atggacatga gggtccccgc tcagctcctg ggcctcctgc tgctctggtt cccaggtgcc     60
aggtgtgcgg tgaatggcac ttcccagttc acatgcttct acaactcgag agccaacatc    120
tcctgtgtct ggagccaaga tgggctctg caggacactt cctgccaagt ccatgcctgg    180
ccggacagac ggcggtggaa ccaaacctgt gagctgctcc ccgtgagtca agcatcctgg    240
gcctgcaacc tgatcctcgg agccccagat tctcagaaac tgaccacagt tgacatcgtc    300
accctgaggg tgctgtgccg tgaggggtg cgatggaggg tgatggccat ccaggacttc    360
aagccctttg agaaccttcg cctgatggcc cccatctccc tccaagttgt ccacgtggag    420
acccacagat gcaacataag ctgggaaatc tcccaagcct cccactactt tgaaagacac    480
ctggagttcg aggcccggac gctgtcccca ggccacacct gggaggaggc ccccctgctg    540
actctcaagc agaagcagga atggatctgc tggagacgc tcaccccaga cacccagtat    600
gagtttcagg tgcgggtcaa gcctctgcaa ggcgagttca cgacctggag ccctggagc    660
cagccctgg ccttcagaac aaagcctgca gcccttggga aggacaccgg agctcaggac    720
aaaactcaca catgcccacc gtgcccagca cctgaactcc tggggggacc gtcagtcttc    780
ctcttccccc caaaacccaa ggacaccctc atgatctccc ggacccctga ggtcacatgc    840
gtggtggtgg acgtgagcca cgaagaccct gaggtcaagt tcaactggta cgtggacggc    900
gtggaggtgc ataatgccaa gacaaagccg cgggaggagc agtacaacag cacgtaccgt    960
gtggtcagcg tcctcaccgt cctgcaccag gactggctga atggcaagga gtacaagtgc   1020
aaggtctcca acaaagccct cccagccccc atcgagaaaa ccatctccaa agccaaaggg   1080
cagccccgag aaccacaggt gtgcaccctg cccccatccc gggatgagct gaccaagaac   1140
caggtcagcc tctcgtgcgc agtcaaaggc ttctatccca gcgacatcgc cgtggagtgg   1200
gagagcaatg ggcagccgga gaacaactac aagaccacgc tcccgtgctg gactccgac   1260
ggctccttct tcctcgtgag caagctcacc gtggacaaga gcaggtggca gcaggggaac   1320
gtcttctcat gctccgtgat gcatgaggct ctgcacaacc actacacgca gaagagcctc   1380
tccctgtctc cgggtaaatg a                                              1401
```

<210> SEQ ID NO 23

<211> LENGTH: 492
<212> TYPE: PRT
<213> ORGANISM: Artificial Sequence
<220> FEATURE:
<223> OTHER INFORMATION: Human IL-2R-gamma-Fc(knob) fusion protein

<400> SEQUENCE: 23

```
Met Leu Lys Pro Ser Leu Pro Phe Thr Ser Leu Leu Phe Leu Gln Leu
1               5                   10                  15

Pro Leu Leu Gly Val Gly Leu Asn Thr Thr Ile Leu Thr Pro Asn Gly
            20                  25                  30

Asn Glu Asp Thr Thr Ala Asp Phe Phe Leu Thr Thr Met Pro Thr Asp
        35                  40                  45

Ser Leu Ser Val Ser Thr Leu Pro Leu Pro Glu Val Gln Cys Phe Val
    50                  55                  60

Phe Asn Val Glu Tyr Met Asn Cys Thr Trp Asn Ser Ser Ser Glu Pro
65                  70                  75                  80

Gln Pro Thr Asn Leu Thr Leu His Tyr Trp Tyr Lys Asn Ser Asp Asn
                85                  90                  95

Asp Lys Val Gln Lys Cys Ser His Tyr Leu Phe Ser Glu Glu Ile Thr
            100                 105                 110

Ser Gly Cys Gln Leu Gln Lys Lys Glu Ile His Leu Tyr Gln Thr Phe
        115                 120                 125

Val Val Gln Leu Gln Asp Pro Arg Glu Pro Arg Arg Gln Ala Thr Gln
    130                 135                 140

Met Leu Lys Leu Gln Asn Leu Val Ile Pro Trp Ala Pro Glu Asn Leu
145                 150                 155                 160

Thr Leu His Lys Leu Ser Glu Ser Gln Leu Glu Leu Asn Trp Asn Asn
                165                 170                 175

Arg Phe Leu Asn His Cys Leu Glu His Leu Val Gln Tyr Arg Thr Asp
            180                 185                 190

Trp Asp His Ser Trp Thr Glu Gln Ser Val Asp Tyr Arg His Lys Phe
        195                 200                 205

Ser Leu Pro Ser Val Asp Gly Gln Lys Arg Tyr Thr Phe Arg Val Arg
    210                 215                 220

Ser Arg Phe Asn Pro Leu Cys Gly Ser Ala Gln His Trp Ser Glu Trp
225                 230                 235                 240

Ser His Pro Ile His Trp Gly Ser Asn Thr Ser Lys Glu Asn Pro Phe
                245                 250                 255

Leu Phe Ala Leu Glu Ala Gly Ala Gln Asp Lys Thr His Thr Cys Pro
            260                 265                 270

Pro Cys Pro Ala Pro Glu Leu Leu Gly Gly Pro Ser Val Phe Leu Phe
        275                 280                 285

Pro Pro Lys Pro Lys Asp Thr Leu Met Ile Ser Arg Thr Pro Glu Val
    290                 295                 300

Thr Cys Val Val Val Asp Val Ser His Glu Asp Pro Glu Val Lys Phe
305                 310                 315                 320

Asn Trp Tyr Val Asp Gly Val Glu Val His Asn Ala Lys Thr Lys Pro
                325                 330                 335

Arg Glu Glu Gln Tyr Asn Ser Thr Tyr Arg Val Val Ser Val Leu Thr
            340                 345                 350

Val Leu His Gln Asp Trp Leu Asn Gly Lys Glu Tyr Lys Cys Lys Val
        355                 360                 365

Ser Asn Lys Ala Leu Pro Ala Pro Ile Glu Lys Thr Ile Ser Lys Ala
    370                 375                 380
```

```
Lys Gly Gln Pro Arg Glu Pro Gln Val Tyr Thr Leu Pro Pro Cys Arg
385                 390                 395                 400

Asp Glu Leu Thr Lys Asn Gln Val Ser Leu Trp Cys Leu Val Lys Gly
                405                 410                 415

Phe Tyr Pro Ser Asp Ile Ala Val Glu Trp Glu Ser Asn Gly Gln Pro
            420                 425                 430

Glu Asn Asn Tyr Lys Thr Thr Pro Pro Val Leu Asp Ser Asp Gly Ser
            435                 440                 445

Phe Phe Leu Tyr Ser Lys Leu Thr Val Asp Lys Ser Arg Trp Gln Gln
    450                 455                 460

Gly Asn Val Phe Ser Cys Ser Val Met His Glu Ala Leu His Asn His
465                 470                 475                 480

Tyr Thr Gln Lys Ser Leu Ser Leu Ser Pro Gly Lys
                485                 490
```

<210> SEQ ID NO 24
<211> LENGTH: 1479
<212> TYPE: DNA
<213> ORGANISM: Artificial Sequence
<220> FEATURE:
<223> OTHER INFORMATION: Human IL-2R-gamma-Fc(knob) fusion protein

<400> SEQUENCE: 24

```
atgttgaagc catcattacc attcacatcc ctcttattcc tgcagctgcc cctgctggga      60
gtggggctga acacgacaat tctgacgccc aatgggaatg aagacaccac agctgatttc    120
ttcctgacca ctatgcccac tgactccctc agtgtttcca ctctgcccct cccagaggtt    180
cagtgttttg tgttcaatgt cgagtacatg aattgcactt ggaacagcag ctctgagccc    240
cagcctacca acctcactct gcattattgg tacaagaact cggataatga taaagtccag    300
aagtgcagcc actatctatt ctctgaagaa tcacttctg gctgtcagtt gcaaaaaaag      360
gagatccacc tctaccaaac atttgttgtt cagctccagg acccacggga acccaggaga    420
caggccacac agatgctaaa actgcagaat ctggtgatcc cctgggctcc agagaaccta    480
acacttcaca aactgagtga atcccagcta gaactgaact ggaacaacag attcttgaac    540
cactgtttgg agcacttggt gcagtaccgg actgactggg accacagctg gactgaacaa    600
tcagtggatt atagacataa gttctccttg cctagtgtgg atgggcagaa acgctacacg    660
tttcgtgttc ggagccgctt taacccactc tgtggaagtg ctcagcattg gagtgaatgg    720
agccacccaa tccactgggg gagcaatact tcaaaagaga tcctttcct gtttgcattg      780 gaagccggag ctcaggacaa aactcacaca tgcccaccgt gcccagcacc tgaactcctg    840
gggggaccgt cagtcttcct cttcccccca aaacccaagg acaccctcat gatctcccgg    900
acccctgagg tcacatgcgt ggtggtggac gtgagccacg aagaccctga ggtcaagttc    960
aactggtacg tggacggcgt ggaggtgcat aatgccaaga caaagccgcg ggaggagcag    1020
tacaacagca cgtaccgtgt ggtcagcgtc ctcaccgtcc tgcaccagga ctggctgaat    1080
ggcaaggagt acaagtgcaa ggtctccaac aaagccctcc cagcccccat cgagaaaacc    1140
atctccaaag ccaaagggca gccccgagaa ccacaggtgt acaccctgcc cccatgccgg    1200
gatgagctga ccaagaacca ggtcagcctg tggtgcctgg tcaaaggctt ctatcccagc    1260
gacatcgccg tggagtggga gagcaatggg cagccggaga caactacaa gaccacgcct     1320 cccgtgctgg actccgacgg ctccttcttc ctctacagca agctcaccgt ggacaagagc    1380
aggtggcagc aggggaacgt cttctcatgc tccgtgatgc atgaggctct gcacaaccac    1440
```
tacacgcaga agagcctctc cctgtctccg ggtaaatga          1479

<210> SEQ ID NO 25
<211> LENGTH: 219
<212> TYPE: PRT
<213> ORGANISM: Artificial Sequence
<220> FEATURE:
<223> OTHER INFORMATION: Human IL-2R alpha subunit + Avi-tag + His-tag

<400> SEQUENCE: 25

Met Gly Trp Ser Cys Ile Ile Leu Phe Leu Val Ala Thr Ala Thr Gly
1               5                   10                  15

Val His Ser Glu Leu Cys Asp Asp Pro Pro Glu Ile Pro His Ala
            20                  25                  30

Thr Phe Lys Ala Met Ala Tyr Lys Glu Gly Thr Met Leu Asn Cys Glu
        35                  40                  45

Cys Lys Arg Gly Phe Arg Arg Ile Lys Ser Gly Ser Leu Tyr Met Leu
    50                  55                  60

Cys Thr Gly Asn Ser Ser His Ser Ser Trp Asp Asn Gln Cys Gln Cys
65                  70                  75                  80

Thr Ser Ser Ala Thr Arg Asn Thr Thr Lys Gln Val Thr Pro Gln Pro
                85                  90                  95

Glu Glu Gln Lys Glu Arg Lys Thr Thr Glu Met Gln Ser Pro Met Gln
            100                 105                 110

Pro Val Asp Gln Ala Ser Leu Pro Gly His Cys Arg Glu Pro Pro Pro
        115                 120                 125

Trp Glu Asn Glu Ala Thr Glu Arg Ile Tyr His Phe Val Val Gly Gln
    130                 135                 140

Met Val Tyr Tyr Gln Cys Val Gln Gly Tyr Arg Ala Leu His Arg Gly
145                 150                 155                 160

Pro Ala Glu Ser Val Cys Lys Met Thr His Gly Lys Thr Arg Trp Thr
                165                 170                 175

Gln Pro Gln Leu Ile Cys Thr Gly Val Asp Glu Gln Leu Tyr Phe Gln
            180                 185                 190

Gly Gly Ser Gly Leu Asn Asp Ile Phe Glu Ala Gln Lys Ile Glu Trp
        195                 200                 205

His Glu Ala Arg Ala His His His His His His
    210                 215

<210> SEQ ID NO 26
<211> LENGTH: 660
<212> TYPE: DNA
<213> ORGANISM: Artificial Sequence
<220> FEATURE:
<223> OTHER INFORMATION: Human IL-2R alpha subunit + Avi-tag + His-tag

<400> SEQUENCE: 26
atgggatgga gctgtatcat cctcttcttg gtagcaacag ctaccggtgt gcattccgag     60
ctctgtgacg atgacccgcc agagatccca cacgccacat tcaaagccat ggcctacaag    120
gaaggaacca tgttgaactg tgaatgcaag agaggtttcc gcagaataaa aagcgggtca   180
ctctatatgc tctgtacagg aaactctagc cactcgtcct gggacaacca atgtcaatgc   240
acaagctctg ccactcggaa cacaacgaaa caagtgacac tcaacctga gaacagaaa    300 gaaaggaaaa ccacagaaat gcaaagtcca atgcagccag tggaccaagc gagccttcca    360
ggtcactgca gggaacctcc accatgggaa atgaagccaca gagagaat ttatcatttc    420

-continued

```
gtggtggggc agatggttta ttatcagtgc gtccaggat  acagggctct acacagaggt   480
cctgctgaga gcgtctgcaa aatgacccac gggaagacaa ggtggaccca gccccagctc   540
atatgcacag gtgtcgacga acagttatat tttcagggcg gctcaggcct gaacgacatc   600
ttcgaggccc agaagatcga gtggcacgag gctcgagctc accaccatca ccatcactga   660
```

<210> SEQ ID NO 27
<211> LENGTH: 473
<212> TYPE: PRT
<213> ORGANISM: Artificial Sequence
<220> FEATURE:
<223> OTHER INFORMATION: Murine IL-2R-beta-Fc(hole) fusion protein

<400> SEQUENCE: 27

```
Met Asp Met Arg Val Pro Ala Gln Leu Leu Gly Leu Leu Leu Leu Trp
1               5                   10                  15

Phe Pro Leu Leu Leu Trp Phe Pro Gly Ala Arg Cys Ala Val Lys
            20                  25                  30

Asn Cys Ser His Leu Glu Cys Phe Tyr Asn Ser Arg Ala Asn Val Ser
        35                  40                  45

Cys Met Trp Ser His Glu Glu Ala Leu Asn Val Thr Thr Cys His Val
    50                  55                  60

His Ala Lys Ser Asn Leu Arg His Trp Asn Lys Thr Cys Glu Leu Thr
65                  70                  75                  80

Leu Val Arg Gln Ala Ser Trp Ala Cys Asn Leu Ile Leu Gly Ser Phe
                85                  90                  95

Pro Glu Ser Gln Ser Leu Thr Ser Val Asp Leu Leu Asp Ile Asn Val
            100                 105                 110

Val Cys Trp Glu Glu Lys Gly Trp Arg Arg Val Lys Thr Cys Asp Phe
        115                 120                 125

His Pro Phe Asp Asn Leu Arg Leu Val Ala Pro His Ser Leu Gln Val
    130                 135                 140

Leu His Ile Asp Thr Gln Arg Cys Asn Ile Ser Trp Lys Val Ser Gln
145                 150                 155                 160

Val Ser His Tyr Ile Glu Pro Tyr Leu Glu Phe Glu Ala Arg Arg Arg
                165                 170                 175

Leu Leu Gly His Ser Trp Glu Asp Ala Ser Val Leu Ser Leu Lys Gln
            180                 185                 190

Arg Gln Gln Trp Leu Phe Leu Glu Met Leu Ile Pro Ser Thr Ser Tyr
        195                 200                 205

Glu Val Gln Val Arg Val Lys Ala Gln Arg Asn Asn Thr Gly Thr Trp
    210                 215                 220

Ser Pro Trp Ser Gln Pro Leu Thr Phe Arg Thr Arg Pro Ala Asp Pro
225                 230                 235                 240

Met Lys Glu Gly Ala Gln Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
```

```
                     325                 330                 335
Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
            355                 360                 365

Pro Arg Glu Pro Gln Val Cys Thr Leu Pro Pro Ser Arg Asp Glu Leu
        370                 375                 380

Thr Lys Asn Gln Val Ser Leu Ser Cys Ala Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Val Ser Lys Leu Thr Val Asp Lys Ser Arg Trp Gln Gln Gly Asn Val
            435                 440                 445

Phe Ser Cys Ser Val Met His Glu Ala Leu His Asn His Tyr Thr Gln
        450                 455                 460

Lys Ser Leu Ser Leu Ser Pro Gly Lys
465                 470
```

<210> SEQ ID NO 28
<211> LENGTH: 1422
<212> TYPE: DNA
<213> ORGANISM: Artificial Sequence
<220> FEATURE:
<223> OTHER INFORMATION: Murine IL-2R-beta-Fc(hole) fusion protein

<400> SEQUENCE: 28

| | | | | | |
|---|---|---|---|---|---|
| atggacatga | gggtccccgc | tcagctcctg | ggcctcctgc | tgctctggtt | ccccctcctg | 60 |
| ctgctctggt | tcccaggtgc | caggtgtgca | gtgaaaaact | gttcccatct | tgaatgcttc | 120 |
| tacaactcaa | gagccaatgt | ctcttgcatg | tggagccatg | aagaggctct | gaatgtcaca | 180 |
| acctgccacg | tccatgccaa | gtcgaacctg | cgacactgga | caaaacctg | tgagctaact | 240 |
| cttgtgaggc | aggcatcctg | ggcctgcaac | ctgatcctcg | ggtcgttccc | agagtcccag | 300 |
| tcactgacct | ccgtggacct | ccttgacata | aatgtggtgt | gctgggaaga | gaagggttgg | 360 |
| cgtagggtaa | agacctgcga | cttccatccc | tttgacaacc | ttcgcctggt | ggcccctcat | 420 |
| tccctccaag | ttctgcacat | tgatacccag | agatgtaaca | taagctggaa | ggtctcccag | 480 |
| gtctctcact | acattgaacc | atacttggaa | tttgaggccc | gtagacgtct | tctgggccac | 540 |
| agctggagg | atgcatccgt | attaagcctc | aagcagagac | agcagtggct | cttcttggag | 600 |
| atgctgatcc | ctagtacctc | atatgaggtc | caggtgaggg | tcaaagctca | acgaaacaat | 660 |
| accgggacct | ggagtccctg | gagccagccc | ctgacctttc | ggacaaggcc | agcagatccc | 720 |
| atgaaggagg | gagctcagga | caaaactcac | acatgcccac | cgtgcccagc | acctgaactc | 780 |
| ctggggggac | cgtcagtctt | cctcttcccc | ccaaaaccca | aggacaccct | catgatctcc | 840 |
| cggacccctg | aggtcacatg | cgtggtggtg | gacgtgagcc | acgaagaccc | tgaggtcaag | 900 |
| ttcaactggt | acgtggacgg | cgtggaggtg | cataatgcca | agacaaagcc | gcggaggag | 960 |
| cagtacaaca | gcacgtaccg | tgtggtcagc | gtcctcaccg | tcctgcacca | ggactggctg | 1020 |
| aatggcaagg | agtacaagtg | caaggtctcc | aacaaagccc | tcccagcccc | catcgagaaa | 1080 |
| accatctcca | aagccaaagg | gcagcccga | gaaccacagg | tgtgcaccct | gcccccatcc | 1140 |
| cgggatgagc | tgaccaagaa | ccaggtcagc | ctctcgtgcg | cagtcaaagg | cttctatccc | 1200 |

-continued

```
agcgacatcg ccgtggagtg ggagagcaat gggcagccgg agaacaacta caagaccacg      1260
cctcccgtgc tggactccga cggctccttc ttcctcgtga gcaagctcac cgtggacaag      1320
agcaggtggc agcaggggaa cgtcttctca tgctccgtga tgcatgaggc tctgcacaac      1380
cactacacgc agaagagcct ctccctgtct ccgggtaaat ga                         1422
```

<210> SEQ ID NO 29
<211> LENGTH: 500
<212> TYPE: PRT
<213> ORGANISM: Artificial Sequence
<220> FEATURE:
<223> OTHER INFORMATION: Murine IL-2R-gamma-Fc(knob) fusion protein

<400> SEQUENCE: 29

```
Met Asp Met Arg Val Pro Ala Gln Leu Leu Gly Leu Leu Leu Leu Trp
1               5                  10                  15

Phe Pro Leu Leu Leu Leu Trp Phe Pro Gly Ala Arg Cys Trp Ser Ser
                20                  25                  30

Lys Val Leu Met Ser Ser Ala Asn Glu Asp Ile Lys Ala Asp Leu Ile
            35                  40                  45

Leu Thr Ser Thr Ala Pro Glu His Leu Ser Ala Pro Thr Leu Pro Leu
        50                  55                  60

Pro Glu Val Gln Cys Phe Val Phe Asn Ile Glu Tyr Met Asn Cys Thr
65                  70                  75                  80

Trp Asn Ser Ser Ser Glu Pro Gln Ala Thr Asn Leu Thr Leu His Tyr
                85                  90                  95

Arg Tyr Lys Val Ser Asp Asn Asn Thr Phe Gln Glu Cys Ser His Tyr
                100                 105                 110

Leu Phe Ser Lys Glu Ile Thr Ser Gly Cys Gln Ile Gln Lys Glu Asp
            115                 120                 125

Ile Gln Leu Tyr Gln Thr Phe Val Val Gln Leu Gln Asp Pro Gln Lys
        130                 135                 140

Pro Gln Arg Arg Ala Val Gln Lys Leu Asn Leu Gln Asn Leu Val Ile
145                 150                 155                 160

Pro Arg Ala Pro Glu Asn Leu Thr Leu Ser Asn Leu Ser Glu Ser Gln
                165                 170                 175

Leu Glu Leu Arg Trp Lys Ser Arg His Ile Lys Glu Arg Cys Leu Gln
                180                 185                 190

Tyr Leu Val Gln Tyr Arg Ser Asn Arg Asp Arg Ser Trp Thr Glu Leu
            195                 200                 205

Ile Val Asn His Glu Pro Arg Phe Ser Leu Pro Ser Val Asp Glu Leu
        210                 215                 220

Lys Arg Tyr Thr Phe Arg Val Arg Ser Arg Tyr Asn Pro Ile Cys Gly
225                 230                 235                 240

Ser Ser Gln Gln Trp Ser Lys Trp Ser Gln Pro Val His Trp Gly Ser
                245                 250                 255

His Thr Val Glu Glu Asn Pro Ser Leu Phe Ala Leu Glu Ala Gly Ala
                260                 265                 270

Gln Asp Lys Thr His Thr Cys Pro Pro Cys Pro Ala Pro Glu Leu Leu
            275                 280                 285

Gly Gly Pro Ser Val Phe Leu Phe Pro Pro Lys Pro Lys Asp Thr Leu
        290                 295                 300

Met Ile Ser Arg Thr Pro Glu Val Thr Cys Val Val Val Asp Val Ser
305                 310                 315                 320

His Glu Asp Pro Glu Val Lys Phe Asn Trp Tyr Val Asp Gly Val Glu
```

```
              325                 330                 335
Val His Asn Ala Lys Thr Lys Pro Arg Glu Glu Gln Tyr Asn Ser Thr
        340                 345                 350

Tyr Arg Val Val Ser Val Leu Thr Val Leu His Gln Asp Trp Leu Asn
    355                 360                 365

Gly Lys Glu Tyr Lys Cys Lys Val Ser Asn Lys Ala Leu Pro Ala Pro
370                 375                 380

Ile Glu Lys Thr Ile Ser Lys Ala Lys Gly Gln Pro Arg Glu Pro Gln
385                 390                 395                 400

Val Tyr Thr Leu Pro Pro Cys Arg Asp Glu Leu Thr Lys Asn Gln Val
            405                 410                 415

Ser Leu Trp Cys Leu Val Lys Gly Phe Tyr Pro Ser Asp Ile Ala Val
        420                 425                 430

Glu Trp Glu Ser Asn Gly Gln Pro Glu Asn Asn Tyr Lys Thr Thr Pro
    435                 440                 445

Pro Val Leu Asp Ser Asp Gly Ser Phe Phe Leu Tyr Ser Lys Leu Thr
450                 455                 460

Val Asp Lys Ser Arg Trp Gln Gln Gly Asn Val Phe Ser Cys Ser Val
465                 470                 475                 480

Met His Glu Ala Leu His Asn His Tyr Thr Gln Lys Ser Leu Ser Leu
            485                 490                 495

Ser Pro Gly Lys
            500

<210> SEQ ID NO 30
<211> LENGTH: 1503
<212> TYPE: DNA
<213> ORGANISM: Artificial Sequence
<220> FEATURE:
<223> OTHER INFORMATION: Murine IL-2R-gamma-Fc(knob) fusion protein

<400> SEQUENCE: 30
atggacatga gggtccccgc tcagctcctg ggcctcctgc tgctctggtt cccccTcctg      60
ctgctctggt tcccaggtgc caggtgttgg agttccaagg tcctcatgtc cagtgcgaat     120
gaagacatca aagctgattt gatcctgact tctacagccc ctgaacacct cagtgctcct     180
actctgcccc ttccagaggt tcagtgcttt gtgttcaaca tagagtacat gaattgcact     240
tggaatagca gttctgagcc tcaggcaacc aacctcacgc tgcactatag gtacaaggta     300
tctgataata tacattcca ggagtgcagt cactatttgt ctccaaaga gattacttct      360 ggctgtcaga tacaaaaaga agatatccag ctctaccaga catttgttgt ccagctccag     420
gacccccaga accccagag gcgagctgta cagaagctaa acctacagaa tcttgtgatc      480
ccacgggctc cagaaaatct aacactcagc aatctgagtg aatcccagct agagctgaga     540
tggaaaagca gacatattaa agaacgctgt ttacaatact ggtgcagta ccggagcaac      600 agagatcgaa gctggacgga actaatagtg aatcatgaac ctagattctc cctgcctagt     660
gtggatgagc tgaaacggta cacatttcgg gttcggagcc gctataaccc aatctgtgga     720
agttctcaac agtggagtaa atggagccag cctgtccact ggggagtca tactgtagag      780 gagaatcctt ccttgtttgc actggaagct ggagctcagg acaaaactca cacatgccca     840
ccgtgcccag cacctgaact cctgggggga ccgtcagtct tcctcttccc cccaaaaccc     900
aaggacaccc tcatgatctc ccggaccct gaggtcacat gcgtggtggt ggacgtgagc       960
cacgaagacc ctgaggtcaa gttcaactgg tacgtggacg gcgtggaggt gcataatgcc    1020
```

```
aagacaaagc cgcgggagga gcagtacaac agcacgtacc gtgtggtcag cgtcctcacc   1080
gtcctgcacc aggactggct gaatggcaag gagtacaagt gcaaggtctc caacaaagcc   1140
ctcccagccc ccatcgagaa aaccatctcc aaagccaaag gcagccccg agaaccacag    1200 gtgtacaccc tgcccccatg ccgggatgag ctgaccaaga accaggtcag cctgtggtgc   1260
ctggtcaaag gcttctatcc cagcgacatc gccgtggagt gggagagcaa tgggcagccg   1320
gagaacaact acaagaccac gcctcccgtg ctggactccg acggctcctt cttcctctac   1380
agcaagctca ccgtggacaa gagcaggtgg cagcagggga acgtcttctc atgctccgtg   1440
atgcatgagg ctctgcacaa ccactacacg cagaagagcc tctccctgtc tccgggtaaa   1500
tga                                                                 1503
```

<210> SEQ ID NO 31
<211> LENGTH: 213
<212> TYPE: PRT
<213> ORGANISM: Artificial Sequence
<220> FEATURE:
<223> OTHER INFORMATION: Murine IL-2R alpha subunit + Avi-tag + His-tag

<400> SEQUENCE: 31

```
Met Gly Trp Ser Cys Ile Ile Leu Phe Leu Val Ala Thr Ala Thr Gly
  1               5                  10                  15

Val His Ser Glu Leu Cys Leu Tyr Asp Pro Pro Glu Val Pro Asn Ala
             20                  25                  30

Thr Phe Lys Ala Leu Ser Tyr Lys Asn Gly Thr Ile Leu Asn Cys Glu
         35                  40                  45

Cys Lys Arg Gly Phe Arg Arg Leu Lys Glu Leu Val Tyr Met Arg Cys
     50                  55                  60

Leu Gly Asn Ser Trp Ser Ser Asn Cys Gln Cys Thr Ser Asn Ser His
 65                  70                  75                  80

Asp Lys Ser Arg Lys Gln Val Thr Ala Gln Leu Glu His Gln Lys Glu
                 85                  90                  95

Gln Gln Thr Thr Thr Asp Met Gln Lys Pro Thr Gln Ser Met His Gln
            100                 105                 110

Glu Asn Leu Thr Gly His Cys Arg Glu Pro Pro Trp Lys His Glu
        115                 120                 125

Asp Ser Lys Arg Ile Tyr His Phe Val Glu Gly Gln Ser Val His Tyr
    130                 135                 140

Glu Cys Ile Pro Gly Tyr Lys Ala Leu Gln Arg Gly Pro Ala Ile Ser
145                 150                 155                 160

Ile Cys Lys Met Lys Cys Gly Lys Thr Gly Trp Thr Gln Pro Gln Leu
                165                 170                 175

Thr Cys Val Asp Glu Gln Leu Tyr Phe Gln Gly Gly Ser Gly Leu Asn
            180                 185                 190

Asp Ile Phe Glu Ala Gln Lys Ile Glu Trp His Glu Ala Arg Ala His
        195                 200                 205

His His His His His
    210
```

<210> SEQ ID NO 32
<211> LENGTH: 642
<212> TYPE: DNA
<213> ORGANISM: Artificial Sequence
<220> FEATURE:
<223> OTHER INFORMATION: Murine IL-2R alpha subunit + Avi-tag + His-tag

<400> SEQUENCE: 32

```
atgggatgga gctgtatcat cctcttcttg gtagcaacag ctaccggtgt gcattccgaa      60
ctgtgtctgt atgacccacc cgaggtcccc aatgccacat tcaaagccct ctcctacaag     120
aacggcacca tcctaaactg tgaatgcaag agaggtttcc gaagactaaa ggaattggtc     180
tatatgcgtt gcttaggaaa ctcctggagc agcaactgcc agtgcaccag caactcccat     240
gacaaatcga gaaagcaagt tacagctcaa cttgaacacc agaaagagca acaaaccaca     300
acagacatgc agaagccaac acagtctatg caccaagaga accttacagg tcactgcagg     360
gagccacctc cttggaaaca tgaagattcc aagagaatct atcatttcgt ggaaggacag     420
agtgttcact acgagtgtat tccgggatac aaggctctac agagaggtcc tgctattagc     480
atctgcaaga tgaagtgtgg gaaaacgggg tggactcagc cccagctcac atgtgtcgac     540
gaacagttat attttcaggg cggctcaggc ctgaacgaca tcttcgaggc ccagaagatc     600
gagtggcacg aggctcgagc tcaccaccat caccatcact ga                        642
```

<210> SEQ ID NO 33
<211> LENGTH: 480
<212> TYPE: PRT
<213> ORGANISM: Artificial Sequence
<220> FEATURE:
<223> OTHER INFORMATION: Cynomolgous IL-2R-beta-Fc(knob) fusion
      protein + Avi-tag

<400> SEQUENCE: 33

```
Met Gly Trp Ser Cys Ile Ile Leu Phe Leu Val Ala Thr Ala Thr Gly
1               5                   10                  15

Val His Ser Ala Val Asn Gly Thr Ser Arg Phe Thr Cys Phe Tyr Asn
            20                  25                  30

Ser Arg Ala Asn Ile Ser Cys Val Trp Ser Gln Asp Gly Ala Leu Gln
        35                  40                  45

Asp Thr Ser Cys Gln Val His Ala Trp Pro Asp Arg Arg Arg Trp Asn
    50                  55                  60

Gln Thr Cys Glu Leu Leu Pro Val Ser Gln Ala Ser Trp Ala Cys Asn
65                  70                  75                  80

Leu Ile Leu Gly Thr Pro Asp Ser Gln Lys Leu Thr Ala Val Asp Ile
                85                  90                  95

Val Thr Leu Arg Val Met Cys Arg Glu Gly Val Arg Trp Arg Met Met
            100                 105                 110

Ala Ile Gln Asp Phe Lys Pro Phe Glu Asn Leu Arg Leu Met Ala Pro
        115                 120                 125

Ile Ser Leu Gln Val Val His Val Glu Thr His Arg Cys Asn Ile Ser
    130                 135                 140

Trp Lys Ile Ser Gln Ala Ser His Tyr Phe Glu Arg His Leu Glu Phe
145                 150                 155                 160

Glu Ala Arg Thr Leu Ser Pro Gly His Thr Trp Glu Glu Ala Pro Leu
                165                 170                 175

Met Thr Leu Lys Gln Lys Gln Glu Trp Ile Cys Leu Glu Thr Leu Thr
            180                 185                 190

Pro Asp Thr Gln Tyr Glu Phe Gln Val Arg Val Lys Pro Leu Gln Gly
        195                 200                 205

Glu Phe Thr Thr Trp Ser Pro Trp Ser Gln Pro Leu Ala Phe Arg Thr
    210                 215                 220

Lys Pro Ala Ala Leu Gly Lys Asp Thr Gly Ala Gln Asp Lys Thr His
225                 230                 235                 240
```

| | | | | | | | | | | | |
|---|---|---|---|---|---|---|---|---|---|---|---|
|Thr|Cys|Pro|Pro|Cys|Pro|Ala|Pro|Glu|Leu|Gly|Gly|Pro|Ser|Val|
| | | |245| | | |250| | | |255| |

Phe Leu Phe Pro Pro Lys Pro Lys Asp Thr Leu Met Ile Ser Arg Thr
        260                  265                270

Pro Glu Val Thr Cys Val Val Val Asp Val Ser His Glu Asp Pro Glu
        275                  280                285

Val Lys Phe Asn Trp Tyr Val Asp Gly Val Glu Val His Asn Ala Lys
        290                  295                300

Thr Lys Pro Arg Glu Glu Gln Tyr Asn Ser Thr Tyr Arg Val Val Ser
305                310                315                320

Val Leu Thr Val Leu His Gln Asp Trp Leu Asn Gly Lys Glu Tyr Lys
        325                  330                335

Cys Lys Val Ser Asn Lys Ala Leu Pro Ala Pro Ile Glu Lys Thr Ile
        340                  345                350

Ser Lys Ala Lys Gly Gln Pro Arg Glu Pro Gln Val Tyr Thr Leu Pro
        355                  360                365

Pro Cys Arg Asp Glu Leu Thr Lys Asn Gln Val Ser Leu Trp Cys Leu
        370                  375                380

Val Lys Gly Phe Tyr Pro Ser Asp Ile Ala Val Glu Trp Glu Ser Asn
385                390                395                400

Gly Gln Pro Glu Asn Asn Tyr Lys Thr Thr Pro Pro Val Leu Asp Ser
        405                  410                415

Asp Gly Ser Phe Phe Leu Tyr Ser Lys Leu Thr Val Asp Lys Ser Arg
        420                  425                430

Trp Gln Gln Gly Asn Val Phe Ser Cys Ser Val Met His Glu Ala Leu
        435                  440                445

His Asn His Tyr Thr Gln Lys Ser Leu Ser Leu Ser Pro Gly Lys Ser
        450                  455                460

Gly Gly Leu Asn Asp Ile Phe Glu Ala Gln Lys Ile Glu Trp His Glu
465                470                475                480

<210> SEQ ID NO 34
<211> LENGTH: 1443
<212> TYPE: DNA
<213> ORGANISM: Artificial Sequence
<220> FEATURE:
<223> OTHER INFORMATION: Cynomolgous IL-2R-beta-Fc(knob) fusion
    protein + Avi-tag

<400> SEQUENCE: 34

```
atgggatgga gctgtatcat cctcttcttg gtagcaacag ctaccggtgt gcattccgcg      60
gtcaacggca cttcccggtt cacatgcttc tacaactcga gagccaacat ctcctgtgtc     120
tggagccaag atgggctct gcaggacact tcctgccaag tccacgcctg ccgggacaga      180
cggcggtgga accaaacctg tgagctgctc cctgtgagtc aagcatcctg ggcctgcaac     240
ctgatcctcg aaccccaga ttctcagaaa ctgaccgcag tggatatcgt caccctgagg      300
gtgatgtgcc gtgaagggt gcgatggagg atgatggcca tccaggactt caaacccttt     360
gagaaccttc gcctgatggc ccccatctcc ctccaagtcg tccacgtgga gacccacaga     420
tgcaacataa gctggaaaat ctcccaagcc tccactact tgaaagaca cctggagttt       480 gaggcccgga cgctgtcccc aggccacacc tgggaggagg cccccctgat gaccctcaag     540
cagaagcagg aatggatctg cctggagacg ctcacccag acacccagta tgagtttcag      600
gtgcgggtca gcctctgca aggcgagttc acgacctgga gccccggag ccagcccctg       660 gccttcagga caaagcctgc agcccttggg aaggacaccg gagctcagga caaaactcac     720
```

```
acatgcccac cgtgcccagc acctgaactc ctggggggac cgtcagtctt cctcttcccc      780
ccaaaaccca aggacaccct catgatctcc cggacccctg aggtcacatg cgtggtggtg      840
gacgtgagcc acgaagaccc tgaggtcaag ttcaactggt acgtggacgg cgtggaggtg      900
cataatgcca agacaaagcc gcgggaggag cagtacaaca gcacgtaccg tgtggtcagc      960
gtcctcaccg tcctgcacca ggactggctg aatggcaagg agtacaagtg caaggtctcc     1020
aacaaagccc tcccagcccc catcgagaaa accatctcca aagccaaagg cagccccga      1080 gaaccacagg tgtacaccct gcccccatgc cgggatgagc tgaccaagaa ccaggtcagc     1140
ctgtggtgcc tggtcaaagg cttctatccc agcgacatcg ccgtggagtg ggagagcaat     1200
gggcagccgg agaacaacta caagaccacg cctcccgtgc tggactccga cggctccttc     1260
ttcctctaca gcaagctcac cgtggacaag agcaggtggc agcaggggaa cgtcttctca     1320
tgctccgtga tgcatgaggc tctgcacaac cactacacgc agaagagcct ctccctgtct     1380
ccgggtaaat ccggaggcct gaacgacatc ttcgaggccc agaagattga atggcacgag     1440
tga                                                                    1443
```

<210> SEQ ID NO 35
<211> LENGTH: 489
<212> TYPE: PRT
<213> ORGANISM: Artificial Sequence
<220> FEATURE:
<223> OTHER INFORMATION: Cynomolgous IL-2R-gamma-Fc(hole) fusion protein

<400> SEQUENCE: 35

```
Met Gly Trp Ser Cys Ile Ile Leu Phe Leu Val Ala Thr Ala Thr Gly
1               5                   10                  15

Val His Ser Leu Asn Thr Thr Ile Leu Thr Pro Asn Gly Asn Glu Asp
            20                  25                  30

Ala Thr Thr Asp Phe Phe Leu Thr Ser Met Pro Thr Asp Ser Leu Ser
        35                  40                  45

Val Ser Thr Leu Pro Leu Pro Glu Val Gln Cys Phe Val Phe Asn Val
    50                  55                  60

Glu Tyr Met Asn Cys Thr Trp Asn Ser Ser Ser Glu Pro Gln Pro Thr
65                  70                  75                  80

Asn Leu Thr Leu His Tyr Trp Tyr Lys Asn Ser Asp Asn Asp Lys Val
                85                  90                  95

Gln Lys Cys Ser His Tyr Leu Phe Ser Glu Glu Ile Thr Ser Gly Cys
            100                 105                 110

Gln Leu Gln Lys Lys Glu Ile His Leu Tyr Gln Thr Phe Val Val Gln
        115                 120                 125

Leu Gln Asp Pro Arg Glu Pro Arg Arg Gln Ala Thr Gln Met Leu Lys
    130                 135                 140

Leu Gln Asn Leu Val Ile Pro Trp Ala Pro Glu Asn Leu Thr Leu Arg
145                 150                 155                 160

Lys Leu Ser Glu Ser Gln Leu Glu Leu Asn Trp Asn Asn Arg Phe Leu
                165                 170                 175

Asn His Cys Leu Glu His Leu Val Gln Tyr Arg Thr Asp Trp Asp His
            180                 185                 190

Ser Trp Thr Glu Gln Ser Val Asp Tyr Arg His Lys Phe Ser Leu Pro
        195                 200                 205

Ser Val Asp Gly Gln Lys Arg Tyr Thr Phe Arg Val Arg Ser Arg Phe
    210                 215                 220
```

Asn Pro Leu Cys Gly Ser Ala Gln His Trp Ser Glu Trp Ser His Pro
225                 230                 235                 240

Ile His Trp Gly Ser Asn Ser Lys Glu Asn Pro Phe Leu Phe Ala
            245                 250                 255

Leu Glu Ala Gly Ala Gln Asp Lys Thr His Thr Cys Pro Pro Cys Pro
        260                 265                 270

Ala Pro Glu Leu Leu Gly Gly Pro Ser Val Phe Leu Phe Pro Pro Lys
    275                 280                 285

Pro Lys Asp Thr Leu Met Ile Ser Arg Thr Pro Glu Val Thr Cys Val
290                 295                 300

Val Val Asp Val Ser His Glu Asp Pro Glu Val Lys Phe Asn Trp Tyr
305                 310                 315                 320

Val Asp Gly Val Glu Val His Asn Ala Lys Thr Lys Pro Arg Glu Glu
            325                 330                 335

Gln Tyr Asn Ser Thr Tyr Arg Val Val Ser Val Leu Thr Val Leu His
        340                 345                 350

Gln Asp Trp Leu Asn Gly Lys Glu Tyr Lys Cys Lys Val Ser Asn Lys
    355                 360                 365

Ala Leu Gly Ala Pro Ile Glu Lys Thr Ile Ser Lys Ala Lys Gly Gln
370                 375                 380

Pro Arg Glu Pro Gln Val Cys Thr Leu Pro Pro Ser Arg Asp Glu Leu
385                 390                 395                 400

Thr Lys Asn Gln Val Ser Leu Ser Cys Ala Val Lys Gly Phe Tyr Pro
            405                 410                 415

Ser Asp Ile Ala Val Glu Trp Glu Ser Asn Gly Gln Pro Glu Asn Asn
        420                 425                 430

Tyr Lys Thr Thr Pro Pro Val Leu Asp Ser Asp Gly Ser Phe Phe Leu
    435                 440                 445

Val Ser Lys Leu Thr Val Asp Lys Ser Arg Trp Gln Gln Gly Asn Val
450                 455                 460

Phe Ser Cys Ser Val Met His Glu Ala Leu His Asn His Tyr Thr Gln
465                 470                 475                 480

Lys Ser Leu Ser Leu Ser Pro Gly Lys
            485

<210> SEQ ID NO 36
<211> LENGTH: 1470
<212> TYPE: DNA
<213> ORGANISM: Artificial Sequence
<220> FEATURE:
<223> OTHER INFORMATION: Cynomolgous IL-2R-gamma-Fc(hole) fusion protein

<400> SEQUENCE: 36
atgggatgga gctgtatcat cctcttcttg gtagcaacag ctaccggtgt gcattccctg      60
aacacgacaa ttctgacgcc aatgggaat gaagacgcca caactgattt cttcctgacc     120
tctatgccca ctgactccct cagtgttttcc actctgcccc tcccagaggt tcagtgtttt     180
gtgttcaatg tcgagtacat gaattgcact tggaacagca gctctgagcc ccagcctacc     240
aacctcactc tgcattattg gtacaagaat tcggataatg ataaagtcca gaagtgcagc     300
cactatctat tctctgaaga aatcacttct ggctgtcagt tgcaaaaaaa ggagatccac     360
ctctaccaaa cgtttgttgt tcagctccag gacccacggg aacccaggag acaggccaca     420
cagatgctaa aactgcagaa tctggtgatc ccctgggctc cggagaacct aacacttcgc     480
aaactgagtg aatcccagct agaactgaac tggaacaaca gattcttgaa ccactgtttg     540

```
gagcacttgg tgcagtaccg gactgactgg gaccacagct ggactgaaca atcagtggat    600
tatagacata agttctcctt gcctagtgtg gatgggcaga aacgctacac gtttcgtgtc    660
cggagccgct ttaacccact ctgtggaagt gctcagcatt ggagtgaatg gagccaccca    720
atccactggg ggagcaatag ttcaaaagag aatcctttcc tgtttgcatt ggaagccgga    780
gctcaggaca aaactcacac atgcccaccg tgcccagcac ctgaactcct ggggggaccg    840
tcagtcttcc tcttcccccc aaaacccaag gacaccctca tgatctcccg gacccctgag    900
gtcacatgcg tggtggtgga cgtgagccac gaagaccctg aggtcaagtt caactggtac    960
gtggacggcg tggaggtgca taatgccaag acaaagccgc gggaggagca gtacaacagc   1020
acgtaccgtg tggtcagcgt cctcaccgtc ctgcaccagg actggctgaa tggcaaggag   1080
tacaagtgca aggtctccaa caaagccctc ggcgccccca tcgagaaaac catctccaaa   1140
gccaagggc agccccgaga ccacaggtg tgcaccctgc cccatcccg ggatgagctg    1200
accaagaacc aggtcagcct ctcgtgcgca gtcaaaggct tctatcccag cgacatcgcc   1260
gtggagtggg agagcaatgg gcagccggag aacaactaca agaccacgcc tcccgtgctg   1320
gactccgacg gctccttctt cctcgtgagc aagctcaccg tggacaagag caggtggcag   1380
caggggaacg tcttctcatg ctccgtgatg catgaggctc tgcacaacca ctacacgcag   1440
aagagcctct ccctgtctcc gggtaaatga                                    1470

<210> SEQ ID NO 37
<211> LENGTH: 217
<212> TYPE: PRT
<213> ORGANISM: Artificial Sequence
<220> FEATURE:
<223> OTHER INFORMATION: Cynomolgous IL-2R alpha subunit + Avi-tag +
      His-tag

<400> SEQUENCE: 37

Met Gly Trp Ser Cys Ile Ile Leu Phe Leu Val Ala Thr Ala Thr Gly
1               5                   10                  15

Glu Leu Cys Asp Asp Asp Pro Pro Lys Ile Thr His Ala Thr Phe Lys
            20                  25                  30

Ala Met Ala Tyr Lys Glu Gly Thr Met Leu Asn Cys Glu Cys Lys Arg
        35                  40                  45

Gly Phe Arg Arg Ile Lys Ser Gly Ser Pro Tyr Met Leu Cys Thr Gly
    50                  55                  60

Asn Ser Ser His Ser Ser Trp Asp Asn Gln Cys Gln Cys Thr Ser Ser
65                  70                  75                  80

Ala Ala Arg Asn Thr Thr Lys Gln Val Thr Pro Gln Pro Glu Glu Gln
                85                  90                  95

Lys Glu Arg Lys Thr Thr Glu Met Gln Ser Gln Met Gln Leu Ala Asp
            100                 105                 110

Gln Val Ser Leu Pro Gly His Cys Arg Glu Pro Pro Trp Glu Asn
        115                 120                 125

Glu Ala Thr Glu Arg Ile Tyr His Phe Val Val Gly Gln Thr Val Tyr
    130                 135                 140

Tyr Gln Cys Val Gln Gly Tyr Arg Ala Leu His Arg Gly Pro Ala Glu
145                 150                 155                 160

Ser Val Cys Lys Met Thr His Gly Lys Thr Arg Trp Thr Gln Pro Gln
                165                 170                 175

Leu Ile Cys Thr Gly Glu Val Asp Glu Gln Leu Tyr Phe Gln Gly Gly
            180                 185                 190
```

Ser Gly Leu Asn Asp Ile Phe Glu Ala Gln Lys Ile Glu Trp His Glu
            195                 200                 205

Ala Arg Ala His His His His His His
    210                 215

<210> SEQ ID NO 38
<211> LENGTH: 654
<212> TYPE: DNA
<213> ORGANISM: Artificial Sequence
<220> FEATURE:
<223> OTHER INFORMATION: Cynomolgous IL-2R alpha subunit + Avi-tag +
      His-tag

<400> SEQUENCE: 38
atgggatgga gctgtatcat cctcttcttg gtagcaacag ctaccggtga gctctgtgac      60
gatgacccgc aaaaatcac acatgccaca ttcaaagcca tggcctacaa ggaaggaacc     120
atgttgaact gtgaatgcaa gagaggtttc gcagaataa aaagcgggtc accctatatg     180
ctctgtacag gaaactctag ccactcgtcc tgggacaacc aatgtcaatg cacaagctct     240
gctgctcgga acacaacaaa acaagtgaca cctcaacctg aagaacagaa agaaagaaaa     300
accacagaaa tgcaaagtca atgcagctg gcggaccaag tgagccttcc aggtcactgc     360
agggaacctc caccgtggga aaatgaagcc acagaaagaa tttatcattt cgtggtgggg     420
cagacggttt actaccagtg cgtccaggga tacagggctc tacacagagg tcctgctgag     480
agcgtctgca aaatgaccca cggaagaca agatggaccc agccccagct catatgcaca     540
ggtgaagtcg acgaacagtt atattttcag ggcggctcag gcctgaacga catcttcgag     600
gcccagaaga tcgagtggca cgaggctcga gctcaccacc atcaccatca ctga         654

<210> SEQ ID NO 39
<211> LENGTH: 19
<212> TYPE: PRT
<213> ORGANISM: Artificial Sequence
<220> FEATURE:
<223> OTHER INFORMATION: leader sequence

<400> SEQUENCE: 39

Met Asp Trp Thr Trp Arg Ile Leu Phe Leu Val Ala Ala Ala Thr Gly
1               5                   10                  15

Ala His Ser

<210> SEQ ID NO 40
<211> LENGTH: 57
<212> TYPE: DNA
<213> ORGANISM: Artificial Sequence
<220> FEATURE:
<223> OTHER INFORMATION: leader sequence

<400> SEQUENCE: 40
atggactgga cctggagaat cctcttcttg gtggcagcag ccacaggagc ccactcc        57

<210> SEQ ID NO 41
<211> LENGTH: 57
<212> TYPE: DNA
<213> ORGANISM: Artificial Sequence
<220> FEATURE:
<223> OTHER INFORMATION: leader sequence

<400> SEQUENCE: 41
atggactgga cctggaggat cctcttcttg gtggcagcag ccacaggagc ccactcc        57

```
<210> SEQ ID NO 42
<211> LENGTH: 22
<212> TYPE: PRT
<213> ORGANISM: Artificial Sequence
<220> FEATURE:
<223> OTHER INFORMATION: leader sequence

<400> SEQUENCE: 42

Met Asp Met Arg Val Pro Ala Gln Leu Leu Gly Leu Leu Leu Leu Trp
1               5                   10                  15

Phe Pro Gly Ala Arg Cys
            20

<210> SEQ ID NO 43
<211> LENGTH: 66
<212> TYPE: DNA
<213> ORGANISM: Artificial Sequence
<220> FEATURE:
<223> OTHER INFORMATION: leader sequence

<400> SEQUENCE: 43
atggacatga gggtccccgc tcagctcctg ggcctcctgc tgctctggtt cccaggtgcc      60
aggtgt                                                                66

<210> SEQ ID NO 44
<211> LENGTH: 19
<212> TYPE: PRT
<213> ORGANISM: Artificial Sequence
<220> FEATURE:
<223> OTHER INFORMATION: leader sequence

<400> SEQUENCE: 44

Met Gly Trp Ser Cys Ile Ile Leu Phe Leu Val Ala Thr Ala Thr Gly
1               5                   10                  15

Val His Ser

<210> SEQ ID NO 45
<211> LENGTH: 57
<212> TYPE: DNA
<213> ORGANISM: Artificial Sequence
<220> FEATURE:
<223> OTHER INFORMATION: leader sequence

<400> SEQUENCE: 45
atgggatgga gctgtatcat cctcttcttg gtagcaacag ctaccggtgt gcattcc         57

<210> SEQ ID NO 46
<211> LENGTH: 57
<212> TYPE: DNA
<213> ORGANISM: Artificial Sequence
<220> FEATURE:
<223> OTHER INFORMATION: leader sequence

<400> SEQUENCE: 46
atgggctggt cctgcatcat cctgtttctg gtggctaccg ccactggagt gcattcc         57

<210> SEQ ID NO 47
<211> LENGTH: 57
<212> TYPE: DNA
<213> ORGANISM: Artificial Sequence
<220> FEATURE:
<223> OTHER INFORMATION: leader sequence

<400> SEQUENCE: 47
atgggctggt cctgcatcat cctgtttctg gtcgccacag ccaccggcgt gcactct         57
```

<210> SEQ ID NO 48
<211> LENGTH: 592
<212> TYPE: PRT
<213> ORGANISM: Artificial Sequence
<220> FEATURE:
<223> OTHER INFORMATION: DP47GS HC(Fc knob,P329G LALA)-IL2 N88D

<400> SEQUENCE: 48

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ser Gly Phe Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Gly Ala Pro Ile Glu Lys Thr Ile Ser Lys
                325                 330                 335

Ala Lys Gly Gln Pro Arg Glu Pro Gln Val Tyr Thr Leu Pro Pro Cys
            340                 345                 350

Arg Asp Glu Leu Thr Lys Asn Gln Val Ser Leu Trp Cys Leu Val Lys
        355                 360                 365
```

```
Gly Phe Tyr Pro Ser Asp Ile Ala Val Glu Trp Glu Ser Asn Gly Gln
        370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Gly Gly Gly Gly
        435                 440                 445

Ser Gly Gly Gly Gly Ser Gly Gly Gly Gly Ser Ala Pro Ala Ser Ser
    450                 455                 460

Ser Thr Lys Lys Thr Gln Leu Gln Leu Glu His Leu Leu Leu Asp Leu
465                 470                 475                 480

Gln Met Ile Leu Asn Gly Ile Asn Asn Tyr Lys Asn Pro Lys Leu Thr
                485                 490                 495

Arg Met Leu Thr Phe Lys Phe Tyr Met Pro Lys Lys Ala Thr Glu Leu
                500                 505                 510

Lys His Leu Gln Cys Leu Glu Glu Glu Leu Lys Pro Leu Glu Glu Val
            515                 520                 525

Leu Asn Leu Ala Gln Ser Lys Asn Phe His Leu Arg Pro Arg Asp Leu
530                 535                 540

Ile Ser Asp Ile Asn Val Ile Val Leu Glu Leu Lys Gly Ser Glu Thr
545                 550                 555                 560

Thr Phe Met Cys Glu Tyr Ala Asp Glu Thr Ala Thr Ile Val Glu Phe
                565                 570                 575

Leu Asn Arg Trp Ile Thr Phe Ala Gln Ser Ile Ile Ser Thr Leu Thr
                580                 585                 590

<210> SEQ ID NO 49
<211> LENGTH: 1776
<212> TYPE: DNA
<213> ORGANISM: Artificial Sequence
<220> FEATURE:
<223> OTHER INFORMATION: DP47GS HC(Fc knob,P329G LALA)-IL2 N88D

<400> SEQUENCE: 49
gaggtgcaat tgttggagtc tgggggaggc ttggtacagc ctggggggtc cctgagactc      60
tcctgtgcag cctccggatt cacctttagc agttatgcca tgagctgggt ccgccaggct     120
ccagggaagg gctggagtg gtctcagct attagtggta gtggtggtag cacatactac      180
gcagactccg tgaagggccg gttcaccatc tccagagaca attccaagaa cacgctgtat     240
ctgcagatga acagcctgag agccgaggac acggccgtat attactgtgc gaaaggcagc     300
ggatttgact actggggcca aggaaccctg gtcaccgtct cgagtgctag caccaagggc     360
ccatcggtct tccccctggc accctcctcc aagagcacct ctgggggcac agcggccctg     420
ggctgcctgg tcaaggacta cttccccgaa ccggtgacgg tgtcgtggaa ctcaggcgcc     480
ctgaccagcg gcgtgcacac cttcccggct gtcctacagt cctcaggact ctactccctc     540
agcagcgtgg tgaccgtgcc ctccagcagc ttgggcaccc agacctacat ctgcaacgtg     600
aatcacaagc ccagcaacac caaggtggac aagaaagttg agcccaaatc ttgtgacaaa     660
actcacacat gcccaccgtg cccagcacct gaagctgcag gggaccgtc agtcttcctc      720 ttccccccaa aacccaagga caccctcatg atctcccgga cccctgaggt cacatgcgtg     780
```

```
gtggtggacg tgagccacga agaccctgag gtcaagttca actggtacgt ggacggcgtg      840
gaggtgcata atgccaagac aaagccgcgg gaggagcagt acaacagcac gtaccgtgtg      900
gtcagcgtcc tcaccgtcct gcaccaggac tggctgaatg gcaaggagta caagtgcaag      960
gtctccaaca aagccctcgg cgccccatc gagaaaacca tctccaaagc caaagggcag      1020
ccccgagaac acaggtgta caccctgccc ccatgccggg atgagctgac caagaaccag      1080
gtcagcctgt ggtgcctggt caaaggcttc tatcccagcg acatcgccgt ggagtgggag      1140
agcaatgggc agccggagaa caactacaag accacgcctc ccgtgctgga ctccgacggc      1200
tccttcttcc tctacagcaa gctcaccgtg gacaagagca ggtggcagca ggggaacgtc      1260
ttctcatgct ccgtgatgca tgaggctctg cacaaccact acacgcagaa gagcctctcc      1320
ctgtctccgg gtggcggcgg aggctccgga ggcggaggtt ctggaggcgg aggtccgca      1380 cctgcctcaa gttctacaaa gaaaacacag ctacaactgg agcatttact gctggattta      1440
cagatgattt tgaatggaat taataattac aagaatccca aactcaccag gatgctcaca      1500
tttaagtttt acatgcccaa gaaggccaca gaactgaaac atcttcagtg tctagaagaa      1560
gaactcaaac ctctggagga agtgctaaat ttagctcaaa gcaaaaactt tcacttaaga      1620
cccagggact taatcagcga tatcaacgta atagttctgg aactaaaggg atctgaaaca      1680
acattcatgt gtgaatatgc tgatgagaca gcaaccattg tagaatttct gaacagatgg      1740
attacctttg cccaaagcat catctcaaca ctgact                                1776
```

<210> SEQ ID NO 50
<211> LENGTH: 592
<212> TYPE: PRT
<213> ORGANISM: Artificial Sequence
<220> FEATURE:
<223> OTHER INFORMATION: DP47GS HC(Fc wt,P329G LALA)-IL2 N88D

<400> SEQUENCE: 50

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ser Gly Phe Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190
```

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
                275                 280                 285

Pro Arg Glu Glu Gln Tyr Asn Ser Thr Tyr Arg Val Val Ser Val Leu
        290                 295                 300

Thr Val Leu His Gln Asp Trp Leu Asn Gly Lys Glu Tyr Lys Cys Lys
305                 310                 315                 320

Val Ser Asn Lys Ala Leu Gly Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Gly Gly Gly Gly
        435                 440                 445

Ser Gly Gly Gly Gly Ser Gly Gly Gly Gly Ser Ala Pro Ala Ser Ser
450                 455                 460

Ser Thr Lys Lys Thr Gln Leu Gln Leu Glu His Leu Leu Leu Asp Leu
465                 470                 475                 480

Gln Met Ile Leu Asn Gly Ile Asn Asn Tyr Lys Asn Pro Lys Leu Thr
                485                 490                 495

Arg Met Leu Thr Phe Lys Phe Tyr Met Pro Lys Lys Ala Thr Glu Leu
            500                 505                 510

Lys His Leu Gln Cys Leu Glu Glu Glu Leu Lys Pro Leu Glu Glu Val
        515                 520                 525

Leu Asn Leu Ala Gln Ser Lys Asn Phe His Leu Arg Pro Arg Asp Leu
530                 535                 540

Ile Ser Asp Ile Asn Val Ile Val Leu Glu Leu Lys Gly Ser Glu Thr
545                 550                 555                 560

Thr Phe Met Cys Glu Tyr Ala Asp Glu Thr Ala Thr Ile Val Glu Phe
                565                 570                 575

Leu Asn Arg Trp Ile Thr Phe Ala Gln Ser Ile Ile Ser Thr Leu Thr
            580                 585                 590

<210> SEQ ID NO 51
<211> LENGTH: 1776

<210> SEQ ID NO 51
<211> LENGTH: 1776
<212> TYPE: DNA
<213> ORGANISM: Artificial Sequence
<220> FEATURE:
<223> OTHER INFORMATION: DP47GS HC(Fc wt,P329G LALA)-IL2 N88D

<400> SEQUENCE: 51

```
gaggtgcaat tgttggagtc tgggggaggc ttggtacagc ctggggggtc cctgagactc        60
tcctgtgcag cctccggatt cacctttagc agttatgcca tgagctgggt ccgccaggct       120
ccagggaagg gctggagtg gtctcagct attagtggta gtggtggtag cacatactac        180
gcagactccg tgaagggccg gttcaccatc tccagagaca attccaagaa cacgctgtat       240
ctgcagatga acagcctgag agccgaggac acggccgtat attactgtgc gaaaggcagc       300
ggatttgact actggggcca aggaaccctg gtcaccgtct cgagtgctag caccaagggc       360
ccatcggtct tccccctggc accctcctcc aagagcacct ctgggggcac agcggccctg       420
ggctgcctgg tcaaggacta cttccccgaa ccggtgacgg tgtcgtggaa ctcaggcgcc       480
ctgaccagcg gcgtgcacac cttcccggct gtcctacagt cctcaggact ctactccctc       540
agcagcgtgg tgaccgtgcc ctccagcagc ttgggcaccc agacctacat ctgcaacgtg       600
aatcacaagc ccagcaacac caaggtggac aagaaagttg agcccaaatc ttgtgacaaa       660
actcacacat gcccaccgtg cccagcacct gaagctgcag ggggaccgtc agtcttcctc       720
ttccccccaa aacccaagga caccctcatg atctcccgga cccctgaggt cacatgcgtg       780
gtggtggacg tgagccacga agaccctgag gtcaagttca actggtacgt ggacggcgtg       840
gaggtgcata atgccaagac aaagccgcgg gaggagcagt acaacagcac gtaccgtgtg       900
gtcagcgtcc tcaccgtcct gcaccaggac tggctgaatg gcaaggagta caagtgcaag       960
gtctccaaca aagccctcgg cgcccccatc gagaaaacca tctccaaagc caaagggcag      1020
ccccgagaac cacaggtgta caccctgccc ccatcccggg atgagctgac caagaaccag      1080
gtcagcctga cctgcctggt caaaggcttc tatcccagcg acatcgccgt ggagtgggag      1140
agcaatgggc agccggagaa caactacaag accacgcctc ccgtgctgga ctccgacggc      1200
tccttcttcc tctacagcaa gctcaccgtg gacaagagca ggtggcagca ggggaacgtc      1260
ttctcatgct ccgtgatgca tgaggctctg cacaaccact acacgcagaa gagcctctcc      1320
ctgtctccgg gtggcggcgg aggctccgga ggcggaggtt ctggaggcgg aggctccgca      1380
cctgcctcaa gttctacaaa gaaaacacag ctacaactgg agcatttact gctggattta      1440
cagatgattt tgaatggaat taataattac aagaatccca aactcaccag gatgctcaca      1500
tttaagtttt acatgcccaa gaaggccaca gaactgaaac atcttcagtg tctagaagaa      1560
gaactcaaac ctctggagga agtgctaaat ttagctcaaa gcaaaaactt tcacttaaga      1620
cccagggact aatcagcga tatcaacgta atagttctgg aactaagggg atctgaaaca      1680
acattcatgt gtgaatatgc tgatgagaca gcaaccattg tagaatttct gaacagatgg      1740
attacctttg cccaaagcat catctcaaca ctgact                                1776
```

<210> SEQ ID NO 52
<211> LENGTH: 592
<212> TYPE: PRT
<213> ORGANISM: Artificial Sequence
<220> FEATURE:
<223> OTHER INFORMATION: DP47GS HC(Fc wt, P329G LALA)-IL2 E95A

<400> SEQUENCE: 52

```
Glu Val Gln Leu Leu Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Ser Tyr
         20                  25                  30

Ala Met Ser Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                 85                  90                  95

Ala Lys Gly Ser Gly Phe Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Gly Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430
```

```
His Tyr Thr Gln Lys Ser Leu Ser Leu Ser Pro Gly Gly Gly Gly
            435                 440                 445
Ser Gly Gly Gly Gly Ser Gly Gly Gly Gly Ser Ala Pro Ala Ser Ser
    450                 455                 460
Ser Thr Lys Lys Thr Gln Leu Gln Leu Glu His Leu Leu Asp Leu
465                 470                 475                 480
Gln Met Ile Leu Asn Gly Ile Asn Asn Tyr Lys Asn Pro Lys Leu Thr
                    485                 490                 495
Arg Met Leu Thr Phe Lys Phe Tyr Met Pro Lys Lys Ala Thr Glu Leu
                500                 505                 510
Lys His Leu Gln Cys Leu Glu Glu Leu Lys Pro Leu Glu Glu Val
            515                 520                 525
Leu Asn Leu Ala Gln Ser Lys Asn Phe His Leu Arg Pro Arg Asp Leu
        530                 535                 540
Ile Ser Asn Ile Asn Val Ile Val Leu Pro Leu Lys Gly Ser Glu Thr
545                 550                 555                 560
Thr Phe Met Cys Glu Tyr Ala Asp Glu Thr Ala Thr Ile Val Glu Phe
                565                 570                 575
Leu Asn Arg Trp Ile Thr Phe Ala Gln Ser Ile Ile Ser Thr Leu Thr
                580                 585                 590

<210> SEQ ID NO 53
<211> LENGTH: 1776
<212> TYPE: DNA
<213> ORGANISM: Artificial Sequence
<220> FEATURE:
<223> OTHER INFORMATION: DP47GS HC(Fc wt, P329G LALA)-IL2 E95A

<400> SEQUENCE: 53
gaggtgcaat tgttggagtc tgggggaggc ttggtacagc ctggggggtc cctgagactc      60
tcctgtgcag cctccggatt cacctttagc agttatgcca tgagctgggt ccgccaggct     120
ccagggaagg gctgagtg gtctcagct attagtggta gtggtggtag cacatactac        180
gcagactccg tgaagggccg gttcaccatc tccagagaca attccaagaa cacgctgtat     240
ctgcagatga acagcctgag agccgaggac acggccgtat attactgtgc gaaaggcagc    300
ggatttgact actggggcca aggaaccctg gtcaccgtct cgagtgctag caccaagggc     360
ccatcggtct tccccctggc accctcctcc aagagcacct ctgggggcac agcggccctg     420
ggctgcctgg tcaaggacta cttccccgaa ccggtgacgg tgtcgtggaa ctcaggcgcc     480
ctgaccagcg gcgtgcacac cttcccggct gtcctacagt cctcaggact ctactccctc     540
agcagcgtgg tgaccgtgcc ctccagcagc ttgggcaccc agacctacat ctgcaacgtg     600
aatcacaagc ccagcaacac caaggtggac aagaaagttg agcccaaatc ttgtgacaaa     660
actcacacat gcccaccgtg cccagcacct gaagctgcag ggggaccgtc agtcttcctc     720
ttccccccaa aacccaagga caccctcatg atctcccgga cccctgaggt cacatgcgtg     780
gtggtggacg tgagccacga agaccctgag gtcaagttca actggtacgt ggacggcgtg     840
gaggtgcata atgccaagac aaagccgcgg gaggagcagt acaacagcac gtaccgtgtg     900
gtcagcgtcc tcaccgtcct gcaccaggac tggctgaatg gcaaggagta caagtgcaag     960
gtctccaaca aagccctcgg cgcccccatc gagaaaacca tctccaaagc caagggcag    1020
ccccgagaac acaggtgta caccctgccc ccatcccggg atgagctgac caagaaccag    1080
gtcagcctga cctgcctggt caaaggcttc tatcccagcg acatcgccgt ggagtgggag    1140
agcaatgggc agccggagaa caactacaag accacgcctc ccgtgctgga ctccgacggc    1200
```

```
tccttcttcc tctacagcaa gctcaccgtg acaagagca ggtggcagca ggggaacgtc    1260
ttctcatgct ccgtgatgca tgaggctctg cacaaccact acacgcagaa gagcctctcc    1320
ctgtctccgg gtggcggcgg aggctccgga ggcggaggtt ctggaggcgg aggctccgca    1380
cctgcctcaa gttctacaaa gaaaacacag ctacaactgg agcatttact gctggattta    1440
cagatgattt tgaatggaat taataattac aagaatccca aactcaccag gatgctcaca    1500
tttaagtttt acatgcccaa gaaggccaca gaactgaaac atcttcagtg tctagaagaa    1560
gaactcaaac ctctggagga agtgctaaat ttagctcaaa gcaaaaactt tcacttaaga    1620
cccagggact aatcagcaa tatcaacgta atagttctgc cactaaaggg atctgaaaca    1680
acattcatgt gtgaatatgc tgatgagaca gcaaccattg tagaatttct gaacagatgg    1740
attacctttg cccaaagcat catctcaaca ctgact                             1776
```

<210> SEQ ID NO 54
<211> LENGTH: 42
<212> TYPE: DNA
<213> ORGANISM: Artificial Sequence
<220> FEATURE:
<223> OTHER INFORMATION: FOXP3 forward primer

<400> SEQUENCE: 54

```
tgtaaaacga cggccagttt tagaagttgt atgggggatg tt                      42
```

<210> SEQ ID NO 55
<211> LENGTH: 44
<212> TYPE: DNA
<213> ORGANISM: Artificial Sequence
<220> FEATURE:
<223> OTHER INFORMATION: FOXP3 reverse primer

<400> SEQUENCE: 55

```
caggaaacag ctatgaccaa aatatctacc ctcttctctt cctc                    44
```

<210> SEQ ID NO 56
<211> LENGTH: 42
<212> TYPE: DNA
<213> ORGANISM: Artificial Sequence
<220> FEATURE:
<223> OTHER INFORMATION: CTLA-4 forward primer

<400> SEQUENCE: 56

```
tgtaaaacga cggccagtgg gtttggttat gaaggagtat ga                      42
```

<210> SEQ ID NO 57
<211> LENGTH: 45
<212> TYPE: DNA
<213> ORGANISM: Artificial Sequence
<220> FEATURE:
<223> OTHER INFORMATION: CTLA-4 reverse primer

<400> SEQUENCE: 57

```
caggaaacag ctatgacctt cacttaattt ccactaaaaa taccc                   45
```

<210> SEQ ID NO 58
<211> LENGTH: 133
<212> TYPE: PRT
<213> ORGANISM: Artificial Sequence
<220> FEATURE:
<223> OTHER INFORMATION: IL-2 N88D T3A C125A

<400> SEQUENCE: 58

Ala Pro Ala Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asp Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
            115                 120                 125

Ile Ser Thr Leu Thr
        130

<210> SEQ ID NO 59
<211> LENGTH: 399
<212> TYPE: DNA
<213> ORGANISM: Artificial Sequence
<220> FEATURE:
<223> OTHER INFORMATION: IL-2 N88D T3A C125A

<400> SEQUENCE: 59
gcacctgcct caagttctac aaagaaaaca cagctacaac tggagcattt actgctggat      60
ttacagatga ttttgaatgg aattaataat tacaagaatc ccaaactcac caggatgctc     120
acatttaagt tttacatgcc caagaaggcc acagaactga acatcttca gtgtctagaa      180 gaagaactca aacctctgga ggaagtgcta aatttagctc aaagcaaaaa ctttcactta     240
agacccaggg acttaatcag cgatatcaac gtaaagtttc tggaactaaa gggatctgaa     300
acaacattca tgtgtgaata tgctgatgag acagcaacca ttgtagaatt tctgaacaga     360
tggattacct ttgcccaaag catcatctca acactgact                             399

<210> SEQ ID NO 60
<211> LENGTH: 133
<212> TYPE: PRT
<213> ORGANISM: Artificial Sequence
<220> FEATURE:
<223> OTHER INFORMATION: IL-2 N88D

<400> SEQUENCE: 60

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asp Ile Asn Val Ile Val Leu Glu Leu
                85                  90                  95

```
Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130
```

<210> SEQ ID NO 61
<211> LENGTH: 399
<212> TYPE: DNA
<213> ORGANISM: Artificial Sequence
<220> FEATURE:
<223> OTHER INFORMATION: IL-2 N88D

<400> SEQUENCE: 61

```
gcacctactt caagttctac aaagaaaaca cagctacaac tggagcattt actgctggat    60
ttacagatga ttttgaatgg aattaataat acaagaatc ccaaactcac caggatgctc    120
acatttaagt tttacatgcc caagaaggcc acagaactga acatcttca gtgtctagaa    180
gaagaactca aacctctgga ggaagtgcta aatttagctc aaagcaaaaa ctttcactta    240
agacccaggg acttaatcag cgatatcaac gtaatagttc tggaactaaa gggatctgaa    300
acaacattca tgtgtgaata tgctgatgag acagcaacca ttgtagaatt tctgaacaga    360
tggattacct tttgtcaaag catcatctca acactgact                           399
```

<210> SEQ ID NO 62
<211> LENGTH: 133
<212> TYPE: PRT
<213> ORGANISM: Artificial Sequence
<220> FEATURE:
<223> OTHER INFORMATION: IL-2 N88D C125A

<400> SEQUENCE: 62

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asp Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125

Ile Ser Thr Leu Thr
    130
```

<210> SEQ ID NO 63
<211> LENGTH: 399
<212> TYPE: DNA
<213> ORGANISM: Artificial Sequence
<220> FEATURE:
<223> OTHER INFORMATION: IL-2 N88D C125A

<400> SEQUENCE: 63

```
gcacctactt caagttctac aaagaaaaca cagctacaac tggagcattt actgctggat    60
ttacagatga ttttgaatgg aattaataat tacaagaatc ccaaactcac caggatgctc   120
acatttaagt tttacatgcc caagaaggcc acagaactga acatcttca gtgtctagaa    180 gaagaactca aacctctgga ggaagtgcta aatttagctc aaagcaaaaa ctttcactta   240
agacccaggg acttaatcag cgatatcaac gtaatagttc tggaactaaa gggatctgaa   300
acaacattca tgtgtgaata tgctgatgag acagcaacca ttgtagaatt tctgaacaga   360
tggattacct ttgcccaaag catcatctca acactgact                          399
```

<210> SEQ ID NO 64
<211> LENGTH: 133
<212> TYPE: PRT
<213> ORGANISM: Artificial Sequence
<220> FEATURE:
<223> OTHER INFORMATION: IL-2 N88D T3A

<400> SEQUENCE: 64

```
Ala Pro Ala Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asp Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130
```

<210> SEQ ID NO 65
<211> LENGTH: 399
<212> TYPE: DNA
<213> ORGANISM: Artificial Sequence
<220> FEATURE:
<223> OTHER INFORMATION: IL-2 N88D T3A

<400> SEQUENCE: 65

```
gcacctgcct caagttctac aaagaaaaca cagctacaac tggagcattt actgctggat    60
ttacagatga ttttgaatgg aattaataat tacaagaatc ccaaactcac caggatgctc   120
acatttaagt tttacatgcc caagaaggcc acagaactga acatcttca gtgtctagaa    180 gaagaactca aacctctgga ggaagtgcta aatttagctc aaagcaaaaa ctttcactta   240
agacccaggg acttaatcag cgatatcaac gtaatagttc tggaactaaa gggatctgaa   300
acaacattca tgtgtgaata tgctgatgag acagcaacca ttgtagaatt tctgaacaga   360
tggattacct tttgtcaaag catcatctca acactgact                          399
```

<210> SEQ ID NO 66
<211> LENGTH: 15

```
<212> TYPE: PRT
<213> ORGANISM: Artificial Sequence
<220> FEATURE:
<223> OTHER INFORMATION: (G4S)3 linker

<400> SEQUENCE: 66

Gly Gly Gly Gly Ser Gly Gly Gly Gly Ser Gly Gly Gly Gly Ser
1               5                   10                  15
```